(12) United States Patent
Hutzler et al.

(10) Patent No.: US 10,226,046 B2
(45) Date of Patent: Mar. 12, 2019

(54) HERBICIDAL COMPOSITIONS COMPRISING ISOXAZOLO[5,4-B]PYRIDINES

(71) Applicant: BASF SE, Ludwigshafen (DE)

(72) Inventors: Johannes Hutzler, Waldsee (DE); Helmut Kraus, Wissembourg (FR); Anna Aleksandra Michrowska-Pianowska, Mannheim (DE); Yogesh Oturkar, Mumbai (IN); Trevor William Newton, Neustadt (DE); Stefan Tresch, Kirchheim (DE); Jens Lerchl, Potsdam OT Golm (DE); Thomas Seitz, Viernheim (DE); Richard Roger Evans, Limburgerhof (DE); Klaus Kreuz, Denzlingen (DE); Ulrich Steinbrenner, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/302,663

(22) PCT Filed: Apr. 8, 2015

(86) PCT No.: PCT/EP2015/057613
§ 371 (c)(1),
(2) Date: Oct. 7, 2016

(87) PCT Pub. No.: WO2015/155236
PCT Pub. Date: Oct. 15, 2015

(65) Prior Publication Data
US 2017/0112130 A1 Apr. 27, 2017

Related U.S. Application Data

(60) Provisional application No. 61/977,663, filed on Apr. 10, 2014.

(51) Int. Cl.
| | |
|---|---|
| *A01N 41/10* | (2006.01) |
| *A01N 43/40* | (2006.01) |
| *A01N 43/56* | (2006.01) |
| *A01N 43/80* | (2006.01) |
| *A01N 43/90* | (2006.01) |
| *A01N 61/00* | (2006.01) |
| *A01N 33/18* | (2006.01) |
| *A01N 33/22* | (2006.01) |
| *A01N 35/10* | (2006.01) |
| *A01N 37/02* | (2006.01) |
| *A01N 37/22* | (2006.01) |
| *A01N 37/30* | (2006.01) |
| *A01N 37/40* | (2006.01) |
| *A01N 39/04* | (2006.01) |
| *A01N 41/06* | (2006.01) |
| *A01N 43/10* | (2006.01) |
| *A01N 43/18* | (2006.01) |
| *A01N 43/42* | (2006.01) |
| *A01N 43/50* | (2006.01) |
| *A01N 43/54* | (2006.01) |
| *A01N 43/60* | (2006.01) |
| *A01N 43/66* | (2006.01) |
| *A01N 43/70* | (2006.01) |
| *A01N 43/76* | (2006.01) |
| *A01N 43/82* | (2006.01) |
| *A01N 43/84* | (2006.01) |
| *A01N 43/88* | (2006.01) |
| *A01N 47/06* | (2006.01) |
| *A01N 47/22* | (2006.01) |
| *A01N 47/30* | (2006.01) |
| *A01N 47/36* | (2006.01) |
| *A01N 47/38* | (2006.01) |
| *A01N 57/20* | (2006.01) |
| *A01N 43/653* | (2006.01) |
| *A01N 43/707* | (2006.01) |

(52) U.S. Cl.
CPC .......... *A01N 43/90* (2013.01); *A01N 61/00* (2013.01)

(58) Field of Classification Search
CPC combination set(s) only.
See application file for complete search history.

(56) References Cited

U.S. PATENT DOCUMENTS

| | | |
|---|---|---|
| 8,642,660 B2 | 2/2014 | Goldfarb |
| 2009/0163545 A1 | 6/2009 | Goldfarb |
| 2013/0123105 A1 | 5/2013 | Michrowska-Pianowska et al. |

FOREIGN PATENT DOCUMENTS

| | | |
|---|---|---|
| WO | WO 2009015208 | 1/2009 |
| WO | WO 2012010633 | 1/2012 |

OTHER PUBLICATIONS

Frequency herbicide label, BASF The Chemical Company, 2009.*
Armezon herbicide technical information brochure, BASF The Chemical Company, 2011.*

(Continued)

*Primary Examiner* — John Pak
(74) *Attorney, Agent, or Firm* — Brinks Gilson & Lione

(57) ABSTRACT

The present invention relates to herbicidal compositions comprising an isoxazolo[5,4-b]pyridine and at least one further compound selected from herbicidally active compounds and, if desired, safeners. The present invention also relates to the use of such a composition for controlling unwanted vegetation and to a method for controlling unwanted vegetation, which comprises allowing a composition to act on plants, their seeds and/or their habitat.

17 Claims, No Drawings

(56) References Cited

OTHER PUBLICATIONS

Rummens, F.H.A., "An improved definition of synergistic and antagonistic effects," Weed Science, vol. 23(1), pp. 4-6 (1975).*
Volochnyuk et al., "Approach to the Library of Fused Pyridine-4-carboxylic Acids by Combes-Type Reaction of Acyl Pyruvates and Electron-Rich Amino Heterocycles," J. Comb. Chem., vol. 12, (2010), pp. 510-517.
Elbannany et al., "Synthesis of New Isoxazolo[4,3-b]pyridine Derivatives," Pharmazie, vol. 43, (1988), pp. 128-129.
International Search Report, issued in PCT/EP2015/057613, dated May 29, 2015.
International Preliminary Report on Patentability, issued in PCT/EP2015/057613, dated Oct. 12, 2016.

\* cited by examiner

HERBICIDAL COMPOSITIONS COMPRISING ISOXAZOLO[5,4-B]PYRIDINES

This application is a National Stage application of International Application No. PCT/EP2015/057613, filed Apr. 8, 2015, which claims the benefit of U.S. Provisional Application No. 61/977,663, filed Apr. 10, 2014.

The present invention relates to herbicidal compositions comprising an isoxazolo[5,4-b]pyridine and at least one further compound selected from herbicidally active compounds and, if desired, safeners. The present invention also relates to the use of such a composition for controlling unwanted vegetation and to a method for controlling unwanted vegetation, which comprises allowing a composition to act on plants, their seeds and/or their habitat.

In the case of crop protection compositions, it is desirable in principle to increase the specific activity of an active compound and the reliability of the effect. It is particularly desirable for the crop protection composition to control the harmful plants effectively, but at the same time to be compatible with the useful plants in question. Also desirable is a broad spectrum of activity allowing the simultaneous control of a variety of harmful plants. Frequently, this cannot be achieved using a single herbicidally active compound.

With many highly effective herbicides, there is the problem that their compatibility with useful plants, in particular dicotyledonous crop plants, such as cotton, oilseed rape and graminaceous plants, such as barley, millet, corn, rice, wheat and sugar cane, is not always satisfactory, i.e. in addition to the harmful plants, the crop plants, too, are damaged on a scale which cannot be tolerated. By reducing the application rates, the useful plants are spared; however, naturally, the extent of the control of harmful plants decreases too.

Frequently, it is a problem that herbicides can only be applied within a narrow time frame in order to achieve the desired herbicidal action, which time frame may be unpredictably influenced by weather conditions.

It is known that special combinations of different specifically active herbicides may result in enhanced activity of an herbicide component in the sense of a synergistic effect. In this manner, it may be feasible to reduce the application rates of herbicidally active compounds required for controlling the harmful plants.

Furthermore, it is known that in some cases joint application of specifically acting herbicides with organic active compounds, some of which may also have herbicidal activity, provides better crop plant compatibility. In these cases, the active compounds act as antidotes or antagonists and are also referred to as safeners, since they reduce or even prevent damage of herbicides to the crop plants.

Isoxazolo[5,4-b]pyridines of formula (I) and their agriculturally useful salts have been described for example in WO 2012010633 for use as herbicides.

US 2009163545 describes such compounds as lifespan-altering for eukaryotic organisms. According to WO 2009015208, particular urea derivatives show an antibacterial effect. Potential routes for synthesis of isoxazolo[5,4-b]pyridine compounds are known from Elbannany et al, Pharmazie (1988) 43(2), 128-129 and Volochnyuk et al, Journal of Combinatorial Chemistry (2010) 12(4), 510-517.

It is an object of the present invention to provide herbicidal compositions which are highly active against unwanted harmful plants, showing enhanced activity in the sense of a synergistic effect. At the same time, the compositions should have good compatibility with useful plants. In addition, the compositions according to the invention should have a broad spectrum of activity.

These and further objects are achieved by the herbicidal compositions below.

Accordingly, the present invention relates to herbicidal compositions comprising as component
A) an isoxazolo[5,4-b]pyridine compound of formula I

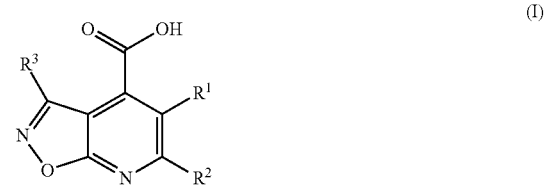

wherein the variables are as defined below:
$R^1$ is hydrogen, halogen, $C_1$-$C_6$-alkyl or $C_1$-$C_6$-haloalkyl;
$R^2$ is hydrogen, $C_1$-$C_6$-alkyl, $C_1$-$C_6$-haloalkyl, $C_1$-$C_6$-hydroxyalkyl, $C_3$-$C_6$-cycloalkyl, $C_3$-$C_6$-halocycloalkyl, $C_2$-$C_6$-alkenyl or $C_2$-$C_6$-alkynyl;
$R^3$ is hydrogen, halogen, hydroxy, $C_1$-$C_6$-alkyl, $C_1$-$C_6$-haloalkyl, $C_1$-$C_6$-hydroxyalkyl, $C_1$-$C_6$-alkoxy-$C_1$-$C_6$-alkyl, $C_1$-$C_6$-haloalkoxy-$C_1$-$C_6$-alkyl, $C_3$-$C_6$-cycloalkyl-$C_1$-$C_6$-alkyl, $C_3$-$C_6$-halocycloalkyl-$C_1$-$C_6$-alkyl, $C_3$-$C_6$-cycloalkyl, $C_3$-$C_6$-halocycloalkyl, $C_1$-$C_4$-alkyl-$C_3$-$C_6$-cycloalkyl, $C_3$-$C_6$-cycloalkenyl, $C_3$-$C_6$-halocycloalkenyl, phenyl-$C_1$-$C_6$-alkyl, heterocyclyl-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylthio, $C_1$-$C_6$-haloalkylthio, amino, $C_1$-$C_6$-alkylamino, N,N-di-($C_1$-$C_6$)-alkylamino, heterocyclyl or phenyl; wherein heterocyclyl is a 5- or 6-membered saturated, partially unsaturated or aromatic monocyclic ring, which contains 1, 2, 3 or 4 heteroatoms from the group consisting of O, N and S as ring members; and wherein the heterocyclyl and phenyl moieties of $R^3$ can be unsubstituted or substituted with one or more radicals selected from halogen, hydroxy, nitro, cyano, $C_1$-$C_4$-alkyl, $C_1$-$C_4$-haloalkyl, $C_1$-$C_4$-alkoxy-$C_1$-$C_4$-alkyl, $C_3$-$C_6$-cycloalkyl, $C_2$-$C_6$-alkenyl, $C_2$-$C_6$-alkynyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl, $C_1$-$C_4$-alkylsulfonyl, amino, $C_1$-$C_4$-alkylamino, N,N-di-($C_1$-$C_4$)-alkylamino, heterocyclyl and phenyl; or its agriculturally acceptable salt, carboxylic ester, thioester or amide;
and as component
B) at least one further herbicide (herbicide B) selected from the classes b1) to b15):
  b1) lipid biosynthesis inhibitors;
  b2) acetolactate synthase inhibitors (ALS inhibitors);
  b3) photosynthesis inhibitors;
  b4) protoporphyrinogen-IX oxidase inhibitors,
  b5) bleacher herbicides;
  b6) enolpyruvyl shikimate 3-phosphate synthase inhibitors (EPSP inhibitors);
  b7) glutamine synthetase inhibitors;
  b8) 7,8-dihydropteroate synthase inhibitors (DHP inhibitors);
  b9) mitosis inhibitors;
  b10) inhibitors of the synthesis of very long chain fatty acids (VLCFA inhibitors);
  b11) cellulose biosynthesis inhibitors;
  b12) decoupler herbicides;

b13) auxinic herbicides;
b14) auxin transport inhibitors; and
b15) other herbicides selected from the group consisting of bromobutide, chlorflurenol, chlorflurenol-methyl, (1RS,2SR,4SR)-1,4-epoxy-p-menth-2-yl 2-methylbenzyl ether, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3);
including their agriculturally acceptable salts or derivatives;
and as component C), if desired, safeners.

The compounds A of the formula (I) and their synthesis are known from WO 2012/010633 A1.

The invention relates in particular to compositions in the form of herbicidally active agrochemical compositions comprising a herbicidally effective amount of an active compound combination comprising at least one isoxazolo[5,4-b]pyridine of formula (I) and at least one further herbicide selected from the herbicides B and, if desired, the safeners C, as defined above, and also at least one liquid and/or solid carrier and/or one or more surfactants and, if desired, one or more further auxiliaries customary for agrochemical compositions.

The invention also relates to compositions in the form of an agrochemical composition formulated as a 1-component composition comprising as component A an active compound combination comprising at least one compound of formula (I) and, as component B), at least one further herbicide selected from the herbicides B, and, if desired, the safeners C, and at least one solid or liquid carrier and/or one or more surfactants and, if desired, one or more further auxiliaries customary for agrochemical compositions.

The invention also relates to compositions in the form of a agrochemical composition formulated as a 2-component composition comprising a first component comprising as component A) at least one isoxazolo[5,4-b]pyridine of formula (I), a solid or liquid carrier and/or one or more surfactants, and, as component B), at least one further herbicide selected from the herbicides B and, if desired, safeners C, a solid or liquid carrier and/or one or more surfactants, where additionally both components may also comprise further auxiliaries customary for agrochemical compositions.

Surprisingly, the compositions according to the invention comprising as component A) at least one isoxazolo[5,4-b]pyridine of formula (I) and, as component B), at least one herbicide B, have better herbicidal activity, i.e. better activity against harmful plants, than would have been expected based on the herbicidal activity observed for the individual compounds, or a broader activity spectrum. The herbicidal activity to be expected for compositions based on the individual compound can be calculated using Colby's formula (see below). If the activity observed exceeds the expected additive activity of the individual compounds, synergism is present.

Moreover, the time frame, within which the desired herbicidal action can be achieved, may be expanded by the compositions according to the invention comprising as component A) at least one isoxazolo[5,4-b]pyridine of formula (I) and, as component B), at least one herbicide B, and, if desired, a safener C. This allows a more flexibly timed application of the compositions according to the present invention in comparison with the single compounds.

The invention furthermore relates to a method for controlling unwanted vegetation, in particular in fields where crop plants are cultivated.

The invention also relates to a method for the desiccation or defoliation of plants.

As used herein, the terms "controlling" and "combating" are synonyms.

As used herein, the terms "undesirable vegetation" and "harmful plants" are synonyms.

If the isoxazolo[5,4-b]pyridine of formula (I), the herbicides B and/or the safeners C as described herein are capable of forming geometrical isomers, for example E/Z isomers, it is possible to use both, the pure isomers and mixtures thereof, in the compositions according to the invention.

If the isoxazolo[5,4-b]pyridine of formula (I), the herbicides B and/or the safeners C as described herein have one or more centers of chirality and, as a consequence, are present as enantiomers or diastereomers, it is possible to use both, the pure enantiomers and diastereomers and their mixtures, in the compositions according to the invention.

If the isoxazolo[5,4-b]pyridine of formula (I), the herbicides B and/or the safeners C as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)-ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Isoxazolo[5,4-b]pyridines of formula (I), herbicides B and/or safeners C as described herein having a carboxyl group can be employed in the form of the acid, in the form of an agriculturally suitable salt as mentioned above or else in the form of an agriculturally acceptable derivative, for example as amides, as esters, and also as thioesters.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

The terms used for organic groups in the definition of the variables are, for example the expression "alkyl", collective terms which represent the individual members of these groups of organic units.

The prefix $C_x$-$C_y$ denotes the number of possible carbon atoms in the particular case. halogen: fluorine, chlorine, bromine or iodine, especially fluorine, chlorine or bromine; alkyl and the alkyl moieties of composite groups such as alkoxy, alkylamino, alkylthio, alkoxycarbonyl: saturated straight-chain or branched hydrocarbon radicals having 1 to 10 carbon atoms, preferably $C_1$-$C_6$-alkyl or $C_1$-$C_4$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; heptyl, octyl, 2-ethylhexyl and positional isomers thereof; nonyl, decyl and positional isomers thereof;

haloalkyl: straight-chain or branched alkyl groups having 1 to 10 carbon atoms (as mentioned above), preferably $C_1$-$C_6$-haloalkyl or $C_1$-$C_4$-haloalkyl, where some or all of the hydrogen atoms in these groups are replaced by halogen atoms as mentioned above. In one embodiment, the alkyl groups are substituted at least once or completely by a particular halogen atom, preferably fluorine, chlorine or bromine. In a further embodiment, the alkyl groups are partially or fully halogenated by different halogen atoms; in the case of mixed halogen substitutions, the combination of chlorine and fluorine is preferred. Particular preference is given to ($C_1$-$C_3$)-haloalkyl, more preferably ($C_1$-$C_2$)-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl; alkenyl and also the alkenyl moieties in composite groups, such as alkenyloxy: unsaturated straight-chain or branched hydrocarbon radicals having 2 to 10 carbon atoms and one double bond in any position. According to the invention, it may be preferred to use small alkenyl groups, such as ($C_2$-$C_6$)-alkenyl; on the other hand, it may also be preferred to employ larger alkenyl groups, such as ($C_5$-$C_8$)-alkenyl. Examples of $C_2$-$C_6$-alkenyl groups are: ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl and the alkynyl moieties in composite groups: straight-chain or branched hydrocarbon groups having 2 to 10 carbon atoms and one triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl and also the cycloalkyl moieties in composite groups: mono- or bicyclic saturated hydrocarbon groups having 3 to 10, in particular 3 to 6, carbon ring members. Examples for $C_3$-$C_6$-cycloalkyl are: cyclopropyl, cyclobutyl, cyclopentyl, cyclohexyl, cycloheptyl or cyclooctyl. Examples of bicyclic radicals comprise bicyclo[2.2.1]heptyl, bicyclo[3.1.1]heptyl, bicyclo[2.2.2]octyl and bicyclo[3.2.1]octyl; halocycloalkyl and the halocycloalkyl moieties in composite groups: monocyclic saturated hydrocarbon groups having 3 to 10 carbon ring members (as mentioned above) in which some or all of the hydrogen atoms may be replaced by halogen atoms as mentioned above, in particular fluorine, chlorine and bromine;

cycloalkenyl: monocyclic monounsaturated hydrocarbon groups having 3 to 10, 3 to 8, 3 to 6, preferably 5 to 6, carbon ring members, such as cyclopenten-1-yl, cyclopenten-3-yl, cyclohexen-1-yl, cyclohexen-3-yl, cyclohexen-4-yl and the like;

alkoxy: an alkyl group as defined above, which is attached via an oxygen, preferably having 1 to 10, more preferably 1 to 6 or 1 to 4 carbon atoms. Examples are: methoxy, ethoxy, n-propoxy, 1-methylethoxy, butoxy, 1-methylpropoxy, 2-methylpropoxy or 1,1-dimethylethoxy, and also for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1, 2-trimethylpropoxy, 1,2,2-trimethylpropoxy, 1-ethyl-1-methylpropoxy or 1-ethyl-2-methylpropoxy;

haloalkoxy: alkoxy as defined above, where some or all of the hydrogen atoms in these groups are replaced by halogen atoms as described above under haloalkyl, in particular by fluorine, chlorine or bromine. Examples are $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy; and also 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy; aryl: 6 to 10-membered, aromatic carbocycle with 6, 7, 8, 9 or 10 carbon atoms.

Examples of preferred aryl are phenyl or naphthyl;

heterocyclyl: 5- or 6-membered saturated, partially unsaturated or aromatic monocyclic ring system, which contains 1, 2, 3 or 4 heteroatoms from the group consisting of O, N and S as ring members, where the heterocycle in question may be attached via a carbon atom or, if present, via a nitrogen atom. In particular:

a five- or six-membered saturated or partially unsaturated heterocycle which comprises one, two, three or four heteroatoms from the group consisting of O, N and S as ring members: for example monocyclic saturated or partially unsaturated heterocycles which, in addition to carbon ring members, comprise one, two or three nitrogen atoms and/or one oxygen or sulfur atom or one or two oxygen and/or sulfur atoms, for example aziridine, oxirane, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals;

a five- or six-membered aromatic heterocyclyl (=heteroaromatic radical) which contains one, two, three or four heteroatoms from the group consisting of oxygen, nitrogen and sulfur, for example 5-membered heteroaryl which is attached via carbon and contains one to three nitrogen atoms or one or two nitrogen atoms and one sulfur or oxygen atom as ring members, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 5-membered heteroaryl which is attached via nitrogen and contains one to three nitrogen atoms as ring members, such as pyrrol-1-yl, pyrazol-1-yl, imidazol-1-yl, 1,2,3-triazol-1-yl and 1,2,4-triazol-1-yl; 6-membered heteroaryl, which contains one, two or three nitrogen atoms as ring members, such as pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

The preferred embodiments of the invention mentioned herein below have to be understood as being preferred either independently from each other or in combination with one another.

According to a preferred embodiment of the invention preference is given to those compositions comprising an isoxazolo[5,4-b]pyridine of formula I, wherein $R^1$ is hydrogen, halogen, $C_1$-$C_6$-alkyl or $C_1$-$C_6$-haloalkyl. Particularly preferred are those compositions comprising an isoxazolo [5,4-b]pyridine of formula I, wherein $R^1$ is hydrogen.

According to another preferred embodiment of the invention, preference is given to those compositions comprising an isoxazolo[5,4-b]pyridine of formula I, wherein $R^2$ is $C_1$-$C_6$-alkyl, $C_1$-$C_6$-haloalkyl, $C_1$-$C_6$-hydroxyalkyl, $C_3$-$C_6$-cycloalkyl, $C_3$-$C_6$-halocycloalkyl, $C_2$-$C_6$-alkenyl or $C_2$-$C_6$-alkynyl. Particularly preferred are those compositions comprising an isoxazolo[5,4-b]pyridine of formula I, wherein $R^2$ is $C_3$-$C_6$-cycloalkyl or $C_3$-$C_6$-halocycloalkyl; most particularly preferred are those compositions comprising an isoxazolo[5,4-b]pyridine of formula I, wherein $R^2$ is cyclopropyl or 1-fluorocyclopropyl.

According to another preferred embodiment of the invention, preference is also given to those compositions comprising an isoxazolo[5,4-b]pyridine of formula I, wherein $R^3$ is $C_1$-$C_6$-alkyl, $C_1$-$C_6$-haloalkyl, $C_3$-$C_6$-cycloalkyl-$C_1$-$C_6$-alkyl, $C_3$-$C_6$-halocycloalkyl-$C_1$-$C_6$-alkyl, $C_3$-$C_6$-cycloalkyl, $C_3$-$C_6$-halocycloalkyl, $C_1$-$C_4$-alkyl-$C_3$-$C_6$-cycloalkyl, $C_1$-$C_6$-alkoxy, $C_1$-$C_6$-haloalkoxy or phenyl; wherein the phenyl moieties of $R^3$ can be unsubstituted or substituted with one or more radicals selected from halogen, hydroxy, nitro, cyano, $C_1$-$C_4$-alkyl, $C_1$-$C_4$-haloalkyl, $C_1$-$C_4$-alkoxy-$C_1$-$C_4$-alkyl, $C_3$-$C_6$-cycloalkyl, $C_2$-$C_6$-alkenyl, $C_2$-$C_6$-alkynyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl, $C_1$-$C_4$-alkylsulfonyl, amino, $C_1$-$C_4$-alkylamino, N,N-di-($C_1$-$C_4$)-alkylamino, heterocyclyl and phenyl.

Particularly preferred are those compositions comprising an isoxazolo[5,4-b]pyridine of formula I, wherein $R^3$ is $C_1$-$C_6$-alkyl, $C_1$-$C_6$-haloalkyl, $C_3$-$C_6$-cycloalkyl-$C_1$-$C_6$-alkyl, $C_3$-$C_6$-halocycloalkyl-$C_1$-$C_6$-alkyl, $C_3$-$C_6$-cycloalkyl, $C_3$-$C_6$-halocycloalkyl, $C_1$-$C_4$-alkyl-$C_3$-$C_6$-cycloalkyl, $C_1$-$C_6$-alkoxy or $C_1$-$C_6$-haloalkoxy. In a very particularly preferred aspect $R^3$ is methyl, cyclopropyl or 1,1-dimethylethoxy; even more particularly preferred $R^3$ is cyclopropyl.

Another preferred embodiment of the invention relates to compositions comprising an isoxazolo[5,4-b]pyridine of formula I, wherein
$R^1$ is hydrogen;
$R^2$ is hydrogen, $C_1$-$C_6$-alkyl, $C_1$-$C_6$-haloalkyl, $C_1$-$C_6$-hydroxyalkyl, $C_3$-$C_6$-cycloalkyl, $C_3$-$C_6$-halocycloalkyl, $C_2$-$C_6$-alkenyl or $C_2$-$C_6$-alkynyl;
$R^3$ is hydrogen, halogen, hydroxy, $C_1$-$C_6$-alkyl, $C_1$-$C_6$-haloalkyl, $C_1$-$C_6$-hydroxyalkyl, $C_1$-$C_6$-alkoxy-$C_1$-$C_6$-alkyl, $C_1$-$C_6$-haloalkoxy-$C_1$-$C_6$-alkyl, $C_3$-$C_6$-cycloalkyl-$C_1$-$C_6$-alkyl, $C_3$-$C_6$-halocycloalkyl-$C_1$-$C_6$-alkyl, $C_3$-$C_6$-cycloalkyl, $C_3$-$C_6$-halocycloalkyl, $C_1$-$C_4$-alkyl-$C_3$-$C_6$-cycloalkyl, $C_3$-$C_6$-cycloalkenyl, $C_3$-$C_6$-halocycloalkenyl, phenyl-$C_1$-$C_6$-alkyl, heterocyclyl-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylthio, $C_1$-$C_6$-haloalkylthio, amino, $C_1$-$C_6$-alkylamino, N,N-di-($C_1$-$C_6$)-alkylamino, heterocyclyl or phenyl; wherein the heterocyclyl and phenyl moieties of $R^3$ can be unsubstituted or substituted with one or more radicals selected from halogen, hydroxy, nitro, cyano, $C_1$-$C_4$-alkyl, $C_1$-$C_4$-haloalkyl, $C_1$-$C_4$-alkoxy-$C_1$-$C_4$-alkyl, $C_3$-$C_6$-cycloalkyl, $C_2$-$C_6$-alkenyl, $C_2$-$C_6$-alkynyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl, $C_1$-$C_4$-alkylsulfonyl, amino, $C_1$-$C_4$-alkylamino, N,N-di-($C_1$-$C_4$)-alkylamino, heterocyclyl and phenyl;
or its agriculturally acceptable salt, carboxylic ester, thioester or amide.

A further preferred embodiment of the invention relates to compositions comprising an isoxazolo[5,4-b]pyridine of formula I, wherein
$R^1$ is hydrogen;
$R^2$ is hydrogen, $C_1$-$C_6$-alkyl, $C_1$-$C_6$-haloalkyl, $C_1$-$C_6$-hydroxyalkyl, $C_3$-$C_6$-cycloalkyl, $C_3$-$C_6$-halocycloalkyl, $C_2$-$C_6$-alkenyl or $C_2$-$C_6$-alkynyl;
$R^3$ is $C_1$-$C_6$-alkyl, $C_1$-$C_6$-haloalkyl, $C_3$-$C_6$-cycloalkyl-$C_1$-$C_6$-alkyl, $C_3$-$C_6$-halocycloalkyl-$C_1$-$C_6$-alkyl, $C_3$-$C_6$-cycloalkyl, $C_3$-$C_6$-halocycloalkyl, $C_1$-$C_4$-alkyl-$C_3$-$C_6$-cycloalkyl, $C_1$-$C_6$-alkoxy, $C_1$-$C_6$-haloalkoxy or phenyl; wherein the phenyl moieties of $R^3$ can be unsubstituted or substituted with one or more radicals selected from halogen, hydroxy, nitro, cyano, $C_1$-$C_4$-alkyl, $C_1$-$C_4$-haloalkyl, $C_1$-$C_4$-alkoxy-$C_1$-$C_4$-alkyl, $C_3$-$C_6$-cycloalkyl, $C_2$-$C_6$-alkenyl, $C_2$-$C_6$-alkynyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl, $C_1$-$C_4$-alkylsulfonyl, amino, $C_1$-$C_4$-alkylamino, N,N-di-($C_1$-$C_4$)-alkylamino, heterocyclyl and phenyl;
or its agriculturally acceptable salt, carboxylic ester, thioester or amide.

One preferred aspect of the invention relates to compositions comprising an isoxazolo[5,4-b]pyridine of formula I, wherein
$R^1$ is hydrogen;
$R^2$ is $C_3$-$C_6$-cycloalkyl or $C_3$-$C_6$-halocycloalkyl; most preferably cyclopropyl or 1-fluorocyclopropyl;
$R^3$ is hydrogen, halogen, hydroxy, $C_1$-$C_6$-alkyl, $C_1$-$C_6$-haloalkyl, $C_1$-$C_6$-hydroxyalkyl, $C_1$-$C_6$-alkoxy-$C_1$-$C_6$-alkyl, $C_1$-$C_6$-haloalkoxy-$C_1$-$C_6$-alkyl, $C_3$-$C_6$-cycloalkyl-$C_1$-$C_6$-alkyl, $C_3$-$C_6$-halocycloalkyl-$C_1$-$C_6$-alkyl, $C_3$-$C_6$-cycloalkyl, $C_3$-$C_6$-halocycloalkyl, $C_1$-$C_4$-alkyl-$C_3$-$C_6$-cycloalkyl, $C_3$-$C_6$-cycloalkenyl, $C_3$-$C_6$-halocycloalkenyl, phenyl-$C_1$-$C_6$-alkyl, heterocyclyl-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylthio, $C_1$-$C_6$-haloalkylthio, amino, $C_1$-$C_6$-alkylamino, N,N-di-($C_1$-$C_6$)-alkylamino, heterocyclyl or phenyl; wherein the heterocyclyl and phenyl moieties of $R^3$ can be unsubstituted or substituted with one or more radicals selected from halogen, hydroxy, nitro, cyano, $C_1$-$C_4$-alkyl, $C_1$-$C_4$-haloalkyl, $C_1$-$C_4$-alkoxy-$C_1$-$C_4$-alkyl, $C_3$-$C_6$-cycloalkyl, $C_2$-$C_6$-alkenyl, $C_2$-$C_6$-alkynyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl, $C_1$-$C_4$-alkylsulfonyl, amino, $C_1$-$C_4$-alkylamino, N,N-di-($C_1$-$C_4$)-alkylamino, heterocyclyl and phenyl;
or its agriculturally acceptable salt, carboxylic ester, thioester or amide.

Another preferred aspect of the invention relates to compositions comprising an isoxazolo[5,4-b]pyridine of formula I, wherein
$R^1$ is hydrogen;
$R^2$ is $C_3$-$C_6$-cycloalkyl or $C_3$-$C_6$-halocycloalkyl; most preferably cyclopropyl or 1-fluorocyclopropyl;
$R^3$ is $C_1$-$C_6$-alkyl, $C_1$-$C_6$-haloalkyl, $C_3$-$C_6$-cycloalkyl-$C_1$-$C_6$-alkyl, $C_3$-$C_6$-halocycloalkyl-$C_1$-$C_6$-alkyl, $C_3$-$C_6$-cycloalkyl, $C_3$-$C_6$-halocycloalkyl or $C_1$-$C_4$-alkyl-$C_3$-$C_6$-cycloalkyl, $C_1$-$C_6$-alkoxy, $C_1$-$C_6$-haloalkoxy or phenyl; wherein the phenyl moieties of $R^3$ can be unsubstituted or substituted with one or more radicals selected from halogen, hydroxy, nitro, cyano, $C_1$-$C_4$-alkyl, $C_1$-$C_4$-haloalkyl, $C_1$-$C_4$-alkoxy-$C_1$-$C_4$-alkyl, $C_3$-$C_6$-cycloalkyl, $C_2$-$C_6$-alkenyl, $C_2$-$C_6$-alkynyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl, $C_1$-$C_4$-alkylsulfonyl, amino, $C_1$-$C_4$-alkylamino, N,N-di-($C_1$-$C_4$)-alkylamino, heterocyclyl, and phenyl;
or its agriculturally acceptable salt, carboxylic ester, thioester or amide.

Still another more preferred embodiment of the invention relates to compositions comprising an isoxazolo[5,4-b]pyridine of formula I, wherein
$R^1$ is hydrogen;
$R^2$ is $C_3$-$C_6$-cycloalkyl or $C_3$-$C_6$-halocycloalkyl; most preferably cyclopropyl or 1-fluorocyclopropyl;
$R^3$ is $C_1$-$C_6$-alkyl, $C_1$-$C_6$-haloalkyl, $C_3$-$C_6$-cycloalkyl-$C_1$-$C_6$-alkyl, $C_3$-$C_6$-halocycloalkyl-$C_1$-$C_6$-alkyl, $C_3$-$C_6$-cycloalkyl, $C_3$-$C_6$-halocycloalkyl, $C_1$-$C_4$-alkyl-$C_3$-$C_6$-cycloalkyl, $C_1$-$C_6$-alkoxy or $C_1$-$C_6$-haloalkoxy;
or its agriculturally acceptable salt, carboxylic ester, thioester or amide.

Still another more preferred embodiment of the invention relates to compositions comprising an isoxazolo[5,4-b]pyridine of formula I, wherein
$R^1$ is hydrogen;
$R^2$ is $C_3$-$C_6$-cycloalkyl or $C_3$-$C_6$-halocycloalkyl; most preferably cyclopropyl or 1-fluorocyclopropyl;
$R^3$ is $C_1$-$C_6$-alkyl, $C_3$-$C_6$-cycloalkyl or $C_1$-$C_6$-alkoxy;

or its agriculturally acceptable salt, carboxylic ester, thioester or amide.

A further more preferred embodiment of the invention relates to compositions comprising an isoxazolo[5,4-b]pyridine of formula I, wherein $R^1$ is hydrogen;
$R^2$ is cyclopropyl;
$R^3$ is $C_1$-$C_6$-alkyl, $C_1$-$C_6$-haloalkyl, $C_3$-$C_6$-cycloalkyl-$C_1$-$C_6$-alkyl, $C_3$-$C_6$-halocycloalkyl-$C_1$-$C_6$-alkyl, $C_3$-$C_6$-cycloalkyl, $C_3$-$C_6$-halocycloalkyl, $C_1$-$C_4$-alkyl-$C_3$-$C_6$-cycloalkyl, $C_1$-$C_6$-alkoxy, $C_1$-$C_6$-haloalkoxy or phenyl; wherein the phenyl moieties of $R^3$ can be unsubstituted or substituted with one or more radicals selected from halogen, hydroxy, nitro, cyano, $C_1$-$C_4$-alkyl, $C_1$-$C_4$-haloalkyl, $C_1$-$C_4$-alkoxy-$C_1$-$C_4$-alkyl, $C_3$-$C_6$-cycloalkyl, $C_2$-$C_6$-alkenyl, $C_2$-$C_6$-alkynyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl, $C_1$-$C_4$-alkylsulfonyl, amino, $C_1$-$C_4$-alkylamino, N,N-di-($C_1$-$C_4$)-alkylamino, heterocyclyl and phenyl;

or its agriculturally acceptable salt, carboxylic ester, thioester or amide.

Still another more preferred embodiment of the invention relates to compositions comprising an isoxazolo[5,4-b]pyridine of formula I, wherein $R^1$ is hydrogen;
$R^2$ is $C_3$-$C_6$-cycloalkyl;
$R^3$ is $C_1$-$C_6$-alkyl, $C_3$-$C_6$-cycloalkyl or $C_1$-$C_6$-alkoxy;

or its agriculturally acceptable salt, carboxylic ester, thioester or amide.

Still another more preferred embodiment of the invention relates to compositions comprising an isoxazolo[5,4-b]pyridine of formula I, wherein $R^1$ is hydrogen;
$R^2$ is cyclopropyl;
$R^3$ is cyclopropyl, methyl or 1,1-dimethylethoxy;

or its agriculturally acceptable salt, carboxylic ester, thioester or amide.

According to a particular preferred embodiment of the invention the composition comprises as component A an isoxazolo[5,4-b]pyridine of formula (I.1) or its agriculturally acceptable salt, carboxylic ester, thioester or amide.

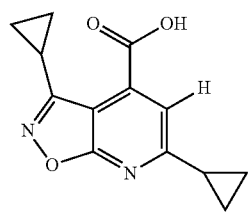

(I.1)

According to a further particular preferred embodiment of the invention the composition comprises as component A an isoxazolo[5,4-b]pyridine of formula (I.2) or its agriculturally acceptable salt, carboxylic ester, thioester or amide.

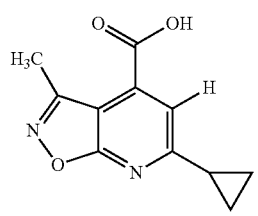

(I.2)

According to a further particular preferred embodiment of the invention the composition comprises as component A an isoxazolo[5,4-b]pyridine of formula (I.3) and its agriculturally acceptable salt, carboxylic ester, thioester or amide.

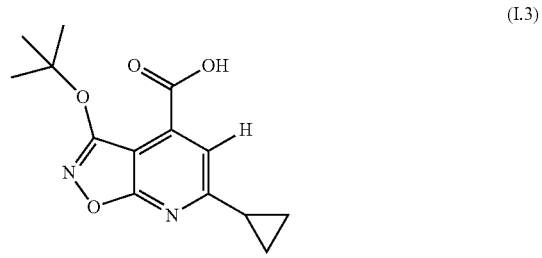 [SMILES: CC(C)(C)Oc1noc2nc(C3CC3)cc(C(=O)O)c12]

(I.3)

In one embodiment of the present invention the compositions according to the present invention comprise as component A at least one isoxazolo[5,4-b]pyridine of formula (I) and at least one further herbicide B as component B.

According to a first embodiment of the invention the compositions comprise at least one inhibitor of the lipid biosynthesis (herbicide b1). These are compounds that inhibit lipid biosynthesis. Inhibition of the lipid biosynthesis can be affected either through inhibition of acetylCoA carboxylase (hereinafter termed ACC herbicides) or through a different mode of action (hereinafter termed non-ACC herbicides). The ACC herbicides belong to the group A of the HRAC classification system whereas the non-ACC herbicides belong to the group N of the HRAC classification.

According to a second embodiment of the invention the compositions comprise at least one ALS inhibitor (herbicide b2). The herbicidal activity of these compounds is based on the inhibition of acetolactate synthase and thus on the inhibition of the branched chain amino acid biosynthesis. These inhibitors belong to the group B of the HRAC classification system.

According to a third embodiment of the invention the compositions comprise at least one inhibitor of photosynthesis (herbicide b3). The herbicidal activity of these compounds is based either on the inhibition of the photosystem II in plants (so-called PSII inhibitors, groups C1, C2 and C3 of HRAC classification) or on diverting the electron transfer in photosystem I in plants (so-called PSI inhibitors, group D of HRAC classification) and thus on an inhibition of photosynthesis. Amongst these, PSII inhibitors are preferred.

According to a fourth embodiment of the invention the compositions comprise at least one inhibitor of protoporphyrinogen-IX-oxidase (herbicide b4). The herbicidal activity of these compounds is based on the inhibition of the protoporphyrinogen-IX-oxidase. These inhibitors belong to the group E of the HRAC classification system.

According to a fifth embodiment of the invention the compositions comprise at least one bleacher-herbicide (herbicide b5). The herbicidal activity of these compounds is based on the inhibition of the carotenoid biosynthesis. These include compounds which inhibit carotenoid biosynthesis by inhibition of phytoene desaturase (so-called PDS inhibitors, group $F_1$ of HRAC classification), compounds that inhibit the 4-hydroxy-phenylpyruvate-dioxygenase (HPPD inhibitors, group $F_2$ of HRAC classification), compounds that inhibit DOXsynthase (group $F_4$ of HRAC class) and compounds which inhibit carotenoid biosynthesis by an unknown mode of action (bleacher—unknown target, group $F_3$ of HRAC classification).

According to a sixth embodiment of the invention the compositions comprise at least one EPSP synthase inhibitor (herbicide b6). The herbicidal activity of these compounds is based on the inhibition of enolpyruvyl shikimate 3-phosphate synthase, and thus on the inhibition of the amino acid biosynthesis in plants. These inhibitors belong to the group G of the HRAC classification system.

According to a seventh embodiment of the invention the compositions comprise at least one glutamine synthetase inhibitor (herbicide b7). The herbicidal activity of these compounds is based on the inhibition of glutamine synthetase, and thus on the inhibition of the aminoacid biosynthesis in plants. These inhibitors belong to the group H of the HRAC classification system.

According to an eighth embodiment of the invention the compositions comprise at least one DHP synthase inhibitor (herbicide b8). The herbicidal activity of these compounds is based on the inhibition of 7,8-dihydropteroate synthase. These inhibitors belong to the group I of the HRAC classification system.

According to a ninth embodiment of the invention the compositions comprise at least one mitosis inhibitor (herbicide b9). The herbicidal activity of these compounds is based on the disturbance or inhibition of microtubule formation or organization, and thus on the inhibition of mitosis. These inhibitors belong to the groups K1 and K2 of the HRAC classification system. Among these, compounds of the group K1, in particular dinitroanilines, are preferred.

According to a tenth embodiment of the invention the compositions comprise at least one VLCFA inhibitor (herbicide b10). The herbicidal activity of these compounds is based on the inhibition of the synthesis of very long chain fatty acids and thus on the disturbance or inhibition of cell division in plants. These inhibitors belong to the group K3 of the HRAC classification system.

According to an eleventh embodiment of the invention the compositions comprise at least one cellulose biosynthesis inhibitor (herbicide b11). The herbicidal activity of these compounds is based on the inhibition of the biosynthesis of cellulose and thus on the inhibition of the synthesis of cell walls in plants. These inhibitors belong to the group L of the HRAC classification system.

According to a twelfth embodiment of the invention the compositions comprise at least one decoupler herbicide (herbicide b12). The herbicidal activity of these compounds is based on the disruption of the cell membrane. These inhibitors belong to the group M of the H RAC classification system.

According to a thirtheenth embodiment of the invention the compositions comprise at least one auxinic herbicide (herbicide b13). These include compounds that mimic auxins, i.e. plant hormones, and affect the growth of the plants. These compounds belong to the group O of the HRAC classification system.

According to a fourteenth embodiment of the invention the compositions comprise at least one auxin transport inhibitor (herbicide b14). The herbicidal activity of these compounds is based on the inhibition of the auxin transport in plants. These compounds belong to the group P of the HRAC classification system.

As to the given mechanisms of action and classification of the active substances, see e.g. "HRAC, Classification of Herbicides According to Mode of Action", http://www.plantprotection.org/hrac/MOA.html).

Preference is given to those compositions according to the present invention comprising as component B at least one herbicide B selected from herbicides of the classes b1, b2, b3, b4, b5, b6, b10 and b13.

Specific preference is given to those compositions according to the present invention which comprise as component B at least one herbicide B selected from the herbicides of the classes b2, b3, b4, b5, b6 and b13.

Particular preference is given to those compositions according to the present invention which comprise as component B at least one herbicide B selected from the herbicides of the classes b2, b3, b5 and b13.

Examples of herbicides B which can be used in combination with an isoxazolo[5,4-b]pyridine of formula (I) according to the present invention are:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuronmethyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:

amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)-pyrimidine (CAS 180608-33-7), HPPD inhibitors: benzobicyclon, benzofenap, bicyclopyrone, clomazone, fenquinotrione, isoxaflutole, mesotrione, pyrasulfotole, pyrazolynate, pyrazoxyfen, sulcotrione, tefuryltrione, tembotrione, tolpyralate, topramezone, bleacher, unknown target: aclonifen, amitrole and flumeturon;

b6) from the group of the EPSP synthase inhibitors:

glyphosate, glyphosate-isopropylammonium, glyposate-potassium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium;

b8) from the group of the DHP synthase inhibitors:

asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl and propham, among these, compounds of group K1, in particular dinitroanilines are preferred;

b10) from the group of the VLCFA inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napronalide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

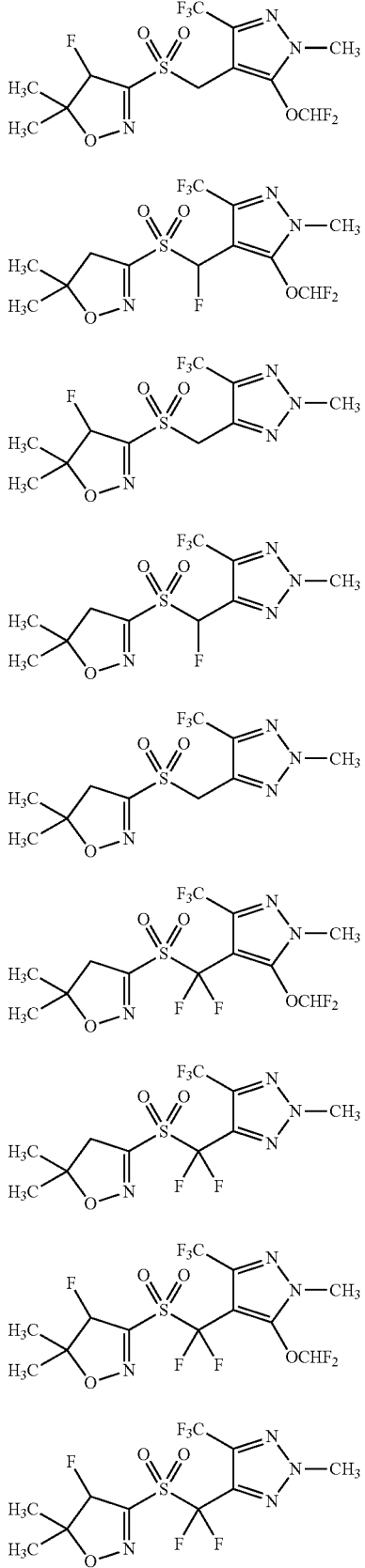

the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors:

chlorthiamid, dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);

b12) from the group of the decoupler herbicides:

dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8), e.g. halauxifen-methyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters, 4-amino-3-chloro-6-(4-chloro-2-fluoro-3-methoxyphenyl)-5-fluoropyridine-2-carboxylic acid and its salts and esters, e.g. benzyl 4-amino-3-chloro-6-(4-chloro-2-fluoro-3-methoxyphenyl)-5-fluoropyridine-2-carboxylate (CAS 1390661-72-9);

b14) from the group of the auxin transport inhibitors:

diflufenzopyr, diflufenzopyr-sodium, naptalam and naptalam-sodium;

b15) from the group of the other herbicides: bromobutide, chlorflurenol, chlorflurenol-methyl, (1RS,2SR,4SR)-1,4-epoxy-p-menth-2-yl 2-methylbenzyl ether, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Preferred herbicides B that can be used in combination with an isoxazolo[5,4-b]pyridine of the formula (I) according to the present invention are:

b1) from the group of the lipid biosynthesis inhibitors:

clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6- dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

More preferred herbicides B that can be used in combination with an isoxazolo[5,4-b]pyridine of the formula (I) according to the present invention are selected from the group b1) clodinafop-propargyl, cyhalofop-butyl, fluazifop-P-butyl, fenoxaprop-P-ethyl, haloxyfop-P-methyl, metamifop, propaquizafop, quizalofop-P-methyl, quizalofop-P-tefuryl, clethodim, cycloxydim, sethoxydim, profoxydim, tepraloxydim, tralkoxydim, pinoxaden, molinate and triallate.

b2) from the group of the ALS inhibitors:

amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone.

More preferred herbicides B from the group b2) that can be used in combination with an isoxazolo[5,4-b]pyridine of the formula (I) according to the present invention are selected from imazamox, imazapyr, imazapic, imazethapyr, imazaquin, pyrithiobac-sodium, bispyribac-sodium, thiencarbazone-methyl, azimsulfuron, cyclosulfamuron, chlorimuron-ethyl, metsulfuron-methyl, mesosulfuron-methyl, halosulfuron-methyl, nicosulfuron, orthosulfamuron, iodosulfuron-methyl-sodium, rimsulfuron, tribenuron-methyl, propyrisulfuron, ethoxysulfuron, foramsulfuron, primisulfuron-methyl, chlorsulfuron, flazasulfuron, sulfosulfuron, penoxsulam, pyroxsulam, florasulam and diclosulam.

Particularly preferred herbicides B from the group b2) that can be used in combination with an isoxazolo[5,4-b]pyridine of the formula (I) according to the present invention are selected from imazamox, imazapyr, imazapic, imazethapyr, bispyribac-sodium, thiencarbazone-methyl, cyclosulfamuron, metsulfuron-methyl, mesosulfuron-methyl, halosulfuron-methyl, nicosulfuron, iodosulfuron-methyl-sodium, rimsulfuron, tribenuron-methyl, propyrisulfuron, foramsulfuron, penoxsulam, pyroxsulam and florasulam.

b3) from the group of the photosynthesis inhibitors:

ametryn, amicarbazone, atrazine, bentazone, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron.

More preferred herbicides B from the group b3) that can be used in combination with an isoxazolo[5,4-b]pyridine of the formula (I) according to the present invention are selected from paraquat, pentanochlor, propanil, bentazone, bromoxynil, phenmedipham, pyridate, atrazine, terbuthylazine, ametryne, metribuzin, hexazinone, amicarbazone, bromacil, chlorotoluron, diuron and isoproturon.

Particularly preferred herbicides B from the group b3) that can be used in combination with an isoxazolo[5,4-b]pyridine of the formula (I) according to the present invention are selected from paraquat, bentazone, bromoxynil, atrazine, terbuthylazine, metribuzin, amicarbazone and chlorotoluron.

b4) from the group of the protoporphyrinogen-IX oxidase inhibitors:

acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen-ethyl, saflufenacil, sulfentrazone, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0); 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), and 3-[7-Chloro-5-fluoro-2-(trifluoromethyl)-1H-benzimidazol-4-yl]-1-methyl-6-(trifluoromethyl)-1H-pyrimidine-2, 4-dione (CAS 212754-02-4);

More preferred herbicides B from the group b4) that can be used in combination with an isoxazolo[5,4-b]pyridine of the formula (I) according to the present invention are selected from acifluorfen-sodium, fomesafen, oxyfluorfen, flumioxazin, cinidon-ethyl, pyraclonil, oxadiargyl, oxadiazon, pentoxazone, saflufenacil, 1,5-dimethyl-6-thioxo-3-(2,2,7-trifluoro-3-oxo-4-(prop-2-ynyl)-3,4-dihydro-2H- benzo[b][1,4]oxazin-6-yl)-1,3,5-triazinane-2,4-dione (CAS 1258836-72-4), carfentrazone-ethyl and sulfentrazone.

Particularly preferred herbicides B from the group b4) that can be used in combination with an isoxazolo[5,4-b]pyridine of the formula (I) according to the present invention are selected from acifluorfen-sodium, fomesafen, flumioxazin, oxadiargyl, saflufenacil, trifludimoxazin, carfentrazone-ethyl and sulfentrazone.

b5) from the group of the bleacher herbicides:
aclonifen, amitrole, beflubutamid, benzobicyclon, bicyclopyrone, clomazone, diflufenican, fenquinotrione, flumeturon, flurochloridone, flurtamone, isoxaflutole, mesotrione, norflurazon, picolinafen, pyrasulfotole, pyrazolynate, sulcotrione, tefuryltrione, tembotrione, topramezone and 4-(3-trifluoromethylphenoxy)-2-(4-trifluoromethylphenyl)pyrimidine (CAS 180608-33-7);

More preferred herbicides B from the group b5) that can be used in combination with an isoxazolo[5,4-b]pyridine of the formula (I) according to the present invention are selected from aclonifen, pyrasulfotole, isoxaflutole, topramezone, benzobicyclon, bicyclopyrone, tembotrione, mesotrione, tefuryltrione, sulcotrione, clomazone, diflufenican and picolinafen.

Particularly preferred herbicides B from the group b5) that can be used in combination with an isoxazolo[5,4-b]pyridine of the formula (I) according to the present invention are selected from pyrasulfotole, isoxaflutole, topramezone, benzobicyclon, bicyclopyrone, tembotrione, mesotrione, tefuryltrione, and picolinafen.

b6) from the group of the EPSP synthase inhibitors:
glyphosate, glyphosate-isopropylammonium, glyphosate-potassium and glyphosate-trimesium (sulfosate).

A more preferred herbicide B from the group b6) that can be used in combination with an isoxazolo[5,4-b]pyridine of the formula (I) according to the present invention is glyphosate.

b7) from the group of the glutamine synthase inhibitors:
glufosinate, glufosinate-P, glufosinate-ammonium.

A more preferred herbicide B from the group b7) that can be used in combination with an isoxazolo[5,4-b]pyridine of the formula (I) according to the present invention is glufosinate-ammonium.

b8) from the group of the DHP synthase inhibitors:
asulam.

b9) from the group of the mitosis inhibitors:
chlorpropham, benfluralin, dithiopyr, ethalfluralin, oryzalin, pendimethalin, propyzamide (=pronamide), thiazopyr and trifluralin.

More preferred herbicides B from the group b9) that can be used in combination with an isoxazolo[5,4-b]pyridine of the formula (I) according to the present invention are selected from chlorpropham, propyzamide (=pronamide), pendimethalin, and trifluralin.

Particularly preferred herbicides B from the group b9) that can be used in combination with an isoxazolo[5,4-b]pyridine of the formula (I) according to the present invention are selected from chlorpropham, propyzamide (=pronamide) and pendimethalin.

b10) from the group of the VLCFA inhibitors:
acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, napropamide-M, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above.

More preferred herbicides B from the group b10) that can be used in combination with an isoxazolo[5,4-b]pyridine of the formula (I) according to the present invention are selected from alachlor, butachlor, cafenstrole, dimethenamid, flufenacet, ipfencarbazone, metazachlor, metolachlor, mefenacet, napropamide, pretilachlor and pyroxasulfone.

Particularly preferred herbicides B from the group b10) that can be used in combination with an isoxazolo[5,4-b]pyridine of the formula (I) according to the present invention are selected from dimethenamid, flufenacet, metazachlor, metolachlor, pretilachlor and pyroxasulfone.

b11) from the group of the cellulose biosynthesis inhibitors: chlorthiamid, dichlobenil, flupoxam, indaziflam, isoxaben, triaziflam and 1-Cyclohexyl-5-pentafluorphenyloxy-1$^4$-[1,2,4,6]thiatriazin-3-ylamine More preferred herbicides B from the group b11) that can be used in combination with an isoxazolo[5,4-b]pyridine of the formula (I) according to the present invention are selected from dichlobenil, flupoxam, indaziflam, isoxaben and triaziflam.

Particularly preferred herbicides B from the group b11) that can be used in combination with an isoxazolo[5,4-b]pyridine of the formula (I) according to the present invention are selected from indaziflam and isoxaben.

b13) from the group of the auxinic herbicides:
2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, dichlorprop-P and its salts and esters, fluroxypyr-meptyl, halauxifen and its salts and esters (CAS 943832-60-8), e.g. halauxifen-methyl, MCPA and its salts and esters, MCPB and its salts and esters, mecoprop-P and its salts and esters, picloram and its salts and esters, quinclorac, quinmerac and triclopyr and its salts and esters, 4-amino-3-chloro-6-(4-chloro-2-fluoro-3-methoxyphenyl)-5-fluoropyridine-2-carboxylic acid and its salts and esters, e.g. benzyl 4-amino-3-chloro-6-(4-chloro-2-fluoro-3-methoxyphenyl)-5-fluoropyridine-2-carboxylate (CAS 1390661-72-9).

More preferred herbicides B from the group b13) that can be used in combination with an isoxazolo[5,4-b]pyridine of the formula (I) according to the present invention are selected from dicamba and its salts and esters, halauxifen and its salts and esters), e.g. halauxifen-methyl, 2,4-D and its salts and esters, MCPA and its salts and esters, picloram and its salts and esters, aminopyralid and its salts and esters, fluroxypyr, quinclorac and its salts and esters, quinmerac and its salts and esters and triclopyr and its salts and esters, 4-amino-3-chloro-6-(4-chloro-2-fluoro-3-methoxyphenyl)-5-fluoropyridine-2-carboxylic acid and its salts and esters, e.g. benzyl 4-amino-3-chloro-6-(4-chloro-2-fluoro-3-methoxyphenyl)-5-fluoropyridine-2-carboxylate (CAS 1390661-72-9).

Particularly preferred herbicides B from the group b13) that can be used in combination with an isoxazolo[5,4-b]pyridine of the formula (I) according to the present invention are selected from dicamba and its salts and esters, halauxifen and its salts and esters, e.g. halauxifen-methyl, 2,4-D and its salts and esters, MCPA and its salts and esters, aminopyralid and its salts and esters, quinclorac and its salts and esters and quinmerac and its salts and esters, 4-amino-3-chloro-6-(4-chloro-2-fluoro-3-methoxyphenyl)-5-fluoropyridine-2-carboxylic acid and its salts and esters, e.g. benzyl 4-amino-3-chloro-6-(4-chloro-2-fluoro-3-methoxyphenyl)-5-fluoropyridine-2-carboxylate (CAS 1390661-72-9).

b14) from the group of the auxin transport inhibitors: diflufenzopyr, diflufenzopyr-sodium and naptalam.

More preferred herbicides B from the group b14) that can be used in combination with an isoxazolo[5,4-b]pyridine of the formula (I) according to the present invention are selected from naptalam and diflufenzopyr-sodium.

b15) from the group of the other herbicides: bromobutide, (1RS,2SR,4SR)-1,4-epoxy-p-menth-2-yl 2-methylbenzyl ether, cumyluron, cyclopyrimorate (CAS 499223-49-3) and its salts and esters, dalapon, difenzoquat, difenzoquat-metilsulfate, DSMA, dymron (=daimuron), indanofan, metam, methylbromide, MSMA, oxaziclomefone, pyributicarb, and tridiphane.

A more preferred herbicide B from the group b15) that can be used in combination with the an isoxazolo[5,4-b]pyridine of the formula (I) according to the present invention is (1RS,2SR,4SR)-1,4-epoxy-p-menth-2-yl 2-methylbenzyl ether In another embodiment of the present invention the compositions according to the present invention comprise at least one isoxazolo[5,4-b]pyridine of formula (I) and at least one safener C.

Safeners are chemical compounds which prevent or reduce damage on useful plants without having a major impact on the herbicidal action of the herbicidal active components of the present compositions towards unwanted plants. They can be applied either before sowings (e.g. on seed treatments, shoots or seedlings) or in the pre-emergence application or post-emergence application of the useful plant. The safeners and the isoxazolo[5,4-b]pyridine of formula (I) and/or the herbicides B can be applied simultaneously or in succession.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4), N-(2-Methoxybenzoyl)-4-[(methylaminocarbonyl)amino]benzenesulfonamide (CAS 129531-12-0), MG191 (2-dichloromethyl-2-methyl-1,3-dioxolane) or their salts and esters.

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro-[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0) or their salts and esters.

Particularly preferred safeners C are benoxacor, cloquintocet, cyprosulfamide, dichlormid, fenchlorazole, fenclorim, furilazole, isoxadifen, mefenpyr, naphtalic anhydride, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0) or their salts and esters.

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro [4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Composition components B (herbicides B) and C (safeners) having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanol-ammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl) ammonium, 2,4-D-tris(isopropyl)-ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl. Suitable salts of clopyralid are clopyralid-potassium, clopyralid-olamine and clopyralid-tris-(2-hydroxypropyl)ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine.

A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chlorambenmethyl, chloramben-methylammonium and chloramben-sodium.

Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium. Suitable salts of glyphosate are for example glyphosate-ammonium, glyphosate-diammonium, glyphosate-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinmerac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

According to a preferred embodiment of the invention, the composition comprises as herbicidal active component B at least one, preferably exactly one herbicide B.

According to another preferred embodiment of the invention, the composition comprises as herbicidal active component B at least two, preferably exactly two herbicides B different from each other.

According to another preferred embodiment of the invention, the composition comprises as herbicidal active component B at least three, preferably exactly three herbicides B different from each other.

According to another preferred embodiment of the invention, the composition comprises as safening component C at least one, preferably exactly one safener.

According to another preferred embodiment of the invention, the composition comprises as component B at least one, preferably exactly one herbicide B, and as component C at least one, preferably exactly one, safener.

According to another preferred embodiment of the invention, the composition comprises as component B at least two, preferably exactly two, herbicides B different from each other, and as component C at least one, preferably exactly one, safener.

According to another preferred embodiment of the invention, the composition comprises as component B at least three, preferably exactly three, herbicides B different from each other, and as component C at least one, preferably exactly one, safener.

According to another preferred embodiment of the invention, the composition comprises as component A at least one, preferably exactly one isoxazolo[5,4-b]pyridine of formula (I), preferably of formula (I.1), (I.2) or (I.3), especially preferred the compound (I.1), and as component B at least one, preferably exactly one, herbicide B.

According to another preferred embodiment of the invention, the composition comprises as component A at least one, preferably exactly one isoxazolo[5,4-b]pyridine of formula (I), preferably of formula (I.1), (I.2) or (I.3), especially preferred the compound (I.1), and at least two, preferably exactly two, herbicides B different from each other.

According to another preferred embodiment of the invention, the composition comprises as component A at least one, preferably exactly one isoxazolo[5,4-b]pyridine of formula (I), preferably of formula (I.1), (I.2) or (I.3), especially preferred the compound (I.1), and at least three, preferably exactly three, herbicides B different from each other.

According to another preferred embodiment of the invention, the composition comprises as component A at least one, preferably exactly one isoxazolo[5,4-b]pyridine of formula (I), preferably of formula (I.1), (I.2) or (I.3), especially preferred the compound (I.1), and as component C at least one, preferably exactly one, safener C.

According to another preferred embodiment of the invention, the composition comprises as component A at least one, preferably exactly one isoxazolo[5,4-b]pyridine of formula (I), preferably of formula (I.1), (I.2) or (I.3), especially preferred the compound (I.1), as component B at least one, preferably exactly one, herbicide B, and as component C at least one, preferably exactly one safener C.

According to another preferred embodiment of the invention, the composition comprises as component A at least one, preferably exactly one isoxazolo[5,4-b]pyridine of formula (I), preferably of formula (I.1), (I.2) or (I.3), especially preferred the compound (I.1), at least two, preferably exactly two herbicides B different from each other, and as component C at least one, preferably exactly one, safener C.

According to another preferred embodiment of the invention, the composition comprises as component A at least one, preferably exactly one isoxazolo[5,4-b]pyridine of formula (I), preferably of formula (I.1), (I.2) or (I.3), especially preferred the compound (I.1), at least three, preferably exactly three herbicides B different from each other, and as component C at least one, preferably exactly one, safener C.

According to another preferred embodiment of the invention, the composition comprises, in addition to an isoxazolo[5,4-b]pyridine of formula (I), especially an isoxazolo[5,4-b]pyridine from the group consisting of (I.1), (I.2) and (I.3), as component B at least one and especially exactly one herbicide B from group b1), in particular selected from the group consisting of clodinafop-propargyl, cyhalofop-butyl, fluazifop-P-butyl, fenoxaprop-P-ethyl, haloxyfop-P-methyl, metamifop, propaquizafop, quizalofop-P-methyl, quizalofop-P-tefuryl, clethodim, cycloxydim, sethoxydim, profoxydim, tepraloxydim, tralkoxydim, pinoxaden, molinate and tri-allate.

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b2), in particular selected from the group consisting of imazamox, imazapyr, imazapic, imazethapyr, imazaquin, pyrithiobac-sodium, bispyribac-sodium, thiencarbazone-methyl, azimsulfuron, cyclosulfamuron, chlorimuron-ethyl, metsulfuron-methyl, mesosulfuron-methyl, halosulfuron-methyl, nicosulfuron, orthosulfamuron, iodosulfuron-methyl-sodium, rimsulfuron, tribenuron-methyl, propyrisulfuron, ethoxysulfuron, foramsulfuron, primisulfuron-methyl, chlorsulfuron, flazasulfuron, sulfosulfuron, penoxsulam, florasulam and diclosulam.

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b3), in particular selected from the group consisting of paraquat, pentanochlor, propanil, bentazone, bromoxynil, phenmedipham, pyridate, atrazine, terbuthylazine, ametryne, metribuzin, hexazinone, amicarbazone, bromacil, chlorotoluron, diuron and isoproturon.

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b4), in particular selected from the group consisting of acifluorfen-sodium, fomesafen, oxyfluorfen, flumioxazin, cinidon-ethyl, pyraclonil, oxadiargyl, pentoxazone, saflufenacil, trifludimoxazin, carfentrazone-ethyl and sulfentrazone.

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b5), in particular selected from the group consisting of aclonifen, pyrasulfotole, isoxaflutole, topramezone, benzobicyclon, bicyclopyrone, tembotrione, mesotrione, tefuryltrione, sulcotrione, clomazone, diflufenican and picolinafen.

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b6), in particular glyphosate.

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b7), in particular glufosinate-ammonium.

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b9), in particular selected from the group consisting of chlorpropham, ethalfluralin, propyzamide (=pronamide), pendimethalin, oryzalin and trifluralin.

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b10), in particular selected from the group consisting of alachlor, butachlor, cafenstrole, dimethenamid, flufenacet, ipfencarbazone, metazachlor, metolachlor, mefenacet, napropamide, pretilachlor and pyroxasulfone.

Likewise, preference is given to compositions comprising in addition to an isoxazolo[5,4-b]pyridine of formula (I), especially an active compound from the group consisting of (I.1), (I.2) and (I.3), as component B at least one and especially exactly one herbicide B from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b11), in particular selected from the group consisting of dichlobenil, flupoxam, indaziflam, isoxaben and triaziflam.

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b13), in particular selected from the group consisting of dicamba and its salts and esters, 2,4-D and its salts and esters, halauxifen and its salts and esters, e.g. halauxifen-methyl, MCPA, aminopyralid and its salts such as aminopyralid-dimethylammonium, aminopyralid-tris(2-hydroxypropyl)ammonium and its esters, fluroxypyr and its salts and esters, fluroxypyr-meptyl and its salts and esters and triclopyr and its salts and esters, 4-amino-3-chloro-6-(4-chloro-2-fluoro-3-methoxyphenyl)-5-fluoropyridine-2-carboxylic acid and its salts and esters, e.g. benzyl 4-amino-3-chloro-6-(4-chloro-2-fluoro-3-methoxyphenyl)-5-fluoropyridine-2-carboxylate (CAS 1390661-72-9).

According to another preferred embodiment of the invention, the composition comprises, in addition to an isoxazolo[5,4-b]pyridine of formula (I), especially an active compound from the group consisting of (I.1), (I.2) and (I.3), as component B at least one and especially exactly one herbicide B from group b14), in particular selected from the group consisting of naptalam and diflufenzopyr-sodium.

According to another preferred embodiment of the invention, the composition comprises, in addition to an isoxazolo [5,4-b]pyridine of formula (I), especially an active compound from the group consisting of (I.1), (I.2) and (I.3), as component B at least one and especially exactly one herbicide B from group b15), in particular (1RS,2SR,4SR)-1,4-epoxy-p-menth-2-yl 2-methylbenzyl ether.

According to another preferred embodiment of the invention, the composition comprises, in addition to an isoxazolo [5,4-b]pyridine of formula (I), especially an active compound from the group consisting of (I.1), (I.2) and (I.3), at least one and especially exactly one safener C, in particular selected from the group consisting of benoxacor, cloquintocet, cyprosulfamide, dichlormid, fenchlorazole, fenclorim, furilazole, isoxadifen, mefenpyr, naphtalic anhydride, 4-(dichloroacetyl)-1-oxa-4-azaspiro-[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Further preferred embodiments relate to ternary compositions which correspond to the binary compositions mentioned above and additionally comprise a safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Here and below, the term "binary compositions" includes compositions comprising one or more, for example 1, 2 or 3 isoxazolo[5,4-b]pyridines of the formula (I) and either one or more, for example 1, 2 or 3, herbicides B or one or more safeners C.

Correspondingly, the term "ternary compositions" includes compositions comprising one or more, for example 1, 2 or 3 isoxazolo[5,4-b]pyridines of the formula (I), one or more, for example 1, 2 or 3, herbicides B and one or more, for example 1, 2 or 3, safeners C.

In binary compositions comprising at least one isoxazolo [5,4-b]pyridine of the formula (I) as component A and as component B at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one isoxazolo [5,4-b]pyridine of the formula (I) as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising at least one isoxazolo [5,4-b]pyridine of the formula (I) as component A and as component B at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

Particularly preferred herbicides B are the herbicides B as defined above; in particular the herbicides B.1 to B.200 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |

TABLE B-continued

| | Herbicide B |
|---|---|
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | saflufenacil |
| B.93 | sulfentrazone |
| B.94 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl-oxy]acetate (CAS 353292-31-6) |
| B.95 | trifludimoxazin |
| B.96 | benzobicyclon |
| B.97 | clomazone |
| B.98 | diflufenican |
| B.99 | flurochloridone |
| B.100 | isoxaflutole |
| B.101 | mesotrione |
| B.102 | norflurazone |
| B.103 | picolinafen |
| B.104 | sulcotrione |
| B.105 | tefuryltrione |
| B.106 | tembotrione |
| B.107 | topramezone |
| B.108 | topramezone-sodium |
| B.109 | bicyclopyrone |
| B.110 | amitrole |
| B.111 | fluometuron |
| B.112 | fenquinotrione |
| B.113 | glyphosate |
| B.114 | glyphosate-ammonium |
| B.115 | glyphosate-dimethylammonium |
| B.116 | glyphosate-isopropylammonium |
| B.117 | glyphosate-trimesium (sulfosate) |
| B.118 | glyphosate-potassium |
| B.119 | glufosinate |
| B.120 | glufosinate-ammonium |
| B.121 | glufosinate-P |
| B.122 | glufosinate-P-ammonium |
| B.123 | pendimethalin |
| B.124 | trifluralin |
| B.125 | acetochlor |
| B.126 | butachlor |
| B.127 | cafenstrole |
| B.128 | dimethenamid-P |
| B.129 | fentrazamide |
| B.130 | flufenacet |
| B.131 | mefenacet |
| B.132 | metazachlor |
| B.133 | metolachlor |
| B.134 | S-metolachlor |
| B.135 | pretilachlor |
| B.136 | fenoxasulfone |
| B.137 | isoxaben |
| B.138 | ipfencarbazone |
| B.139 | pyroxasulfone |
| B.140 | 2,4-D |
| B.141 | 2,4-D-isobutyl |
| B.142 | 2,4-D-dimethylammonium |
| B.143 | 2,4-D-N,N,N-trimethylethanolammonium |
| B.144 | aminopyralid |
| B.145 | aminopyralid-methyl |
| B.146 | aminopyralid-dimethyl-ammonium |
| B.147 | aminopyralid-tris(2-hydroxypropyl)ammonium |
| B.148 | clopyralid |
| B.149 | clopyralid-methyl |
| B.150 | clopyralid-olamine |
| B.151 | dicamba |
| B.152 | dicamba-butotyl |
| B.153 | dicamba-diglycolamine |
| B.154 | dicamba-dimethylammonium |
| B.155 | dicamba-diolamine |
| B.156 | dicamba-isopropylammonium |
| B.157 | dicamba-potassium |
| B.158 | dicamba-sodium |
| B.159 | dicamba-trolamine |
| B.160 | dicamba-N,N-bis-(3-aminopropyl)methylamine |
| B.161 | dicamba-diethylenetriamine |
| B.162 | fluroxypyr |
| B.163 | fluroxypyr-meptyl |
| B.164 | MCPA |
| B.165 | MCPA-2-ethylhexyl |
| B.166 | MCPA-dimethylammonium |
| B.167 | quinclorac |
| B.168 | quinclorac-dimethylammonium |
| B.169 | quimnerac |
| B.170 | quimnerac-dimethylammonium |
| B.171 | aminocyclopyrachlor |
| B.172 | aminocyclopyrachlor-potassium |
| B.173 | aminocyclopyrachlor-methyl |
| B.174 | diflufenzopyr |
| B.175 | diflufenzopyr-sodium |
| B.176 | dymron |
| B.177 | indanofan |
| B.178 | indaziflam |
| B.179 | oxaziclomefone |
| B.180 | triaziflam |
| B.181 | II.1 |
| B.182 | II.2 |
| B.183 | II.3 |
| B.184 | II.4 |
| B.185 | II.5 |
| B.186 | II.6 |
| B.187 | II.7 |
| B.188 | II.8 |
| B.189 | II.9 |
| B.190 | chlorotoluron |
| B.191 | pyridate |
| B.192 | phenmedipham |
| B.193 | (1RS,2SR,4SR)-1,4-epoxy-p-menth-2-yl 2-methylbenzyl ether |
| B.194 | pyraflufen |
| B.195 | pyraflufen-ethyl |
| B.196 | tolpyralate |
| B.197 | halauxifen |
| B.198 | halauxifen-methyl |
| B.199 | 4-amino-3-chloro-6-(4-chloro-2-fluoro-3-methoxyphenyl)-5-fluoropyridine-2-carboxylic acid |

TABLE B-continued

| | Herbicide B |
|---|---|
| B.200 | benzyl 4-amino-3-chloro-6-(4-chloro-2-fluoro-3-methoxyphenyl)-5-fluoropyridine-2-carboxylate (CAS 1390661-72-9) |

Particularly preferred safeners C, which, as component C, are constituent of the composition according to the invention are the safeners C as defined above; in particular the safeners C.1 to C.17 listed below in table C:

TABLE C

| | Safener C |
|---|---|
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (CAS 71526-07-3) |
| C.16 | 2,2,5-trimethyl-3-(dichloro-acetyl)-1,3-oxazolidine (CAS 52836-31-4) |
| C.17 | N-(2-Methoxybenzoyl)-4-[(methylaminocarbonyl)amino]benzenesulfonamide (CAS 129531-12-0) |

The weight ratios of the individual components in the preferred compositions mentioned below are within the limits given above, in particular within the preferred limits.

Particularly preferred are the compositions mentioned below comprising an isoxazolo[5,4-b]pyridine of formula I as defined and the substance(s) as defined in the respective row of table 1; especially preferred comprising as only herbicidal active compounds an isoxazolo[5,4-b]pyridine of formula I as defined and the substance(s) as defined in the respective row of table 1; most preferably comprising as only active compounds an isoxazolo[5,4-b]pyridine of formula I as defined and the substance(s) as defined in the respective row of table 1.

Particularly preferred are compositions (composition no. 1.1 to 1.3617), comprising as component A an isoxazolo[5,4-b]pyridine of formula (I.1) and as component B the herbicide(s) B and/or the safener C as defined in the respective row of table 1:

TABLE 1

(compositions 1.1 to 1.3617):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |

TABLE 1-continued (compositions 1.1 to 1.3617):

| comp. no. | herbicide B | safener C |
|---|---|---|
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | — |
| 1.191 | B.191 | — |
| 1.192 | B.192 | — |
| 1.193 | B.193 | — |
| 1.194 | B-194 | — |
| 1.195 | B-195 | — |
| 1.196 | B-196 | — |
| 1.197 | B-197 | — |
| 1.198 | B-198 | — |
| 1.199 | B-199 | — |
| 1.200 | B-200 | — |
| 1.201 | B.1 | C.1 |
| 1.202 | B.2 | C.1 |
| 1.203 | B.3 | C.1 |
| 1.204 | B.4 | C.1 |
| 1.205 | B.5 | C.1 |
| 1.206 | B.6 | C.1 |
| 1.207 | B.7 | C.1 |
| 1.208 | B.8 | C.1 |
| 1.209 | B.9 | C.1 |
| 1.210 | B.10 | C.1 |
| 1.211 | B.11 | C.1 |
| 1.212 | B.12 | C.1 |
| 1.213 | B.13 | C.1 |
| 1.214 | B.14 | C.1 |
| 1.215 | B.15 | C.1 |
| 1.216 | B.16 | C.1 |
| 1.217 | B.17 | C.1 |
| 1.218 | B.18 | C.1 |
| 1.219 | B.19 | C.1 |
| 1.220 | B.20 | C.1 |
| 1.221 | B.21 | C.1 |
| 1.222 | B.22 | C.1 |
| 1.223 | B.23 | C.1 |
| 1.224 | B.24 | C.1 |
| 1.225 | B.25 | C.1 |
| 1.226 | B.26 | C.1 |
| 1.227 | B.27 | C.1 |
| 1.228 | B.28 | C.1 |
| 1.229 | B.29 | C.1 |
| 1.230 | B.30 | C.1 |
| 1.231 | B.31 | C.1 |
| 1.232 | B.32 | C.1 |
| 1.233 | B.33 | C.1 |

TABLE 1-continued (compositions 1.1 to 1.3617):

| comp. no. | herbicide B | safener C |
|---|---|---|
| 1.234 | B.34 | C.1 |
| 1.235 | B.35 | C.1 |
| 1.236 | B.36 | C.1 |
| 1.237 | B.37 | C.1 |
| 1.238 | B.38 | C.1 |
| 1.239 | B.39 | C.1 |
| 1.240 | B.40 | C.1 |
| 1.241 | B.41 | C.1 |
| 1.242 | B.42 | C.1 |
| 1.243 | B.43 | C.1 |
| 1.244 | B.44 | C.1 |
| 1.245 | B.45 | C.1 |
| 1.246 | B.46 | C.1 |
| 1.247 | B.47 | C.1 |
| 1.248 | B.48 | C.1 |
| 1.249 | B.49 | C.1 |
| 1.250 | B.50 | C.1 |
| 1.251 | B.51 | C.1 |
| 1.252 | B.52 | C.1 |
| 1.253 | B.53 | C.1 |
| 1.254 | B.54 | C.1 |
| 1.255 | B.55 | C.1 |
| 1.256 | B.56 | C.1 |
| 1.257 | B.57 | C.1 |
| 1.258 | B.58. | C.1 |
| 1.259 | B.59 | C.1 |
| 1.260 | B.60 | C.1 |
| 1.261 | B.61 | C.1 |
| 1.262 | B.62 | C.1 |
| 1.263 | B.63 | C.1 |
| 1.264 | B.64 | C.1 |
| 1.265 | B.65 | C.1 |
| 1.266 | B.66 | C.1 |
| 1.267 | B.67 | C.1 |
| 1.268 | B.68 | C.1 |
| 1.269 | B.69 | C.1 |
| 1.270 | B.70 | C.1 |
| 1.271 | B.71 | C.1 |
| 1.272 | B.72 | C.1 |
| 1.273 | B.73 | C.1 |
| 1.274 | B.74 | C.1 |
| 1.275 | B.75 | C.1 |
| 1.276 | B.76 | C.1 |
| 1.277 | B.77 | C.1 |
| 1.278 | B.78 | C.1 |
| 1.279 | B.79 | C.1 |
| 1.280 | B.80 | C.1 |
| 1.281 | B.81 | C.1 |
| 1.282 | B.82 | C.1 |
| 1.283 | B.83 | C.1 |
| 1.284 | B.84 | C.1 |
| 1.285 | B.85 | C.1 |
| 1.286 | B.86 | C.1 |
| 1.287 | B.87 | C.1 |
| 1.288 | B.88 | C.1 |
| 1.289 | B.89 | C.1 |
| 1.290 | B.90 | C.1 |
| 1.291 | B.91 | C.1 |
| 1.292 | B.92 | C.1 |
| 1.293 | B.93 | C.1 |
| 1.294 | B.94 | C.1 |
| 1.295 | B.95 | C.1 |
| 1.296 | B.96 | C.1 |
| 1.297 | B.97 | C.1 |
| 1.298 | B.98 | C.1 |
| 1.299 | B.99 | C.1 |
| 1.300 | B.100 | C.1 |
| 1.301 | B.101 | C.1 |
| 1.302 | B.102 | C.1 |
| 1.303 | B.103 | C.1 |
| 1.304 | B.104 | C.1 |
| 1.305 | B.105 | C.1 |
| 1.306 | B.106 | C.1 |
| 1.307 | B.107 | C.1 |
| 1.308 | B.108 | C.1 |
| 1.309 | B.109 | C.1 |
| 1.310 | B.110 | C.1 |
| 1.311 | B.111 | C.1 |
| 1.312 | B.112 | C.1 |
| 1.313 | B.113 | C.1 |
| 1.314 | B.114 | C.1 |
| 1.315 | B.115 | C.1 |
| 1.316 | B.116 | C.1 |
| 1.317 | B.117 | C.1 |
| 1.318 | B.118 | C.1 |
| 1.319 | B.119 | C.1 |
| 1.320 | B.120 | C.1 |
| 1.321 | B.121 | C.1 |
| 1.322 | B.122 | C.1 |
| 1.323 | B.123 | C.1 |
| 1.324 | B.124 | C.1 |
| 1.325 | B.125 | C.1 |
| 1.326 | B.126 | C.1 |
| 1.327 | B.127 | C.1 |
| 1.328 | B.128 | C.1 |
| 1.329 | B.129 | C.1 |
| 1.330 | B.130 | C.1 |
| 1.331 | B.131 | C.1 |
| 1.332 | B.132 | C.1 |
| 1.333 | B.133 | C.1 |
| 1.334 | B.134 | C.1 |
| 1.335 | B.135 | C.1 |
| 1.336 | B.136 | C.1 |
| 1.337 | B.137 | C.1 |
| 1.338 | B.138 | C.1 |
| 1.339 | B.139 | C.1 |
| 1.340 | B.140 | C.1 |
| 1.341 | B.141 | C.1 |
| 1.342 | B.142 | C.1 |
| 1.343 | B.143 | C.1 |
| 1.344 | B.144 | C.1 |
| 1.345 | B.145 | C.1 |
| 1.346 | B.146 | C.1 |
| 1.347 | B.147 | C.1 |
| 1.348 | B.148 | C.1 |
| 1.349 | B.149 | C.1 |
| 1.350 | B.150 | C.1 |
| 1.351 | B.151 | C.1 |
| 1.352 | B.152 | C.1 |
| 1.353 | B.153 | C.1 |
| 1.354 | B.154 | C.1 |
| 1.355 | B.155 | C.1 |
| 1.356 | B.156 | C.1 |
| 1.357 | B.157 | C.1 |
| 1.358 | B.158 | C.1 |
| 1.359 | B.159 | C.1 |
| 1.360 | B.160 | C.1 |
| 1.361 | B.161 | C.1 |
| 1.362 | B.162 | C.1 |
| 1.363 | B.163 | C.1 |
| 1.364 | B.164 | C.1 |
| 1.365 | B.165 | C.1 |
| 1.366 | B.166 | C.1 |
| 1.367 | B.167 | C.1 |
| 1.368 | B.168 | C.1 |
| 1.369 | B.169 | C.1 |
| 1.370 | B.170 | C.1 |
| 1.371 | B.171 | C.1 |
| 1.372 | B.172 | C.1 |
| 1.373 | B.173 | C.1 |
| 1.374 | B.174 | C.1 |
| 1.375 | B.175 | C.1 |
| 1.376 | B.176 | C.1 |
| 1.377 | B.177 | C.1 |
| 1.378 | B.178 | C.1 |
| 1.379 | B.179 | C.1 |
| 1.380 | B.180 | C.1 |
| 1.381 | B.181 | C.1 |
| 1.382 | B.182 | C.1 |
| 1.383 | B.183 | C.1 |
| 1.384 | B.184 | C.1 |
| 1.385 | B.185 | C.1 |

TABLE 1-continued

(compositions 1.1 to 1.3617):

| comp. no. | herbicide B | safener C |
|---|---|---|
| 1.386 | B.186 | C.1 |
| 1.387 | B.187 | C.1 |
| 1.388 | B.188 | C.1 |
| 1.389 | B.189 | C.1 |
| 1.390 | B.190 | C.1 |
| 1.391 | B.191 | C.1 |
| 1.392 | B.192 | C.1 |
| 1.393 | B.193 | C.1 |
| 1.394 | B-194 | C.1 |
| 1.395 | B-195 | C.1 |
| 1.396 | B-196 | C.1 |
| 1.397 | B-197 | C.1 |
| 1.398 | B-198 | C.1 |
| 1.399 | B-199 | C.1 |
| 1.400 | B-200 | C.1 |
| 1.401 | B.1 | C.2 |
| 1.402 | B.2 | C.2 |
| 1.403 | B.3 | C.2 |
| 1.404 | B.4 | C.2 |
| 1.405 | B.5 | C.2 |
| 1.406 | B.6 | C.2 |
| 1.407 | B.7 | C.2 |
| 1.408 | B.8 | C.2 |
| 1.409 | B.9 | C.2 |
| 1.410 | B.10 | C.2 |
| 1.411 | B.11 | C.2 |
| 1.412 | B.12 | C.2 |
| 1.413 | B.13 | C.2 |
| 1.414 | B.14 | C.2 |
| 1.415 | B.15 | C.2 |
| 1.416 | B.16 | C.2 |
| 1.417 | B.17 | C.2 |
| 1.418 | B.18 | C.2 |
| 1.419 | B.19 | C.2 |
| 1.420 | B.20 | C.2 |
| 1.421 | B.21 | C.2 |
| 1.422 | B.22 | C.2 |
| 1.423 | B.23 | C.2 |
| 1.424 | B.24 | C.2 |
| 1.425 | B.25 | C.2 |
| 1.426 | B.26 | C.2 |
| 1.427 | B.27 | C.2 |
| 1.428 | B.28 | C.2 |
| 1.429 | B.29 | C.2 |
| 1.430 | B.30 | C.2 |
| 1.431 | B.31 | C.2 |
| 1.432 | B.32 | C.2 |
| 1.433 | B.33 | C.2 |
| 1.434 | B.34 | C.2 |
| 1.435 | B.35 | C.2 |
| 1.436 | B.36 | C.2 |
| 1.437 | B.37 | C.2 |
| 1.438 | B.38 | C.2 |
| 1.439 | B.39 | C.2 |
| 1.440 | B.40 | C.2 |
| 1.441 | B.41 | C.2 |
| 1.442 | B.42 | C.2 |
| 1.443 | B.43 | C.2 |
| 1.444 | B.44 | C.2 |
| 1.445 | B.45 | C.2 |
| 1.446 | B.46 | C.2 |
| 1.447 | B.47 | C.2 |
| 1.448 | B.48 | C.2 |
| 1.449 | B.49 | C.2 |
| 1.450 | B.50 | C.2 |
| 1.451 | B.51 | C.2 |
| 1.452 | B.52 | C.2 |
| 1.453 | B.53 | C.2 |
| 1.454 | B.54 | C.2 |
| 1.455 | B.55 | C.2 |
| 1.456 | B.56 | C.2 |
| 1.457 | B.57 | C.2 |
| 1.458 | B.58. | C.2 |
| 1.459 | B.59 | C.2 |
| 1.460 | B.60 | C.2 |
| 1.461 | B.61 | C.2 |
| 1.462 | B.62 | C.2 |
| 1.463 | B.63 | C.2 |
| 1.464 | B.64 | C.2 |
| 1.465 | B.65 | C.2 |
| 1.466 | B.66 | C.2 |
| 1.467 | B.67 | C.2 |
| 1.468 | B.68 | C.2 |
| 1.469 | B.69 | C.2 |
| 1.470 | B.70 | C.2 |
| 1.471 | B.71 | C.2 |
| 1.472 | B.72 | C.2 |
| 1.473 | B.73 | C.2 |
| 1.474 | B.74 | C.2 |
| 1.475 | B.75 | C.2 |
| 1.476 | B.76 | C.2 |
| 1.477 | B.77 | C.2 |
| 1.478 | B.78 | C.2 |
| 1.479 | B.79 | C.2 |
| 1.480 | B.80 | C.2 |
| 1.481 | B.81 | C.2 |
| 1.482 | B.82 | C.2 |
| 1.483 | B.83 | C.2 |
| 1.484 | B.84 | C.2 |
| 1.485 | B.85 | C.2 |
| 1.486 | B.86 | C.2 |
| 1.487 | B.87 | C.2 |
| 1.488 | B.88 | C.2 |
| 1.489 | B.89 | C.2 |
| 1.490 | B.90 | C.2 |
| 1.491 | B.91 | C.2 |
| 1.492 | B.92 | C.2 |
| 1.493 | B.93 | C.2 |
| 1.494 | B.94 | C.2 |
| 1.495 | B.95 | C.2 |
| 1.496 | B.96 | C.2 |
| 1.497 | B.97 | C.2 |
| 1.498 | B.98 | C.2 |
| 1.499 | B.99 | C.2 |
| 1.500 | B.100 | C.2 |
| 1.501 | B.101 | C.2 |
| 1.502 | B.102 | C.2 |
| 1.503 | B.103 | C.2 |
| 1.504 | B.104 | C.2 |
| 1.505 | B.105 | C.2 |
| 1.506 | B.106 | C.2 |
| 1.507 | B.107 | C.2 |
| 1.508 | B.108 | C.2 |
| 1.509 | B.109 | C.2 |
| 1.510 | B.110 | C.2 |
| 1.511 | B.111 | C.2 |
| 1.512 | B.112 | C.2 |
| 1.513 | B.113 | C.2 |
| 1.514 | B.114 | C.2 |
| 1.515 | B.115 | C.2 |
| 1.516 | B.116 | C.2 |
| 1.517 | B.117 | C.2 |
| 1.518 | B.118 | C.2 |
| 1.519 | B.119 | C.2 |
| 1.520 | B.120 | C.2 |
| 1.521 | B.121 | C.2 |
| 1.522 | B.122 | C.2 |
| 1.523 | B.123 | C.2 |
| 1.524 | B.124 | C.2 |
| 1.525 | B.125 | C.2 |
| 1.526 | B.126 | C.2 |
| 1.527 | B.127 | C.2 |
| 1.528 | B.128 | C.2 |
| 1.529 | B.129 | C.2 |
| 1.530 | B.130 | C.2 |
| 1.531 | B.131 | C.2 |
| 1.532 | B.132 | C.2 |
| 1.533 | B.133 | C.2 |
| 1.534 | B.134 | C.2 |
| 1.535 | B.135 | C.2 |
| 1.536 | B.136 | C.2 |
| 1.537 | B.137 | C.2 |

TABLE 1-continued (compositions 1.1 to 1.3617):

| comp. no. | herbicide B | safener C |
|---|---|---|
| 1.538 | B.138 | C.2 |
| 1.539 | B.139 | C.2 |
| 1.540 | B.140 | C.2 |
| 1.541 | B.141 | C.2 |
| 1.542 | B.142 | C.2 |
| 1.543 | B.143 | C.2 |
| 1.544 | B.144 | C.2 |
| 1.545 | B.145 | C.2 |
| 1.546 | B.146 | C.2 |
| 1.547 | B.147 | C.2 |
| 1.548 | B.148 | C.2 |
| 1.549 | B.149 | C.2 |
| 1.550 | B.150 | C.2 |
| 1.551 | B.151 | C.2 |
| 1.552 | B.152 | C.2 |
| 1.553 | B.153 | C.2 |
| 1.554 | B.154 | C.2 |
| 1.555 | B.155 | C.2 |
| 1.556 | B.156 | C.2 |
| 1.557 | B.157 | C.2 |
| 1.558 | B.158 | C.2 |
| 1.559 | B.159 | C.2 |
| 1.560 | B.160 | C.2 |
| 1.561 | B.161 | C.2 |
| 1.562 | B.162 | C.2 |
| 1.563 | B.163 | C.2 |
| 1.564 | B.164 | C.2 |
| 1.565 | B.165 | C.2 |
| 1.566 | B.166 | C.2 |
| 1.567 | B.167 | C.2 |
| 1.568 | B.168 | C.2 |
| 1.569 | B.169 | C.2 |
| 1.570 | B.170 | C.2 |
| 1.571 | B.171 | C.2 |
| 1.572 | B.172 | C.2 |
| 1.573 | B.173 | C.2 |
| 1.574 | B.174 | C.2 |
| 1.575 | B.175 | C.2 |
| 1.576 | B.176 | C.2 |
| 1.577 | B.177 | C.2 |
| 1.578 | B.178 | C.2 |
| 1.579 | B.179 | C.2 |
| 1.580 | B.180 | C.2 |
| 1.581 | B.181 | C.2 |
| 1.582 | B.182 | C.2 |
| 1.583 | B.183 | C.2 |
| 1.584 | B.184 | C.2 |
| 1.585 | B.185 | C.2 |
| 1.586 | B.186 | C.2 |
| 1.587 | B.187 | C.2 |
| 1.588 | B.188 | C.2 |
| 1.589 | B.189 | C.2 |
| 1.590 | B.190 | C.2 |
| 1.591 | B.191 | C.2 |
| 1.592 | B.192 | C.2 |
| 1.593 | B.193 | C.2 |
| 1.594 | B-194 | C.2 |
| 1.595 | B-195 | C.2 |
| 1.596 | B-196 | C.2 |
| 1.597 | B-197 | C.2 |
| 1.598 | B-198 | C.2 |
| 1.599 | B-199 | C.2 |
| 1.600 | B-200 | C.2 |
| 1.601 | B.1 | C.3 |
| 1.602 | B.2 | C.3 |
| 1.603 | B.3 | C.3 |
| 1.604 | B.4 | C.3 |
| 1.605 | B.5 | C.3 |
| 1.606 | B.6 | C.3 |
| 1.607 | B.7 | C.3 |
| 1.608 | B.8 | C.3 |
| 1.609 | B.9 | C.3 |
| 1.610 | B.10 | C.3 |
| 1.611 | B.11 | C.3 |
| 1.612 | B.12 | C.3 |
| 1.613 | B.13 | C.3 |
| 1.614 | B.14 | C.3 |
| 1.615 | B.15 | C.3 |
| 1.616 | B.16 | C.3 |
| 1.617 | B.17 | C.3 |
| 1.618 | B.18 | C.3 |
| 1.619 | B.19 | C.3 |
| 1.620 | B.20 | C.3 |
| 1.621 | B.21 | C.3 |
| 1.622 | B.22 | C.3 |
| 1.623 | B.23 | C.3 |
| 1.624 | B.24 | C.3 |
| 1.625 | B.25 | C.3 |
| 1.626 | B.26 | C.3 |
| 1.627 | B.27 | C.3 |
| 1.628 | B.28 | C.3 |
| 1.629 | B.29 | C.3 |
| 1.630 | B.30 | C.3 |
| 1.631 | B.31 | C.3 |
| 1.632 | B.32 | C.3 |
| 1.633 | B.33 | C.3 |
| 1.634 | B.34 | C.3 |
| 1.635 | B.35 | C.3 |
| 1.636 | B.36 | C.3 |
| 1.637 | B.37 | C.3 |
| 1.638 | B.38 | C.3 |
| 1.639 | B.39 | C.3 |
| 1.640 | B.40 | C.3 |
| 1.641 | B.41 | C.3 |
| 1.642 | B.42 | C.3 |
| 1.643 | B.43 | C.3 |
| 1.644 | B.44 | C.3 |
| 1.645 | B.45 | C.3 |
| 1.646 | B.46 | C.3 |
| 1.647 | B.47 | C.3 |
| 1.648 | B.48 | C.3 |
| 1.649 | B.49 | C.3 |
| 1.650 | B.50 | C.3 |
| 1.651 | B.51 | C.3 |
| 1.652 | B.52 | C.3 |
| 1.653 | B.53 | C.3 |
| 1.654 | B.54 | C.3 |
| 1.655 | B.55 | C.3 |
| 1.656 | B.56 | C.3 |
| 1.657 | B.57 | C.3 |
| 1.658 | B.58. | C.3 |
| 1.659 | B.59 | C.3 |
| 1.660 | B.60 | C.3 |
| 1.661 | B.61 | C.3 |
| 1.662 | B.62 | C.3 |
| 1.663 | B.63 | C.3 |
| 1.664 | B.64 | C.3 |
| 1.665 | B.65 | C.3 |
| 1.666 | B.66 | C.3 |
| 1.667 | B.67 | C.3 |
| 1.668 | B.68 | C.3 |
| 1.669 | B.69 | C.3 |
| 1.670 | B.70 | C.3 |
| 1.671 | B.71 | C.3 |
| 1.672 | B.72 | C.3 |
| 1.673 | B.73 | C.3 |
| 1.674 | B.74 | C.3 |
| 1.675 | B.75 | C.3 |
| 1.676 | B.76 | C.3 |
| 1.677 | B.77 | C.3 |
| 1.678 | B.78 | C.3 |
| 1.679 | B.79 | C.3 |
| 1.680 | B.80 | C.3 |
| 1.681 | B.81 | C.3 |
| 1.682 | B.82 | C.3 |
| 1.683 | B.83 | C.3 |
| 1.684 | B.84 | C.3 |
| 1.685 | B.85 | C.3 |
| 1.686 | B.86 | C.3 |
| 1.687 | B.87 | C.3 |
| 1.688 | B.88 | C.3 |
| 1.689 | B.89 | C.3 |

TABLE 1-continued (compositions 1.1 to 1.3617):

| comp. no. | herbicide B | safener C |
|---|---|---|
| 1.690 | B.90 | C.3 |
| 1.691 | B.91 | C.3 |
| 1.692 | B.92 | C.3 |
| 1.693 | B.93 | C.3 |
| 1.694 | B.94 | C.3 |
| 1.695 | B.95 | C.3 |
| 1.696 | B.96 | C.3 |
| 1.697 | B.97 | C.3 |
| 1.698 | B.98 | C.3 |
| 1.699 | B.99 | C.3 |
| 1.700 | B.100 | C.3 |
| 1.701 | B.101 | C.3 |
| 1.702 | B.102 | C.3 |
| 1.703 | B.103 | C.3 |
| 1.704 | B.104 | C.3 |
| 1.705 | B.105 | C.3 |
| 1.706 | B.106 | C.3 |
| 1.707 | B.107 | C.3 |
| 1.708 | B.108 | C.3 |
| 1.709 | B.109 | C.3 |
| 1.710 | B.110 | C.3 |
| 1.711 | B.111 | C.3 |
| 1.712 | B.112 | C.3 |
| 1.713 | B.113 | C.3 |
| 1.714 | B.114 | C.3 |
| 1.715 | B.115 | C.3 |
| 1.716 | B.116 | C.3 |
| 1.717 | B.117 | C.3 |
| 1.718 | B.118 | C.3 |
| 1.719 | B.119 | C.3 |
| 1.720 | B.120 | C.3 |
| 1.721 | B.121 | C.3 |
| 1.722 | B.122 | C.3 |
| 1.723 | B.123 | C.3 |
| 1.724 | B.124 | C.3 |
| 1.725 | B.125 | C.3 |
| 1.726 | B.126 | C.3 |
| 1.727 | B.127 | C.3 |
| 1.728 | B.128 | C.3 |
| 1.729 | B.129 | C.3 |
| 1.730 | B.130 | C.3 |
| 1.731 | B.131 | C.3 |
| 1.732 | B.132 | C.3 |
| 1.733 | B.133 | C.3 |
| 1.734 | B.134 | C.3 |
| 1.735 | B.135 | C.3 |
| 1.736 | B.136 | C.3 |
| 1.737 | B.137 | C.3 |
| 1.738 | B.138 | C.3 |
| 1.739 | B.139 | C.3 |
| 1.740 | B.140 | C.3 |
| 1.741 | B.141 | C.3 |
| 1.742 | B.142 | C.3 |
| 1.743 | B.143 | C.3 |
| 1.744 | B.144 | C.3 |
| 1.745 | B.145 | C.3 |
| 1.746 | B.146 | C.3 |
| 1.747 | B.147 | C.3 |
| 1.748 | B.148 | C.3 |
| 1.749 | B.149 | C.3 |
| 1.750 | B.150 | C.3 |
| 1.751 | B.151 | C.3 |
| 1.752 | B.152 | C.3 |
| 1.753 | B.153 | C.3 |
| 1.754 | B.154 | C.3 |
| 1.755 | B.155 | C.3 |
| 1.756 | B.156 | C.3 |
| 1.757 | B.157 | C.3 |
| 1.758 | B.158 | C.3 |
| 1.759 | B.159 | C.3 |
| 1.760 | B.160 | C.3 |
| 1.761 | B.161 | C.3 |
| 1.762 | B.162 | C.3 |
| 1.763 | B.163 | C.3 |
| 1.764 | B.164 | C.3 |
| 1.765 | B.165 | C.3 |
| 1.766 | B.166 | C.3 |
| 1.767 | B.167 | C.3 |
| 1.768 | B.168 | C.3 |
| 1.769 | B.169 | C.3 |
| 1.770 | B.170 | C.3 |
| 1.771 | B.171 | C.3 |
| 1.772 | B.172 | C.3 |
| 1.773 | B.173 | C.3 |
| 1.774 | B.174 | C.3 |
| 1.775 | B.175 | C.3 |
| 1.776 | B.176 | C.3 |
| 1.777 | B.177 | C.3 |
| 1.778 | B.178 | C.3 |
| 1.779 | B.179 | C.3 |
| 1.780 | B.180 | C.3 |
| 1.781 | B.181 | C.3 |
| 1.782 | B.182 | C.3 |
| 1.783 | B.183 | C.3 |
| 1.784 | B.184 | C.3 |
| 1.785 | B.185 | C.3 |
| 1.786 | B.186 | C.3 |
| 1.787 | B.187 | C.3 |
| 1.788 | B.188 | C.3 |
| 1.789 | B.189 | C.3 |
| 1.790 | B.190 | C.3 |
| 1.791 | B.191 | C.3 |
| 1.792 | B.192 | C.3 |
| 1.793 | B.193 | C.3 |
| 1.794 | B-194 | C.3 |
| 1.795 | B-195 | C.3 |
| 1.796 | B-196 | C.3 |
| 1.797 | B-197 | C.3 |
| 1.798 | B-198 | C.3 |
| 1.799 | B-199 | C.3 |
| 1.800 | B-200 | C.3 |
| 1.801 | B.1 | C.4 |
| 1.802 | B.2 | C.4 |
| 1.803 | B.3 | C.4 |
| 1.804 | B.4 | C.4 |
| 1.805 | B.5 | C.4 |
| 1.806 | B.6 | C.4 |
| 1.807 | B.7 | C.4 |
| 1.808 | B.8 | C.4 |
| 1.809 | B.9 | C.4 |
| 1.810 | B.10 | C.4 |
| 1.811 | B.11 | C.4 |
| 1.812 | B.12 | C.4 |
| 1.813 | B.13 | C.4 |
| 1.814 | B.14 | C.4 |
| 1.815 | B.15 | C.4 |
| 1.816 | B.16 | C.4 |
| 1.817 | B.17 | C.4 |
| 1.818 | B.18 | C.4 |
| 1.819 | B.19 | C.4 |
| 1.820 | B.20 | C.4 |
| 1.821 | B.21 | C.4 |
| 1.822 | B.22 | C.4 |
| 1.823 | B.23 | C.4 |
| 1.824 | B.24 | C.4 |
| 1.825 | B.25 | C.4 |
| 1.826 | B.26 | C.4 |
| 1.827 | B.27 | C.4 |
| 1.828 | B.28 | C.4 |
| 1.829 | B.29 | C.4 |
| 1.830 | B.30 | C.4 |
| 1.831 | B.31 | C.4 |
| 1.832 | B.32 | C.4 |
| 1.833 | B.33 | C.4 |
| 1.834 | B.34 | C.4 |
| 1.835 | B.35 | C.4 |
| 1.836 | B.36 | C.4 |
| 1.837 | B.37 | C.4 |
| 1.838 | B.38 | C.4 |
| 1.839 | B.39 | C.4 |
| 1.840 | B.40 | C.4 |
| 1.841 | B.41 | C.4 |

TABLE 1-continued (compositions 1.1 to 1.3617):

| comp. no. | herbicide B | safener C |
|---|---|---|
| 1.842 | B.42 | C.4 |
| 1.843 | B.43 | C.4 |
| 1.844 | B.44 | C.4 |
| 1.845 | B.45 | C.4 |
| 1.846 | B.46 | C.4 |
| 1.847 | B.47 | C.4 |
| 1.848 | B.48 | C.4 |
| 1.849 | B.49 | C.4 |
| 1.850 | B.50 | C.4 |
| 1.851 | B.51 | C.4 |
| 1.852 | B.52 | C.4 |
| 1.853 | B.53 | C.4 |
| 1.854 | B.54 | C.4 |
| 1.855 | B.55 | C.4 |
| 1.856 | B.56 | C.4 |
| 1.857 | B.57 | C.4 |
| 1.858 | B.58. | C.4 |
| 1.859 | B.59 | C.4 |
| 1.860 | B.60 | C.4 |
| 1.861 | B.61 | C.4 |
| 1.862 | B.62 | C.4 |
| 1.863 | B.63 | C.4 |
| 1.864 | B.64 | C.4 |
| 1.865 | B.65 | C.4 |
| 1.866 | B.66 | C.4 |
| 1.867 | B.67 | C.4 |
| 1.868 | B.68 | C.4 |
| 1.869 | B.69 | C.4 |
| 1.870 | B.70 | C.4 |
| 1.871 | B.71 | C.4 |
| 1.872 | B.72 | C.4 |
| 1.873 | B.73 | C.4 |
| 1.874 | B.74 | C.4 |
| 1.875 | B.75 | C.4 |
| 1.876 | B.76 | C.4 |
| 1.877 | B.77 | C.4 |
| 1.878 | B.78 | C.4 |
| 1.879 | B.79 | C.4 |
| 1.880 | B.80 | C.4 |
| 1.881 | B.81 | C.4 |
| 1.882 | B.82 | C.4 |
| 1.883 | B.83 | C.4 |
| 1.884 | B.84 | C.4 |
| 1.885 | B.85 | C.4 |
| 1.886 | B.86 | C.4 |
| 1.887 | B.87 | C.4 |
| 1.888 | B.88 | C.4 |
| 1.889 | B.89 | C.4 |
| 1.890 | B.90 | C.4 |
| 1.891 | B.91 | C.4 |
| 1.892 | B.92 | C.4 |
| 1.893 | B.93 | C.4 |
| 1.894 | B.94 | C.4 |
| 1.895 | B.95 | C.4 |
| 1.896 | B.96 | C.4 |
| 1.897 | B.97 | C.4 |
| 1.898 | B.98 | C.4 |
| 1.899 | B.99 | C.4 |
| 1.900 | B.100 | C.4 |
| 1.901 | B.101 | C.4 |
| 1.902 | B.102 | C.4 |
| 1.903 | B.103 | C.4 |
| 1.904 | B.104 | C.4 |
| 1.905 | B.105 | C.4 |
| 1.906 | B.106 | C.4 |
| 1.907 | B.107 | C.4 |
| 1.908 | B.108 | C.4 |
| 1.909 | B.109 | C.4 |
| 1.910 | B.110 | C.4 |
| 1.911 | B.111 | C.4 |
| 1.912 | B.112 | C.4 |
| 1.913 | B.113 | C.4 |
| 1.914 | B.114 | C.4 |
| 1.915 | B.115 | C.4 |
| 1.916 | B.116 | C.4 |
| 1.917 | B.117 | C.4 |
| 1.918 | B.118 | C.4 |
| 1.919 | B.119 | C.4 |
| 1.920 | B.120 | C.4 |
| 1.921 | B.121 | C.4 |
| 1.922 | B.122 | C.4 |
| 1.923 | B.123 | C.4 |
| 1.924 | B.124 | C.4 |
| 1.925 | B.125 | C.4 |
| 1.926 | B.126 | C.4 |
| 1.927 | B.127 | C.4 |
| 1.928 | B.128 | C.4 |
| 1.929 | B.129 | C.4 |
| 1.930 | B.130 | C.4 |
| 1.931 | B.131 | C.4 |
| 1.932 | B.132 | C.4 |
| 1.933 | B.133 | C.4 |
| 1.934 | B.134 | C.4 |
| 1.935 | B.135 | C.4 |
| 1.936 | B.136 | C.4 |
| 1.937 | B.137 | C.4 |
| 1.938 | B.138 | C.4 |
| 1.939 | B.139 | C.4 |
| 1.940 | B.140 | C.4 |
| 1.941 | B.141 | C.4 |
| 1.942 | B.142 | C.4 |
| 1.943 | B.143 | C.4 |
| 1.944 | B.144 | C.4 |
| 1.945 | B.145 | C.4 |
| 1.946 | B.146 | C.4 |
| 1.947 | B.147 | C.4 |
| 1.948 | B.148 | C.4 |
| 1.949 | B.149 | C.4 |
| 1.950 | B.150 | C.4 |
| 1.951 | B.151 | C.4 |
| 1.952 | B.152 | C.4 |
| 1.953 | B.153 | C.4 |
| 1.954 | B.154 | C.4 |
| 1.955 | B.155 | C.4 |
| 1.956 | B.156 | C.4 |
| 1.957 | B.157 | C.4 |
| 1.958 | B.158 | C.4 |
| 1.959 | B.159 | C.4 |
| 1.960 | B.160 | C.4 |
| 1.961 | B.161 | C.4 |
| 1.962 | B.162 | C.4 |
| 1.963 | B.163 | C.4 |
| 1.964 | B.164 | C.4 |
| 1.965 | B.165 | C.4 |
| 1.966 | B.166 | C.4 |
| 1.967 | B.167 | C.4 |
| 1.968 | B.168 | C.4 |
| 1.969 | B.169 | C.4 |
| 1.970 | B.170 | C.4 |
| 1.971 | B.171 | C.4 |
| 1.972 | B.172 | C.4 |
| 1.973 | B.173 | C.4 |
| 1.974 | B.174 | C.4 |
| 1.975 | B.175 | C.4 |
| 1.976 | B.176 | C.4 |
| 1.977 | B.177 | C.4 |
| 1.978 | B.178 | C.4 |
| 1.979 | B.179 | C.4 |
| 1.980 | B.180 | C.4 |
| 1.981 | B.181 | C.4 |
| 1.982 | B.182 | C.4 |
| 1.983 | B.183 | C.4 |
| 1.984 | B.184 | C.4 |
| 1.985 | B.185 | C.4 |
| 1.986 | B.186 | C.4 |
| 1.987 | B.187 | C.4 |
| 1.988 | B.188 | C.4 |
| 1.989 | B.189 | C.4 |
| 1.990 | B.190 | C.4 |
| 1.991 | B.191 | C.4 |
| 1.992 | B.192 | C.4 |
| 1.993 | B.193 | C.4 |

TABLE 1-continued (compositions 1.1 to 1.3617):

| comp. no. | herbicide B | safener C |
|---|---|---|
| 1.994 | B-194 | C.4 |
| 1.995 | B-195 | C.4 |
| 1.996 | B-196 | C.4 |
| 1.997 | B-197 | C.4 |
| 1.998 | B-198 | C.4 |
| 1.999 | B-199 | C.4 |
| 1.1000 | B-200 | C.4 |
| 1.1001 | B.1 | C.5 |
| 1.1002 | B.2 | C.5 |
| 1.1003 | B.3 | C.5 |
| 1.1004 | B.4 | C.5 |
| 1.1005 | B.5 | C.5 |
| 1.1006 | B.6 | C.5 |
| 1.1007 | B.7 | C.5 |
| 1.1008 | B.8 | C.5 |
| 1.1009 | B.9 | C.5 |
| 1.1010 | B.10 | C.5 |
| 1.1011 | B.11 | C.5 |
| 1.1012 | B.12 | C.5 |
| 1.1013 | B.13 | C.5 |
| 1.1014 | B.14 | C.5 |
| 1.1015 | B.15 | C.5 |
| 1.1016 | B.16 | C.5 |
| 1.1017 | B.17 | C.5 |
| 1.1018 | B.18 | C.5 |
| 1.1019 | B.19 | C.5 |
| 1.1020 | B.20 | C.5 |
| 1.1021 | B.21 | C.5 |
| 1.1022 | B.22 | C.5 |
| 1.1023 | B.23 | C.5 |
| 1.1024 | B.24 | C.5 |
| 1.1025 | B.25 | C.5 |
| 1.1026 | B.26 | C.5 |
| 1.1027 | B.27 | C.5 |
| 1.1028 | B.28 | C.5 |
| 1.1029 | B.29 | C.5 |
| 1.1030 | B.30 | C.5 |
| 1.1031 | B.31 | C.5 |
| 1.1032 | B.32 | C.5 |
| 1.1033 | B.33 | C.5 |
| 1.1034 | B.34 | C.5 |
| 1.1035 | B.35 | C.5 |
| 1.1036 | B.36 | C.5 |
| 1.1037 | B.37 | C.5 |
| 1.1038 | B.38 | C.5 |
| 1.1039 | B.39 | C.5 |
| 1.1040 | B.40 | C.5 |
| 1.1041 | B.41 | C.5 |
| 1.1042 | B.42 | C.5 |
| 1.1043 | B.43 | C.5 |
| 1.1044 | B.44 | C.5 |
| 1.1045 | B.45 | C.5 |
| 1.1046 | B.46 | C.5 |
| 1.1047 | B.47 | C.5 |
| 1.1048 | B.48 | C.5 |
| 1.1049 | B.49 | C.5 |
| 1.1050 | B.50 | C.5 |
| 1.1051 | B.51 | C.5 |
| 1.1052 | B.52 | C.5 |
| 1.1053 | B.53 | C.5 |
| 1.1054 | B.54 | C.5 |
| 1.1055 | B.55 | C.5 |
| 1.1056 | B.56 | C.5 |
| 1.1057 | B.57 | C.5 |
| 1.1058 | B.58. | C.5 |
| 1.1059 | B.59 | C.5 |
| 1.1060 | B.60 | C.5 |
| 1.1061 | B.61 | C.5 |
| 1.1062 | B.62 | C.5 |
| 1.1063 | B.63 | C.5 |
| 1.1064 | B.64 | C.5 |
| 1.1065 | B.65 | C.5 |
| 1.1066 | B.66 | C.5 |
| 1.1067 | B.67 | C.5 |
| 1.1068 | B.68 | C.5 |
| 1.1069 | B.69 | C.5 |
| 1.1070 | B.70 | C.5 |
| 1.1071 | B.71 | C.5 |
| 1.1072 | B.72 | C.5 |
| 1.1073 | B.73 | C.5 |
| 1.1074 | B.74 | C.5 |
| 1.1075 | B.75 | C.5 |
| 1.1076 | B.76 | C.5 |
| 1.1077 | B.77 | C.5 |
| 1.1078 | B.78 | C.5 |
| 1.1079 | B.79 | C.5 |
| 1.1080 | B.80 | C.5 |
| 1.1081 | B.81 | C.5 |
| 1.1082 | B.82 | C.5 |
| 1.1083 | B.83 | C.5 |
| 1.1084 | B.84 | C.5 |
| 1.1085 | B.85 | C.5 |
| 1.1086 | B.86 | C.5 |
| 1.1087 | B.87 | C.5 |
| 1.1088 | B.88 | C.5 |
| 1.1089 | B.89 | C.5 |
| 1.1090 | B.90 | C.5 |
| 1.1091 | B.91 | C.5 |
| 1.1092 | B.92 | C.5 |
| 1.1093 | B.93 | C.5 |
| 1.1094 | B.94 | C.5 |
| 1.1095 | B.95 | C.5 |
| 1.1096 | B.96 | C.5 |
| 1.1097 | B.97 | C.5 |
| 1.1098 | B.98 | C.5 |
| 1.1099 | B.99 | C.5 |
| 1.1100 | B.100 | C.5 |
| 1.1101 | B.101 | C.5 |
| 1.1102 | B.102 | C.5 |
| 1.1103 | B.103 | C.5 |
| 1.1104 | B.104 | C.5 |
| 1.1105 | B.105 | C.5 |
| 1.1106 | B.106 | C.5 |
| 1.1107 | B.107 | C.5 |
| 1.1108 | B.108 | C.5 |
| 1.1109 | B.109 | C.5 |
| 1.1110 | B.110 | C.5 |
| 1.1111 | B.111 | C.5 |
| 1.1112 | B.112 | C.5 |
| 1.1113 | B.113 | C.5 |
| 1.1114 | B.114 | C.5 |
| 1.1115 | B.115 | C.5 |
| 1.1116 | B.116 | C.5 |
| 1.1117 | B.117 | C.5 |
| 1.1118 | B.118 | C.5 |
| 1.1119 | B.119 | C.5 |
| 1.1120 | B.120 | C.5 |
| 1.1121 | B.121 | C.5 |
| 1.1122 | B.122 | C.5 |
| 1.1123 | B.123 | C.5 |
| 1.1124 | B.124 | C.5 |
| 1.1125 | B.125 | C.5 |
| 1.1126 | B.126 | C.5 |
| 1.1127 | B.127 | C.5 |
| 1.1128 | B.128 | C.5 |
| 1.1129 | B.129 | C.5 |
| 1.1130 | B.130 | C.5 |
| 1.1131 | B.131 | C.5 |
| 1.1132 | B.132 | C.5 |
| 1.1133 | B.133 | C.5 |
| 1.1134 | B.134 | C.5 |
| 1.1135 | B.135 | C.5 |
| 1.1136 | B.136 | C.5 |
| 1.1137 | B.137 | C.5 |
| 1.1138 | B.138 | C.5 |
| 1.1139 | B.139 | C.5 |
| 1.1140 | B.140 | C.5 |
| 1.1141 | B.141 | C.5 |
| 1.1142 | B.142 | C.5 |
| 1.1143 | B.143 | C.5 |
| 1.1144 | B.144 | C.5 |
| 1.1145 | B.145 | C.5 |

TABLE 1-continued (compositions 1.1 to 1.3617):

| comp. no. | herbicide B | safener C |
|---|---|---|
| 1.1146 | B.146 | C.5 |
| 1.1147 | B.147 | C.5 |
| 1.1148 | B.148 | C.5 |
| 1.1149 | B.149 | C.5 |
| 1.1150 | B.150 | C.5 |
| 1.1151 | B.151 | C.5 |
| 1.1152 | B.152 | C.5 |
| 1.1153 | B.153 | C.5 |
| 1.1154 | B.154 | C.5 |
| 1.1155 | B.155 | C.5 |
| 1.1156 | B.156 | C.5 |
| 1.1157 | B.157 | C.5 |
| 1.1158 | B.158 | C.5 |
| 1.1159 | B.159 | C.5 |
| 1.1160 | B.160 | C.5 |
| 1.1161 | B.161 | C.5 |
| 1.1162 | B.162 | C.5 |
| 1.1163 | B.163 | C.5 |
| 1.1164 | B.164 | C.5 |
| 1.1165 | B.165 | C.5 |
| 1.1166 | B.166 | C.5 |
| 1.1167 | B.167 | C.5 |
| 1.1168 | B.168 | C.5 |
| 1.1169 | B.169 | C.5 |
| 1.1170 | B.170 | C.5 |
| 1.1171 | B.171 | C.5 |
| 1.1172 | B.172 | C.5 |
| 1.1173 | B.173 | C.5 |
| 1.1174 | B.174 | C.5 |
| 1.1175 | B.175 | C.5 |
| 1.1176 | B.176 | C.5 |
| 1.1177 | B.177 | C.5 |
| 1.1178 | B.178 | C.5 |
| 1.1179 | B.179 | C.5 |
| 1.1180 | B.180 | C.5 |
| 1.1181 | B.181 | C.5 |
| 1.1182 | B.182 | C.5 |
| 1.1183 | B.183 | C.5 |
| 1.1184 | B.184 | C.5 |
| 1.1185 | B.185 | C.5 |
| 1.1186 | B.186 | C.5 |
| 1.1187 | B.187 | C.5 |
| 1.1188 | B.188 | C.5 |
| 1.1189 | B.189 | C.5 |
| 1.1190 | B.190 | C.5 |
| 1.1191 | B.191 | C.5 |
| 1.1192 | B.192 | C.5 |
| 1.1193 | B.193 | C.5 |
| 1.1194 | B-194 | C.5 |
| 1.1195 | B-195 | C.5 |
| 1.1196 | B-196 | C.5 |
| 1.1197 | B-197 | C.5 |
| 1.1198 | B-198 | C.5 |
| 1.1199 | B-199 | C.5 |
| 1.1200 | B-200 | C.5 |
| 1.1201 | B.1 | C.6 |
| 1.1202 | B.2 | C.6 |
| 1.1203 | B.3 | C.6 |
| 1.1204 | B.4 | C.6 |
| 1.1205 | B.5 | C.6 |
| 1.1206 | B.6 | C.6 |
| 1.1207 | B.7 | C.6 |
| 1.1208 | B.8 | C.6 |
| 1.1209 | B.9 | C.6 |
| 1.1210 | B.10 | C.6 |
| 1.1211 | B.11 | C.6 |
| 1.1212 | B.12 | C.6 |
| 1.1213 | B.13 | C.6 |
| 1.1214 | B.14 | C.6 |
| 1.1215 | B.15 | C.6 |
| 1.1216 | B.16 | C.6 |
| 1.1217 | B.17 | C.6 |
| 1.1218 | B.18 | C.6 |
| 1.1219 | B.19 | C.6 |
| 1.1220 | B.20 | C.6 |
| 1.1221 | B.21 | C.6 |
| 1.1222 | B.22 | C.6 |
| 1.1223 | B.23 | C.6 |
| 1.1224 | B.24 | C.6 |
| 1.1225 | B.25 | C.6 |
| 1.1226 | B.26 | C.6 |
| 1.1227 | B.27 | C.6 |
| 1.1228 | B.28 | C.6 |
| 1.1229 | B.29 | C.6 |
| 1.1230 | B.30 | C.6 |
| 1.1231 | B.31 | C.6 |
| 1.1232 | B.32 | C.6 |
| 1.1233 | B.33 | C.6 |
| 1.1234 | B.34 | C.6 |
| 1.1235 | B.35 | C.6 |
| 1.1236 | B.36 | C.6 |
| 1.1237 | B.37 | C.6 |
| 1.1238 | B.38 | C.6 |
| 1.1239 | B.39 | C.6 |
| 1.1240 | B.40 | C.6 |
| 1.1241 | B.41 | C.6 |
| 1.1242 | B.42 | C.6 |
| 1.1243 | B.43 | C.6 |
| 1.1244 | B.44 | C.6 |
| 1.1245 | B.45 | C.6 |
| 1.1246 | B.46 | C.6 |
| 1.1247 | B.47 | C.6 |
| 1.1248 | B.48 | C.6 |
| 1.1249 | B.49 | C.6 |
| 1.1250 | B.50 | C.6 |
| 1.1251 | B.51 | C.6 |
| 1.1252 | B.52 | C.6 |
| 1.1253 | B.53 | C.6 |
| 1.1254 | B.54 | C.6 |
| 1.1255 | B.55 | C.6 |
| 1.1256 | B.56 | C.6 |
| 1.1257 | B.57 | C.6 |
| 1.1258 | B.58. | C.6 |
| 1.1259 | B.59 | C.6 |
| 1.1260 | B.60 | C.6 |
| 1.1261 | B.61 | C.6 |
| 1.1262 | B.62 | C.6 |
| 1.1263 | B.63 | C.6 |
| 1.1264 | B.64 | C.6 |
| 1.1265 | B.65 | C.6 |
| 1.1266 | B.66 | C.6 |
| 1.1267 | B.67 | C.6 |
| 1.1268 | B.68 | C.6 |
| 1.1269 | B.69 | C.6 |
| 1.1270 | B.70 | C.6 |
| 1.1271 | B.71 | C.6 |
| 1.1272 | B.72 | C.6 |
| 1.1273 | B.73 | C.6 |
| 1.1274 | B.74 | C.6 |
| 1.1275 | B.75 | C.6 |
| 1.1276 | B.76 | C.6 |
| 1.1277 | B.77 | C.6 |
| 1.1278 | B.78 | C.6 |
| 1.1279 | B.79 | C.6 |
| 1.1280 | B.80 | C.6 |
| 1.1281 | B.81 | C.6 |
| 1.1282 | B.82 | C.6 |
| 1.1283 | B.83 | C.6 |
| 1.1284 | B.84 | C.6 |
| 1.1285 | B.85 | C.6 |
| 1.1286 | B.86 | C.6 |
| 1.1287 | B.87 | C.6 |
| 1.1288 | B.88 | C.6 |
| 1.1289 | B.89 | C.6 |
| 1.1290 | B.90 | C.6 |
| 1.1291 | B.91 | C.6 |
| 1.1292 | B.92 | C.6 |
| 1.1293 | B.93 | C.6 |
| 1.1294 | B.94 | C.6 |
| 1.1295 | B.95 | C.6 |
| 1.1296 | B.96 | C.6 |
| 1.1297 | B.97 | C.6 |

TABLE 1-continued (compositions 1.1 to 1.3617):

| comp. no. | herbicide B | safener C |
|---|---|---|
| 1.1298 | B.98 | C.6 |
| 1.1299 | B.99 | C.6 |
| 1.1300 | B.100 | C.6 |
| 1.1301 | B.101 | C.6 |
| 1.1302 | B.102 | C.6 |
| 1.1303 | B.103 | C.6 |
| 1.1304 | B.104 | C.6 |
| 1.1305 | B.105 | C.6 |
| 1.1306 | B.106 | C.6 |
| 1.1307 | B.107 | C.6 |
| 1.1308 | B.108 | C.6 |
| 1.1309 | B.109 | C.6 |
| 1.1310 | B.110 | C.6 |
| 1.1311 | B.111 | C.6 |
| 1.1312 | B.112 | C.6 |
| 1.1313 | B.113 | C.6 |
| 1.1314 | B.114 | C.6 |
| 1.1315 | B.115 | C.6 |
| 1.1316 | B.116 | C.6 |
| 1.1317 | B.117 | C.6 |
| 1.1318 | B.118 | C.6 |
| 1.1319 | B.119 | C.6 |
| 1.1320 | B.120 | C.6 |
| 1.1321 | B.121 | C.6 |
| 1.1322 | B.122 | C.6 |
| 1.1323 | B.123 | C.6 |
| 1.1324 | B.124 | C.6 |
| 1.1325 | B.125 | C.6 |
| 1.1326 | B.126 | C.6 |
| 1.1327 | B.127 | C.6 |
| 1.1328 | B.128 | C.6 |
| 1.1329 | B.129 | C.6 |
| 1.1330 | B.130 | C.6 |
| 1.1331 | B.131 | C.6 |
| 1.1332 | B.132 | C.6 |
| 1.1333 | B.133 | C.6 |
| 1.1334 | B.134 | C.6 |
| 1.1335 | B.135 | C.6 |
| 1.1336 | B.136 | C.6 |
| 1.1337 | B.137 | C.6 |
| 1.1338 | B.138 | C.6 |
| 1.1339 | B.139 | C.6 |
| 1.1340 | B.140 | C.6 |
| 1.1341 | B.141 | C.6 |
| 1.1342 | B.142 | C.6 |
| 1.1343 | B.143 | C.6 |
| 1.1344 | B.144 | C.6 |
| 1.1345 | B.145 | C.6 |
| 1.1346 | B.146 | C.6 |
| 1.1347 | B.147 | C.6 |
| 1.1348 | B.148 | C.6 |
| 1.1349 | B.149 | C.6 |
| 1.1350 | B.150 | C.6 |
| 1.1351 | B.151 | C.6 |
| 1.1352 | B.152 | C.6 |
| 1.1353 | B.153 | C.6 |
| 1.1354 | B.154 | C.6 |
| 1.1355 | B.155 | C.6 |
| 1.1356 | B.156 | C.6 |
| 1.1357 | B.157 | C.6 |
| 1.1358 | B.158 | C.6 |
| 1.1359 | B.159 | C.6 |
| 1.1360 | B.160 | C.6 |
| 1.1361 | B.161 | C.6 |
| 1.1362 | B.162 | C.6 |
| 1.1363 | B.163 | C.6 |
| 1.1364 | B.164 | C.6 |
| 1.1365 | B.165 | C.6 |
| 1.1366 | B.166 | C.6 |
| 1.1367 | B.167 | C.6 |
| 1.1368 | B.168 | C.6 |
| 1.1369 | B.169 | C.6 |
| 1.1370 | B.170 | C.6 |
| 1.1371 | B.171 | C.6 |
| 1.1372 | B.172 | C.6 |
| 1.1373 | B.173 | C.6 |
| 1.1374 | B.174 | C.6 |
| 1.1375 | B.175 | C.6 |
| 1.1376 | B.176 | C.6 |
| 1.1377 | B.177 | C.6 |
| 1.1378 | B.178 | C.6 |
| 1.1379 | B.179 | C.6 |
| 1.1380 | B.180 | C.6 |
| 1.1381 | B.181 | C.6 |
| 1.1382 | B.182 | C.6 |
| 1.1383 | B.183 | C.6 |
| 1.1384 | B.184 | C.6 |
| 1.1385 | B.185 | C.6 |
| 1.1386 | B.186 | C.6 |
| 1.1387 | B.187 | C.6 |
| 1.1388 | B.188 | C.6 |
| 1.1389 | B.189 | C.6 |
| 1.1390 | B.190 | C.6 |
| 1.1391 | B.191 | C.6 |
| 1.1392 | B.192 | C.6 |
| 1.1393 | B.193 | C.6 |
| 1.1394 | B-194 | C.6 |
| 1.1395 | B-195 | C.6 |
| 1.1396 | B-196 | C.6 |
| 1.1397 | B-197 | C.6 |
| 1.1398 | B-198 | C.6 |
| 1.1399 | B-199 | C.6 |
| 1.1400 | B-200 | C.6 |
| 1.1401 | B.1 | C.7 |
| 1.1402 | B.2 | C.7 |
| 1.1403 | B.3 | C.7 |
| 1.1404 | B.4 | C.7 |
| 1.1405 | B.5 | C.7 |
| 1.1406 | B.6 | C.7 |
| 1.1407 | B.7 | C.7 |
| 1.1408 | B.8 | C.7 |
| 1.1409 | B.9 | C.7 |
| 1.1410 | B.10 | C.7 |
| 1.1411 | B.11 | C.7 |
| 1.1412 | B.12 | C.7 |
| 1.1413 | B.13 | C.7 |
| 1.1414 | B.14 | C.7 |
| 1.1415 | B.15 | C.7 |
| 1.1416 | B.16 | C.7 |
| 1.1417 | B.17 | C.7 |
| 1.1418 | B.18 | C.7 |
| 1.1419 | B.19 | C.7 |
| 1.1420 | B.20 | C.7 |
| 1.1421 | B.21 | C.7 |
| 1.1422 | B.22 | C.7 |
| 1.1423 | B.23 | C.7 |
| 1.1424 | B.24 | C.7 |
| 1.1425 | B.25 | C.7 |
| 1.1426 | B.26 | C.7 |
| 1.1427 | B.27 | C.7 |
| 1.1428 | B.28 | C.7 |
| 1.1429 | B.29 | C.7 |
| 1.1430 | B.30 | C.7 |
| 1.1431 | B.31 | C.7 |
| 1.1432 | B.32 | C.7 |
| 1.1433 | B.33 | C.7 |
| 1.1434 | B.34 | C.7 |
| 1.1435 | B.35 | C.7 |
| 1.1436 | B.36 | C.7 |
| 1.1437 | B.37 | C.7 |
| 1.1438 | B.38 | C.7 |
| 1.1439 | B.39 | C.7 |
| 1.1440 | B.40 | C.7 |
| 1.1441 | B.41 | C.7 |
| 1.1442 | B.42 | C.7 |
| 1.1443 | B.43 | C.7 |
| 1.1444 | B.44 | C.7 |
| 1.1445 | B.45 | C.7 |
| 1.1446 | B.46 | C.7 |
| 1.1447 | B.47 | C.7 |
| 1.1448 | B.48 | C.7 |
| 1.1449 | B.49 | C.7 |

TABLE 1-continued (compositions 1.1 to 1.3617):

| comp. no. | herbicide B | safener C |
|---|---|---|
| 1.1450 | B.50 | C.7 |
| 1.1451 | B.51 | C.7 |
| 1.1452 | B.52 | C.7 |
| 1.1453 | B.53 | C.7 |
| 1.1454 | B.54 | C.7 |
| 1.1455 | B.55 | C.7 |
| 1.1456 | B.56 | C.7 |
| 1.1457 | B.57 | C.7 |
| 1.1458 | B.58. | C.7 |
| 1.1459 | B.59 | C.7 |
| 1.1460 | B.60 | C.7 |
| 1.1461 | B.61 | C.7 |
| 1.1462 | B.62 | C.7 |
| 1.1463 | B.63 | C.7 |
| 1.1464 | B.64 | C.7 |
| 1.1465 | B.65 | C.7 |
| 1.1466 | B.66 | C.7 |
| 1.1467 | B.67 | C.7 |
| 1.1468 | B.68 | C.7 |
| 1.1469 | B.69 | C.7 |
| 1.1470 | B.70 | C.7 |
| 1.1471 | B.71 | C.7 |
| 1.1472 | B.72 | C.7 |
| 1.1473 | B.73 | C.7 |
| 1.1474 | B.74 | C.7 |
| 1.1475 | B.75 | C.7 |
| 1.1476 | B.76 | C.7 |
| 1.1477 | B.77 | C.7 |
| 1.1478 | B.78 | C.7 |
| 1.1479 | B.79 | C.7 |
| 1.1480 | B.80 | C.7 |
| 1.1481 | B.81 | C.7 |
| 1.1482 | B.82 | C.7 |
| 1.1483 | B.83 | C.7 |
| 1.1484 | B.84 | C.7 |
| 1.1485 | B.85 | C.7 |
| 1.1486 | B.86 | C.7 |
| 1.1487 | B.87 | C.7 |
| 1.1488 | B.88 | C.7 |
| 1.1489 | B.89 | C.7 |
| 1.1490 | B.90 | C.7 |
| 1.1491 | B.91 | C.7 |
| 1.1492 | B.92 | C.7 |
| 1.1493 | B.93 | C.7 |
| 1.1494 | B.94 | C.7 |
| 1.1495 | B.95 | C.7 |
| 1.1496 | B.96 | C.7 |
| 1.1497 | B.97 | C.7 |
| 1.1498 | B.98 | C.7 |
| 1.1499 | B.99 | C.7 |
| 1.1500 | B.100 | C.7 |
| 1.1501 | B.101 | C.7 |
| 1.1502 | B.102 | C.7 |
| 1.1503 | B.103 | C.7 |
| 1.1504 | B.104 | C.7 |
| 1.1505 | B.105 | C.7 |
| 1.1506 | B.106 | C.7 |
| 1.1507 | B.107 | C.7 |
| 1.1508 | B.108 | C.7 |
| 1.1509 | B.109 | C.7 |
| 1.1510 | B.110 | C.7 |
| 1.1511 | B.111 | C.7 |
| 1.1512 | B.112 | C.7 |
| 1.1513 | B.113 | C.7 |
| 1.1514 | B.114 | C.7 |
| 1.1515 | B.115 | C.7 |
| 1.1516 | B.116 | C.7 |
| 1.1517 | B.117 | C.7 |
| 1.1518 | B.118 | C.7 |
| 1.1519 | B.119 | C.7 |
| 1.1520 | B.120 | C.7 |
| 1.1521 | B.121 | C.7 |
| 1.1522 | B.122 | C.7 |
| 1.1523 | B.123 | C.7 |
| 1.1524 | B.124 | C.7 |
| 1.1525 | B.125 | C.7 |
| 1.1526 | B.126 | C.7 |
| 1.1527 | B.127 | C.7 |
| 1.1528 | B.128 | C.7 |
| 1.1529 | B.129 | C.7 |
| 1.1530 | B.130 | C.7 |
| 1.1531 | B.131 | C.7 |
| 1.1532 | B.132 | C.7 |
| 1.1533 | B.133 | C.7 |
| 1.1534 | B.134 | C.7 |
| 1.1535 | B.135 | C.7 |
| 1.1536 | B.136 | C.7 |
| 1.1537 | B.137 | C.7 |
| 1.1538 | B.138 | C.7 |
| 1.1539 | B.139 | C.7 |
| 1.1540 | B.140 | C.7 |
| 1.1541 | B.141 | C.7 |
| 1.1542 | B.142 | C.7 |
| 1.1543 | B.143 | C.7 |
| 1.1544 | B.144 | C.7 |
| 1.1545 | B.145 | C.7 |
| 1.1546 | B.146 | C.7 |
| 1.1547 | B.147 | C.7 |
| 1.1548 | B.148 | C.7 |
| 1.1549 | B.149 | C.7 |
| 1.1550 | B.150 | C.7 |
| 1.1551 | B.151 | C.7 |
| 1.1552 | B.152 | C.7 |
| 1.1553 | B.153 | C.7 |
| 1.1554 | B.154 | C.7 |
| 1.1555 | B.155 | C.7 |
| 1.1556 | B.156 | C.7 |
| 1.1557 | B.157 | C.7 |
| 1.1558 | B.158 | C.7 |
| 1.1559 | B.159 | C.7 |
| 1.1560 | B.160 | C.7 |
| 1.1561 | B.161 | C.7 |
| 1.1562 | B.162 | C.7 |
| 1.1563 | B.163 | C.7 |
| 1.1564 | B.164 | C.7 |
| 1.1565 | B.165 | C.7 |
| 1.1566 | B.166 | C.7 |
| 1.1567 | B.167 | C.7 |
| 1.1568 | B.168 | C.7 |
| 1.1569 | B.169 | C.7 |
| 1.1570 | B.170 | C.7 |
| 1.1571 | B.171 | C.7 |
| 1.1572 | B.172 | C.7 |
| 1.1573 | B.173 | C.7 |
| 1.1574 | B.174 | C.7 |
| 1.1575 | B.175 | C.7 |
| 1.1576 | B.176 | C.7 |
| 1.1577 | B.177 | C.7 |
| 1.1578 | B.178 | C.7 |
| 1.1579 | B.179 | C.7 |
| 1.1580 | B.180 | C.7 |
| 1.1581 | B.181 | C.7 |
| 1.1582 | B.182 | C.7 |
| 1.1583 | B.183 | C.7 |
| 1.1584 | B.184 | C.7 |
| 1.1585 | B.185 | C.7 |
| 1.1586 | B.186 | C.7 |
| 1.1587 | B.187 | C.7 |
| 1.1588 | B.188 | C.7 |
| 1.1589 | B.189 | C.7 |
| 1.1590 | B.190 | C.7 |
| 1.1591 | B.191 | C.7 |
| 1.1592 | B.192 | C.7 |
| 1.1593 | B.193 | C.7 |
| 1.1594 | B-194 | C.7 |
| 1.1595 | B-195 | C.7 |
| 1.1596 | B-196 | C.7 |
| 1.1597 | B-197 | C.7 |
| 1.1598 | B-198 | C.7 |
| 1.1599 | B-199 | C.7 |
| 1.1600 | B-200 | C.7 |
| 1.1601 | B.1 | C.8 |

TABLE 1-continued (compositions 1.1 to 1.3617):

| comp. no. | herbicide B | safener C |
|---|---|---|
| 1.1602 | B.2 | C.8 |
| 1.1603 | B.3 | C.8 |
| 1.1604 | B.4 | C.8 |
| 1.1605 | B.5 | C.8 |
| 1.1606 | B.6 | C.8 |
| 1.1607 | B.7 | C.8 |
| 1.1608 | B.8 | C.8 |
| 1.1609 | B.9 | C.8 |
| 1.1610 | B.10 | C.8 |
| 1.1611 | B.11 | C.8 |
| 1.1612 | B.12 | C.8 |
| 1.1613 | B.13 | C.8 |
| 1.1614 | B.14 | C.8 |
| 1.1615 | B.15 | C.8 |
| 1.1616 | B.16 | C.8 |
| 1.1617 | B.17 | C.8 |
| 1.1618 | B.18 | C.8 |
| 1.1619 | B.19 | C.8 |
| 1.1620 | B.20 | C.8 |
| 1.1621 | B.21 | C.8 |
| 1.1622 | B.22 | C.8 |
| 1.1623 | B.23 | C.8 |
| 1.1624 | B.24 | C.8 |
| 1.1625 | B.25 | C.8 |
| 1.1626 | B.26 | C.8 |
| 1.1627 | B.27 | C.8 |
| 1.1628 | B.28 | C.8 |
| 1.1629 | B.29 | C.8 |
| 1.1630 | B.30 | C.8 |
| 1.1631 | B.31 | C.8 |
| 1.1632 | B.32 | C.8 |
| 1.1633 | B.33 | C.8 |
| 1.1634 | B.34 | C.8 |
| 1.1635 | B.35 | C.8 |
| 1.1636 | B.36 | C.8 |
| 1.1637 | B.37 | C.8 |
| 1.1638 | B.38 | C.8 |
| 1.1639 | B.39 | C.8 |
| 1.1640 | B.40 | C.8 |
| 1.1641 | B.41 | C.8 |
| 1.1642 | B.42 | C.8 |
| 1.1643 | B.43 | C.8 |
| 1.1644 | B.44 | C.8 |
| 1.1645 | B.45 | C.8 |
| 1.1646 | B.46 | C.8 |
| 1.1647 | B.47 | C.8 |
| 1.1648 | B.48 | C.8 |
| 1.1649 | B.49 | C.8 |
| 1.1650 | B.50 | C.8 |
| 1.1651 | B.51 | C.8 |
| 1.1652 | B.52 | C.8 |
| 1.1653 | B.53 | C.8 |
| 1.1654 | B.54 | C.8 |
| 1.1655 | B.55 | C.8 |
| 1.1656 | B.56 | C.8 |
| 1.1657 | B.57 | C.8 |
| 1.1658 | B.58. | C.8 |
| 1.1659 | B.59 | C.8 |
| 1.1660 | B.60 | C.8 |
| 1.1661 | B.61 | C.8 |
| 1.1662 | B.62 | C.8 |
| 1.1663 | B.63 | C.8 |
| 1.1664 | B.64 | C.8 |
| 1.1665 | B.65 | C.8 |
| 1.1666 | B.66 | C.8 |
| 1.1667 | B.67 | C.8 |
| 1.1668 | B.68 | C.8 |
| 1.1669 | B.69 | C.8 |
| 1.1670 | B.70 | C.8 |
| 1.1671 | B.71 | C.8 |
| 1.1672 | B.72 | C.8 |
| 1.1673 | B.73 | C.8 |
| 1.1674 | B.74 | C.8 |
| 1.1675 | B.75 | C.8 |
| 1.1676 | B.76 | C.8 |
| 1.1677 | B.77 | C.8 |
| 1.1678 | B.78 | C.8 |
| 1.1679 | B.79 | C.8 |
| 1.1680 | B.80 | C.8 |
| 1.1681 | B.81 | C.8 |
| 1.1682 | B.82 | C.8 |
| 1.1683 | B.83 | C.8 |
| 1.1684 | B.84 | C.8 |
| 1.1685 | B.85 | C.8 |
| 1.1686 | B.86 | C.8 |
| 1.1687 | B.87 | C.8 |
| 1.1688 | B.88 | C.8 |
| 1.1689 | B.89 | C.8 |
| 1.1690 | B.90 | C.8 |
| 1.1691 | B.91 | C.8 |
| 1.1692 | B.92 | C.8 |
| 1.1693 | B.93 | C.8 |
| 1.1694 | B.94 | C.8 |
| 1.1695 | B.95 | C.8 |
| 1.1696 | B.96 | C.8 |
| 1.1697 | B.97 | C.8 |
| 1.1698 | B.98 | C.8 |
| 1.1699 | B.99 | C.8 |
| 1.1700 | B.100 | C.8 |
| 1.1701 | B.101 | C.8 |
| 1.1702 | B.102 | C.8 |
| 1.1703 | B.103 | C.8 |
| 1.1704 | B.104 | C.8 |
| 1.1705 | B.105 | C.8 |
| 1.1706 | B.106 | C.8 |
| 1.1707 | B.107 | C.8 |
| 1.1708 | B.108 | C.8 |
| 1.1709 | B.109 | C.8 |
| 1.1710 | B.110 | C.8 |
| 1.1711 | B.111 | C.8 |
| 1.1712 | B.112 | C.8 |
| 1.1713 | B.113 | C.8 |
| 1.1714 | B.114 | C.8 |
| 1.1715 | B.115 | C.8 |
| 1.1716 | B.116 | C.8 |
| 1.1717 | B.117 | C.8 |
| 1.1718 | B.118 | C.8 |
| 1.1719 | B.119 | C.8 |
| 1.1720 | B.120 | C.8 |
| 1.1721 | B.121 | C.8 |
| 1.1722 | B.122 | C.8 |
| 1.1723 | B.123 | C.8 |
| 1.1724 | B.124 | C.8 |
| 1.1725 | B.125 | C.8 |
| 1.1726 | B.126 | C.8 |
| 1.1727 | B.127 | C.8 |
| 1.1728 | B.128 | C.8 |
| 1.1729 | B.129 | C.8 |
| 1.1730 | B.130 | C.8 |
| 1.1731 | B.131 | C.8 |
| 1.1732 | B.132 | C.8 |
| 1.1733 | B.133 | C.8 |
| 1.1734 | B.134 | C.8 |
| 1.1735 | B.135 | C.8 |
| 1.1736 | B.136 | C.8 |
| 1.1737 | B.137 | C.8 |
| 1.1738 | B.138 | C.8 |
| 1.1739 | B.139 | C.8 |
| 1.1740 | B.140 | C.8 |
| 1.1741 | B.141 | C.8 |
| 1.1742 | B.142 | C.8 |
| 1.1743 | B.143 | C.8 |
| 1.1744 | B.144 | C.8 |
| 1.1745 | B.145 | C.8 |
| 1.1746 | B.146 | C.8 |
| 1.1747 | B.147 | C.8 |
| 1.1748 | B.148 | C.8 |
| 1.1749 | B.149 | C.8 |
| 1.1750 | B.150 | C.8 |
| 1.1751 | B.151 | C.8 |
| 1.1752 | B.152 | C.8 |
| 1.1753 | B.153 | C.8 |

TABLE 1-continued (compositions 1.1 to 1.3617):

| comp. no. | herbicide B | safener C |
|---|---|---|
| 1.1754 | B.154 | C.8 |
| 1.1755 | B.155 | C.8 |
| 1.1756 | B.156 | C.8 |
| 1.1757 | B.157 | C.8 |
| 1.1758 | B.158 | C.8 |
| 1.1759 | B.159 | C.8 |
| 1.1760 | B.160 | C.8 |
| 1.1761 | B.161 | C.8 |
| 1.1762 | B.162 | C.8 |
| 1.1763 | B.163 | C.8 |
| 1.1764 | B.164 | C.8 |
| 1.1765 | B.165 | C.8 |
| 1.1766 | B.166 | C.8 |
| 1.1767 | B.167 | C.8 |
| 1.1768 | B.168 | C.8 |
| 1.1769 | B.169 | C.8 |
| 1.1770 | B.170 | C.8 |
| 1.1771 | B.171 | C.8 |
| 1.1772 | B.172 | C.8 |
| 1.1773 | B.173 | C.8 |
| 1.1774 | B.174 | C.8 |
| 1.1775 | B.175 | C.8 |
| 1.1776 | B.176 | C.8 |
| 1.1777 | B.177 | C.8 |
| 1.1778 | B.178 | C.8 |
| 1.1779 | B.179 | C.8 |
| 1.1780 | B.180 | C.8 |
| 1.1781 | B.181 | C.8 |
| 1.1782 | B.182 | C.8 |
| 1.1783 | B.183 | C.8 |
| 1.1784 | B.184 | C.8 |
| 1.1785 | B.185 | C.8 |
| 1.1786 | B.186 | C.8 |
| 1.1787 | B.187 | C.8 |
| 1.1788 | B.188 | C.8 |
| 1.1789 | B.189 | C.8 |
| 1.1790 | B.190 | C.8 |
| 1.1791 | B.191 | C.8 |
| 1.1792 | B.192 | C.8 |
| 1.1793 | B.193 | C.8 |
| 1.1794 | B-194 | C.8 |
| 1.1795 | B-195 | C.8 |
| 1.1796 | B-196 | C.8 |
| 1.1797 | B-197 | C.8 |
| 1.1798 | B-198 | C.8 |
| 1.1799 | B-199 | C.8 |
| 1.1800 | B-200 | C.8 |
| 1.1801 | B.1 | C.9 |
| 1.1802 | B.2 | C.9 |
| 1.1803 | B.3 | C.9 |
| 1.1804 | B.4 | C.9 |
| 1.1805 | B.5 | C.9 |
| 1.1806 | B.6 | C.9 |
| 1.1807 | B.7 | C.9 |
| 1.1808 | B.8 | C.9 |
| 1.1809 | B.9 | C.9 |
| 1.1810 | B.10 | C.9 |
| 1.1811 | B.11 | C.9 |
| 1.1812 | B.12 | C.9 |
| 1.1813 | B.13 | C.9 |
| 1.1814 | B.14 | C.9 |
| 1.1815 | B.15 | C.9 |
| 1.1816 | B.16 | C.9 |
| 1.1817 | B.17 | C.9 |
| 1.1818 | B.18 | C.9 |
| 1.1819 | B.19 | C.9 |
| 1.1820 | B.20 | C.9 |
| 1.1821 | B.21 | C.9 |
| 1.1822 | B.22 | C.9 |
| 1.1823 | B.23 | C.9 |
| 1.1824 | B.24 | C.9 |
| 1.1825 | B.25 | C.9 |
| 1.1826 | B.26 | C.9 |
| 1.1827 | B.27 | C.9 |
| 1.1828 | B.28 | C.9 |
| 1.1829 | B.29 | C.9 |
| 1.1830 | B.30 | C.9 |
| 1.1831 | B.31 | C.9 |
| 1.1832 | B.32 | C.9 |
| 1.1833 | B.33 | C.9 |
| 1.1834 | B.34 | C.9 |
| 1.1835 | B.35 | C.9 |
| 1.1836 | B.36 | C.9 |
| 1.1837 | B.37 | C.9 |
| 1.1838 | B.38 | C.9 |
| 1.1839 | B.39 | C.9 |
| 1.1840 | B.40 | C.9 |
| 1.1841 | B.41 | C.9 |
| 1.1842 | B.42 | C.9 |
| 1.1843 | B.43 | C.9 |
| 1.1844 | B.44 | C.9 |
| 1.1845 | B.45 | C.9 |
| 1.1846 | B.46 | C.9 |
| 1.1847 | B.47 | C.9 |
| 1.1848 | B.48 | C.9 |
| 1.1849 | B.49 | C.9 |
| 1.1850 | B.50 | C.9 |
| 1.1851 | B.51 | C.9 |
| 1.1852 | B.52 | C.9 |
| 1.1853 | B.53 | C.9 |
| 1.1854 | B.54 | C.9 |
| 1.1855 | B.55 | C.9 |
| 1.1856 | B.56 | C.9 |
| 1.1857 | B.57 | C.9 |
| 1.1858 | B.58. | C.9 |
| 1.1859 | B.59 | C.9 |
| 1.1860 | B.60 | C.9 |
| 1.1861 | B.61 | C.9 |
| 1.1862 | B.62 | C.9 |
| 1.1863 | B.63 | C.9 |
| 1.1864 | B.64 | C.9 |
| 1.1865 | B.65 | C.9 |
| 1.1866 | B.66 | C.9 |
| 1.1867 | B.67 | C.9 |
| 1.1868 | B.68 | C.9 |
| 1.1869 | B.69 | C.9 |
| 1.1870 | B.70 | C.9 |
| 1.1871 | B.71 | C.9 |
| 1.1872 | B.72 | C.9 |
| 1.1873 | B.73 | C.9 |
| 1.1874 | B.74 | C.9 |
| 1.1875 | B.75 | C.9 |
| 1.1876 | B.76 | C.9 |
| 1.1877 | B.77 | C.9 |
| 1.1878 | B.78 | C.9 |
| 1.1879 | B.79 | C.9 |
| 1.1880 | B.80 | C.9 |
| 1.1881 | B.81 | C.9 |
| 1.1882 | B.82 | C.9 |
| 1.1883 | B.83 | C.9 |
| 1.1884 | B.84 | C.9 |
| 1.1885 | B.85 | C.9 |
| 1.1886 | B.86 | C.9 |
| 1.1887 | B.87 | C.9 |
| 1.1888 | B.88 | C.9 |
| 1.1889 | B.89 | C.9 |
| 1.1890 | B.90 | C.9 |
| 1.1891 | B.91 | C.9 |
| 1.1892 | B.92 | C.9 |
| 1.1893 | B.93 | C.9 |
| 1.1894 | B.94 | C.9 |
| 1.1895 | B.95 | C.9 |
| 1.1896 | B.96 | C.9 |
| 1.1897 | B.97 | C.9 |
| 1.1898 | B.98 | C.9 |
| 1.1899 | B.99 | C.9 |
| 1.1900 | B.100 | C.9 |
| 1.1901 | B.101 | C.9 |
| 1.1902 | B.102 | C.9 |
| 1.1903 | B.103 | C.9 |
| 1.1904 | B.104 | C.9 |
| 1.1905 | B.105 | C.9 |

TABLE 1-continued (compositions 1.1 to 1.3617):

| comp. no. | herbicide B | safener C |
|---|---|---|
| 1.1906 | B.106 | C.9 |
| 1.1907 | B.107 | C.9 |
| 1.1908 | B.108 | C.9 |
| 1.1909 | B.109 | C.9 |
| 1.1910 | B.110 | C.9 |
| 1.1911 | B.111 | C.9 |
| 1.1912 | B.112 | C.9 |
| 1.1913 | B.113 | C.9 |
| 1.1914 | B.114 | C.9 |
| 1.1915 | B.115 | C.9 |
| 1.1916 | B.116 | C.9 |
| 1.1917 | B.117 | C.9 |
| 1.1918 | B.118 | C.9 |
| 1.1919 | B.119 | C.9 |
| 1.1920 | B.120 | C.9 |
| 1.1921 | B.121 | C.9 |
| 1.1922 | B.122 | C.9 |
| 1.1923 | B.123 | C.9 |
| 1.1924 | B.124 | C.9 |
| 1.1925 | B.125 | C.9 |
| 1.1926 | B.126 | C.9 |
| 1.1927 | B.127 | C.9 |
| 1.1928 | B.128 | C.9 |
| 1.1929 | B.129 | C.9 |
| 1.1930 | B.130 | C.9 |
| 1.1931 | B.131 | C.9 |
| 1.1932 | B.132 | C.9 |
| 1.1933 | B.133 | C.9 |
| 1.1934 | B.134 | C.9 |
| 1.1935 | B.135 | C.9 |
| 1.1936 | B.136 | C.9 |
| 1.1937 | B.137 | C.9 |
| 1.1938 | B.138 | C.9 |
| 1.1939 | B.139 | C.9 |
| 1.1940 | B.140 | C.9 |
| 1.1941 | B.141 | C.9 |
| 1.1942 | B.142 | C.9 |
| 1.1943 | B.143 | C.9 |
| 1.1944 | B.144 | C.9 |
| 1.1945 | B.145 | C.9 |
| 1.1946 | B.146 | C.9 |
| 1.1947 | B.147 | C.9 |
| 1.1948 | B.148 | C.9 |
| 1.1949 | B.149 | C.9 |
| 1.1950 | B.150 | C.9 |
| 1.1951 | B.151 | C.9 |
| 1.1952 | B.152 | C.9 |
| 1.1953 | B.153 | C.9 |
| 1.1954 | B.154 | C.9 |
| 1.1955 | B.155 | C.9 |
| 1.1956 | B.156 | C.9 |
| 1.1957 | B.157 | C.9 |
| 1.1958 | B.158 | C.9 |
| 1.1959 | B.159 | C.9 |
| 1.1960 | B.160 | C.9 |
| 1.1961 | B.161 | C.9 |
| 1.1962 | B.162 | C.9 |
| 1.1963 | B.163 | C.9 |
| 1.1964 | B.164 | C.9 |
| 1.1965 | B.165 | C.9 |
| 1.1966 | B.166 | C.9 |
| 1.1967 | B.167 | C.9 |
| 1.1968 | B.168 | C.9 |
| 1.1969 | B.169 | C.9 |
| 1.1970 | B.170 | C.9 |
| 1.1971 | B.171 | C.9 |
| 1.1972 | B.172 | C.9 |
| 1.1973 | B.173 | C.9 |
| 1.1974 | B.174 | C.9 |
| 1.1975 | B.175 | C.9 |
| 1.1976 | B.176 | C.9 |
| 1.1977 | B.177 | C.9 |
| 1.1978 | B.178 | C.9 |
| 1.1979 | B.179 | C.9 |
| 1.1980 | B.180 | C.9 |
| 1.1981 | B.181 | C.9 |
| 1.1982 | B.182 | C.9 |
| 1.1983 | B.183 | C.9 |
| 1.1984 | B.184 | C.9 |
| 1.1985 | B.185 | C.9 |
| 1.1986 | B.186 | C.9 |
| 1.1987 | B.187 | C.9 |
| 1.1988 | B.188 | C.9 |
| 1.1989 | B.189 | C.9 |
| 1.1990 | B.190 | C.9 |
| 1.1991 | B.191 | C.9 |
| 1.1992 | B.192 | C.9 |
| 1.1993 | B.193 | C.9 |
| 1.1994 | B-194 | C.9 |
| 1.1995 | B-195 | C.9 |
| 1.1996 | B-196 | C.9 |
| 1.1997 | B-197 | C.9 |
| 1.1998 | B-198 | C.9 |
| 1.1999 | B-199 | C.9 |
| 1.2000 | B-200 | C.9 |
| 1.2001 | B.1 | C.10 |
| 1.2002 | B.2 | C.10 |
| 1.2003 | B.3 | C.10 |
| 1.2004 | B.4 | C.10 |
| 1.2005 | B.5 | C.10 |
| 1.2006 | B.6 | C.10 |
| 1.2007 | B.7 | C.10 |
| 1.2008 | B.8 | C.10 |
| 1.2009 | B.9 | C.10 |
| 1.2010 | B.10 | C.10 |
| 1.2011 | B.11 | C.10 |
| 1.2012 | B.12 | C.10 |
| 1.2013 | B.13 | C.10 |
| 1.2014 | B.14 | C.10 |
| 1.2015 | B.15 | C.10 |
| 1.2016 | B.16 | C.10 |
| 1.2017 | B.17 | C.10 |
| 1.2018 | B.18 | C.10 |
| 1.2019 | B.19 | C.10 |
| 1.2020 | B.20 | C.10 |
| 1.2021 | B.21 | C.10 |
| 1.2022 | B.22 | C.10 |
| 1.2023 | B.23 | C.10 |
| 1.2024 | B.24 | C.10 |
| 1.2025 | B.25 | C.10 |
| 1.2026 | B.26 | C.10 |
| 1.2027 | B.27 | C.10 |
| 1.2028 | B.28 | C.10 |
| 1.2029 | B.29 | C.10 |
| 1.2030 | B.30 | C.10 |
| 1.2031 | B.31 | C.10 |
| 1.2032 | B.32 | C.10 |
| 1.2033 | B.33 | C.10 |
| 1.2034 | B.34 | C.10 |
| 1.2035 | B.35 | C.10 |
| 1.2036 | B.36 | C.10 |
| 1.2037 | B.37 | C.10 |
| 1.2038 | B.38 | C.10 |
| 1.2039 | B.39 | C.10 |
| 1.2040 | B.40 | C.10 |
| 1.2041 | B.41 | C.10 |
| 1.2042 | B.42 | C.10 |
| 1.2043 | B.43 | C.10 |
| 1.2044 | B.44 | C.10 |
| 1.2045 | B.45 | C.10 |
| 1.2046 | B.46 | C.10 |
| 1.2047 | B.47 | C.10 |
| 1.2048 | B.48 | C.10 |
| 1.2049 | B.49 | C.10 |
| 1.2050 | B.50 | C.10 |
| 1.2051 | B.51 | C.10 |
| 1.2052 | B.52 | C.10 |
| 1.2053 | B.53 | C.10 |
| 1.2054 | B.54 | C.10 |
| 1.2055 | B.55 | C.10 |
| 1.2056 | B.56 | C.10 |
| 1.2057 | B.57 | C.10 |

TABLE 1-continued (compositions 1.1 to 1.3617):

| comp. no. | herbicide B | safener C |
|---|---|---|
| 1.2058 | B.58. | C.10 |
| 1.2059 | B.59 | C.10 |
| 1.2060 | B.60 | C.10 |
| 1.2061 | B.61 | C.10 |
| 1.2062 | B.62 | C.10 |
| 1.2063 | B.63 | C.10 |
| 1.2064 | B.64 | C.10 |
| 1.2065 | B.65 | C.10 |
| 1.2066 | B.66 | C.10 |
| 1.2067 | B.67 | C.10 |
| 1.2068 | B.68 | C.10 |
| 1.2069 | B.69 | C.10 |
| 1.2070 | B.70 | C.10 |
| 1.2071 | B.71 | C.10 |
| 1.2072 | B.72 | C.10 |
| 1.2073 | B.73 | C.10 |
| 1.2074 | B.74 | C.10 |
| 1.2075 | B.75 | C.10 |
| 1.2076 | B.76 | C.10 |
| 1.2077 | B.77 | C.10 |
| 1.2078 | B.78 | C.10 |
| 1.2079 | B.79 | C.10 |
| 1.2080 | B.80 | C.10 |
| 1.2081 | B.81 | C.10 |
| 1.2082 | B.82 | C.10 |
| 1.2083 | B.83 | C.10 |
| 1.2084 | B.84 | C.10 |
| 1.2085 | B.85 | C.10 |
| 1.2086 | B.86 | C.10 |
| 1.2087 | B.87 | C.10 |
| 1.2088 | B.88 | C.10 |
| 1.2089 | B.89 | C.10 |
| 1.2090 | B.90 | C.10 |
| 1.2091 | B.91 | C.10 |
| 1.2092 | B.92 | C.10 |
| 1.2093 | B.93 | C.10 |
| 1.2094 | B.94 | C.10 |
| 1.2095 | B.95 | C.10 |
| 1.2096 | B.96 | C.10 |
| 1.2097 | B.97 | C.10 |
| 1.2098 | B.98 | C.10 |
| 1.2099 | B.99 | C.10 |
| 1.2100 | B.100 | C.10 |
| 1.2101 | B.101 | C.10 |
| 1.2102 | B.102 | C.10 |
| 1.2103 | B.103 | C.10 |
| 1.2104 | B.104 | C.10 |
| 1.2105 | B.105 | C.10 |
| 1.2106 | B.106 | C.10 |
| 1.2107 | B.107 | C.10 |
| 1.2108 | B.108 | C.10 |
| 1.2109 | B.109 | C.10 |
| 1.2110 | B.110 | C.10 |
| 1.2111 | B.111 | C.10 |
| 1.2112 | B.112 | C.10 |
| 1.2113 | B.113 | C.10 |
| 1.2114 | B.114 | C.10 |
| 1.2115 | B.115 | C.10 |
| 1.2116 | B.116 | C.10 |
| 1.2117 | B.117 | C.10 |
| 1.2118 | B.118 | C.10 |
| 1.2119 | B.119 | C.10 |
| 1.2120 | B.120 | C.10 |
| 1.2121 | B.121 | C.10 |
| 1.2122 | B.122 | C.10 |
| 1.2123 | B.123 | C.10 |
| 1.2124 | B.124 | C.10 |
| 1.2125 | B.125 | C.10 |
| 1.2126 | B.126 | C.10 |
| 1.2127 | B.127 | C.10 |
| 1.2128 | B.128 | C.10 |
| 1.2129 | B.129 | C.10 |
| 1.2130 | B.130 | C.10 |
| 1.2131 | B.131 | C.10 |
| 1.2132 | B.132 | C.10 |
| 1.2133 | B.133 | C.10 |
| 1.2134 | B.134 | C.10 |
| 1.2135 | B.135 | C.10 |
| 1.2136 | B.136 | C.10 |
| 1.2137 | B.137 | C.10 |
| 1.2138 | B.138 | C.10 |
| 1.2139 | B.139 | C.10 |
| 1.2140 | B.140 | C.10 |
| 1.2141 | B.141 | C.10 |
| 1.2142 | B.142 | C.10 |
| 1.2143 | B.143 | C.10 |
| 1.2144 | B.144 | C.10 |
| 1.2145 | B.145 | C.10 |
| 1.2146 | B.146 | C.10 |
| 1.2147 | B.147 | C.10 |
| 1.2148 | B.148 | C.10 |
| 1.2149 | B.149 | C.10 |
| 1.2150 | B.150 | C.10 |
| 1.2151 | B.151 | C.10 |
| 1.2152 | B.152 | C.10 |
| 1.2153 | B.153 | C.10 |
| 1.2154 | B.154 | C.10 |
| 1.2155 | B.155 | C.10 |
| 1.2156 | B.156 | C.10 |
| 1.2157 | B.157 | C.10 |
| 1.2158 | B.158 | C.10 |
| 1.2159 | B.159 | C.10 |
| 1.2160 | B.160 | C.10 |
| 1.2161 | B.161 | C.10 |
| 1.2162 | B.162 | C.10 |
| 1.2163 | B.163 | C.10 |
| 1.2164 | B.164 | C.10 |
| 1.2165 | B.165 | C.10 |
| 1.2166 | B.166 | C.10 |
| 1.2167 | B.167 | C.10 |
| 1.2168 | B.168 | C.10 |
| 1.2169 | B.169 | C.10 |
| 1.2170 | B.170 | C.10 |
| 1.2171 | B.171 | C.10 |
| 1.2172 | B.172 | C.10 |
| 1.2173 | B.173 | C.10 |
| 1.2174 | B.174 | C.10 |
| 1.2175 | B.175 | C.10 |
| 1.2176 | B.176 | C.10 |
| 1.2177 | B.177 | C.10 |
| 1.2178 | B.178 | C.10 |
| 1.2179 | B.179 | C.10 |
| 1.2180 | B.180 | C.10 |
| 1.2181 | B.181 | C.10 |
| 1.2182 | TABLE.182 | C.10 |
| 1.2183 | B.183 | C.10 |
| 1.2184 | B.184 | C.10 |
| 1.2185 | B.185 | C.10 |
| 1.2186 | B.186 | C.10 |
| 1.2187 | B.187 | C.10 |
| 1.2188 | B.188 | C.10 |
| 1.2189 | B.189 | C.10 |
| 1.2190 | B.190 | C.10 |
| 1.2191 | B.191 | C.10 |
| 1.2192 | B.192 | C.10 |
| 1.2193 | B.193 | C.10 |
| 1.2194 | B-194 | C.10 |
| 1.2195 | B-195 | C.10 |
| 1.2196 | B-196 | C.10 |
| 1.2197 | B-197 | C.10 |
| 1.2198 | B-198 | C.10 |
| 1.2199 | B-199 | C.10 |
| 1.2200 | B-200 | C.10 |
| 1.2201 | B.1 | C.11 |
| 1.2202 | B.2 | C.11 |
| 1.2203 | B.3 | C.11 |
| 1.2204 | B.4 | C.11 |
| 1.2205 | B.5 | C.11 |
| 1.2206 | B.6 | C.11 |
| 1.2207 | B.7 | C.11 |
| 1.2208 | B.8 | C.11 |
| 1.2209 | B.9 | C.11 |

TABLE 1-continued (compositions 1.1 to 1.3617):

| comp. no. | herbicide B | safener C |
|---|---|---|
| 1.2210 | B.10 | C.11 |
| 1.2211 | B.11 | C.11 |
| 1.2212 | B.12 | C.11 |
| 1.2213 | B.13 | C.11 |
| 1.2214 | B.14 | C.11 |
| 1.2215 | B.15 | C.11 |
| 1.2216 | B.16 | C.11 |
| 1.2217 | B.17 | C.11 |
| 1.2218 | B.18 | C.11 |
| 1.2219 | B.19 | C.11 |
| 1.2220 | B.20 | C.11 |
| 1.2221 | B.21 | C.11 |
| 1.2222 | B.22 | C.11 |
| 1.2223 | B.23 | C.11 |
| 1.2224 | B.24 | C.11 |
| 1.2225 | B.25 | C.11 |
| 1.2226 | B.26 | C.11 |
| 1.2227 | B.27 | C.11 |
| 1.2228 | B.28 | C.11 |
| 1.2229 | B.29 | C.11 |
| 1.2230 | B.30 | C.11 |
| 1.2231 | B.31 | C.11 |
| 1.2232 | B.32 | C.11 |
| 1.2233 | B.33 | C.11 |
| 1.2234 | B.34 | C.11 |
| 1.2235 | B.35 | C.11 |
| 1.2236 | B.36 | C.11 |
| 1.2237 | B.37 | C.11 |
| 1.2238 | B.38 | C.11 |
| 1.2239 | B.39 | C.11 |
| 1.2240 | B.40 | C.11 |
| 1.2241 | B.41 | C.11 |
| 1.2242 | B.42 | C.11 |
| 1.2243 | B.43 | C.11 |
| 1.2244 | B.44 | C.11 |
| 1.2245 | B.45 | C.11 |
| 1.2246 | B.46 | C.11 |
| 1.2247 | B.47 | C.11 |
| 1.2248 | B.48 | C.11 |
| 1.2249 | B.49 | C.11 |
| 1.2250 | B.50 | C.11 |
| 1.2251 | B.51 | C.11 |
| 1.2252 | B.52 | C.11 |
| 1.2253 | B.53 | C.11 |
| 1.2254 | B.54 | C.11 |
| 1.2255 | B.55 | C.11 |
| 1.2256 | B.56 | C.11 |
| 1.2257 | B.57 | C.11 |
| 1.2258 | B.58. | C.11 |
| 1.2259 | B.59 | C.11 |
| 1.2260 | B.60 | C.11 |
| 1.2261 | B.61 | C.11 |
| 1.2262 | B.62 | C.11 |
| 1.2263 | B.63 | C.11 |
| 1.2264 | B.64 | C.11 |
| 1.2265 | B.65 | C.11 |
| 1.2266 | B.66 | C.11 |
| 1.2267 | B.67 | C.11 |
| 1.2268 | B.68 | C.11 |
| 1.2269 | B.69 | C.11 |
| 1.2270 | B.70 | C.11 |
| 1.2271 | B.71 | C.11 |
| 1.2272 | B.72 | C.11 |
| 1.2273 | B.73 | C.11 |
| 1.2274 | B.74 | C.11 |
| 1.2275 | B.75 | C.11 |
| 1.2276 | B.76 | C.11 |
| 1.2277 | B.77 | C.11 |
| 1.2278 | B.78 | C.11 |
| 1.2279 | B.79 | C.11 |
| 1.2280 | B.80 | C.11 |
| 1.2281 | B.81 | C.11 |
| 1.2282 | B.82 | C.11 |
| 1.2283 | B.83 | C.11 |
| 1.2284 | B.84 | C.11 |
| 1.2285 | B.85 | C.11 |
| 1.2286 | B.86 | C.11 |
| 1.2287 | B.87 | C.11 |
| 1.2288 | B.88 | C.11 |
| 1.2289 | B.89 | C.11 |
| 1.2290 | B.90 | C.11 |
| 1.2291 | B.91 | C.11 |
| 1.2292 | B.92 | C.11 |
| 1.2293 | B.93 | C.11 |
| 1.2294 | B.94 | C.11 |
| 1.2295 | B.95 | C.11 |
| 1.2296 | B.96 | C.11 |
| 1.2297 | B.97 | C.11 |
| 1.2298 | B.98 | C.11 |
| 1.2299 | B.99 | C.11 |
| 1.2300 | B.100 | C.11 |
| 1.2301 | B.101 | C.11 |
| 1.2302 | B.102 | C.11 |
| 1.2303 | B.103 | C.11 |
| 1.2304 | B.104 | C.11 |
| 1.2305 | B.105 | C.11 |
| 1.2306 | B.106 | C.11 |
| 1.2307 | B.107 | C.11 |
| 1.2308 | B.108 | C.11 |
| 1.2309 | B.109 | C.11 |
| 1.2310 | B.110 | C.11 |
| 1.2311 | B.111 | C.11 |
| 1.2312 | B.112 | C.11 |
| 1.2313 | B.113 | C.11 |
| 1.2314 | B.114 | C.11 |
| 1.2315 | B.115 | C.11 |
| 1.2316 | B.116 | C.11 |
| 1.2317 | B.117 | C.11 |
| 1.2318 | B.118 | C.11 |
| 1.2319 | B.119 | C.11 |
| 1.2320 | B.120 | C.11 |
| 1.2321 | B.121 | C.11 |
| 1.2322 | B.122 | C.11 |
| 1.2323 | B.123 | C.11 |
| 1.2324 | B.124 | C.11 |
| 1.2325 | B.125 | C.11 |
| 1.2326 | B.126 | C.11 |
| 1.2327 | B.127 | C.11 |
| 1.2328 | B.128 | C.11 |
| 1.2329 | B.129 | C.11 |
| 1.2330 | B.130 | C.11 |
| 1.2331 | B.131 | C.11 |
| 1.2332 | B.132 | C.11 |
| 1.2333 | B.133 | C.11 |
| 1.2334 | B.134 | C.11 |
| 1.2335 | B.135 | C.11 |
| 1.2336 | B.136 | C.11 |
| 1.2337 | B.137 | C.11 |
| 1.2338 | B.138 | C.11 |
| 1.2339 | B.139 | C.11 |
| 1.2340 | B.140 | C.11 |
| 1.2341 | B.141 | C.11 |
| 1.2342 | B.142 | C.11 |
| 1.2343 | B.143 | C.11 |
| 1.2344 | B.144 | C.11 |
| 1.2345 | B.145 | C.11 |
| 1.2346 | B.146 | C.11 |
| 1.2347 | B.147 | C.11 |
| 1.2348 | B.148 | C.11 |
| 1.2349 | B.149 | C.11 |
| 1.2350 | B.150 | C.11 |
| 1.2351 | B.151 | C.11 |
| 1.2352 | B.152 | C.11 |
| 1.2353 | B.153 | C.11 |
| 1.2354 | B.154 | C.11 |
| 1.2355 | B.155 | C.11 |
| 1.2356 | B.156 | C.11 |
| 1.2357 | B.157 | C.11 |
| 1.2358 | B.158 | C.11 |
| 1.2359 | B.159 | C.11 |
| 1.2360 | B.160 | C.11 |
| 1.2361 | B.161 | C.11 |

TABLE 1-continued (compositions 1.1 to 1.3617):

| comp. no. | herbicide B | safener C |
|---|---|---|
| 1.2362 | B.162 | C.11 |
| 1.2363 | B.163 | C.11 |
| 1.2364 | B.164 | C.11 |
| 1.2365 | B.165 | C.11 |
| 1.2366 | B.166 | C.11 |
| 1.2367 | B.167 | C.11 |
| 1.2368 | B.168 | C.11 |
| 1.2369 | B.169 | C.11 |
| 1.2370 | B.170 | C.11 |
| 1.2371 | B.171 | C.11 |
| 1.2372 | B.172 | C.11 |
| 1.2373 | B.173 | C.11 |
| 1.2374 | B.174 | C.11 |
| 1.2375 | B.175 | C.11 |
| 1.2376 | B.176 | C.11 |
| 1.2377 | B.177 | C.11 |
| 1.2378 | B.178 | C.11 |
| 1.2379 | B.179 | C.11 |
| 1.2380 | B.180 | C.11 |
| 1.2381 | B.181 | C.11 |
| 1.2382 | B.182 | C.11 |
| 1.2383 | B.183 | C.11 |
| 1.2384 | B.184 | C.11 |
| 1.2385 | B.185 | C.11 |
| 1.2386 | B.186 | C.11 |
| 1.2387 | B.187 | C.11 |
| 1.2388 | B.188 | C.11 |
| 1.2389 | B.189 | C.11 |
| 1.2390 | B.190 | C.11 |
| 1.2391 | B.191 | C.11 |
| 1.2392 | B.192 | C.11 |
| 1.2393 | B.193 | C.11 |
| 1.2394 | B-194 | C.11 |
| 1.2395 | B-195 | C.11 |
| 1.2396 | B-196 | C.11 |
| 1.2397 | B-197 | C.11 |
| 1.2398 | B-198 | C.11 |
| 1.2399 | B-199 | C.11 |
| 1.2400 | B-200 | C.11 |
| 1.2401 | B.1 | C.12 |
| 1.2402 | B.2 | C.12 |
| 1.2403 | B.3 | C.12 |
| 1.2404 | B.4 | C.12 |
| 1.2405 | B.5 | C.12 |
| 1.2406 | B.6 | C.12 |
| 1.2407 | B.7 | C.12 |
| 1.2408 | B.8 | C.12 |
| 1.2409 | B.9 | C.12 |
| 1.2410 | B.10 | C.12 |
| 1.2411 | B.11 | C.12 |
| 1.2412 | B.12 | C.12 |
| 1.2413 | B.13 | C.12 |
| 1.2414 | B.14 | C.12 |
| 1.2415 | B.15 | C.12 |
| 1.2416 | B.16 | C.12 |
| 1.2417 | B.17 | C.12 |
| 1.2418 | B.18 | C.12 |
| 1.2419 | B.19 | C.12 |
| 1.2420 | B.20 | C.12 |
| 1.2421 | B.21 | C.12 |
| 1.2422 | B.22 | C.12 |
| 1.2423 | B.23 | C.12 |
| 1.2424 | B.24 | C.12 |
| 1.2425 | B.25 | C.12 |
| 1.2426 | B.26 | C.12 |
| 1.2427 | B.27 | C.12 |
| 1.2428 | B.28 | C.12 |
| 1.2429 | B.29 | C.12 |
| 1.2430 | B.30 | C.12 |
| 1.2431 | B.31 | C.12 |
| 1.2432 | B.32 | C.12 |
| 1.2433 | B.33 | C.12 |
| 1.2434 | B.34 | C.12 |
| 1.2435 | B.35 | C.12 |
| 1.2436 | B.36 | C.12 |
| 1.2437 | B.37 | C.12 |
| 1.2438 | B.38 | C.12 |
| 1.2439 | B.39 | C.12 |
| 1.2440 | B.40 | C.12 |
| 1.2441 | B.41 | C.12 |
| 1.2442 | B.42 | C.12 |
| 1.2443 | B.43 | C.12 |
| 1.2444 | B.44 | C.12 |
| 1.2445 | B.45 | C.12 |
| 1.2446 | B.46 | C.12 |
| 1.2447 | B.47 | C.12 |
| 1.2448 | B.48 | C.12 |
| 1.2449 | B.49 | C.12 |
| 1.2450 | B.50 | C.12 |
| 1.2451 | B.51 | C.12 |
| 1.2452 | B.52 | C.12 |
| 1.2453 | B.53 | C.12 |
| 1.2454 | B.54 | C.12 |
| 1.2455 | B.55 | C.12 |
| 1.2456 | B.56 | C.12 |
| 1.2457 | B.57 | C.12 |
| 1.2458 | B.58. | C.12 |
| 1.2459 | B.59 | C.12 |
| 1.2460 | B.60 | C.12 |
| 1.2461 | B.61 | C.12 |
| 1.2462 | B.62 | C.12 |
| 1.2463 | B.63 | C.12 |
| 1.2464 | B.64 | C.12 |
| 1.2465 | B.65 | C.12 |
| 1.2466 | B.66 | C.12 |
| 1.2467 | B.67 | C.12 |
| 1.2468 | B.68 | C.12 |
| 1.2469 | B.69 | C.12 |
| 1.2470 | B.70 | C.12 |
| 1.2471 | B.71 | C.12 |
| 1.2472 | B.72 | C.12 |
| 1.2473 | B.73 | C.12 |
| 1.2474 | B.74 | C.12 |
| 1.2475 | B.75 | C.12 |
| 1.2476 | B.76 | C.12 |
| 1.2477 | B.77 | C.12 |
| 1.2478 | B.78 | C.12 |
| 1.2479 | B.79 | C.12 |
| 1.2480 | B.80 | C.12 |
| 1.2481 | B.81 | C.12 |
| 1.2482 | B.82 | C.12 |
| 1.2483 | B.83 | C.12 |
| 1.2484 | B.84 | C.12 |
| 1.2485 | B.85 | C.12 |
| 1.2486 | B.86 | C.12 |
| 1.2487 | B.87 | C.12 |
| 1.2488 | B.88 | C.12 |
| 1.2489 | B.89 | C.12 |
| 1.2490 | B.90 | C.12 |
| 1.2491 | B.91 | C.12 |
| 1.2492 | B.92 | C.12 |
| 1.2493 | B.93 | C.12 |
| 1.2494 | B.94 | C.12 |
| 1.2495 | B.95 | C.12 |
| 1.2496 | B.96 | C.12 |
| 1.2497 | B.97 | C.12 |
| 1.2498 | B.98 | C.12 |
| 1.2499 | B.99 | C.12 |
| 1.2500 | B.100 | C.12 |
| 1.2501 | B.101 | C.12 |
| 1.2502 | B.102 | C.12 |
| 1.2503 | B.103 | C.12 |
| 1.2504 | B.104 | C.12 |
| 1.2505 | B.105 | C.12 |
| 1.2506 | B.106 | C.12 |
| 1.2507 | B.107 | C.12 |
| 1.2508 | B.108 | C.12 |
| 1.2509 | B.109 | C.12 |
| 1.2510 | B.110 | C.12 |
| 1.2511 | B.111 | C.12 |
| 1.2512 | B.112 | C.12 |
| 1.2513 | B.113 | C.12 |

TABLE 1-continued (compositions 1.1 to 1.3617):

| comp. no. | herbicide B | safener C |
|---|---|---|
| 1.2514 | B.114 | C.12 |
| 1.2515 | B.115 | C.12 |
| 1.2516 | B.116 | C.12 |
| 1.2517 | B.117 | C.12 |
| 1.2518 | B.118 | C.12 |
| 1.2519 | B.119 | C.12 |
| 1.2520 | B.120 | C.12 |
| 1.2521 | B.121 | C.12 |
| 1.2522 | B.122 | C.12 |
| 1.2523 | B.123 | C.12 |
| 1.2524 | B.124 | C.12 |
| 1.2525 | B.125 | C.12 |
| 1.2526 | B.126 | C.12 |
| 1.2527 | B.127 | C.12 |
| 1.2528 | B.128 | C.12 |
| 1.2529 | B.129 | C.12 |
| 1.2530 | B.130 | C.12 |
| 1.2531 | B.131 | C.12 |
| 1.2532 | B.132 | C.12 |
| 1.2533 | B.133 | C.12 |
| 1.2534 | B.134 | C.12 |
| 1.2535 | B.135 | C.12 |
| 1.2536 | B.136 | C.12 |
| 1.2537 | B.137 | C.12 |
| 1.2538 | B.138 | C.12 |
| 1.2539 | B.139 | C.12 |
| 1.2540 | B.140 | C.12 |
| 1.2541 | B.141 | C.12 |
| 1.2542 | B.142 | C.12 |
| 1.2543 | B.143 | C.12 |
| 1.2544 | B.144 | C.12 |
| 1.2545 | B.145 | C.12 |
| 1.2546 | B.146 | C.12 |
| 1.2547 | B.147 | C.12 |
| 1.2548 | B.148 | C.12 |
| 1.2549 | B.149 | C.12 |
| 1.2550 | B.150 | C.12 |
| 1.2551 | B.151 | C.12 |
| 1.2552 | B.152 | C.12 |
| 1.2553 | B.153 | C.12 |
| 1.2554 | B.154 | C.12 |
| 1.2555 | B.155 | C.12 |
| 1.2556 | B.156 | C.12 |
| 1.2557 | B.157 | C.12 |
| 1.2558 | B.158 | C.12 |
| 1.2559 | B.159 | C.12 |
| 1.2560 | B.160 | C.12 |
| 1.2561 | B.161 | C.12 |
| 1.2562 | B.162 | C.12 |
| 1.2563 | B.163 | C.12 |
| 1.2564 | B.164 | C.12 |
| 1.2565 | B.165 | C.12 |
| 1.2566 | B.166 | C.12 |
| 1.2567 | B.167 | C.12 |
| 1.2568 | B.168 | C.12 |
| 1.2569 | B.169 | C.12 |
| 1.2570 | B.170 | C.12 |
| 1.2571 | B.171 | C.12 |
| 1.2572 | B.172 | C.12 |
| 1.2573 | B.173 | C.12 |
| 1.2574 | B.174 | C.12 |
| 1.2575 | B.175 | C.12 |
| 1.2576 | B.176 | C.12 |
| 1.2577 | B.177 | C.12 |
| 1.2578 | B.178 | C.12 |
| 1.2579 | B.179 | C.12 |
| 1.2580 | B.180 | C.12 |
| 1.2581 | B.181 | C.12 |
| 1.2582 | B.182 | C.12 |
| 1.2583 | B.183 | C.12 |
| 1.2584 | B.184 | C.12 |
| 1.2585 | B.185 | C.12 |
| 1.2586 | B.186 | C.12 |
| 1.2587 | B.187 | C.12 |
| 1.2588 | B.188 | C.12 |
| 1.2589 | B.189 | C.12 |
| 1.2590 | B.190 | C.12 |
| 1.2591 | B.191 | C.12 |
| 1.2592 | B.192 | C.12 |
| 1.2593 | B.193 | C.12 |
| 1.2594 | B-194 | C.12 |
| 1.2595 | B-195 | C.12 |
| 1.2596 | B-196 | C.12 |
| 1.2597 | B-197 | C.12 |
| 1.2598 | B-198 | C.12 |
| 1.2599 | B-199 | C.12 |
| 1.2600 | B-200 | C.12 |
| 1.2601 | B.1 | C.13 |
| 1.2602 | B.2 | C.13 |
| 1.2603 | B.3 | C.13 |
| 1.2604 | B.4 | C.13 |
| 1.2605 | B.5 | C.13 |
| 1.2606 | B.6 | C.13 |
| 1.2607 | B.7 | C.13 |
| 1.2608 | B.8 | C.13 |
| 1.2609 | B.9 | C.13 |
| 1.2610 | B.10 | C.13 |
| 1.2611 | B.11 | C.13 |
| 1.2612 | B.12 | C.13 |
| 1.2613 | B.13 | C.13 |
| 1.2614 | B.14 | C.13 |
| 1.2615 | B.15 | C.13 |
| 1.2616 | B.16 | C.13 |
| 1.2617 | B.17 | C.13 |
| 1.2618 | B.18 | C.13 |
| 1.2619 | B.19 | C.13 |
| 1.2620 | B.20 | C.13 |
| 1.2621 | B.21 | C.13 |
| 1.2622 | B.22 | C.13 |
| 1.2623 | B.23 | C.13 |
| 1.2624 | B.24 | C.13 |
| 1.2625 | B.25 | C.13 |
| 1.2626 | B.26 | C.13 |
| 1.2627 | B.27 | C.13 |
| 1.2628 | B.28 | C.13 |
| 1.2629 | B.29 | C.13 |
| 1.2630 | B.30 | C.13 |
| 1.2631 | B.31 | C.13 |
| 1.2632 | B.32 | C.13 |
| 1.2633 | B.33 | C.13 |
| 1.2634 | B.34 | C.13 |
| 1.2635 | B.35 | C.13 |
| 1.2636 | B.36 | C.13 |
| 1.2637 | B.37 | C.13 |
| 1.2638 | B.38 | C.13 |
| 1.2639 | B.39 | C.13 |
| 1.2640 | B.40 | C.13 |
| 1.2641 | B.41 | C.13 |
| 1.2642 | B.42 | C.13 |
| 1.2643 | B.43 | C.13 |
| 1.2644 | B.44 | C.13 |
| 1.2645 | B.45 | C.13 |
| 1.2646 | B.46 | C.13 |
| 1.2647 | B.47 | C.13 |
| 1.2648 | B.48 | C.13 |
| 1.2649 | B.49 | C.13 |
| 1.2650 | B.50 | C.13 |
| 1.2651 | B.51 | C.13 |
| 1.2652 | B.52 | C.13 |
| 1.2653 | B.53 | C.13 |
| 1.2654 | B.54 | C.13 |
| 1.2655 | B.55 | C.13 |
| 1.2656 | B.56 | C.13 |
| 1.2657 | B.57 | C.13 |
| 1.2658 | B.58. | C.13 |
| 1.2659 | B.59 | C.13 |
| 1.2660 | B.60 | C.13 |
| 1.2661 | B.61 | C.13 |
| 1.2662 | B.62 | C.13 |
| 1.2663 | B.63 | C.13 |
| 1.2664 | B.64 | C.13 |
| 1.2665 | B.65 | C.13 |

TABLE 1-continued (compositions 1.1 to 1.3617):

| comp. no. | herbicide B | safener C |
|---|---|---|
| 1.2666 | B.66 | C.13 |
| 1.2667 | B.67 | C.13 |
| 1.2668 | B.68 | C.13 |
| 1.2669 | B.69 | C.13 |
| 1.2670 | B.70 | C.13 |
| 1.2671 | B.71 | C.13 |
| 1.2672 | B.72 | C.13 |
| 1.2673 | B.73 | C.13 |
| 1.2674 | B.74 | C.13 |
| 1.2675 | B.75 | C.13 |
| 1.2676 | B.76 | C.13 |
| 1.2677 | B.77 | C.13 |
| 1.2678 | B.78 | C.13 |
| 1.2679 | B.79 | C.13 |
| 1.2680 | B.80 | C.13 |
| 1.2681 | B.81 | C.13 |
| 1.2682 | B.82 | C.13 |
| 1.2683 | B.83 | C.13 |
| 1.2684 | B.84 | C.13 |
| 1.2685 | B.85 | C.13 |
| 1.2686 | B.86 | C.13 |
| 1.2687 | B.87 | C.13 |
| 1.2688 | B.88 | C.13 |
| 1.2689 | B.89 | C.13 |
| 1.2690 | B.90 | C.13 |
| 1.2691 | B.91 | C.13 |
| 1.2692 | B.92 | C.13 |
| 1.2693 | B.93 | C.13 |
| 1.2694 | B.94 | C.13 |
| 1.2695 | B.95 | C.13 |
| 1.2696 | B.96 | C.13 |
| 1.2697 | B.97 | C.13 |
| 1.2698 | B.98 | C.13 |
| 1.2699 | B.99 | C.13 |
| 1.2700 | B.100 | C.13 |
| 1.2701 | B.101 | C.13 |
| 1.2702 | B.102 | C.13 |
| 1.2703 | B.103 | C.13 |
| 1.2704 | B.104 | C.13 |
| 1.2705 | B.105 | C.13 |
| 1.2706 | B.106 | C.13 |
| 1.2707 | B.107 | C.13 |
| 1.2708 | B.108 | C.13 |
| 1.2709 | B.109 | C.13 |
| 1.2710 | B.110 | C.13 |
| 1.2711 | B.111 | C.13 |
| 1.2712 | B.112 | C.13 |
| 1.2713 | B.113 | C.13 |
| 1.2714 | B.114 | C.13 |
| 1.2715 | B.115 | C.13 |
| 1.2716 | B.116 | C.13 |
| 1.2717 | B.117 | C.13 |
| 1.2718 | B.118 | C.13 |
| 1.2719 | B.119 | C.13 |
| 1.2720 | B.120 | C.13 |
| 1.2721 | B.121 | C.13 |
| 1.2722 | B.122 | C.13 |
| 1.2723 | B.123 | C.13 |
| 1.2724 | B.124 | C.13 |
| 1.2725 | B.125 | C.13 |
| 1.2726 | B.126 | C.13 |
| 1.2727 | B.127 | C.13 |
| 1.2728 | B.128 | C.13 |
| 1.2729 | B.129 | C.13 |
| 1.2730 | B.130 | C.13 |
| 1.2731 | B.131 | C.13 |
| 1.2732 | B.132 | C.13 |
| 1.2733 | B.133 | C.13 |
| 1.2734 | B.134 | C.13 |
| 1.2735 | B.135 | C.13 |
| 1.2736 | B.136 | C.13 |
| 1.2737 | B.137 | C.13 |
| 1.2738 | B.138 | C.13 |
| 1.2739 | B.139 | C.13 |
| 1.2740 | B.140 | C.13 |
| 1.2741 | B.141 | C.13 |
| 1.2742 | B.142 | C.13 |
| 1.2743 | B.143 | C.13 |
| 1.2744 | B.144 | C.13 |
| 1.2745 | B.145 | C.13 |
| 1.2746 | B.146 | C.13 |
| 1.2747 | B.147 | C.13 |
| 1.2748 | B.148 | C.13 |
| 1.2749 | B.149 | C.13 |
| 1.2750 | B.150 | C.13 |
| 1.2751 | B.151 | C.13 |
| 1.2752 | B.152 | C.13 |
| 1.2753 | B.153 | C.13 |
| 1.2754 | B.154 | C.13 |
| 1.2755 | B.155 | C.13 |
| 1.2756 | B.156 | C.13 |
| 1.2757 | B.157 | C.13 |
| 1.2758 | B.158 | C.13 |
| 1.2759 | B.159 | C.13 |
| 1.2760 | B.160 | C.13 |
| 1.2761 | B.161 | C.13 |
| 1.2762 | B.162 | C.13 |
| 1.2763 | B.163 | C.13 |
| 1.2764 | B.164 | C.13 |
| 1.2765 | B.165 | C.13 |
| 1.2766 | B.166 | C.13 |
| 1.2767 | B.167 | C.13 |
| 1.2768 | B.168 | C.13 |
| 1.2769 | B.169 | C.13 |
| 1.2770 | B.170 | C.13 |
| 1.2771 | B.171 | C.13 |
| 1.2772 | B.172 | C.13 |
| 1.2773 | B.173 | C.13 |
| 1.2774 | B.174 | C.13 |
| 1.2775 | B.175 | C.13 |
| 1.2776 | B.176 | C.13 |
| 1.2777 | B.177 | C.13 |
| 1.2778 | B.178 | C.13 |
| 1.2779 | B.179 | C.13 |
| 1.2780 | B.180 | C.13 |
| 1.2781 | B.181 | C.13 |
| 1.2782 | B.182 | C.13 |
| 1.2783 | B.183 | C.13 |
| 1.2784 | B.184 | C.13 |
| 1.2785 | B.185 | C.13 |
| 1.2786 | B.186 | C.13 |
| 1.2787 | B.187 | C.13 |
| 1.2788 | B.188 | C.13 |
| 1.2789 | B.189 | C.13 |
| 1.2790 | B.190 | C.13 |
| 1.2791 | B.191 | C.13 |
| 1.2792 | B.192 | C.13 |
| 1.2793 | B.193 | C.13 |
| 1.2794 | B-194 | C.13 |
| 1.2795 | B-195 | C.13 |
| 1.2796 | B-196 | C.13 |
| 1.2797 | B-197 | C.13 |
| 1.2798 | B-198 | C.13 |
| 1.2799 | B-199 | C.13 |
| 1.2800 | B-200 | C.13 |
| 1.2801 | B.1 | C.14 |
| 1.2802 | B.2 | C.14 |
| 1.2803 | B.3 | C.14 |
| 1.2804 | B.4 | C.14 |
| 1.2805 | B.5 | C.14 |
| 1.2806 | B.6 | C.14 |
| 1.2807 | B.7 | C.14 |
| 1.2808 | B.8 | C.14 |
| 1.2809 | B.9 | C.14 |
| 1.2810 | B.10 | C.14 |
| 1.2811 | B.11 | C.14 |
| 1.2812 | B.12 | C.14 |
| 1.2813 | B.13 | C.14 |
| 1.2814 | B.14 | C.14 |
| 1.2815 | B.15 | C.14 |
| 1.2816 | B.16 | C.14 |
| 1.2817 | B.17 | C.14 |

TABLE 1-continued (compositions 1.1 to 1.3617):

| comp. no. | herbicide B | safener C |
|---|---|---|
| 1.2818 | B.18 | C.14 |
| 1.2819 | B.19 | C.14 |
| 1.2820 | B.20 | C.14 |
| 1.2821 | B.21 | C.14 |
| 1.2822 | B.22 | C.14 |
| 1.2823 | B.23 | C.14 |
| 1.2824 | B.24 | C.14 |
| 1.2825 | B.25 | C.14 |
| 1.2826 | B.26 | C.14 |
| 1.2827 | B.27 | C.14 |
| 1.2828 | B.28 | C.14 |
| 1.2829 | B.29 | C.14 |
| 1.2830 | B.30 | C.14 |
| 1.2831 | B.31 | C.14 |
| 1.2832 | B.32 | C.14 |
| 1.2833 | B.33 | C.14 |
| 1.2834 | B.34 | C.14 |
| 1.2835 | B.35 | C.14 |
| 1.2836 | B.36 | C.14 |
| 1.2837 | B.37 | C.14 |
| 1.2838 | B.38 | C.14 |
| 1.2839 | B.39 | C.14 |
| 1.2840 | B.40 | C.14 |
| 1.2841 | B.41 | C.14 |
| 1.2842 | B.42 | C.14 |
| 1.2843 | B.43 | C.14 |
| 1.2844 | B.44 | C.14 |
| 1.2845 | B.45 | C.14 |
| 1.2846 | B.46 | C.14 |
| 1.2847 | B.47 | C.14 |
| 1.2848 | B.48 | C.14 |
| 1.2849 | B.49 | C.14 |
| 1.2850 | B.50 | C.14 |
| 1.2851 | B.51 | C.14 |
| 1.2852 | B.52 | C.14 |
| 1.2853 | B.53 | C.14 |
| 1.2854 | B.54 | C.14 |
| 1.2855 | B.55 | C.14 |
| 1.2856 | B.56 | C.14 |
| 1.2857 | B.57 | C.14 |
| 1.2858 | B.58. | C.14 |
| 1.2859 | B.59 | C.14 |
| 1.2860 | B.60 | C.14 |
| 1.2861 | B.61 | C.14 |
| 1.2862 | B.62 | C.14 |
| 1.2863 | B.63 | C.14 |
| 1.2864 | B.64 | C.14 |
| 1.2865 | B.65 | C.14 |
| 1.2866 | B.66 | C.14 |
| 1.2867 | B.67 | C.14 |
| 1.2868 | B.68 | C.14 |
| 1.2869 | B.69 | C.14 |
| 1.2870 | B.70 | C.14 |
| 1.2871 | B.71 | C.14 |
| 1.2872 | B.72 | C.14 |
| 1.2873 | B.73 | C.14 |
| 1.2874 | B.74 | C.14 |
| 1.2875 | B.75 | C.14 |
| 1.2876 | B.76 | C.14 |
| 1.2877 | B.77 | C.14 |
| 1.2878 | B.78 | C.14 |
| 1.2879 | B.79 | C.14 |
| 1.2880 | B.80 | C.14 |
| 1.2881 | B.81 | C.14 |
| 1.2882 | B.82 | C.14 |
| 1.2883 | B.83 | C.14 |
| 1.2884 | B.84 | C.14 |
| 1.2885 | B.85 | C.14 |
| 1.2886 | B.86 | C.14 |
| 1.2887 | B.87 | C.14 |
| 1.2888 | B.88 | C.14 |
| 1.2889 | B.89 | C.14 |
| 1.2890 | B.90 | C.14 |
| 1.2891 | B.91 | C.14 |
| 1.2892 | B.92 | C.14 |
| 1.2893 | B.93 | C.14 |
| 1.2894 | B.94 | C.14 |
| 1.2895 | B.95 | C.14 |
| 1.2896 | B.96 | C.14 |
| 1.2897 | B.97 | C.14 |
| 1.2898 | B.98 | C.14 |
| 1.2899 | B.99 | C.14 |
| 1.2900 | B.100 | C.14 |
| 1.2901 | B.101 | C.14 |
| 1.2902 | B.102 | C.14 |
| 1.2903 | B.103 | C.14 |
| 1.2904 | B.104 | C.14 |
| 1.2905 | B.105 | C.14 |
| 1.2906 | B.106 | C.14 |
| 1.2907 | B.107 | C.14 |
| 1.2908 | B.108 | C.14 |
| 1.2909 | B.109 | C.14 |
| 1.2910 | B.110 | C.14 |
| 1.2911 | B.111 | C.14 |
| 1.2912 | B.112 | C.14 |
| 1.2913 | B.113 | C.14 |
| 1.2914 | B.114 | C.14 |
| 1.2915 | B.115 | C.14 |
| 1.2916 | B.116 | C.14 |
| 1.2917 | B.117 | C.14 |
| 1.2918 | B.118 | C.14 |
| 1.2919 | B.119 | C.14 |
| 1.2920 | B.120 | C.14 |
| 1.2921 | B.121 | C.14 |
| 1.2922 | B.122 | C.14 |
| 1.2923 | B.123 | C.14 |
| 1.2924 | B.124 | C.14 |
| 1.2925 | B.125 | C.14 |
| 1.2926 | B.126 | C.14 |
| 1.2927 | B.127 | C.14 |
| 1.2928 | B.128 | C.14 |
| 1.2929 | B.129 | C.14 |
| 1.2930 | B.130 | C.14 |
| 1.2931 | B.131 | C.14 |
| 1.2932 | B.132 | C.14 |
| 1.2933 | B.133 | C.14 |
| 1.2934 | B.134 | C.14 |
| 1.2935 | B.135 | C.14 |
| 1.2936 | B.136 | C.14 |
| 1.2937 | B.137 | C.14 |
| 1.2938 | B.138 | C.14 |
| 1.2939 | B.139 | C.14 |
| 1.2940 | B.140 | C.14 |
| 1.2941 | B.141 | C.14 |
| 1.2942 | B.142 | C.14 |
| 1.2943 | B.143 | C.14 |
| 1.2944 | B.144 | C.14 |
| 1.2945 | B.145 | C.14 |
| 1.2946 | B.146 | C.14 |
| 1.2947 | B.147 | C.14 |
| 1.2948 | B.148 | C.14 |
| 1.2949 | B.149 | C.14 |
| 1.2950 | B.150 | C.14 |
| 1.2951 | B.151 | C.14 |
| 1.2952 | B.152 | C.14 |
| 1.2953 | B.153 | C.14 |
| 1.2954 | B.154 | C.14 |
| 1.2955 | B.155 | C.14 |
| 1.2956 | B.156 | C.14 |
| 1.2957 | B.157 | C.14 |
| 1.2958 | B.158 | C.14 |
| 1.2959 | B.159 | C.14 |
| 1.2960 | B.160 | C.14 |
| 1.2961 | B.161 | C.14 |
| 1.2962 | B.162 | C.14 |
| 1.2963 | B.163 | C.14 |
| 1.2964 | B.164 | C.14 |
| 1.2965 | B.165 | C.14 |
| 1.2966 | B.166 | C.14 |
| 1.2967 | B.167 | C.14 |
| 1.2968 | B.168 | C.14 |
| 1.2969 | B.169 | C.14 |

TABLE 1-continued (compositions 1.1 to 1.3617):

| comp. no. | herbicide B | safener C |
|---|---|---|
| 1.2970 | B.170 | C.14 |
| 1.2971 | B.171 | C.14 |
| 1.2972 | B.172 | C.14 |
| 1.2973 | B.173 | C.14 |
| 1.2974 | B.174 | C.14 |
| 1.2975 | B.175 | C.14 |
| 1.2976 | B.176 | C.14 |
| 1.2977 | B.177 | C.14 |
| 1.2978 | B.178 | C.14 |
| 1.2979 | B.179 | C.14 |
| 1.2980 | B.180 | C.14 |
| 1.2981 | B.181 | C.14 |
| 1.2982 | B.182 | C.14 |
| 1.2983 | B.183 | C.14 |
| 1.2984 | B.184 | C.14 |
| 1.2985 | B.185 | C.14 |
| 1.2986 | B.186 | C.14 |
| 1.2987 | B.187 | C.14 |
| 1.2988 | B.188 | C.14 |
| 1.2989 | B.189 | C.14 |
| 1.2990 | B.190 | C.14 |
| 1.2991 | B.191 | C.14 |
| 1.2992 | B.192 | C.14 |
| 1.2993 | B.193 | C.14 |
| 1.2994 | B-194 | C.14 |
| 1.2995 | B-195 | C.14 |
| 1.2996 | B-196 | C.14 |
| 1.2997 | B-197 | C.14 |
| 1.2998 | B-198 | C.14 |
| 1.2999 | B-199 | C.14 |
| 1.3000 | B-200 | C.14 |
| 1.3001 | B.1 | C.15 |
| 1.3002 | B.2 | C.15 |
| 1.3003 | B.3 | C.15 |
| 1.3004 | B.4 | C.15 |
| 1.3005 | B.5 | C.15 |
| 1.3006 | B.6 | C.15 |
| 1.3007 | B.7 | C.15 |
| 1.3008 | B.8 | C.15 |
| 1.3009 | B.9 | C.15 |
| 1.3010 | B.10 | C.15 |
| 1.3011 | B.11 | C.15 |
| 1.3012 | B.12 | C.15 |
| 1.3013 | B.13 | C.15 |
| 1.3014 | B.14 | C.15 |
| 1.3015 | B.15 | C.15 |
| 1.3016 | B.16 | C.15 |
| 1.3017 | B.17 | C.15 |
| 1.3018 | B.18 | C.15 |
| 1.3019 | B.19 | C.15 |
| 1.3020 | B.20 | C.15 |
| 1.3021 | B.21 | C.15 |
| 1.3022 | B.22 | C.15 |
| 1.3023 | B.23 | C.15 |
| 1.3024 | B.24 | C.15 |
| 1.3025 | B.25 | C.15 |
| 1.3026 | B.26 | C.15 |
| 1.3027 | B.27 | C.15 |
| 1.3028 | B.28 | C.15 |
| 1.3029 | B.29 | C.15 |
| 1.3030 | B.30 | C.15 |
| 1.3031 | B.31 | C.15 |
| 1.3032 | B.32 | C.15 |
| 1.3033 | B.33 | C.15 |
| 1.3034 | B.34 | C.15 |
| 1.3035 | B.35 | C.15 |
| 1.3036 | B.36 | C.15 |
| 1.3037 | B.37 | C.15 |
| 1.3038 | B.38 | C.15 |
| 1.3039 | B.39 | C.15 |
| 1.3040 | B.40 | C.15 |
| 1.3041 | B.41 | C.15 |
| 1.3042 | B.42 | C.15 |
| 1.3043 | B.43 | C.15 |
| 1.3044 | B.44 | C.15 |
| 1.3045 | B.45 | C.15 |
| 1.3046 | B.46 | C.15 |
| 1.3047 | B.47 | C.15 |
| 1.3048 | B.48 | C.15 |
| 1.3049 | B.49 | C.15 |
| 1.3050 | B.50 | C.15 |
| 1.3051 | B.51 | C.15 |
| 1.3052 | B.52 | C.15 |
| 1.3053 | B.53 | C.15 |
| 1.3054 | B.54 | C.15 |
| 1.3055 | B.55 | C.15 |
| 1.3056 | B.56 | C.15 |
| 1.3057 | B.57 | C.15 |
| 1.3058 | B.58. | C.15 |
| 1.3059 | B.59 | C.15 |
| 1.3060 | B.60 | C.15 |
| 1.3061 | B.61 | C.15 |
| 1.3062 | B.62 | C.15 |
| 1.3063 | B.63 | C.15 |
| 1.3064 | B.64 | C.15 |
| 1.3065 | B.65 | C.15 |
| 1.3066 | B.66 | C.15 |
| 1.3067 | B.67 | C.15 |
| 1.3068 | B.68 | C.15 |
| 1.3069 | B.69 | C.15 |
| 1.3070 | B.70 | C.15 |
| 1.3071 | B.71 | C.15 |
| 1.3072 | B.72 | C.15 |
| 1.3073 | B.73 | C.15 |
| 1.3074 | B.74 | C.15 |
| 1.3075 | B.75 | C.15 |
| 1.3076 | B.76 | C.15 |
| 1.3077 | B.77 | C.15 |
| 1.3078 | B.78 | C.15 |
| 1.3079 | B.79 | C.15 |
| 1.3080 | B.80 | C.15 |
| 1.3081 | B.81 | C.15 |
| 1.3082 | B.82 | C.15 |
| 1.3083 | B.83 | C.15 |
| 1.3084 | B.84 | C.15 |
| 1.3085 | B.85 | C.15 |
| 1.3086 | B.86 | C.15 |
| 1.3087 | B.87 | C.15 |
| 1.3088 | B.88 | C.15 |
| 1.3089 | B.89 | C.15 |
| 1.3090 | B.90 | C.15 |
| 1.3091 | B.91 | C.15 |
| 1.3092 | B.92 | C.15 |
| 1.3093 | B.93 | C.15 |
| 1.3094 | B.94 | C.15 |
| 1.3095 | B.95 | C.15 |
| 1.3096 | B.96 | C.15 |
| 1.3097 | B.97 | C.15 |
| 1.3098 | B.98 | C.15 |
| 1.3099 | B.99 | C.15 |
| 1.3100 | B.100 | C.15 |
| 1.3101 | B.101 | C.15 |
| 1.3102 | B.102 | C.15 |
| 1.3103 | B.103 | C.15 |
| 1.3104 | B.104 | C.15 |
| 1.3105 | B.105 | C.15 |
| 1.3106 | B.106 | C.15 |
| 1.3107 | B.107 | C.15 |
| 1.3108 | B.108 | C.15 |
| 1.3109 | B.109 | C.15 |
| 1.3110 | B.110 | C.15 |
| 1.3111 | B.111 | C.15 |
| 1.3112 | B.112 | C.15 |
| 1.3113 | B.113 | C.15 |
| 1.3114 | B.114 | C.15 |
| 1.3115 | B.115 | C.15 |
| 1.3116 | B.116 | C.15 |
| 1.3117 | B.117 | C.15 |
| 1.3118 | B.118 | C.15 |
| 1.3119 | B.119 | C.15 |
| 1.3120 | B.120 | C.15 |
| 1.3121 | B.121 | C.15 |

TABLE 1-continued

(compositions 1.1 to 1.3617):

| comp. no. | herbicide B | safener C |
|---|---|---|
| 1.3122 | B.122 | C.15 |
| 1.3123 | B.123 | C.15 |
| 1.3124 | B.124 | C.15 |
| 1.3125 | B.125 | C.15 |
| 1.3126 | B.126 | C.15 |
| 1.3127 | B.127 | C.15 |
| 1.3128 | B.128 | C.15 |
| 1.3129 | B.129 | C.15 |
| 1.3130 | B.130 | C.15 |
| 1.3131 | B.131 | C.15 |
| 1.3132 | B.132 | C.15 |
| 1.3133 | B.133 | C.15 |
| 1.3134 | B.134 | C.15 |
| 1.3135 | B.135 | C.15 |
| 1.3136 | B.136 | C.15 |
| 1.3137 | B.137 | C.15 |
| 1.3138 | B.138 | C.15 |
| 1.3139 | B.139 | C.15 |
| 1.3140 | B.140 | C.15 |
| 1.3141 | B.141 | C.15 |
| 1.3142 | B.142 | C.15 |
| 1.3143 | B.143 | C.15 |
| 1.3144 | B.144 | C.15 |
| 1.3145 | B.145 | C.15 |
| 1.3146 | B.146 | C.15 |
| 1.3147 | B.147 | C.15 |
| 1.3148 | B.148 | C.15 |
| 1.3149 | B.149 | C.15 |
| 1.3150 | B.150 | C.15 |
| 1.3151 | B.151 | C.15 |
| 1.3152 | B.152 | C.15 |
| 1.3153 | B.153 | C.15 |
| 1.3154 | B.154 | C.15 |
| 1.3155 | B.155 | C.15 |
| 1.3156 | B.156 | C.15 |
| 1.3157 | B.157 | C.15 |
| 1.3158 | B.158 | C.15 |
| 1.3159 | B.159 | C.15 |
| 1.3160 | B.160 | C.15 |
| 1.3161 | B.161 | C.15 |
| 1.3162 | B.162 | C.15 |
| 1.3163 | B.163 | C.15 |
| 1.3164 | B.164 | C.15 |
| 1.3165 | B.165 | C.15 |
| 1.3166 | B.166 | C.15 |
| 1.3167 | B.167 | C.15 |
| 1.3168 | B.168 | C.15 |
| 1.3169 | B.169 | C.15 |
| 1.3170 | B.170 | C.15 |
| 1.3171 | B.171 | C.15 |
| 1.3172 | B.172 | C.15 |
| 1.3173 | B.173 | C.15 |
| 1.3174 | B.174 | C.15 |
| 1.3175 | B.175 | C.15 |
| 1.3176 | B.176 | C.15 |
| 1.3177 | B.177 | C.15 |
| 1.3178 | B.178 | C.15 |
| 1.3179 | B.179 | C.15 |
| 1.3180 | B.180 | C.15 |
| 1.3181 | B.181 | C.15 |
| 1.3182 | B.182 | C.15 |
| 1.3183 | B.183 | C.15 |
| 1.3184 | B.184 | C.15 |
| 1.3185 | B.185 | C.15 |
| 1.3186 | B.186 | C.15 |
| 1.3187 | B.187 | C.15 |
| 1.3188 | B.188 | C.15 |
| 1.3189 | B.189 | C.15 |
| 1.3190 | B.190 | C.15 |
| 1.3191 | B.191 | C.15 |
| 1.3192 | B.192 | C.15 |
| 1.3193 | B.193 | C.15 |
| 1.3194 | B-194 | C.15 |
| 1.3195 | B-195 | C.15 |
| 1.3196 | B-196 | C.15 |
| 1.3197 | B-197 | C.15 |
| 1.3198 | B-198 | C.15 |
| 1.3199 | B-199 | C.15 |
| 1.3200 | B-200 | C.15 |
| 1.3201 | B.1 | C.16 |
| 1.3202 | B.2 | C.16 |
| 1.3203 | B.3 | C.16 |
| 1.3204 | B.4 | C.16 |
| 1.3205 | B.5 | C.16 |
| 1.3206 | B.6 | C.16 |
| 1.3207 | B.7 | C.16 |
| 1.3208 | B.8 | C.16 |
| 1.3209 | B.9 | C.16 |
| 1.3210 | B.10 | C.16 |
| 1.3211 | B.11 | C.16 |
| 1.3212 | B.12 | C.16 |
| 1.3213 | B.13 | C.16 |
| 1.3214 | B.14 | C.16 |
| 1.3215 | B.15 | C.16 |
| 1.3216 | B.16 | C.16 |
| 1.3217 | B.17 | C.16 |
| 1.3218 | B.18 | C.16 |
| 1.3219 | B.19 | C.16 |
| 1.3220 | B.20 | C.16 |
| 1.3221 | B.21 | C.16 |
| 1.3222 | B.22 | C.16 |
| 1.3223 | B.23 | C.16 |
| 1.3224 | B.24 | C.16 |
| 1.3225 | B.25 | C.16 |
| 1.3226 | B.26 | C.16 |
| 1.3227 | B.27 | C.16 |
| 1.3228 | B.28 | C.16 |
| 1.3229 | B.29 | C.16 |
| 1.3230 | B.30 | C.16 |
| 1.3231 | B.31 | C.16 |
| 1.3232 | B.32 | C.16 |
| 1.3233 | B.33 | C.16 |
| 1.3234 | B.34 | C.16 |
| 1.3235 | B.35 | C.16 |
| 1.3236 | B.36 | C.16 |
| 1.3237 | B.37 | C.16 |
| 1.3238 | B.38 | C.16 |
| 1.3239 | B.39 | C.16 |
| 1.3240 | B.40 | C.16 |
| 1.3241 | B.41 | C.16 |
| 1.3242 | B.42 | C.16 |
| 1.3243 | B.43 | C.16 |
| 1.3244 | B.44 | C.16 |
| 1.3245 | B.45 | C.16 |
| 1.3246 | B.46 | C.16 |
| 1.3247 | B.47 | C.16 |
| 1.3248 | B.48 | C.16 |
| 1.3249 | B.49 | C.16 |
| 1.3250 | B.50 | C.16 |
| 1.3251 | B.51 | C.16 |
| 1.3252 | B.52 | C.16 |
| 1.3253 | B.53 | C.16 |
| 1.3254 | B.54 | C.16 |
| 1.3255 | B.55 | C.16 |
| 1.3256 | B.56 | C.16 |
| 1.3257 | B.57 | C.16 |
| 1.3258 | B.58. | C.16 |
| 1.3259 | B.59 | C.16 |
| 1.3260 | B.60 | C.16 |
| 1.3261 | B.61 | C.16 |
| 1.3262 | B.62 | C.16 |
| 1.3263 | B.63 | C.16 |
| 1.3264 | B.64 | C.16 |
| 1.3265 | B.65 | C.16 |
| 1.3266 | B.66 | C.16 |
| 1.3267 | B.67 | C.16 |
| 1.3268 | B.68 | C.16 |
| 1.3269 | B.69 | C.16 |
| 1.3270 | B.70 | C.16 |
| 1.3271 | B.71 | C.16 |
| 1.3272 | B.72 | C.16 |
| 1.3273 | B.73 | C.16 |

TABLE 1-continued (compositions 1.1 to 1.3617):

| comp. no. | herbicide B | safener C |
|---|---|---|
| 1.3274 | B.74 | C.16 |
| 1.3275 | B.75 | C.16 |
| 1.3276 | B.76 | C.16 |
| 1.3277 | B.77 | C.16 |
| 1.3278 | B.78 | C.16 |
| 1.3279 | B.79 | C.16 |
| 1.3280 | B.80 | C.16 |
| 1.3281 | B.81 | C.16 |
| 1.3282 | B.82 | C.16 |
| 1.3283 | B.83 | C.16 |
| 1.3284 | B.84 | C.16 |
| 1.3285 | B.85 | C.16 |
| 1.3286 | B.86 | C.16 |
| 1.3287 | B.87 | C.16 |
| 1.3288 | B.88 | C.16 |
| 1.3289 | B.89 | C.16 |
| 1.3290 | B.90 | C.16 |
| 1.3291 | B.91 | C.16 |
| 1.3292 | B.92 | C.16 |
| 1.3293 | B.93 | C.16 |
| 1.3294 | B.94 | C.16 |
| 1.3295 | B.95 | C.16 |
| 1.3296 | B.96 | C.16 |
| 1.3297 | B.97 | C.16 |
| 1.3298 | B.98 | C.16 |
| 1.3299 | B.99 | C.16 |
| 1.3300 | B.100 | C.16 |
| 1.3301 | B.101 | C.16 |
| 1.3302 | B.102 | C.16 |
| 1.3303 | B.103 | C.16 |
| 1.3304 | B.104 | C.16 |
| 1.3305 | B.105 | C.16 |
| 1.3306 | B.106 | C.16 |
| 1.3307 | B.107 | C.16 |
| 1.3308 | B.108 | C.16 |
| 1.3309 | B.109 | C.16 |
| 1.3310 | B.110 | C.16 |
| 1.3311 | B.111 | C.16 |
| 1.3312 | B.112 | C.16 |
| 1.3313 | B.113 | C.16 |
| 1.3314 | B.114 | C.16 |
| 1.3315 | B.115 | C.16 |
| 1.3316 | B.116 | C.16 |
| 1.3317 | B.117 | C.16 |
| 1.3318 | B.118 | C.16 |
| 1.3319 | B.119 | C.16 |
| 1.3320 | B.120 | C.16 |
| 1.3321 | B.121 | C.16 |
| 1.3322 | B.122 | C.16 |
| 1.3323 | B.123 | C.16 |
| 1.3324 | B.124 | C.16 |
| 1.3325 | B.125 | C.16 |
| 1.3326 | B.126 | C.16 |
| 1.3327 | B.127 | C.16 |
| 1.3328 | B.128 | C.16 |
| 1.3329 | B.129 | C.16 |
| 1.3330 | B.130 | C.16 |
| 1.3331 | B.131 | C.16 |
| 1.3332 | B.132 | C.16 |
| 1.3333 | B.133 | C.16 |
| 1.3334 | B.134 | C.16 |
| 1.3335 | B.135 | C.16 |
| 1.3336 | B.136 | C.16 |
| 1.3337 | B.137 | C.16 |
| 1.3338 | B.138 | C.16 |
| 1.3339 | B.139 | C.16 |
| 1.3340 | B.140 | C.16 |
| 1.3341 | B.141 | C.16 |
| 1.3342 | B.142 | C.16 |
| 1.3343 | B.143 | C.16 |
| 1.3344 | B.144 | C.16 |
| 1.3345 | B.145 | C.16 |
| 1.3346 | B.146 | C.16 |
| 1.3347 | B.147 | C.16 |
| 1.3348 | B.148 | C.16 |
| 1.3349 | B.149 | C.16 |
| 1.3350 | B.150 | C.16 |
| 1.3351 | B.151 | C.16 |
| 1.3352 | B.152 | C.16 |
| 1.3353 | B.153 | C.16 |
| 1.3354 | B.154 | C.16 |
| 1.3355 | B.155 | C.16 |
| 1.3356 | B.156 | C.16 |
| 1.3357 | B.157 | C.16 |
| 1.3358 | B.158 | C.16 |
| 1.3359 | B.159 | C.16 |
| 1.3360 | B.160 | C.16 |
| 1.3361 | B.161 | C.16 |
| 1.3362 | B.162 | C.16 |
| 1.3363 | B.163 | C.16 |
| 1.3364 | B.164 | C.16 |
| 1.3365 | B.165 | C.16 |
| 1.3366 | B.166 | C.16 |
| 1.3367 | B.167 | C.16 |
| 1.3368 | B.168 | C.16 |
| 1.3369 | B.169 | C.16 |
| 1.3370 | B.170 | C.16 |
| 1.3371 | B.171 | C.16 |
| 1.3372 | B.172 | C.16 |
| 1.3373 | B.173 | C.16 |
| 1.3374 | B.174 | C.16 |
| 1.3375 | B.175 | C.16 |
| 1.3376 | B.176 | C.16 |
| 1.3377 | B.177 | C.16 |
| 1.3378 | B.178 | C.16 |
| 1.3379 | B.179 | C.16 |
| 1.3380 | B.180 | C.16 |
| 1.3381 | B.181 | C.16 |
| 1.3382 | B.182 | C.16 |
| 1.3383 | B.183 | C.16 |
| 1.3384 | B.184 | C.16 |
| 1.3385 | B.185 | C.16 |
| 1.3386 | B.186 | C.16 |
| 1.3387 | B.187 | C.16 |
| 1.3388 | B.188 | C.16 |
| 1.3389 | B.189 | C.16 |
| 1.3390 | B.190 | C.16 |
| 1.3391 | B.191 | C.16 |
| 1.3392 | B.192 | C.16 |
| 1.3393 | B.193 | C.16 |
| 1.3394 | B-194 | C.16 |
| 1.3395 | B-195 | C.16 |
| 1.3396 | B-196 | C.16 |
| 1.3397 | B-197 | C.16 |
| 1.3398 | B-198 | C.16 |
| 1.3399 | B-199 | C.16 |
| 1.3400 | B-200 | C.16 |
| 1.3401 | B.1 | C.17 |
| 1.3402 | B.2 | C.17 |
| 1.3403 | B.3 | C.17 |
| 1.3404 | B.4 | C.17 |
| 1.3405 | B.5 | C.17 |
| 1.3406 | B.6 | C.17 |
| 1.3407 | B.7 | C.17 |
| 1.3408 | B.8 | C.17 |
| 1.3409 | B.9 | C.17 |
| 1.3410 | B.10 | C.17 |
| 1.3411 | B.11 | C.17 |
| 1.3412 | B.12 | C.17 |
| 1.3413 | B.13 | C.17 |
| 1.3414 | B.14 | C.17 |
| 1.3415 | B.15 | C.17 |
| 1.3416 | B.16 | C.17 |
| 1.3417 | B.17 | C.17 |
| 1.3418 | B.18 | C.17 |
| 1.3419 | B.19 | C.17 |
| 1.3420 | B.20 | C.17 |
| 1.3421 | B.21 | C.17 |
| 1.3422 | B.22 | C.17 |
| 1.3423 | B.23 | C.17 |
| 1.3424 | B.24 | C.17 |
| 1.3425 | B.25 | C.17 |

TABLE 1-continued (compositions 1.1 to 1.3617):

| comp. no. | herbicide B | safener C |
|---|---|---|
| 1.3426 | B.26 | C.17 |
| 1.3427 | B.27 | C.17 |
| 1.3428 | B.28 | C.17 |
| 1.3429 | B.29 | C.17 |
| 1.3430 | B.30 | C.17 |
| 1.3431 | B.31 | C.17 |
| 1.3432 | B.32 | C.17 |
| 1.3433 | B.33 | C.17 |
| 1.3434 | B.34 | C.17 |
| 1.3435 | B.35 | C.17 |
| 1.3436 | B.36 | C.17 |
| 1.3437 | B.37 | C.17 |
| 1.3438 | B.38 | C.17 |
| 1.3439 | B.39 | C.17 |
| 1.3440 | B.40 | C.17 |
| 1.3441 | B.41 | C.17 |
| 1.3442 | B.42 | C.17 |
| 1.3443 | B.43 | C.17 |
| 1.3444 | B.44 | C.17 |
| 1.3445 | B.45 | C.17 |
| 1.3446 | B.46 | C.17 |
| 1.3447 | B.47 | C.17 |
| 1.3448 | B.48 | C.17 |
| 1.3449 | B.49 | C.17 |
| 1.3450 | B.50 | C.17 |
| 1.3451 | B.51 | C.17 |
| 1.3452 | B.52 | C.17 |
| 1.3453 | B.53 | C.17 |
| 1.3454 | B.54 | C.17 |
| 1.3455 | B.55 | C.17 |
| 1.3456 | B.56 | C.17 |
| 1.3457 | B.57 | C.17 |
| 1.3458 | B.58. | C.17 |
| 1.3459 | B.59 | C.17 |
| 1.3460 | B.60 | C.17 |
| 1.3461 | B.61 | C.17 |
| 1.3462 | B.62 | C.17 |
| 1.3463 | B.63 | C.17 |
| 1.3464 | B.64 | C.17 |
| 1.3465 | B.65 | C.17 |
| 1.3466 | B.66 | C.17 |
| 1.3467 | B.67 | C.17 |
| 1.3468 | B.68 | C.17 |
| 1.3469 | B.69 | C.17 |
| 1.3470 | B.70 | C.17 |
| 1.3471 | B.71 | C.17 |
| 1.3472 | B.72 | C.17 |
| 1.3473 | B.73 | C.17 |
| 1.3474 | B.74 | C.17 |
| 1.3475 | B.75 | C.17 |
| 1.3476 | B.76 | C.17 |
| 1.3477 | B.77 | C.17 |
| 1.3478 | B.78 | C.17 |
| 1.3479 | B.79 | C.17 |
| 1.3480 | B.80 | C.17 |
| 1.3481 | B.81 | C.17 |
| 1.3482 | B.82 | C.17 |
| 1.3483 | B.83 | C.17 |
| 1.3484 | B.84 | C.17 |
| 1.3485 | B.85 | C.17 |
| 1.3486 | B.86 | C.17 |
| 1.3487 | B.87 | C.17 |
| 1.3488 | B.88 | C.17 |
| 1.3489 | B.89 | C.17 |
| 1.3490 | B.90 | C.17 |
| 1.3491 | B.91 | C.17 |
| 1.3492 | B.92 | C.17 |
| 1.3493 | B.93 | C.17 |
| 1.3494 | B.94 | C.17 |
| 1.3495 | B.95 | C.17 |
| 1.3496 | B.96 | C.17 |
| 1.3497 | B.97 | C.17 |
| 1.3498 | B.98 | C.17 |
| 1.3499 | B.99 | C.17 |
| 1.3500 | B.100 | C.17 |
| 1.3501 | B.101 | C.17 |
| 1.3502 | B.102 | C.17 |
| 1.3503 | B.103 | C.17 |
| 1.3504 | B.104 | C.17 |
| 1.3505 | B.105 | C.17 |
| 1.3506 | B.106 | C.17 |
| 1.3507 | B.107 | C.17 |
| 1.3508 | B.108 | C.17 |
| 1.3509 | B.109 | C.17 |
| 1.3510 | B.110 | C.17 |
| 1.3511 | B.111 | C.17 |
| 1.3512 | B.112 | C.17 |
| 1.3513 | B.113 | C.17 |
| 1.3514 | B.114 | C.17 |
| 1.3515 | B.115 | C.17 |
| 1.3516 | B.116 | C.17 |
| 1.3517 | B.117 | C.17 |
| 1.3518 | B.118 | C.17 |
| 1.3519 | B.119 | C.17 |
| 1.3520 | B.120 | C.17 |
| 1.3521 | B.121 | C.17 |
| 1.3522 | B.122 | C.17 |
| 1.3523 | B.123 | C.17 |
| 1.3524 | B.124 | C.17 |
| 1.3525 | B.125 | C.17 |
| 1.3526 | B.126 | C.17 |
| 1.3527 | B.127 | C.17 |
| 1.3528 | B.128 | C.17 |
| 1.3529 | B.129 | C.17 |
| 1.3530 | B.130 | C.17 |
| 1.3531 | B.131 | C.17 |
| 1.3532 | B.132 | C.17 |
| 1.3533 | B.133 | C.17 |
| 1.3534 | B.134 | C.17 |
| 1.3535 | B.135 | C.17 |
| 1.3536 | B.136 | C.17 |
| 1.3537 | B.137 | C.17 |
| 1.3538 | B.138 | C.17 |
| 1.3539 | B.139 | C.17 |
| 1.3540 | B.140 | C.17 |
| 1.3541 | B.141 | C.17 |
| 1.3542 | B.142 | C.17 |
| 1.3543 | B.143 | C.17 |
| 1.3544 | B.144 | C.17 |
| 1.3545 | B.145 | C.17 |
| 1.3546 | B.146 | C.17 |
| 1.3547 | B.147 | C.17 |
| 1.3548 | B.148 | C.17 |
| 1.3549 | B.149 | C.17 |
| 1.3550 | B.150 | C.17 |
| 1.3551 | B.151 | C.17 |
| 1.3552 | B.152 | C.17 |
| 1.3553 | B.153 | C.17 |
| 1.3554 | B.154 | C.17 |
| 1.3555 | B.155 | C.17 |
| 1.3556 | B.156 | C.17 |
| 1.3557 | B.157 | C.17 |
| 1.3558 | B.158 | C.17 |
| 1.3559 | B.159 | C.17 |
| 1.3560 | B.160 | C.17 |
| 1.3561 | B.161 | C.17 |
| 1.3562 | B.162 | C.17 |
| 1.3563 | B.163 | C.17 |
| 1.3564 | B.164 | C.17 |
| 1.3565 | B.165 | C.17 |
| 1.3566 | B.166 | C.17 |
| 1.3567 | B.167 | C.17 |
| 1.3568 | B.168 | C.17 |
| 1.3569 | B.169 | C.17 |
| 1.3570 | B.170 | C.17 |
| 1.3571 | B.171 | C.17 |
| 1.3572 | B.172 | C.17 |
| 1.3573 | B.173 | C.17 |
| 1.3574 | B.174 | C.17 |
| 1.3575 | B.175 | C.17 |
| 1.3576 | B.176 | C.17 |
| 1.3577 | B.177 | C.17 |

TABLE 1-continued (compositions 1.1 to 1.3617):

| comp. no. | herbicide B | safener C |
|---|---|---|
| 1.3578 | B.178 | C.17 |
| 1.3579 | B.179 | C.17 |
| 1.3580 | B.180 | C.17 |
| 1.3581 | B.181 | C.17 |
| 1.3582 | B.182 | C.17 |
| 1.3583 | B.183 | C.17 |
| 1.3584 | B.184 | C.17 |
| 1.3585 | B.185 | C.17 |
| 1.3586 | B.186 | C.17 |
| 1.3587 | B.187 | C.17 |
| 1.3588 | B.188 | C.17 |
| 1.3589 | B.189 | C.17 |
| 1.3590 | B.190 | C.17 |
| 1.3591 | B.191 | C.17 |
| 1.3592 | B.192 | C.17 |
| 1.3593 | B.193 | C.17 |
| 1.3594 | B-194 | C.17 |
| 1.3595 | B-195 | C.17 |
| 1.3596 | B-196 | C.17 |
| 1.3597 | B-197 | C.17 |
| 1.3598 | B-198 | C.17 |
| 1.3599 | B-199 | C.17 |
| 1.3600 | B-200 | C.17 |
| 1.3601 | — | C.1 |
| 1.3602 | — | C.2 |
| 1.3603 | — | C.3 |
| 1.3604 | — | C.4 |
| 1.3605 | — | C.5 |
| 1.3606 | — | C.6 |
| 1.3607 | — | C.7 |
| 1.3608 | — | C.8 |
| 1.3609 | — | C.9 |
| 1.3610 | — | C.10 |
| 1.3611 | — | C.11 |
| 1.3612 | — | C.12 |
| 1.3613 | — | C.13 |
| 1.3614 | — | C.14 |
| 1.3615 | — | C.15 |
| 1.3616 | — | C.16 |
| 1.3617 | — | C.17 |

The specific number for each single composition is deductible as follows:

Composition 1.854 for example comprises a compound of the formula (I.1), pyrazosulfuron-ethyl (B.54) and cyprosulfamide (C.4) (see table 1, entry 1.854; as well as table B, entry B.54 and table C, entry C.4).

Also especially preferred are compositions 2.1 to 2.3617 which differ from the corresponding compositions 1.1 to 1.3617 only in that they comprise as the active component A, instead of the isoxazolo[5,4-b]pyridine of formula (I.1), the an isoxazolo[5,4-b]pyridine of formula (I.2).

Also especially preferred are compositions 3.1 to 3.3617 which differ from the corresponding compositions 1.1 to 1.3617 only in that they comprise as the active compound A, instead of the an isoxazolo[5,4-b]pyridine of formula (I.1), the an isoxazolo[5,4-b]pyridine of formula (I.3).

Also especially preferred are compositions 1a.1 to 1a.3617, 2a.1 to 2a.3617, 3a.1 to 3a.3617 which differ from the corresponding compositions 1.1 to 1.3617, 2.1 to 2.3617 and 3.1 to 3.3617, respectively, only in that they comprise as the component A an isoxazolo[5,4-b]pyridine of formula (I.1), (I.2) or (I.3), respectively, each in the form of its carboxylic acid ester, thioester or amide formed with the carboxylic acid moiety of the isoxazolo[5,4-b]pyridine of the formula (I).

Also especially preferred are compositions 4.1 to 4.3617 which differ from the corresponding compositions 1.1 to 1.3617 only in that they additionally comprise B.8 pinoxaden as further herbicide B.

Also especially preferred are compositions 5.1 to 5.3617 which differ from the corresponding compositions 1.1 to 1.3617 only in that they additionally comprise B.30 imazamox as further herbicide B.

Also especially preferred are compositions 6.1 to 6.3617 which differ from the corresponding compositions 1.1 to 1.3617 only in that they additionally comprise B.32 imazapic as further herbicide B.

Also especially preferred are compositions 7.1 to 7.3617 which differ from the corresponding compositions 1.1 to 1.3617 only in that they additionally comprise B.35 imazapyr as further herbicide B.

Also especially preferred are compositions 8.1 to 8.3617 which differ from the corresponding compositions 1.1 to 1.3617 only in that they additionally comprise B.38 imazaquin as further herbicide B.

Also especially preferred are compositions 9.1 to 9.3617 which differ from the corresponding compositions 1.1 to 1.3617 only in that they additionally comprise B.40 imazethapyr as further herbicide B.

Also especially preferred are compositions 10.1 to 10.3617 which differ from the corresponding compositions 1.1 to 1.3617 only in that they additionally comprise B.51 nicosulfuron as further herbicide B.

Also especially preferred are compositions 11.1 to 11.3617 which differ from the corresponding compositions 1.1 to 1.3617 only in that they additionally comprise B.55 pyribenzoxim as further herbicide B.

Also especially preferred are compositions 12.1 to 12.3617 which differ from the corresponding compositions 1.1 to 1.3617 only in that they additionally comprise B.56 pyriftalid as further herbicide B.

Also especially preferred are compositions 13.1 to 13.3617 which differ from the corresponding compositions 1.1 to 1.3617 only in that they additionally comprise B.64 tritosulfuron as further herbicide B.

Also especially preferred are compositions 14.1 to 14.3617 which differ from the corresponding compositions 1.1 to 1.3617 only in that they additionally comprise B.66 ametryne as further herbicide B.

Also especially preferred are compositions 15.1 to 15.3617 which differ from the corresponding compositions 1.1 to 1.3617 only in that they additionally comprise B.67 atrazine as further herbicide B.

Also especially preferred are compositions 16.1 to 16.3617 which differ from the corresponding compositions 1.1 to 1.3617 only in that they additionally comprise B.68 bentazon as further herbicide B.

Also especially preferred are compositions 17.1 to 17.3617 which differ from the corresponding compositions 1.1 to 1.3617 only in that they additionally comprise B.69 bromoxynil as further herbicide B.

Also especially preferred are compositions 18.1 to 18.3617 which differ from the corresponding compositions 1.1 to 1.3617 only in that they additionally comprise B.73 diuron as further herbicide B.

Also especially preferred are compositions 19.1 to 19.3617 which differ from the corresponding compositions 1.1 to 1.3617 only in that they additionally comprise B.76 isoproturon as further herbicide B.

Also especially preferred are compositions 20.1 to 20.3617 which differ from the corresponding compositions 1.1 to 1.3617 only in that they additionally comprise B.81 simazin as further herbicide B.

Also especially preferred are compositions 21.1 to 21.3617 which differ from the corresponding compositions 1.1 to 1.3617 only in that they additionally comprise B.82 terbuthylazin as further herbicide B.

Also especially preferred are compositions 22.1 to 22.3617 which differ from the corresponding compositions 1.1 to 1.3617 only in that they additionally comprise B.85 acifluorfen as further herbicide B.

Also especially preferred are compositions 23.1 to 23.3617 which differ from the corresponding compositions 1.1 to 1.3617 only in that they additionally comprise B.88 flumioxazin as further herbicide B.

Also especially preferred are compositions 24.1 to 24.3617 which differ from the corresponding compositions 1.1 to 1.3617 only in that they additionally comprise B.89 fomesafen as further herbicide B.

Also especially preferred are compositions 25.1 to 25.3617 which differ from the corresponding compositions 1.1 to 1.3617 only in that they additionally comprise B.92 saflufenacil as further herbicide B.

Also especially preferred are compositions 26.1 to 26.3617 which differ from the corresponding compositions 1.1 to 1.3617 only in that they additionally comprise B.93 sulfentrazone as further herbicide B.

Also especially preferred are compositions 27.1 to 27.3617 which differ from the corresponding compositions 1.1 to 1.3617 only in that they additionally comprise B.96 benzbicyclone as further herbicide B.

Also especially preferred are compositions 28.1 to 28.3617 which differ from the corresponding compositions 1.1 to 1.3617 only in that they additionally comprise B.97 clomazone as further herbicide B.

Also especially preferred are compositions 29.1 to 29.3617 which differ from the corresponding compositions 1.1 to 1.3617 only in that they additionally comprise B.100 isoxaflutole as further herbicide B.

Also especially preferred are compositions 30.1 to 30.3617 which differ from the corresponding compositions 1.1 to 1.3617 only in that they additionally comprise B.100 isoxaflutole and B.67 atrazine as further herbicides B.

Also especially preferred are compositions 31.1 to 31.3617 which differ from the corresponding compositions 1.1 to 1.3617 only in that they additionally comprise B.100 isoxaflutole and B.76 isoproturon as further herbicides B.

Also especially preferred are compositions 32.1 to 32.3617 which differ from the corresponding compositions 1.1 to 1.3617 only in that they additionally comprise B.100 isoxaflutole and B.82 terbutylazin as further herbicides B.

Also especially preferred are compositions 33.1 to 33.3617 which differ from the corresponding compositions 1.1 to 1.3617 only in that they additionally comprise B.101 mesotrione as further herbicide B.

Also especially preferred are compositions 34.1 to 34.3617 which differ from the corresponding compositions 1.1 to 1.3617 only in that they additionally comprise B.101 mesotrione and B.67 atrazine as further herbicides B.

Also especially preferred are compositions 35.1 to 35.3617 which differ from the corresponding compositions 1.1 to 1.3617 only in that they additionally comprise B.101 mesotrione and B.76 isoproturon as further herbicides B.

Also especially preferred are compositions 36.1 to 36.3617 which differ from the corresponding compositions 1.1 to 1.3617 only in that they additionally comprise B.101 mesotrione and B.82 terbutylazin as further herbicides B.

Also especially preferred are compositions 37.1 to 37.3617 which differ from the corresponding compositions 1.1 to 1.3617 only in that they additionally comprise B.103 picolinafen as further herbicide B.

Also especially preferred are compositions 38.1 to 38.3617 which differ from the corresponding compositions 1.1 to 1.3617 only in that they additionally comprise B.104 sulcotrione as further herbicide B.

Also especially preferred are compositions 39.1 to 39.3617 which differ from the corresponding compositions 1.1 to 1.3617 only in that they additionally comprise B.104 sulcotrione and B.67 atrazine as further herbicides B.

Also especially preferred are compositions 40.1 to 40.3617 which differ from the corresponding compositions 1.1 to 1.3617 only in that they additionally comprise B.104 sulcotrione and B.76 isoproturon as further herbicides B.

Also especially preferred are compositions 41.1 to 41.3617 which differ from the corresponding compositions 1.1 to 1.3617 only in that they additionally comprise B.104 sulcotrione and B.82 terbutylazin as further herbicides B.

Also especially preferred are compositions 42.1 to 42.3617 which differ from the corresponding compositions 1.1 to 1.3617 only in that they additionally comprise B.106 tembotrione as further herbicide B.

Also especially preferred are compositions 43.1 to 43.3617 which differ from the corresponding compositions 1.1 to 1.3617 only in that they additionally comprise B.107 topramezone as further herbicide B.

Also especially preferred are compositions 44.1 to 44.3617 which differ from the corresponding compositions 1.1 to 1.3617 only in that they additionally comprise B.107 topramezone and B.67 atrazine as further herbicides B.

Also especially preferred are compositions 45.1 to 45.3617 which differ from the corresponding compositions 1.1 to 1.3617 only in that they additionally comprise B.107 topramezone and B.76 isoproturon as further herbicides B.

Also especially preferred are compositions 46.1 to 46.3617 which differ from the corresponding compositions 1.1 to 1.3617 only in that they additionally comprise B.107 topramezone and B.82 terbutylazin as further herbicides B.

Also especially preferred are compositions 47.1 to 47.3617 which differ from the corresponding compositions 1.1 to 1.3617 only in that they additionally comprise B.112 glyphosate as further herbicide B.

Also especially preferred are compositions 48.1 to 48.3617 which differ from the corresponding compositions 1.1 to 1.3617 only in that they additionally comprise B.112 glyphosate and B.67 atrazine as further herbicides B.

Also especially preferred are compositions 49.1 to 49.3617 which differ from the corresponding compositions 1.1 to 1.3617 only in that they additionally comprise B.112 glyphosate and B.92 saflufenacil as further herbicides B.

Also especially preferred are compositions 50.1 to 50.3617 which differ from the corresponding compositions 1.1 to 1.3617 only in that they additionally comprise B.112 glyphosate and B.100 isoxaflutole as further herbicides B.

Also especially preferred are compositions 51.1 to 51.3617 which differ from the corresponding compositions 1.1 to 1.3617 only in that they additionally comprise B.112 glyphosate and B.124 acetochlor as further herbicides B.

Also especially preferred are compositions 52.1 to 52.3617 which differ from the corresponding compositions 1.1 to 1.3617 only in that they additionally comprise B.112 glyphosate and B.101 mesotrione as further herbicides B.

Also especially preferred are compositions 53.1 to 53.3617 which differ from the corresponding compositions 1.1 to 1.3617 only in that they additionally comprise B.112 glyphosate and B.104 sulcotrione as further herbicides B.

Also especially preferred are compositions 54.1 to 54.3617 which differ from the corresponding compositions 1.1 to 1.3617 only in that they additionally comprise B.112 glyphosate and B.107 topramezone as further herbicides B.

Also especially preferred are compositions 55.1 to 55.3617 which differ from the corresponding compositions 1.1 to 1.3617 only in that they additionally comprise B.118 glufosinate as further herbicide B.

Also especially preferred are compositions 56.1 to 56.3617 which differ from the corresponding compositions 1.1 to 1.3617 only in that they additionally comprise B.122 pendimethalin as further herbicide B.

Also especially preferred are compositions 57.1 to 57.3617 which differ from the corresponding compositions 1.1 to 1.3617 only in that they additionally comprise B.124 acetochlor as further herbicide B.

Also especially preferred are compositions 58.1 to 58.3617 which differ from the corresponding compositions 1.1 to 1.3617 only in that they additionally comprise B.127 dimethenamid-P as further herbicide B.

Also especially preferred are compositions 59.1 to 59.3617 which differ from the corresponding compositions 1.1 to 1.3617 only in that they additionally comprise B.128 fentrazamide as further herbicide B.

Also especially preferred are compositions 60.1 to 60.3617 which differ from the corresponding compositions 1.1 to 1.3617 only in that they additionally comprise B.129 flufenacet as further herbicide B.

Also especially preferred are compositions 61.1 to 61.3617 which differ from the corresponding compositions 1.1 to 1.3617 only in that they additionally comprise B.131 metazachlor as further herbicide B.

Also especially preferred are compositions 62.1 to 62.3617 which differ from the corresponding compositions 1.1 to 1.3617 only in that they additionally comprise B.133 S-metolachlor as further herbicide B.

Also especially preferred are compositions 63.1 to 63.3617 which differ from the corresponding compositions 11.1 to 1.3617 only in that they additionally comprise B.134 pretilachlor as further herbicide B.

Also especially preferred are compositions 64.1 to 64.3617 which differ from the corresponding compositions 1.1 to 1.3617 only in that they additionally comprise B.139 2,4-D as further herbicide B.

Also especially preferred are compositions 65.1 to 65.3617 which differ from the corresponding compositions 1.1 to 1.3617 only in that they additionally comprise B.146 clopyralid as further herbicide B.

Also especially preferred are compositions 66.1 to 66.3617 which differ from the corresponding compositions 1.1 to 1.3617 only in that they additionally comprise B.149 dicamba as further herbicide B.

Also especially preferred are compositions 67.1 to 67.3617 which differ from the corresponding compositions 1.1 to 1.3617 only in that they additionally comprise B.162 MCPA as further herbicide B.

Also especially preferred are compositions 68.1 to 68.3617 which differ from the corresponding compositions 1.1 to 1.3617 only in that they additionally comprise B.165 quinclorac as further herbicide B.

Also especially preferred are compositions 69.1 to 69.3617 which differ from the corresponding compositions 1.1 to 1.3617 only in that they additionally comprise B.176 indaziflam as further herbicide B.

Also especially preferred are compositions 70.1 to 70.3617 which differ from the corresponding compositions 1.1 to 1.3383 only in that they additionally comprise B.2 clodinafop-propargyl as further herbicide B.

Also especially preferred are compositions 71.1 to 71.3617 which differ from the corresponding compositions 2.1 to 2.3617 only in that they additionally comprise B.8 pinoxaden as further herbicide B.

Also especially preferred are compositions 72.1 to 72.3617 which differ from the corresponding compositions 2.1 to 2.3617 only in that they additionally comprise B.30 imazamox as further herbicide B.

Also especially preferred are compositions 73.1 to 73.3617 which differ from the corresponding compositions 2.1 to 2.3617 only in that they additionally comprise B.32 imazapic as further herbicide B.

Also especially preferred are compositions 74.1 to 74.3617 which differ from the corresponding compositions 2.1 to 2.3617 only in that they additionally comprise B.35 imazapyr as further herbicide B.

Also especially preferred are compositions 75.1 to 75.3617 which differ from the corresponding compositions 2.1 to 2.3617 only in that they additionally comprise B.38 imazaquin as further herbicide B.

Also especially preferred are compositions 76.1 to 76.3617 which differ from the corresponding compositions 2.1 to 2.3617 only in that they additionally comprise B.40 imazethapyr as further herbicide B.

Also especially preferred are compositions 77.1 to 77.3617 which differ from the corresponding compositions 2.1 to 2.3617 only in that they additionally comprise B.51 nicosulfuron as further herbicide B.

Also especially preferred are compositions 78.1 to 78.3617 which differ from the corresponding compositions 2.1 to 2.3617 only in that they additionally comprise B.55 pyribenzoxim as further herbicide B.

Also especially preferred are compositions 79.1 to 79.3617 which differ from the corresponding compositions 2.1 to 2.3617 only in that they additionally comprise B.56 pyriftalid as further herbicide B.

Also especially preferred are compositions 80.1 to 80.3617 which differ from the corresponding compositions 2.1 to 2.3617 only in that they additionally comprise B.64 tritosulfuron as further herbicide B.

Also especially preferred are compositions 81.1 to 81.3617 which differ from the corresponding compositions 2.1 to 2.3617 only in that they additionally comprise B.66 ametryne as further herbicide B.

Also especially preferred are compositions 82.1 to 82.3617 which differ from the corresponding compositions 2.1 to 2.3617 only in that they additionally comprise B.67 atrazine as further herbicide B.

Also especially preferred are compositions 83.1 to 83.3617 which differ from the corresponding compositions 2.1 to 2.3617 only in that they additionally comprise B.68 bentazon as further herbicide B.

Also especially preferred are compositions 84.1 to 84.3617 which differ from the corresponding compositions 2.1 to 2.3617 only in that they additionally comprise B.69 bromoxynil as further herbicide B.

Also especially preferred are compositions 85.1 to 85.3617 which differ from the corresponding compositions 2.1 to 2.3617 only in that they additionally comprise B.73 diuron as further herbicide B.

Also especially preferred are compositions 86.1 to 86.3617 which differ from the corresponding compositions 2.1 to 2.3617 only in that they additionally comprise B.76 isoproturon as further herbicide B.

Also especially preferred are compositions 87.1 to 87.3617 which differ from the corresponding compositions 2.1 to 2.3617 only in that they additionally comprise B.81 simazin as further herbicide B.

Also especially preferred are compositions 88.1 to 88.3617 which differ from the corresponding compositions 2.1 to 2.3617 only in that they additionally comprise B.82 terbuthylazin as further herbicide B.

Also especially preferred are compositions 89.1 to 89.3617 which differ from the corresponding compositions 2.1 to 2.3617 only in that they additionally comprise B.85 acifluorfen as further herbicide B.

Also especially preferred are compositions 90.1 to 90.3617 which differ from the corresponding compositions 2.1 to 2.3617 only in that they additionally comprise B.88 flumioxazin as further herbicide B.

Also especially preferred are compositions 91.1 to 91.3617 which differ from the corresponding compositions 2.1 to 2.3617 only in that they additionally comprise B.89 fomesafen as further herbicide B.

Also especially preferred are compositions 92.1 to 92.3617 which differ from the corresponding compositions 2.1 to 2.3617 only in that they additionally comprise B.92 saflufenacil as further herbicide B.

Also especially preferred are compositions 93.1 to 93.3617 which differ from the corresponding compositions 2.1 to 2.3617 only in that they additionally comprise B.93 sulfentrazone as further herbicide B.

Also especially preferred are compositions 94.1 to 94.3617 which differ from the corresponding compositions 2.1 to 2.3617 only in that they additionally comprise B.96 benzbicyclone as further herbicide B.

Also especially preferred are compositions 95.1 to 95.3617 which differ from the corresponding compositions 2.1 to 2.3617 only in that they additionally comprise B.97 clomazone as further herbicide B.

Also especially preferred are compositions 96.1 to 96.3617 which differ from the corresponding compositions 2.1 to 2.3617 only in that they additionally comprise B.100 isoxaflutole as further herbicide B.

Also especially preferred are compositions 97.1 to 97.3617 which differ from the corresponding compositions 2.1 to 2.3617 only in that they additionally comprise B.100 isoxaflutole and B.67 atrazine as further herbicides B.

Also especially preferred are compositions 98.1 to 98.3617 which differ from the corresponding compositions 2.1 to 2.3617 only in that they additionally comprise B.100 isoxaflutole and B.76 isoproturon as further herbicides B.

Also especially preferred are compositions 99.1 to 99.3617 which differ from the corresponding compositions 2.1 to 2.3617 only in that they additionally comprise B.100 isoxaflutole and B.82 terbutylazin as further herbicides B.

Also especially preferred are compositions 100.1 to 100.3617 which differ from the corresponding compositions 2.1 to 2.3617 only in that they additionally comprise B.101 mesotrione as further herbicide B.

Also especially preferred are compositions 101.1 to 101.3617 which differ from the corresponding compositions 2.1 to 2.3617 only in that they additionally comprise B.101 mesotrione and B.67 atrazine as further herbicides B.

Also especially preferred are compositions 102.1 to 102.3617 which differ from the corresponding compositions 2.1 to 2.3617 only in that they additionally comprise B.101 mesotrione and B.76 isoproturon as further herbicides B.

Also especially preferred are compositions 103.1 to 103.3617 which differ from the corresponding compositions 2.1 to 2.3617 only in that they additionally comprise B.101 mesotrione and B.82 terbutylazin as further herbicides B.

Also especially preferred are compositions 104.1 to 104.3617 which differ from the corresponding compositions 2.1 to 2.3617 only in that they additionally comprise B.103 picolinafen as further herbicide B.

Also especially preferred are compositions 105.1 to 105.3617 which differ from the corresponding compositions 2.1 to 2.3617 only in that they additionally comprise B.104 sulcotrione as further herbicide B.

Also especially preferred are compositions 106.1 to 106.3617 which differ from the corresponding compositions 2.1 to 2.3617 only in that they additionally comprise B.104 sulcotrione and B.67 atrazine as further herbicides B.

Also especially preferred are compositions 107.1 to 107.3617 which differ from the corresponding compositions 2.1 to 2.3617 only in that they additionally comprise B.104 sulcotrione and B.76 isoproturon as further herbicides B.

Also especially preferred are compositions 108.1 to 108.3617 which differ from the corresponding compositions 2.1 to 2.3617 only in that they additionally comprise B.104 sulcotrione and B.82 terbutylazin as further herbicides B.

Also especially preferred are compositions 109.1 to 109.3617 which differ from the corresponding compositions 2.1 to 2.3617 only in that they additionally comprise B.106 tembotrione as further herbicide B.

Also especially preferred are compositions 110.1 to 110.3617 which differ from the corresponding compositions 2.1 to 2.3617 only in that they additionally comprise B.107 topramezone as further herbicide B.

Also especially preferred are compositions 111.1 to 111.3617 which differ from the corresponding compositions 2.1 to 2.3617 only in that they additionally comprise B.107 topramezone and B.67 atrazine as further herbicides B.

Also especially preferred are compositions 112.1 to 112.3617 which differ from the corresponding compositions 2.1 to 2.3617 only in that they additionally comprise B.107 topramezone and B.76 isoproturon as further herbicides B.

Also especially preferred are compositions 113.1 to 113.3617 which differ from the corresponding compositions 2.1 to 2.3617 only in that they additionally comprise B.107 topramezone and B.82 terbutylazin as further herbicides B.

Also especially preferred are compositions 114.1 to 114.3617 which differ from the corresponding compositions 2.1 to 2.3617 only in that they additionally comprise B.112 glyphosate as further herbicide B.

Also especially preferred are compositions 115.1 to 115.3617 which differ from the corresponding compositions 2.1 to 2.3617 only in that they additionally comprise B.112 glyphosate and B.67 atrazine as further herbicides B.

Also especially preferred are compositions 116.1 to 116.3617 which differ from the corresponding compositions 2.1 to 2.3617 only in that they additionally comprise B.112 glyphosate and B.92 saflufenacil as further herbicides B.

Also especially preferred are compositions 117.1 to 117.3617 which differ from the corresponding compositions 2.1 to 2.3617 only in that they additionally comprise B.112 glyphosate and B.100 isoxaflutole as further herbicides B.

Also especially preferred are compositions 118.1 to 118.3617 which differ from the corresponding compositions 2.1 to 2.3617 only in that they additionally comprise B.112 glyphosate and B.124 acetochlor as further herbicides B.

Also especially preferred are compositions 119.1 to 119.3617 which differ from the corresponding compositions 2.1 to 2.3617 only in that they additionally comprise B.112 glyphosate and B.101 mesotrione as further herbicides B.

Also especially preferred are compositions 120.1 to 120.3617 which differ from the corresponding compositions 2.1 to 2.3617 only in that they additionally comprise B.112 glyphosate and B.104 sulcotrione as further herbicides B.

Also especially preferred are compositions 121.1 to 121.3617 which differ from the corresponding compositions 2.1 to 2.3617 only in that they additionally comprise B.112 glyphosate and B.107 topramezone as further herbicides B.

Also especially preferred are compositions 122.1 to 122.3617 which differ from the corresponding compositions 2.1 to 2.3617 only in that they additionally comprise B.118 glufosinate as further herbicide B.

Also especially preferred are compositions 123.1 to 123.3617 which differ from the corresponding compositions 2.1 to 2.3617 only in that they additionally comprise B.122 pendimethalin as further herbicide B.

Also especially preferred are compositions 124.1 to 124.3617 which differ from the corresponding compositions 2.1 to 2.3617 only in that they additionally comprise B.124 acetochlor as further herbicide B.

Also especially preferred are compositions 125.1 to 125.3617 which differ from the corresponding compositions 2.1 to 2.3617 only in that they additionally comprise B.127 dimethenamid-P as further herbicide B.

Also especially preferred are compositions 126.1 to 126.3617 which differ from the corresponding compositions 2.1 to 2.3617 only in that they additionally comprise B.128 fentrazamide as further herbicide B.

Also especially preferred are compositions 127.1 to 127.3617 which differ from the corresponding compositions 2.1 to 2.3617 only in that they additionally comprise B.129 flufenacet as further herbicide B.

Also especially preferred are compositions 128.1 to 128.3617 which differ from the corresponding compositions 2.1 to 2.3617 only in that they additionally comprise B.131 metazachlor as further herbicide B.

Also especially preferred are compositions 129.1 to 129.3617 which differ from the corresponding compositions 2.1 to 2.3617 only in that they additionally comprise B.133 S-metolachlor as further herbicide B.

Also especially preferred are compositions 130.1 to 130.3617 which differ from the corresponding compositions 12.1 to 2.3617 only in that they additionally comprise B.134 pretilachlor as further herbicide B.

Also especially preferred are compositions 131.1 to 132.3617 which differ from the corresponding compositions 2.1 to 2.3617 only in that they additionally comprise B.139 2,4-D as further herbicide B.

Also especially preferred are compositions 132.1 to 132.3617 which differ from the corresponding compositions 2.1 to 2.3617 only in that they additionally comprise B.146 clopyralid as further herbicide B.

Also especially preferred are compositions 133.1 to 133.3617 which differ from the corresponding compositions 2.1 to 2.3617 only in that they additionally comprise B.149 dicamba as further herbicide B.

Also especially preferred are compositions 134.1 to 134.3617 which differ from the corresponding compositions 2.1 to 2.3617 only in that they additionally comprise B.162 MCPA as further herbicide B.

Also especially preferred are compositions 135.1 to 135.3617 which differ from the corresponding compositions 2.1 to 2.3617 only in that they additionally comprise B.165 quinclorac as further herbicide B.

Also especially preferred are compositions 136.1 to 136.3617 which differ from the corresponding compositions 2.1 to 2.3617 only in that they additionally comprise B.176 indaziflam as further herbicide B.

Also especially preferred are compositions 137.1 to 137.3617 which differ from the corresponding compositions 2.1 to 2.3383 only in that they additionally comprise B.2 clodinafop-propargyl as further herbicide B.

Also especially preferred are compositions 138.1 to 138.3617 which differ from the corresponding compositions 3.1 to 3.3617 only in that they additionally comprise B.8 pinoxaden as further herbicide B.

Also especially preferred are compositions 139.1 to 139.3617 which differ from the corresponding compositions 3.1 to 3.3617 only in that they additionally comprise B.30 imazamox as further herbicide B.

Also especially preferred are compositions 140.1 to 140.3617 which differ from the corresponding compositions 3.1 to 3.3617 only in that they additionally comprise B.32 imazapic as further herbicide B.

Also especially preferred are compositions 141.1 to 141.3617 which differ from the corresponding compositions 3.1 to 3.3617 only in that they additionally comprise B.35 imazapyr as further herbicide B.

Also especially preferred are compositions 142.1 to 142.3617 which differ from the corresponding compositions 3.1 to 3.3617 only in that they additionally comprise B.38 imazaquin as further herbicide B.

Also especially preferred are compositions 143.1 to 143.3617 which differ from the corresponding compositions 3.1 to 3.3617 only in that they additionally comprise B.40 imazethapyr as further herbicide B.

Also especially preferred are compositions 144.1 to 144.3617 which differ from the corresponding compositions 3.1 to 3.3617 only in that they additionally comprise B.51 nicosulfuron as further herbicide B.

Also especially preferred are compositions 145.1 to 145.3617 which differ from the corresponding compositions 3.1 to 3.3617 only in that they additionally comprise B.55 pyribenzoxim as further herbicide B.

Also especially preferred are compositions 146.1 to 146.3617 which differ from the corresponding compositions 3.1 to 3.3617 only in that they additionally comprise B.56 pyriftalid as further herbicide B.

Also especially preferred are compositions 147.1 to 147.3617 which differ from the corresponding compositions 3.1 to 3.3617 only in that they additionally comprise B.64 tritosulfuron as further herbicide B.

Also especially preferred are compositions 148.1 to 148.3617 which differ from the corresponding compositions 3.1 to 3.3617 only in that they additionally comprise B.66 ametryne as further herbicide B.

Also especially preferred are compositions 149.1 to 149.3617 which differ from the corresponding compositions 3.1 to 3.3617 only in that they additionally comprise B.67 atrazine as further herbicide B.

Also especially preferred are compositions 150.1 to 150.3617 which differ from the corresponding compositions 3.1 to 3.3617 only in that they additionally comprise B.68 bentazon as further herbicide B.

Also especially preferred are compositions 151.1 to 151.3617 which differ from the corresponding compositions 3.1 to 3.3617 only in that they additionally comprise B.69 bromoxynil as further herbicide B.

Also especially preferred are compositions 152.1 to 152.3617 which differ from the corresponding compositions 3.1 to 3.3617 only in that they additionally comprise B.73 diuron as further herbicide B.

Also especially preferred are compositions 153.1 to 153.3617 which differ from the corresponding compositions 3.1 to 3.3617 only in that they additionally comprise B.76 isoproturon as further herbicide B.

Also especially preferred are compositions 154.1 to 154.3617 which differ from the corresponding compositions 3.1 to 3.3617 only in that they additionally comprise B.81 simazin as further herbicide B.

Also especially preferred are compositions 155.1 to 155.3617 which differ from the corresponding compositions 3.1 to 3.3617 only in that they additionally comprise B.82 terbuthylazin as further herbicide B.

Also especially preferred are compositions 156.1 to 156.3617 which differ from the corresponding compositions 3.1 to 3.3617 only in that they additionally comprise B.85 acifluorfen as further herbicide B.

Also especially preferred are compositions 157.1 to 157.3617 which differ from the corresponding compositions 3.1 to 3.3617 only in that they additionally comprise B.88 flumioxazin as further herbicide B.

Also especially preferred are compositions 158.1 to 158.3617 which differ from the corresponding compositions 3.1 to 3.3617 only in that they additionally comprise B.89 fomesafen as further herbicide B.

Also especially preferred are compositions 159.1 to 159.3617 which differ from the corresponding compositions 3.1 to 3.3617 only in that they additionally comprise B.92 saflufenacil as further herbicide B.

Also especially preferred are compositions 160.1 to 160.3617 which differ from the corresponding compositions 3.1 to 3.3617 only in that they additionally comprise B.93 sulfentrazone as further herbicide B.

Also especially preferred are compositions 161.1 to 161.3617 which differ from the corresponding compositions 3.1 to 3.3617 only in that they additionally comprise B.96 benzbicyclone as further herbicide B.

Also especially preferred are compositions 162.1 to 162.3617 which differ from the corresponding compositions 3.1 to 3.3617 only in that they additionally comprise B.97 clomazone as further herbicide B.

Also especially preferred are compositions 163.1 to 163.3617 which differ from the corresponding compositions 3.1 to 3.3617 only in that they additionally comprise B.100 isoxaflutole as further herbicide B.

Also especially preferred are compositions 164.1 to 164.3617 which differ from the corresponding compositions 3.1 to 3.3617 only in that they additionally comprise B.100 isoxaflutole and B.67 atrazine as further herbicides B.

Also especially preferred are compositions 165.1 to 165.3617 which differ from the corresponding compositions 3.1 to 3.3617 only in that they additionally comprise B.100 isoxaflutole and B.76 isoproturon as further herbicides B.

Also especially preferred are compositions 166.1 to 166.3617 which differ from the corresponding compositions 3.1 to 3.3617 only in that they additionally comprise B.100 isoxaflutole and B.82 terbutylazin as further herbicides B.

Also especially preferred are compositions 167.1 to 167.3617 which differ from the corresponding compositions 3.1 to 3.3617 only in that they additionally comprise B.101 mesotrione as further herbicide B.

Also especially preferred are compositions 168.1 to 168.3617 which differ from the corresponding compositions 3.1 to 3.3617 only in that they additionally comprise B.101 mesotrione and B.67 atrazine as further herbicides B.

Also especially preferred are compositions 169.1 to 169.3617 which differ from the corresponding compositions 3.1 to 3.3617 only in that they additionally comprise B.101 mesotrione and B.76 isoproturon as further herbicides B.

Also especially preferred are compositions 170.1 to 170.3617 which differ from the corresponding compositions 3.1 to 3.3617 only in that they additionally comprise B.101 mesotrione and B.82 terbutylazin as further herbicides B.

Also especially preferred are compositions 171.1 to 171.3617 which differ from the corresponding compositions 3.1 to 3.3617 only in that they additionally comprise B.103 picolinafen as further herbicide B.

Also especially preferred are compositions 172.1 to 172.3617 which differ from the corresponding compositions 3.1 to 3.3617 only in that they additionally comprise B.104 sulcotrione as further herbicide B.

Also especially preferred are compositions 173.1 to 173.3617 which differ from the corresponding compositions 3.1 to 3.3617 only in that they additionally comprise B.104 sulcotrione and B.67 atrazine as further herbicides B.

Also especially preferred are compositions 174.1 to 174.3617 which differ from the corresponding compositions 3.1 to 3.3617 only in that they additionally comprise B.104 sulcotrione and B.76 isoproturon as further herbicides B.

Also especially preferred are compositions 175.1 to 175.3617 which differ from the corresponding compositions 3.1 to 3.3617 only in that they additionally comprise B.104 sulcotrione and B.82 terbutylazin as further herbicides B.

Also especially preferred are compositions 176.1 to 176.3617 which differ from the corresponding compositions 3.1 to 3.3617 only in that they additionally comprise B.106 tembotrione as further herbicide B.

Also especially preferred are compositions 177.1 to 177.3617 which differ from the corresponding compositions 3.1 to 3.3617 only in that they additionally comprise B.107 topramezone as further herbicide B.

Also especially preferred are compositions 178.1 to 178.3617 which differ from the corresponding compositions 3.1 to 3.3617 only in that they additionally comprise B.107 topramezone and B.67 atrazine as further herbicides B.

Also especially preferred are compositions 179.1 to 179.3617 which differ from the corresponding compositions 3.1 to 3.3617 only in that they additionally comprise B.107 topramezone and B.76 isoproturon as further herbicides B.

Also especially preferred are compositions 180.1 to 180.3617 which differ from the corresponding compositions 3.1 to 3.3617 only in that they additionally comprise B.107 topramezone and B.82 terbutylazin as further herbicides B.

Also especially preferred are compositions 181.1 to 181.3617 which differ from the corresponding compositions 3.1 to 3.3617 only in that they additionally comprise B.112 glyphosate as further herbicide B.

Also especially preferred are compositions 182.1 to 182.3617 which differ from the corresponding compositions 3.1 to 3.3617 only in that they additionally comprise B.112 glyphosate and B.67 atrazine as further herbicides B.

Also especially preferred are compositions 183.1 to 183.3617 which differ from the corresponding compositions 3.1 to 3.3617 only in that they additionally comprise B.112 glyphosate and B.92 saflufenacil as further herbicides B.

Also especially preferred are compositions 184.1 to 184.3617 which differ from the corresponding compositions 3.1 to 3.3617 only in that they additionally comprise B.112 glyphosate and B.100 isoxaflutole as further herbicides B.

Also especially preferred are compositions 185.1 to 185.3617 which differ from the corresponding compositions 3.1 to 3.3617 only in that they additionally comprise B.112 glyphosate and B.124 acetochlor as further herbicides B.

Also especially preferred are compositions 186.1 to 186.3617 which differ from the corresponding compositions 3.1 to 3.3617 only in that they additionally comprise B.112 glyphosate and B.101 mesotrione as further herbicides B.

Also especially preferred are compositions 187.1 to 187.3617 which differ from the corresponding compositions 3.1 to 3.3617 only in that they additionally comprise B.112 glyphosate and B.104 sulcotrione as further herbicides B.

Also especially preferred are compositions 188.1 to 188.3617 which differ from the corresponding compositions 3.1 to 3.3617 only in that they additionally comprise B.112 glyphosate and B.107 topramezone as further herbicides B.

Also especially preferred are compositions 189.1 to 189.3617 which differ from the corresponding compositions 3.1 to 3.3617 only in that they additionally comprise B.118 glufosinate as further herbicide B.

Also especially preferred are compositions 190.1 to 190.3617 which differ from the corresponding compositions 3.1 to 3.3617 only in that they additionally comprise B.122 pendimethalin as further herbicide B.

Also especially preferred are compositions 191.1 to 191.3617 which differ from the corresponding compositions 3.1 to 3.3617 only in that they additionally comprise B.124 acetochlor as further herbicide B.

Also especially preferred are compositions 192.1 to 192.3617 which differ from the corresponding compositions 3.1 to 3.3617 only in that they additionally comprise B.127 dimethenamid-P as further herbicide B.

Also especially preferred are compositions 193.1 to 193.3617 which differ from the corresponding compositions 3.1 to 3.3617 only in that they additionally comprise B.128 fentrazamide as further herbicide B.

Also especially preferred are compositions 194.1 to 194.3617 which differ from the corresponding compositions 3.1 to 3.3617 only in that they additionally comprise B.129 flufenacet as further herbicide B.

Also especially preferred are compositions 195.1 to 195.3617 which differ from the corresponding compositions 3.1 to 3.3617 only in that they additionally comprise B.131 metazachlor as further herbicide B.

Also especially preferred are compositions 196.1 to 196.3617 which differ from the corresponding compositions 3.1 to 3.3617 only in that they additionally comprise B.133 S-metolachlor as further herbicide B.

Also especially preferred are compositions 197.1 to 197.3617 which differ from the corresponding compositions 13.1 to 3.3617 only in that they additionally comprise B.134 pretilachlor as further herbicide B.

Also especially preferred are compositions 198.1 to 198.3617 which differ from the corresponding compositions 3.1 to 3.3617 only in that they additionally comprise B.139 2,4-D as further herbicide B.

Also especially preferred are compositions 199.1 to 199.3617 which differ from the corresponding compositions 3.1 to 3.3617 only in that they additionally comprise B.146 clopyralid as further herbicide B.

Also especially preferred are compositions 200.1 to 200.3617 which differ from the corresponding compositions 3.1 to 3.3617 only in that they additionally comprise B.149 dicamba as further herbicide B.

Also especially preferred are compositions 201.1 to 201.3617 which differ from the corresponding compositions 3.1 to 3.3617 only in that they additionally comprise B.162 MCPA as further herbicide B.

Also especially preferred are compositions 202.1 to 202.3617 which differ from the corresponding compositions 3.1 to 3.3617 only in that they additionally comprise B.165 quinclorac as further herbicide B.

Also especially preferred are compositions 203.1 to 203.3617 which differ from the corresponding compositions 3.1 to 3.3617 only in that they additionally comprise B.176 indaziflam as further herbicide B.

Also especially preferred are compositions 204.1 to 204.3617 which differ from the corresponding compositions 3.1 to 3.3383 only in that they additionally comprise B.2 clodinafop-propargyl as further herbicide B.

The invention also relates to agrochemical compositions comprising an auxiliary and a composition according to the invention.

An agrochemical composition comprises a pesticidally effective amount of at least one composition according to the invention. The term "effective amount" denotes an amount of the active ingredients, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific composition according to the invention used.

The compounds A and optionally B and/or C, their N-oxides, salts or derivatives can be converted into customary types of agrochemical compositions, e. g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, $6^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-Soluble Concentrates (SL, LS)

10-60 wt % of a composition according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a composition according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a composition according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a composition according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a composition according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a composition according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a composition according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a composition according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

ix) Microemulsion (ME)

5-20 wt % of a composition according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a composition according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable Powders (DP, DS)

1-10 wt % of a composition according to the invention are ground finely and mixed intimately with solid carrier (e.g. finely divided kaolin) ad 100 wt %.

xii) Granules (GR, FG)

0.5-30 wt % of a composition according to the invention is ground finely and associated with solid carrier (e.g. silicate) ad 100 wt %. Granulation is achieved by extrusion, spray-drying or the fluidized bed.

xiii) Ultra-Low Volume Liquids (UL)

1-50 wt % of a composition according to the invention are dissolved in organic solvent (e.g. aromatic hydrocarbon) ad 100 wt %.

The agrochemical composition types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying compounds of formula (I) and compositions comprising them, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the agrochemical composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e. g. agrochemical components comprising an isoxazolo[5,4-b]pyridine of formula (I) and/or active substances from the groups B and/or C may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g. components comprising an isoxazolo[5,4-b]pyridine of formula (I) and active substances from the groups B and/or C, can be applied jointly (e.g. after tank mix) or consecutively.

Accordingly, a first embodiment of the invention relates to compositions in the form of an agrochemical composition formulated as a 1-component composition comprising the at least one isoxazolo[5,4-b]pyridine of formula (I) (component A) and as component B at least one further active compound selected from the herbicides B, and, if desired, the safeners C and also a solid or liquid carrier and, if appropriate, one or more surfactants.

Accordingly, a second embodiment of the invention relates to compositions in the form of a agrochemical composition formulated as a 2-component composition comprising a first formulation (component) comprising the at least one isoxazolo[5,4-b]pyridine of formula (I) (component A), a solid or liquid carrier and, if appropriate, one or more surfactants, and as component B at least one further herbicide B and safeners C, a solid or liquid carrier and, if appropriate, one or more surfactants.

The isoxazolo[5,4-b]pyridine of formula (I) (component A) and the at least one further active herbicide B (component B) and/or C can be formulated and applied jointly or separately, simultaneously or in succession, before, during or after the emergence of the plants. In case of separate application, the order of the application of the components A, B and/or C is of minor importance. The only thing that is important is that the at least one isoxazolo[5,4-b]pyridine of formula (I) and the at least one further herbicide B and/or C are present simultaneously at the site of action, i.e. are at the same time in contact with or taken up by the plant to be controlled.

The compositions according to the invention are suitable as herbicides. They are suitable as such or as an appropriately formulated composition (agrochemical composition).

The compositions according to the invention control vegetation on non-crop areas very efficiently, especially at high rates of application. They act against broad-leafed weeds and grass weeds in crops such as wheat, rice, corn, soybeans and cotton without causing any significant damage to the crop plants. This effect is mainly observed at low rates of application.

The compositions according to the invention are applied to the plants mainly by spraying the leaves. Here, the application can be carried out using, for example, water as carrier by customary spraying techniques using spray liquor amounts of from about 100 to 1000 l/ha (for example from 300 to 400 l/ha). The herbicidal compositions may also be applied by the low-volume or the ultra-low-volume method, or in the form of microgranules.

Application of the herbicidal compositions according to the present invention can be done before, during and/or after, preferably during and/or after, the emergence of the undesirable plants.

The herbicidal compositions according to the present invention can be applied pre- or post-emergence or together with the seed of a crop plant. It is also possible to apply the compounds and compositions by applying seed, pretreated with a composition of the invention, of a crop plant. If the active components A and B, and, if appropriate, C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

In a further embodiment, the composition according to the invention can be applied by treating seed. The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the isoxazolo[5,4-b]pyridine of formula (I) according to the invention or the compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

Moreover, it may be advantageous to apply the compositions of the present invention on their own or jointly in combination with other crop protection agents, for example with agents for controlling pests or phytopathogenic fungi or bacteria or with groups of active compounds which regulate growth. Also of interest is the miscibility with mineral salt solutions which are employed for treating nutritional and trace element deficiencies. Non-phytotoxic oils and oil concentrates can also be added.

When employed in plant protection, the amounts of active substances applied, i.e. components A and B, and, if appropriate, C, without formulation auxiliaries, are, depending on the kind of effect desired, from 0.001 to 3 kg/ha, preferably from 0.005 to 2.5 kg/ha and in particular from 0.01 to 2 kg/ha of active substance (a.s.).

In another preferred embodiment of the invention, the rates of application of the isoxazolo[5,4-b]pyridine of formula (I) according to the present invention (total amount of isoxazolo[5,4-b]pyridine of formula (I)) are from 0.1 g/ha to 3000 g/ha, preferably 10 g/ha to 1000 g/ha, depending on the control target, the season, the target plants and the growth stage.

In another preferred embodiment of the invention, the application rates of the isoxazolo[5,4-b]pyridine of formula (I) are in the range from 0.1 g/ha to 5000 g/ha and preferably in the range from 1 g/ha to 2500 g/ha or from 5 g/ha to 2000 g/ha.

In another preferred embodiment of the invention, the application rate of the isoxazolo[5,4-b]pyridine of formula (I) is 0.1 to 1000 g/ha, preferably 1 to 750 g/ha, more preferably 5 to 500 g/ha.

The required application rates of herbicides B are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of safeners C are generally in the range of from 0.0005 kg/ha to 2.5 kg/ha and preferably in the range of from 0.005 kg/ha to 2 kg/ha or 0.01 kg/ha to 1.5 kg/h of a.s.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of composition components applied, i.e. A and B, and, if appropriate, C, are generally employed in amounts of from 0.001 to 10 kg per 100 kg of seed.

When used in the protection of materials or stored products, the amount of composition components applied depends on the kind of application area and on the desired effect. Amounts customarily applied in the protection of materials are 0.001 g to 2 kg, preferably 0.005 g to 1 kg, of active substance per cubic meter of treated material.

In the methods of the present invention it is immaterial whether the isoxazolo[5,4-b]pyridine of formula (I), and the further herbicide B and/or the safener C are formulated and applied jointly or separately.

In the case of separate application it is of minor importance, in which order the application takes place. It is only necessary, that the isoxazolo[5,4-b]pyridine of formula (I) and the herbicide B and/or the herbicide safener C are applied in a time frame that allows simultaneous action of the active ingredients on the plants, preferably within a time-frame of at most 14 days, in particular at most 7 days.

Depending on the application method in question, the compositions according to the invention can additionally be employed in a further number of crop plants for eliminating undesirable plants. Examples of suitable crops are the following: *Allium cepa, Ananas comosus, Arachis hypogaea, Asparagus officinalis, Avena sativa, Beta vulgaris* spec. *altissima, Beta vulgaris* spec. *rapa, Brassica napus* var.

*napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis and prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera, Zea mays.*

Preferred crops are *Arachis hypogaea, Beta vulgaris* spec. *altissima, Brassica napus* var. *napus, Brassica oleracea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus* spec., *Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (s. vulgare), Triticale, Triticum aestivum, Triticum durum, Vicia faba, Vitis vinifera and Zea mays*

Especially preferred crops are crops of cereals, corn, soybeans, rice, millets, oilseed rape, cotton, sugarcane, potatoes, legumes, turf or permanent crops.

The compositions according to the invention can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides, e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxinic herbicides such as dicamba or 2,4-D; bleacher herbicides such as 4-hydroxyphenylpyruvate dioxygenase (HPPD) inhibitors or phytoene desaturase (PDS) inhibitors; acetolactate synthase (ALS) inhibitors such as sulfonylureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors (PPO); lipid biosynthesis inhibitors such as acetylCoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxinic herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® summer rape (Canola, BASF SE, Germany) being tolerant to imidazolinones, e. g., imazamox, or ExpressSun® sunflowers (DuPont, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e. g., CryIA(b), CryIA(c), CryIF, CryIF(a2), CryIIA(b), CryIIIA, CryIIIB(b1) or Cry9c; vegetative insecticidal proteins (VIP), e. g., VIP1, VIP2, VIP3 or VIP3A; insecticidal proteins of bacteria colonizing nematodes, e. g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451

878, WO 03/18810 and WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S. A., Belgium (corn cultivars producing the Cry3Bb1 toxin), IPC 531 from Monsanto Europe S. A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow Agro-Sciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the compositions according to the invention are also suitable for the defoliation and/or desiccation of plant parts, for which crop plants such as cotton, potato, oilseed rape, sunflower, soybean or field beans, in particular cotton, are suitable. In this regard compositions have been found for the desiccation and/or defoliation of plants, processes for preparing these compositions, and methods for desiccating and/or defoliating plants using the compositions according to the invention.

As desiccants, the compositions according to the invention are suitable in particular for desiccating the above-ground parts of crop plants such as potato, oilseed rape, sunflower and soybean, but also cereals. This makes possible the fully mechanical harvesting of these important crop plants.

Also of economic interest is the facilitation of harvesting, which is made possible by concentrating within a certain period of time the dehiscence, or reduction of adhesion to the tree, in *citrus* fruit, olives and other species and varieties of pomaceous fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

USE EXAMPLES

The following examples serve to illustrate the invention.

The herbicidal action of the compositions according to the invention was demonstrated by the following greenhouse experiments:

The culture containers used were plastic pots containing medium loamy sand with approximately 4.6% of humus and 69.9% sand as substrate. The seeds of the test plants were sown separately for each species.

For the pre-emergence treatment, the active compounds, suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants unless this was adversely affected by the active compounds.

For the post-emergence treatment, the test plants were grown to a plant height of from 1 to 15 cm, depending on the plant habit, and only then treated with the active compounds which had been suspended or emulsified in water. To this end, the test plants were either sown directly, and grown in the same containers, or they were first grown separately as seedlings and transplanted into the test containers a few days prior to treatment.

Depending on the species, the plants were kept at 10-25° C. and 20-35° C., respectively.

The test period extended over 1 to 3 weeks. During this time, the plants were tended and their response to the individual treatments was evaluated 20 days after treatment except mentioned otherwise.

Evaluation was carried out using a scale from 0 to 100. 100 means no emergence of the plants, or complete destruction of at least the above-ground parts, and 0 means no damage or normal course of growth.

The respective stated components A and B, and, if appropriate, C, were formulated as a 10% by weight strength emulsion concentrate and, with addition of the amount of solvent system, introduced into the spray liquor used for applying the active compound.

In the examples, the solvent used was water.

In the examples below, using the method of S. R. Colby (1967) "Calculating synergistic and antagonistic responses of herbicide combinations", Weeds 15, p. 22 ff., the value E, which is expected if the activity of the individual active compounds is only additive, was calculated.

$$E = X + Y - (X \cdot Y/100)$$

where
X = percent activity using active compound A at an application rate a;
Y = percent activity using active compound B at an application rate b;
E = expected activity (in %) by A+B at application rates a+b.

If the value found experimentally is higher than the value E calculated according to Colby, a synergistic effect is present.

The plants used in the greenhouse experiments were of the following species:

| Bayer code | Scientific name |
|---|---|
| ABUTH | Abutilon theophrast |
| ALOMY | Alopecurus myosuroides |
| AMARE | Amaranthus retroflexus |
| AMBEL | Ambrosia artemisiifolia |
| APESV | Apera spica-venti |
| CHEAL | Chenopodium album |
| CONAR | Convolvulus arvensis |
| DIGSA | Digitaria sanguinalis |
| ECHCG | Echinochloa crus-galli |
| ERICA | Conyza canadensis |
| GALAP | Galium aparine |
| GERDI | Geranium dissectum |
| GERPU | Geranium pusillum |
| IPOHE | Ipomoea hederacea |
| KCHSC | Kochia scoparia |
| LAMAM | Lamium amplexicaule |
| LOLMU | Lolium multiflorum |
| MATCH | Matricaria recutita |
| PANMI | Panicum miliaceum |
| PAPRH | Papaver rhoeas |
| POLAV | Polygonum aviculare |
| POLCO | Polygonum convolvulus |
| POLPE | Persicaria maculosa |
| SASKR | Salsola kali |
| SEBEX | Sesbania exaltata |
| SETVI | Setaria viridis |
| STEME | Stellaria media |
| VIOAR | Viola arvensis | note:
100-90%: "very good" 90-80%: "good"

The results of these tests are given below in the use examples and demonstrate the synergistic effect of the mixtures comprising at least one compound of the formula (I) and at least one herbicide B. In this context, a.i. means active ingredient, based on 100% active ingredient.

Use Example 1: Synergistic Herbicidal Action of the Composition 1.190 Applied by the Post Emergence Method: Treatment by the Mixture of Compound (I.1)+Chlorotoluron (B.190)

| application rate a.i. in g/ha | | herbicidal activity against | | | | | | | | | |
|---|---|---|---|---|---|---|---|---|---|---|---|
| | | POLCO | | AMARE | | STEME | | GERDI | | IPOHE | |
| I.1 | B.190 | found | calculated | found | calculated | found | calculated | found | calculated | found | calculated |
| 31.25 | — | 50 | — | 35 | — | 70 | — | 30 | — | 65 | — |
| — | 62.5 | 50 | — | 40 | — | 70 | — | 60 | — | 60 | — |
| 31.25 | 62.5 | 100 | 75 | 98 | 61 | 100 | 91 | 100 | 72 | 100 | 86 |

| application rate a.i. in g/ha | | herbicidal activity against | | | | | | | | | |
|---|---|---|---|---|---|---|---|---|---|---|---|
| | | POLCO | | IPOHE | | POLAV | | AMARE | | CHEAL | |
| I.1 | B.190 | found | calculated | found | calculated | found | calculated | found | calculated | found | calculated |
| 15.6 | — | 30 | — | 50 | — | 45 | — | 30 | — | 70 | — |
| — | 62.5 | 50 | — | 60 | — | 50 | — | 40 | — | 95 | — |
| 15.6 | 62.5 | 100 | 65 | 100 | 80 | 100 | 73 | 98 | 58 | 100 | 99 |

Use Example 2: Synergistic Herbicidal Action Applied by the Post Emergence Method: Treatment by the Mixture of Compound (I.1)+Bentazon in Form of Sodium-Salt (Bentazon Na)

| application rate a.i. in g/ha | | herbicidal activity against | | | | | |
|---|---|---|---|---|---|---|---|
| | | POLCO | | AMARE | | POLAV | |
| I.1 | bentazon Na | found | calculated | found | calculated | found | calculated |
| 31.25 | — | 50 | — | 35 | — | 80 | — |
| — | 125 | 40 | — | 75 | — | 40 | — |
| 31.25 | 125 | 90 | 70 | 98 | 84 | 90 | 88 |

Use Example 3: Synergistic Herbicidal Action of the Composition 1.67 Applied by the Post Emergence Method: Treatment by the Mixture of Compound (I.1)+Atrazine (B.67)

| application rate a.i. in g/ha | | \multicolumn{2}{c|}{LOLMU} | \multicolumn{2}{c|}{PHACA} | \multicolumn{2}{c|}{GERDI} | \multicolumn{2}{c|}{MATCH} | \multicolumn{2}{c|}{CONAR} |
|---|---|---|---|---|---|---|---|---|---|---|---|
| I.1 | B.67 | found | calculated | found | calculated | found | calculated | found | calculated | found | calculated |
| 62.5 | — | 20 | — | 35 | — | 40 | — | 0 | — | 0 | — |
| — | 125 | 35 | — | 30 | — | 70 | — | 50 | — | 65 | — |
| 62.5 | 125 | 80 | 48 | 70 | 55 | 100 | 82 | 100 | 50 | 98 | 65 |

| application rate a.i. in g/ha | | \multicolumn{2}{c|}{ABUTH} | | | | | | | | |
|---|---|---|---|---|---|---|---|---|---|---|---|
| I.1 | B.67 | found | calculated | found | calculated | found | calculated | found | calculated | found | calculated |
| 62.5 | — | 90 | — | — | — | — | — | — | — | — | — |
| — | 125 | 60 | — | — | — | — | — | — | — | — | — |
| 62.5 | 125 | 100 | 96 | — | — | — | — | — | — | — | — |

| application rate a.i. in g/ha | | \multicolumn{2}{c|}{ABUTH} | \multicolumn{2}{c|}{STEME} | \multicolumn{2}{c|}{MATCH} | \multicolumn{2}{c|}{GERDI} | | |
|---|---|---|---|---|---|---|---|---|---|---|---|
| I.1 | B.67 | found | calculated | found | calculated | found | calculated | found | calculated | | |
| 31.25 | — | 60 | — | 70 | — | 30 | — | 30 | — | | |
| — | 125 | 60 | — | 75 | — | 70 | — | 85 | — | | |
| 31.25 | 125 | 95 | 84 | 100 | 93 | 100 | 79 | 100 | 90 | | |

| application rate a.i. in g/ha | | \multicolumn{2}{c|}{LOLMU} | \multicolumn{2}{c|}{PHACA} | \multicolumn{2}{c|}{POLCO} | \multicolumn{2}{c|}{CHEAL} | \multicolumn{2}{c|}{GALAP} |
|---|---|---|---|---|---|---|---|---|---|---|---|
| I.1 | B.67 | found | calculated | found | calculated | found | calculated | found | calculated | found | calculated |
| 31.25 | — | 0 | — | 0 | — | 0 | — | 65 | — | 75 | — |
| — | 125 | 35 | — | 30 | — | 60 | — | 80 | — | 70 | — |
| 31.25 | 125 | 80 | 35 | 70 | 0 | 100 | 60 | 98 | 93 | 100 | 93 |

| application rate a.i. in g/ha | | \multicolumn{2}{c|}{ABUTH} | \multicolumn{2}{c|}{MATCH} | \multicolumn{2}{c|}{CONAR} | \multicolumn{2}{c|}{STEME} | \multicolumn{2}{c|}{GERDI} |
|---|---|---|---|---|---|---|---|---|---|---|---|
| I.1 | B.67 | found | calculated | found | calculated | found | calculated | found | calculated | found | calculated |
| 31.25 | — | 60 | — | 30 | — | 0 | — | 70 | — | 30 | — |
| — | 125 | 60 | — | 70 | — | 65 | — | 75 | — | 85 | — |
| 31.25 | 125 | 95 | 84 | 100 | 79 | 95 | 65 | 100 | 93 | 100 | 90 |

| application rate a.i. in g/ha | | \multicolumn{2}{c|}{CHEAL} | \multicolumn{2}{c|}{GERDI} | \multicolumn{2}{c|}{POLCO} | \multicolumn{2}{c|}{GALAP} | | |
|---|---|---|---|---|---|---|---|---|---|---|---|
| I.1 | B.67 | found | calculated | found | calculated | found | calculated | found | calculated | | |
| 15.6 | — | 0 | — | 0 | — | 0 | — | 20 | — | | |
| — | 125 | 80 | — | 70 | — | 60 | — | 70 | — | | |
| 15.6 | 125 | 98 | 80 | 100 | 70 | 70 | 60 | 85 | 76 | | |

| application rate a.i. in g/ha | | \multicolumn{2}{c|}{LOLMU} | \multicolumn{2}{c|}{ABUTH} | \multicolumn{2}{c|}{STEME} | \multicolumn{2}{c|}{CONAR} | | |
|---|---|---|---|---|---|---|---|---|---|---|---|
| I.1 | B.67 | found | calculated | found | calculated | found | calculated | found | calculated | | |
| 15.6 | — | 0 | — | 30 | — | 0 | — | 0 | — | | |
| — | 125 | 35 | — | 60 | — | 75 | — | 65 | — | | |
| 15.6 | 125 | 70 | 35 | 85 | 72 | 100 | 75 | 98 | 65 | | |

-continued

| application rate | | herbicidal activity against | | | | | | | | |
|---|---|---|---|---|---|---|---|---|---|---|
| a.i. in g/ha | | GERDI | | LOLMU | | ABUTH | | CONAR | | |
| I.1 | B.67 | found | calculated | found | calculated | found | calculated | found | calculated | found | calculated |
| 7.8 | — | 0 | — | 0 | — | 0 | — | 0 | — | — | — |
| — | 125 | 70 | — | 35 | — | 60 | — | 65 | — | — | — |
| 7.8 | 125 | 100 | 70 | 60 | 35 | 80 | 60 | 98 | 65 | | |

| application rate | | herbicidal activity against | | | | | | | | |
|---|---|---|---|---|---|---|---|---|---|---|
| a.i. in g/ha | | ALOMY | | LOLMU | | ECHCG | | GALAP | | CONAR |
| I.1 | B.67 | found | calculated | found | calculated | found | calculated | found | calculated | found | calculated |
| 62.5 | — | 0 | — | 40 | — | 65 | — | 10 | — | 25 | — |
| — | 62.5 | 35 | — | 20 | — | 35 | — | 65 | — | 60 | — |
| 62.5 | 62.5 | 65 | 35 | 65 | 52 | 85 | 77 | 90 | 69 | 85 | 70 |

| application rate | | herbicidal activity against | | | | | | | | |
|---|---|---|---|---|---|---|---|---|---|---|
| a.i. in g/ha | | POLCO | | | | | | | | |
| I.1 | B.67 | found | calculated | found | calculated | found | calculated | found | calculated | found | calculated |
| 62.5 | — | 65 | — | — | — | — | — | — | — | — | — |
| — | 62.5 | 80 | — | — | — | — | — | — | — | — | — |
| 62.5 | 62.5 | 100 | 93 | | | | | | | | |

| application rate | | herbicidal activity against | | | | | | | | |
|---|---|---|---|---|---|---|---|---|---|---|
| a.i. in g/ha | | ALOMY | | POLCO | | CHEAL | | GALAP | | STEME |
| I.1 | B.67 | found | calculated | found | calculated | found | calculated | found | calculated | found | calculated |
| 20.8 | — | 0 | — | 30 | — | 85 | — | 0 | — | 50 | — |
| — | 62.5 | 35 | — | 80 | — | 75 | — | 65 | — | 80 | — |
| 20.8 | 62.5 | 50 | 35 | 100 | 86 | 100 | 96 | 70 | 65 | 100 | 90 |

| application rate | | herbicidal activity against | | | | | | | | |
|---|---|---|---|---|---|---|---|---|---|---|
| a.i. in g/ha | | CONAR | | ECHCG | | | | | | |
| I.1 | B.67 | found | calculated | found | calculated | found | calculated | found | calculated | found | calculated |
| 20.8 | — | 0 | — | 30 | — | — | — | — | — | — | — |
| — | 62.5 | 60 | — | 35 | — | — | — | — | — | — | — |
| 20.8 | 62.5 | 65 | 60 | 60 | 55 | | | | | | |

| application rate | | herbicidal activity against | | | | | | | | |
|---|---|---|---|---|---|---|---|---|---|---|
| a.i. in g/ha | | ALOMY | | STEME | | APESV | | CHEAL | | |
| I.1 | B.67 | found | calculated | found | calculated | found | calculated | found | calculated | found | calculated |
| 6.9 | — | 0 | — | 0 | — | 0 | — | 0 | — | — | — |
| — | 62.5 | 35 | — | 80 | — | 60 | — | 75 | — | — | — |
| 6.9 | 62.5 | 40 | 35 | 100 | 80 | 65 | 60 | 85 | 75 | | |

-continued

| application rate a.i. in g/ha | | herbicidal activity against | | | | | | | | |
|---|---|---|---|---|---|---|---|---|---|---|
| | | STEME | | APESV | | | | | | |
| I.1 | B.67 | found | calculated | found | calculated | found | calculated | found | calculated | found | calculated |
| 2.3 | — | 0 | — | 0 | — | | | | | |
| — | 62.5 | 80 | — | 60 | — | | | | | |
| 2.3 | 62.5 | 100 | 80 | 65 | 60 | | | | | |

Use Example 4: Synergistic Herbicidal Action of the Composition 1.69 Applied by the Post Emergence Method: Treatment by the Mixture of Compound (I.1)+Bromoxynil (B.69)

| application rate a.i. in g/ha | | herbicidal activity against | | | | | | | | |
|---|---|---|---|---|---|---|---|---|---|---|
| | | ABUTH | | CHEAL | | GALAP | | ERICA | | CONAR | |
| I.1 | B.69 | found | calculated | found | calculated | found | calculated | found | calculated | found | calculated |
| 62.5 | — | 50 | — | 60 | — | 65 | — | 90 | — | 65 | — |
| — | 25 | 35 | — | 60 | — | 50 | — | 30 | — | 50 | — |
| 62.5 | 25 | 85 | 68 | 100 | 84 | 100 | 83 | 100 | 93 | 100 | 83 |

| application rate a.i. in g/ha | | herbicidal activity against | | | | | |
|---|---|---|---|---|---|---|---|
| | | CHEAL | | CONAR | | MATCH | |
| I.1 | B.69 | found | calculated | found | calculated | found | calculated |
| 31.25 | — | 30 | — | 70 | — | 30 | — |
| — | 25 | 60 | — | 50 | — | 0 | — |
| 31.25 | 25 | 85 | 72 | 100 | 85 | 100 | 30 |

Use Example 5: Synergistic Herbicidal Action of the Composition 1.191 Applied by the Post Emergence Method: Treatment by the Mixture of Compound (I.1)+Pyridate (B.191)

| application rate a.i. in g/ha | | herbicidal activity against | | | | | | | |
|---|---|---|---|---|---|---|---|---|---|
| | | GALAP | | STEME | | MATCH | | ERICA | |
| I.1 | B.191 | found | calculated | found | calculated | found | calculated | found | calculated |
| 62.5 | — | 65 | — | 85 | — | 30 | — | 90 | — |
| — | 225 | 90 | — | 0 | — | 20 | — | 70 | — |
| 62.5 | 225 | 100 | 97 | 100 | 85 | 95 | 44 | 100 | 97 |

Use Example 6: Synergistic Herbicidal Action of the Composition 1.76 Applied by the Post Emergence Method: Treatment by the Mixture of Compound (I.1)+Isoproturon (B.76)

| application rate a.i. in g/ha | | herbicidal activity against | | | | | |
|---|---|---|---|---|---|---|---|
| | | CHEAL | | CONAR | | DIGSA | |
| I.1 | B.76 | found | calculated | found | calculated | found | calculated |
| 62.5 | — | 60 | — | 65 | — | 40 | — |
| — | 225 | 65 | — | 65 | — | 30 | — |
| 62.5 | 225 | 100 | 86 | 100 | 88 | 65 | 58 |

-continued

| application rate a.i. in g/ha | | herbicidal activity against | | | | | |
|---|---|---|---|---|---|---|---|
| | | AMARE | | CHEAL | | DIGSA | |
| I.1 | B.76 | found | calculated | found | calculated | found | calculated |
| 31.25 | — | 90 | — | 30 | — | 35 | — |
| — | 225 | 50 | — | 65 | — | 30 | — |
| 31.25 | 225 | 98 | 95 | 100 | 76 | 60 | 55 |

Use Example 7: Synergistic Herbicidal Action of the Composition 1.82 Applied by the Post Emergence Method: Treatment by the Mixture of Compound (I.1)+Terbuthylazine (B.82)

| application rate a.i. in g/ha | | herbicidal activity against | | | |
|---|---|---|---|---|---|
| | | CHEAL | | GALAP | |
| I.1 | B.82 | found | calculated | found | calculated |
| 62.5 | — | 60 | — | 65 | — |
| — | 31.25 | 65 | — | 55 | — |
| 62.5 | 31.25 | 100 | 86 | 85 | 84 |

Use Example 8: Synergistic Herbicidal Action of the Composition 1.77 Applied by the Post Emergence Method: Treatment by the Mixture of Compound (I.1)+Linuron (B.77)

| application rate a.i. in g/ha | | herbicidal activity against | | | | | |
|---|---|---|---|---|---|---|---|
| | | LOLMU | | GALAP | | CONAR | |
| I.1 | B.77 | found | calculated | found | calculated | found | calculated |
| 62.5 | — | 20 | — | 10 | — | 25 | — |
| — | 75 | 35 | — | 40 | — | 50 | — |
| 62.5 | 75 | 60 | 48 | 65 | 46 | 85 | 63 |

Use Example 9: Synergistic Herbicidal Action of the Composition 1.79 Applied by the Post Emergence Method: Treatment by the Mixture of Compound (I.1)+Metribuzin (B.79)

| I.1 | B.79 | found | calculated | found | calculated |
|---|---|---|---|---|---|
| application rate a.i. in g/ha | | herbicidal activity against | | | |
| | | ECHCG | | POLCO | |
| 62.5 | — | 65 | — | 75 | — |
| — | 25 | 20 | — | 20 | — |
| 62.5 | 25 | 75 | 72 | 100 | 80 |

| I.1 | B.79 | found | calculated | found | calculated |
|---|---|---|---|---|---|
| application rate a.i. in g/ha | | herbicidal activity against | | | |
| | | POLCO | | MATCH | |
| 20.8 | — | 50 | — | 60 | — |
| — | 25 | 20 | — | 65 | — |
| 20.8 | 25 | 90 | 60 | 98 | 86 |

Use Example 10: Synergistic Herbicidal Action of the Composition 1.192 Applied by the Post Emergence Method: Treatment by the Mixture of Compound (I.1)+Phenmedipham (B.192)

| application rate a.i. in g/ha | | herbicidal activity against | | | | | | | | | |
|---|---|---|---|---|---|---|---|---|---|---|---|
| | | SETVI | | AMARE | | CHEAL | | MATCH | | AMBEL | |
| I.1 | B.192 | found | calculated | found | calculated | found | calculated | found | calculated | found | calculated |
| 20.8 | — | 25 | — | 70 | — | 85 | — | 60 | — | 30 | — |
| — | 62.5 | 65 | — | 35 | — | 50 | — | 50 | — | 90 | — |
| 20.8 | 62.5 | 75 | 74 | 95 | 81 | 95 | 93 | 100 | 80 | 98 | 93 |

Use Example 11: Synergistic Herbicidal Action of the Composition 1.80 Applied by the Post Emergence Method: Treatment by the Mixture of Compound (I.1)+Propanil (B.80)

| application rate a.i. in g/ha | | herbicidal activity against | | | | | |
|---|---|---|---|---|---|---|---|
| | | DIGSA | | CONAR | | ERICA | |
| I.1 | B.80 | found | calculated | found | calculated | found | calculated |
| 62.5 | — | 40 | — | 25 | — | 65 | — |
| — | 250 | 40 | — | 20 | — | 65 | — |
| 62.5 | 250 | 65 | 64 | 70 | 40 | 98 | 88 |

Use Example 12: Synergistic Herbicidal Action of the Composition 1.107 Applied by the Post Emergence Method: Treatment by the Mixture of Compound (I.1)+Topramezone (B.107)

| application rate a.i. in g/ha | | herbicidal activity against | | | | | | | |
|---|---|---|---|---|---|---|---|---|---|
| | | POLCO | | ABUTH | | GALAP | | ERICA | |
| I.1 | B.107 | found | calculated | found | calculated | found | calculated | found | calculated |
| 62.5 | — | 75 | — | 65 | — | 10 | — | 65 | — |
| — | 6 | 35 | — | 85 | — | 70 | — | 65 | — |
| 62.5 | 6 | 100 | 54 | 95 | 95 | 80 | 73 | 98 | 88 |

| application rate a.i. in g/ha | | herbicidal activity against | | | | | |
|---|---|---|---|---|---|---|---|
| | | MATCH | | ERICA | | ABUTH | |
| I.1 | B.107 | found | calculated | found | calculated | found | calculated |
| 20.8 | — | 60 | — | 65 | — | 0 | — |
| — | 6 | 70 | — | 65 | — | 85 | — |
| 20.8 | 6 | 95 | 88 | 100 | 88 | 90 | 85 |

Use Example 13: Synergistic Herbicidal Action of the Composition 1.113 Applied by the Post Emergence Method: Treatment by the Mixture of Compound (I.1)+Glyphosate (B.113)

| application rate a.i. in g/ha | | herbicidal activity against | | | | | |
|---|---|---|---|---|---|---|---|
| | | PANMI | | GALAP | | GERDI | |
| I.1 | B.113 | found | calculated | found | calculated | found | calculated |
| 125 | — | 60 | — | 80 | — | 80 | — |
| — | 135 | 90 | — | 80 | — | 80 | — |
| 125 | 135 | 98 | 96 | 98 | 96 | 98 | 96 |

| application rate a.i. in g/ha | | herbicidal activity against | | | | | |
|---|---|---|---|---|---|---|---|
| | | PANMI | | GALAP | | CONAR | |
| I.1 | B.113 | found | calculated | found | calculated | found | calculated |
| 125 | — | 60 | — | 80 | — | 80 | — |
| — | 33.75 | 80 | — | 50 | — | 45 | — |
| 125 | 33.75 | 95 | 92 | 98 | 90 | 100 | 89 |

Use Example 14: Synergistic Herbicidal Action of the Composition 1.193 Applied by the Post Emergence Method: Treatment by the Mixture of Compound (I.1)+(1RS,2SR,4SR)-1,4-Epoxy-p-Menth-2-yl 2-Methylbenzyl Ether (B.193)

| application rate a.i. in g/ha | | herbicidal activity against | | | | | | | |
|---|---|---|---|---|---|---|---|---|---|
| | | ECHCG | | DIGSA | | GERDI | | ALOMY | |
| I.1 | B.193 | found | calculated | found | calculated | found | calculated | found | calculated |
| 250 | — | 95 | — | 35 | — | 95 | — | 45 | — |
| — | 15 | 40 | — | 20 | — | 40 | — | 0 | — |
| 250 | 15 | 98 | 97 | 80 | 48 | 98 | 97 | 60 | 45 |

Use Example 15: Synergistic Herbicidal Action of the Composition 1.030 Applied by the Post Emergence Method: Treatment by the Mixture of Compound (I.1)+Imazamox (B.30)

| application rate a.i. in g/ha | | herbicidal activity against | | | | | |
|---|---|---|---|---|---|---|---|
| | | VIOAR | | CONAR | | GERDI | |
| I.1 | B.30 | found | calculated | found | calculated | found | calculated |
| 62.5 | — | 0 | — | 25 | — | 85 | — |
| — | 3.75 | 45 | — | 85 | — | 90 | — |
| 62.5 | 3.75 | 65 | 45 | 90 | 89 | 100 | 99 |

Use Example 16: Synergistic Herbicidal Action of the Composition 1.84 Applied by the Post Emergence Method: Treatment by the Mixture of Compound (I.1)+Paraquat-Dichloride (B.84)

| application rate a.i. in g/ha | | herbicidal activity against | | | | | | | | |
|---|---|---|---|---|---|---|---|---|---|---|
| | | AMBEL | | VIOAR | | SASKR | | ERICA | | GALAP |
| I.1 | B.84 | found | calculated | found | calculated | found | calculated | found | calculated | found | calculated |
| 31.25 | — | 65 | — | 40 | — | 10 | — | 55 | — | 65 | — |
| — | 17.5 | 90 | — | 55 | — | 70 | — | 35 | — | 55 | — |
| 31.25 | 17.5 | 100 | 97 | 75 | 73 | 98 | 73 | 75 | 71 | 85 | 84 |

| application rate a.i. in g/ha | | herbicidal activity against | | | | | | | |
|---|---|---|---|---|---|---|---|---|---|
| | | MATCH | | VIOAR | | POLCO | | CONAR | |
| I.1 | B.84 | found | calculated | found | calculated | found | calculated | found | calculated |
| 62.5 | — | 80 | — | 40 | — | 90 | — | 45 | — |
| — | 17.5 | 80 | — | 55 | — | 30 | — | 10 | — |
| 62.5 | 17.5 | 98 | 96 | 75 | 73 | 95 | 93 | 60 | 51 |

Use Example 17: Synergistic Herbicidal Action of the Composition 1.87 Applied by the Post Emergence Method: Treatment by the Mixture of Compound (I.1)+Carfentrazone-Ethyl (B.87)

| application rate a.i. in g/ha | | herbicidal activity against | | | | | | | |
|---|---|---|---|---|---|---|---|---|---|
| | | LAMAM | | PAPRH | | MATCH | | GERDI | |
| I.1 | B.87 | found | calculated | found | calculated | found | calculated | found | calculated |
| 62.5 | — | 85 | — | 85 | — | 80 | — | 85 | — |
| — | 1.75 | 80 | — | 30 | — | 75 | — | 70 | — |
| 62.5 | 1.75 | 100 | 97 | 100 | 90 | 98 | 95 | 98 | 96 |

| application rate a.i. in g/ha | | herbicidal activity against | | | | | | | |
|---|---|---|---|---|---|---|---|---|---|
| | | LALAM | | SEBEX | | MATCH | | GERPU | |
| I.1 | B.87 | found | calculated | found | calculated | found | calculated | found | calculated |
| 31.25 | — | 70 | — | 75 | — | 35 | — | 80 | — |
| — | 1.75 | 80 | — | 75 | — | 75 | — | 75 | — |
| 31.25 | 1.75 | 98 | 94 | 100 | 94 | 95 | 84 | 98 | 95 |

Use Example 18: Synergistic Herbicidal Action of the Composition 1.139 Applied by the Post Emergence Method: Treatment by the Mixture of Compound (I.1)+Pyroxasulfone (B.139)

| application rate a.i. in g/ha | | herbicidal activity against | | | | | | | | |
|---|---|---|---|---|---|---|---|---|---|---|
| | | GERPU | | LAMAM | | SEBEX | | CONAR | | ABUTH | |
| I.1 | B.139 | found | calculated | found | calculated | found | calculated | found | calculated | found | calculated |
| 31.25 | — | 80 | — | 80 | — | 80 | — | 30 | — | 10 | — |
| — | 25 | 25 | — | 45 | — | 35 | — | 60 | — | 60 | — |
| 31.25 | 25 | 98 | 85 | 90 | 89 | 95 | 87 | 75 | 72 | 75 | 64 |

| application rate a.i. in g/ha | | herbicidal activity against | | | | | | | | |
|---|---|---|---|---|---|---|---|---|---|---|
| | | GERPU | | AMBEL | | CONAR | | POLCO | | POLPE | |
| I.1 | B.139 | found | calculated | found | calculated | found | calculated | found | calculated | found | calculated |
| 31.25 | — | 80 | — | 65 | — | 30 | — | 65 | — | 30 | — |
| — | 12.5 | 0 | — | 10 | — | 60 | — | 15 | — | 55 | — |
| 31.25 | 12.5 | 95 | 80 | 75 | 69 | 80 | 72 | 80 | 70 | 80 | 69 |

Use Example 19: Synergistic Herbicidal Action of the Composition 1.92 Applied by the Post Emergence Method: Treatment by the Mixture of Compound (I.1)+Saflufenacil (B.92)

| application rate a.i. in g/ha | | herbicidal activity against | | | |
|---|---|---|---|---|---|
| | | ERICA | | GALAP | |
| I.1 | B.92 | found | calculated | found | calculated |
| 31.25 | — | 25 | — | 65 | — |
| — | 0.5 | 80 | — | 80 | — |
| 31.25 | 0.5 | 100 | 85 | 98 | 93 |

Use Example 20: Synergistic Herbicidal Action of the Composition 1.100 Applied by the Post Emergence Method: Treatment by the Mixture of Compound (I.1)+Isoxaflutole (B.100)

| application rate a.i. in g/ha | | herbicidal activity against | | | | | | | |
|---|---|---|---|---|---|---|---|---|---|
| | | VIOAR | | AMBEL | | ERICA | | GERDI | |
| I.1 | B.100 | found | calculated | found | calculated | found | calculated | found | calculated |
| 62.5 | — | 30 | — | 90 | — | 75 | — | 65 | — |
| — | 12.5 | 70 | — | 45 | — | 80 | — | 0 | — |
| 62.5 | 12.5 | 85 | 79 | 98 | 95 | 100 | 95 | 100 | 65 |

| application rate a.i. in g/ha | | herbicidal activity against | | | | | | | |
|---|---|---|---|---|---|---|---|---|---|
| | | POLCO | | AMBEL | | ERICA | | GERDI | |
| I.1 | B.100 | found | calculated | found | calculated | found | calculated | found | calculated |
| 31.25 | — | 70 | — | 90 | — | 25 | — | 60 | — |
| — | 12.5 | 60 | — | 45 | — | 80 | — | 0 | — |
| 31.25 | 12.5 | 95 | 88 | 98 | 95 | 98 | 85 | 90 | 60 |

Use Example 21: Synergistic Herbicidal Action of the Composition 1.40 Applied by the Post Emergence Method: Treatment by the Mixture of Compound (I.1)+Imazethapyr (B.40)

| application rate a.i. in g/ha | | herbicidal activity against | | | | | |
|---|---|---|---|---|---|---|---|
| | | PAPRH | | IPOHE | | GERDI | |
| I.1 | B.40 | found | calculated | found | calculated | found | calculated |
| 62.5 | — | 65 | — | 95 | — | 70 | — |
| — | 7.5 | 45 | — | 80 | — | 90 | — |
| 62.5 | 7.5 | 100 | 81 | 100 | 99 | 98 | 97 |

| application rate a.i. in g/ha | | herbicidal activity against | | | | | |
|---|---|---|---|---|---|---|---|
| | | ECHCG | | POLCO | | GERDI | |
| I.1 | B.40 | found | calculated | found | calculated | found | calculated |
| 31.25 | — | 0 | — | 20 | — | 30 | — |
| — | 7.5 | 85 | — | 80 | — | 95 | — |
| 31.25 | 7.5 | 90 | 85 | 90 | 84 | 98 | 97 |

Use Example 22: Synergistic Herbicidal Action of the Composition 1.104 Applied by the Post Emergence Method: Treatment by the Mixture of Compound (I.1)+Sulcotrione (B.104)

| application rate a.i. in g/ha | | herbicidal activity against | | | | | |
|---|---|---|---|---|---|---|---|
| | | ECHCG | | VIOAR | | MATCH | |
| I.1 | B.104 | found | calculated | found | calculated | found | calculated |
| 31.25 | — | 0 | — | 0 | — | 10 | — |
| — | 15 | 80 | — | 85 | — | 10 | — |
| 31.25 | 15 | 98 | 80 | 100 | 85 | 100 | 19 |

| application rate a.i. in g/ha | | herbicidal activity against | | | | | | | |
|---|---|---|---|---|---|---|---|---|---|
| | | ERICA | | POLCO | | GERDI | | KCHSC | |
| I.1 | B.104 | found | calculated | found | calculated | found | calculated | found | calculated |
| 31.25 | — | 25 | — | 70 | — | 30 | — | 75 | — |
| — | 15 | 75 | — | 90 | — | 45 | — | 90 | — |
| 31.25 | 15 | 95 | 81 | 98 | 97 | 75 | 62 | 100 | 98 |

Use Example 23: Synergistic Herbicidal Action of the Composition 1.2605 Applied by the Post Emergence Method: Treatment by the Mixture of Compound (I.1)+Fenoxaprop-Ethyl (B.5)+Mefenpyr-Diethyl (C.13)

| application rate a.i. in g/ha | | | herbicidal activity against | | | | | |
|---|---|---|---|---|---|---|---|---|
| | | | APESV | | POLCO | | GALAP | |
| I.1 | B.5 | C.13 | found | calculated | found | calculated | found | calculated |
| 31.25 | — | — | 0 | — | 45 | — | 50 | — |
| — | 7.5 | 8.15 | 65 | — | 0 | — | 0 | — |
| 31.25 | 7.5 | 8.15 | 75 | 65 | 60 | 45 | 60 | 50 |

Use Example 24: Synergistic Herbicidal Action of the Composition 1.59 Applied by the Post Emergence Method: Treatment by the Mixture of Compound (I.1)+Rimsulfuron (B.59)

| application rate a.i. in g/ha | | herbicidal activity against | | | | | |
|---|---|---|---|---|---|---|---|
| | | PAPRH | | ERICA | | IPOHE | |
| I.1 | B.59 | found | calculated | found | calculated | found | calculated |
| 31.25 | — | 50 | — | 25 | — | 75 | — |
| — | 0.5 | 65 | — | 65 | — | 90 | — |
| 31.25 | 0.5 | 85 | 83 | 75 | 74 | 98 | 98 |

-continued

| application rate a.i. in g/ha | | herbicidal activity against | | | |
|---|---|---|---|---|---|
| | | MATCH | | GERDI | |
| I.1 | B.59 | found | calculated | found | calculated |
| 62.5 | — | 50 | — | 90 | — |
| — | 0.5 | 75 | — | 75 | — |
| 62.5 | 0.5 | 100 | 88 | 100 | 98 |

Use Example 25: Synergistic Herbicidal Action of the Composition 1.120 Applied by the Post Emergence Method: Treatment by the Mixture of Compound (I.1)+Glufosinate Ammonium (B.120)

| application rate a.i. in g/ha | | herbicidal activity against | | | | | | | | |
|---|---|---|---|---|---|---|---|---|---|---|
| | | VIOAR | | POLCO | | ABUTH | | GERDI | | GALAP |
| I.1 | B.120 | found | calculated | found | calculated | found | calculated | found | calculated | found | calculated |
| 31.25 | — | 0 | — | 25 | — | 25 | — | 40 | — | 50 | — |
| — | 125 | 15 | — | 65 | — | 70 | — | 90 | — | 80 | — |
| 31.25 | 125 | 80 | 15 | 95 | 74 | 90 | 78 | 98 | 94 | 98 | 90 |

| application rate a.i. in g/ha | | herbicidal activity against | | | | | | | | |
|---|---|---|---|---|---|---|---|---|---|---|
| | | PAPRH | | MATCH | | IPOHE | | GERDI | | KCHSC |
| I.1 | B.120 | found | calculated | found | calculated | found | calculated | found | calculated | found | calculated |
| 31.25 | — | 50 | — | 0 | — | 75 | — | 35 | — | 90 | — |
| — | 62.5 | 30 | — | 55 | — | 80 | — | 40 | — | 45 | — |
| 31.25 | 62.5 | 85 | 65 | 95 | 55 | 98 | 95 | 95 | 61 | 100 | 95 |

Use Example 26: Synergistic Herbicidal Action of the Composition 1.02 Applied by the Post Emergence Method: Treatment by the Mixture of Compound (I.1)+Clodinafop-Propargyl (B.2)

| application rate a.i. in g/ha | | herbicidal activity against | | | | | | | |
|---|---|---|---|---|---|---|---|---|---|
| | | ALOMY | | MATCH | | IPOHE | | ABUTH | |
| I.1 | B.2 | found | calculated | found | calculated | found | calculated | found | calculated |
| 62.5 | — | 20 | — | 70 | — | 90 | — | 25 | — |
| — | 15 | 85 | — | 0 | — | 40 | — | 15 | — |
| 62.5 | 15 | 90 | 88 | 80 | 70 | 98 | 94 | 75 | 36 |

| application rate a.i. in g/ha | | herbicidal activity against | | | | | | | |
|---|---|---|---|---|---|---|---|---|---|
| | | GERDI | | STEME | | IPOHE | | GALAP | |
| I.1 | B.2 | found | calculated | found | calculated | found | calculated | found | calculated |
| 62.5 | — | 90 | — | 65 | — | 90 | — | 50 | — |
| — | 7.5 | 0 | — | 0 | — | 10 | — | 0 | — |
| 62.5 | 7.5 | 98 | 90 | 80 | 65 | 98 | 91 | 65 | 50 |

Use Example 27: Synergistic Herbicidal Action of the Composition 1.44 Applied by the Post Emergence Method: Treatment by the Mixture of Compound (I.1)+Iodosulfuron Methyl Sodium (B.44)

| application rate a.i. in g/ha | | herbicidal activity against | | | |
|---|---|---|---|---|---|
| | | ALOMY | | POLCO | |
| I.1 | B.44 | found | calculated | found | calculated |
| 62.5 | — | 0 | — | 40 | — |
| — | 1 | 20 | — | 90 | — |
| 62.5 | 1 | 55 | 20 | 98 | 94 |

Use Example 28: Synergistic Herbicidal Action of the Composition 1.60 Applied by the Post Emergence Method: Treatment by the Mixture of Compound (I.1)+Sulfosulfuron (B.60)

| application rate a.i. in g/ha | | herbicidal activity against | | | | | | |
|---|---|---|---|---|---|---|---|---|
| | | ALOMY | | APESV | | POLCO | | PAPRH | |
| I.1 | B.60 | found | calculated | found | calculated | found | calculated | found | calculated |
| 62.5 | — | 0 | — | 0 | — | 40 | — | 50 | — |
| — | 3 | 60 | — | 60 | — | 90 | — | 90 | — |
| 62.5 | 3 | 85 | 60 | 85 | 60 | 98 | 94 | 100 | 95 |

| application rate a.i. in g/ha | | herbicidal activity against | | | | | |
|---|---|---|---|---|---|---|---|
| | | VIOAR | | ERICA | | POLCO | |
| I.1 | B.60 | found | calculated | found | calculated | found | calculated |
| 31.25 | — | 20 | — | 0 | — | 30 | — |
| — | 3 | 65 | — | 75 | — | 90 | — |
| 31.25 | 3 | 85 | 72 | 80 | 75 | 95 | 93 |

Use Example 29: Synergistic Herbicidal Action of the Composition 1.26 Applied by the Post Emergence Method: Treatment by the Mixture of Compound (I.1)+Florasulam (B.26)

| application rate a.i. in g/ha | | herbicidal activity against | | | |
|---|---|---|---|---|---|
| | | POLCO | | PAPRH | |
| I.1 | B.26 | found | calculated | found | calculated |
| 31.25 | — | 70 | — | 50 | — |
| — | 2 | 85 | — | 98 | — |
| 31.25 | 2 | 98 | 96 | 100 | 99 |

Use Example 30: Synergistic Herbicidal Action of the Composition 1.35 Applied by the Post Emergence Method: Treatment by the Mixture of Compound (I.1)+Imazapyr (B.35)

| application rate a.i. in g/ha | | herbicidal activity against | | | | | |
|---|---|---|---|---|---|---|---|
| | | ABUTH | | GERDI | | MATCH | |
| I.1 | B.35 | found | calculated | found | calculated | found | calculated |
| 31.25 | — | 10 | — | 30 | — | 40 | — |
| — | 10 | 90 | — | 95 | — | 55 | — |
| 31.25 | 10 | 95 | 91 | 98 | 97 | 98 | 73 |

-continued

| application rate a.i. in g/ha | | herbicidal activity against | | | | | |
|---|---|---|---|---|---|---|---|
| | | POLCO | | VIOAR | | ERICA | |
| I.1 | B.35 | found | calculated | found | calculated | found | calculated |
| 31.25 | — | 30 | — | 25 | — | 0 | — |
| — | 5 | 95 | — | 55 | — | 75 | — |
| 31.25 | 5 | 98 | 97 | 70 | 66 | 80 | 75 |

Use Example 31: Synergistic Herbicidal Action of the Composition 1.101 Applied by the Post Emergence Method: Treatment by the Mixture of Compound (I.1)+Mesotrione (B.101)

| application rate a.i. in g/ha | | herbicidal activity against | | | | | |
|---|---|---|---|---|---|---|---|
| | | PAPRH | | AMBEL | | SASKR | |
| I.1 | B.101 | found | calculated | found | calculated | found | calculated |
| 31.25 | — | 0 | — | 85 | — | 20 | — |
| — | 9.375 | 35 | — | 80 | — | 75 | — |
| 31.25 | 9375 | 75 | 35 | 100 | 97 | 100 | 80 |

| application rate a.i. in g/ha | | herbicidal activity against | | | | | |
|---|---|---|---|---|---|---|---|
| | | MATCH | | ERICA | | GERDI | |
| I.1 | B.101 | found | calculated | found | calculated | found | calculated |
| 31.25 | — | 35 | — | 35 | — | 55 | — |
| — | 9.375 | 75 | — | 80 | — | 0 | — |
| 31.25 | 9375 | 100 | 84 | 95 | 87 | 80 | 55 |

Use Example 32: Synergistic Herbicidal Action of the Composition 1.106 Applied by the Post Emergence Method: Treatment by the Mixture of Compound (I.1)+Tembotrione (B.106)

| application rate a.i. in g/ha | | herbicidal activity against | | | | | | | |
|---|---|---|---|---|---|---|---|---|---|
| | | SASKR | | MATCH | | ERICA | | IPOHE | |
| I.1 | B.106 | found | calculated | found | calculated | found | calculated | found | calculated |
| 31.25 | — | 20 | — | 35 | — | 35 | — | 70 | — |
| — | 9.375 | 65 | — | 65 | — | 90 | — | 70 | — |
| 31.25 | 9375 | 80 | 72 | 100 | 77 | 95 | 94 | 95 | 91 |

Use Example 33: Synergistic Herbicidal Action of the Composition 1.51 Applied by the Post Emergence Method: Treatment by the Mixture of Compound (I.1)+Nicosulfuron (B.51)

| application rate a.i. in g/ha | | herbicidal activity against | | | | | |
|---|---|---|---|---|---|---|---|
| | | AMBEL | | MATCH | | POLPE | |
| I.1 | B.51 | found | calculated | found | calculated | found | calculated |
| 31.25 | — | 85 | — | 35 | — | 45 | — |
| — | 20 | 80 | — | 90 | — | 95 | — |
| 31.25 | 20 | 100 | 97 | 95 | 94 | 98 | 97 |

Use Example 34: Synergistic Herbicidal Action of the Composition 1.164 Applied by the Post Emergence Method: Treatment by the Mixture of Compound (I.1)+MCPA (B.164)

| application rate a.i. in g/ha | | herbicidal activity against | | | | | | | |
|---|---|---|---|---|---|---|---|---|---|
| | | GALAP | | POLAV | | CONAR | | | |
| I.1 | B.164 | found | calculated | found | calculated | found | calculated | found | calculated |
| 125 | — | 80 | — | 65 | — | 70 | — | — | — |
| — | 400 | 30 | — | 85 | — | 90 | — | — | — |
| 125 | 400 | 95 | 86 | 98 | 95 | 100 | 97 | | |

| application rate a.i. in g/ha | | herbicidal activity against | | | | | | | | | |
|---|---|---|---|---|---|---|---|---|---|---|---|
| | | POLAV | | CONAR | | | | | | | |
| I.1 | B.164 | found | calculated | found | calculated | found | calculated | found | calculated | found | calculated |
| 125 | — | 65 | — | 70 | — | — | — | — | — | — | — |
| — | 200 | 85 | — | 90 | — | — | — | — | — | — | — |
| 125 | 200 | 100 | 95 | 100 | 97 | | | | | | |

| application rate a.i. in g/ha | | herbicidal activity against | | | | | | | |
|---|---|---|---|---|---|---|---|---|---|
| | | VIOAR | | POLAV | | CONAR | | POLCO | |
| I.1 | B.164 | found | calculated | found | calculated | found | calculated | found | calculated |
| 62.5 | — | 0 | — | 65 | — | 60 | — | 85 | — |
| — | 400 | 70 | — | 85 | — | 90 | — | 50 | — |
| 62.25 | 400 | 100 | 70 | 100 | 95 | 100 | 96 | 100 | 93 |

| application rate a.i. in g/ha | | herbicidal activity against | | | | | | | |
|---|---|---|---|---|---|---|---|---|---|
| | | VIOAR | | POLAV | | CONAR | | POLCO | |
| I.1 | B.164 | found | calculated | found | calculated | found | calculated | found | calculated |
| 62.5 | — | 0 | — | 65 | — | 60 | — | 85 | — |
| — | 200 | 65 | — | 85 | — | 90 | — | 50 | — |
| 62.5 | 200 | 70 | 65 | 100 | 95 | 100 | 96 | 100 | 93 |

| application rate a.i. in g/ha | | herbicidal activity against | | | |
|---|---|---|---|---|---|
| | | VIOAR | | POLAV | |
| I.1 | B.164 | found | calculated | found | calculated |
| 62.5 | — | 0 | — | 65 | — |
| — | 100 | 60 | — | 70 | — |
| 62.5 | 100 | 75 | 60 | 100 | 90 |

| application rate a.i. in g/ha | | herbicidal activity against | | | | | | | |
|---|---|---|---|---|---|---|---|---|---|
| | | POLPE | | LAMAM | | MATCH | | CONAR | | STEME | |
| I.1 | B.164 | found | calculated | found | calculated | found | calculated | found | calculated | found | calculated |
| 31.25 | — | 70 | — | 70 | — | 0 | — | 40 | — | 70 | — |
| — | 400 | 80 | — | 70 | — | 50 | — | 90 | — | 80 | — |
| 31.25 | 400 | 100 | 94 | 95 | 91 | 55 | 50 | 98 | 94 | 100 | 94 |

| application rate a.i. in g/ha | | herbicidal activity against | | | | | | | |
|---|---|---|---|---|---|---|---|---|---|
| | | POLPE | | PAPRH | | ABUTH | | STEME | | LAMAM | |
| I.1 | B.164 | found | calculated | found | calculated | found | calculated | found | calculated | found | calculated |
| 31.25 | — | 70 | — | 65 | — | 40 | — | 70 | — | 70 | — |
| — | 200 | 65 | — | 65 | — | 80 | — | 60 | — | 65 | — |
| 31.25 | 200 | 100 | 90 | 95 | 88 | 98 | 88 | 95 | 88 | 95 | 90 |

| application rate a.i. in g/ha | | herbicidal activity against | | | | | | | |
|---|---|---|---|---|---|---|---|---|---|
| | | PAPRH | | GERDI | | STEME | | | | | |
| I.1 | B.164 | found | calculated | found | calculated | found | calculated | found | calculated | found | calculated |
| 31.25 | — | 65 | — | 70 | — | 70 | — | — | — | — | — |
| — | 100 | 60 | — | 65 | — | 50 | — | — | — | — | — |
| 31.25 | 100 | 100 | 86 | 98 | 90 | 100 | 85 | — | — | — | — |

Use Example 35: Synergistic Herbicidal Action Applied by the Post Emergence Method: Treatment by the Mixture of Compound (I.1)+Pyrasulfatole

| application rate a.i. in g/ha | | herbicidal activity against | | | | | | | |
|---|---|---|---|---|---|---|---|---|---|
| | | VIOAR | | CONAR | | | | | |
| I.1 | pyrasulfatole | found | calculated | found | calculated | found | calculated | found | calculated |
| 125 | — | 90 | — | 70 | — | — | — | — | — |
| — | 40 | 60 | — | 85 | — | — | — | — | — |
| 125 | 40 | 100 | 96 | 98 | 96 | — | — | — | — |

| application rate a.i. in g/ha | | herbicidal activity against | | | | | | | |
|---|---|---|---|---|---|---|---|---|---|
| | | CONAR | | | | | | | |
| I.1 | pyrasulfatole | found | calculated | found | calculated | found | calculated | found | calculated |
| 125 | — | 70 | — | — | — | — | — | — | — |
| — | 20 | 65 | — | — | — | — | — | — | — |
| 125 | 20 | 98 | 90 | — | — | — | — | — | — |

-continued

| application rate | | herbicidal activity against | | | | | | | | |
|---|---|---|---|---|---|---|---|---|---|---|
| a.i. in g/ha | | VIOAR | | CONAR | | | | | | |
| I.1 | pyrasulfatole | found | calculated | found | calculated | found | calculated | found | calculated | found | calculated |
| 125 | — | 90 | — | 70 | — | | | | | |
| — | 10 | 0 | — | 60 | — | | | | | |
| 125 | 10 | 100 | 90 | 98 | 88 | | | | | |

| application rate | | herbicidal activity against | | | | | | | | |
|---|---|---|---|---|---|---|---|---|---|---|
| a.i. in g/ha | | VIOAR | | | | | | | | |
| I.1 | pyrasulfatole | found | calculated | found | calculated | found | calculated | found | calculated | found | calculated |
| 62.5 | — | 0 | — | | | | | | | |
| — | 40 | 60 | — | | | | | | | |
| 62.5 | 40 | 80 | 60 | | | | | | | |

| application rate | | herbicidal activity against | | | | | | | | |
|---|---|---|---|---|---|---|---|---|---|---|
| a.i. in g/ha | | VIOAR | | POLAV | | CONAR | | | | |
| I.1 | pyrasulfatole | found | calculated | found | calculated | found | calculated | found | calculated | found | calculated |
| 62.5 | — | 0 | — | 65 | — | 60 | — | | | |
| — | 20 | 40 | — | 70 | — | 65 | — | | | |
| 62.5 | 20 | 70 | 40 | 100 | 90 | 90 | 86 | | | |

| application rate | | herbicidal activity against | | | | | | | | |
|---|---|---|---|---|---|---|---|---|---|---|
| a.i. in g/ha | | VIOAR | | | | | | | | |
| I.1 | pyrasulfatole | found | calculated | found | calculated | found | calculated | found | calculated | found | calculated |
| 62.5 | — | 0 | — | | | | | | | |
| — | 10 | 0 | — | | | | | | | |
| 62.5 | 10 | 60 | 0 | | | | | | | |

| application rate | | herbicidal activity against | | | | | | | | |
|---|---|---|---|---|---|---|---|---|---|---|
| a.i. in g/ha | | PAPRH | | MATCH | | CONAR | | GERDI | | VIOAR |
| I.1 | pyrasulfatole | found | calculated | found | calculated | found | calculated | found | calculated | found | calculated |
| 31.25 | — | 65 | — | 0 | — | 40 | — | 70 | — | 0 | — |
| — | 40 | 65 | — | 50 | — | 85 | — | 50 | — | 60 | — |
| 31.25 | 40 | 100 | 88 | 100 | 50 | 100 | 91 | 100 | 85 | 65 | 60 |

| application rate | | herbicidal activity against | | | | | | | | |
|---|---|---|---|---|---|---|---|---|---|---|
| a.i. in g/ha | | PAPRH | | VIOAR | | | | | | |
| I.1 | pyrasulfatole | found | calculated | found | calculated | found | calculated | found | calculated | found | calculated |
| 31.25 | — | 65 | — | 0 | — | | | | | |
| — | 20 | 65 | — | 40 | — | | | | | |
| 31.25 | 20 | 100 | 88 | 50 | 40 | | | | | |

| application rate | | herbicidal activity against | | | | | | | | |
|---|---|---|---|---|---|---|---|---|---|---|
| a.i. in g/ha | | PAPRH | | VIOAR | | MATCH | | CONAR | | SASKAR |
| I.1 | pyrasulfatole | found | calculated | found | calculated | found | calculated | found | calculated | found | calculated |
| 31.25 | — | 65 | — | 0 | — | 0 | — | 40 | — | 60 | — |
| — | 10 | 50 | — | 0 | — | 50 | — | 60 | — | 90 | — |
| 31.25 | 10 | 100 | 83 | 60 | 0 | 100 | 50 | 98 | 76 | 100 | 96 |

Use Example 36: Synergistic Herbicidal Action Applied by the Post Emergence Method: Treatment by the Mixture of Compound (I.1)+Naptalam

| application rate a.i. in g/ha | | herbicidal activity 6 days after treatment against | | | | | | | |
|---|---|---|---|---|---|---|---|---|---|
| | | SORVU | | VIOAR | | POLAV | | SASKR | |
| I.1 | naptalam | found | calculated | found | calculated | found | calculated | found | calculated |
| 62.5 | — | 20 | — | 0 | — | 70 | — | 65 | — |
| — | 200 | 50 | — | 70 | — | 75 | — | 80 | — |
| 62.5 | 200 | 65 | 60 | 80 | 70 | 98 | 93 | 98 | 93 |

| application rate a.i. in g/ha | | herbicidal activity 6 days after treatment against | | | | | | | | | |
|---|---|---|---|---|---|---|---|---|---|---|---|
| | | CONAR | | VIOAR | | POLAV | | SASKR | | KCHAS | |
| I.1 | naptalam | found | calculated | found | calculated | found | calculated | found | calculated | found | calculated |
| 31.25 | — | 5 | — | 0 | — | 70 | — | 65 | — | 10 | — |
| — | 200 | 80 | — | 70 | — | 75 | — | 80 | — | 85 | — |
| 31.25 | 200 | 95 | 81 | 75 | 70 | 98 | 93 | 98 | 93 | 95 | 87 |

| application rate a.i. in g/ha | | herbicidal activity 6 days after treatment against | | | | | | | | | |
|---|---|---|---|---|---|---|---|---|---|---|---|
| | | CONAR | | | | | | | | | |
| I.1 | naptalam | found | calculated | found | calculated | found | calculated | found | calculated | found | calculated |
| 125 | — | 70 | — | — | — | — | — | — | — | — | — |
| — | 100 | 80 | — | — | — | — | — | — | — | — | — |
| 125 | 100 | 98 | 94 | — | — | — | — | — | — | — | — |

| application rate a.i. in g/ha | | herbicidal activity 6 days after treatment against | | | | | | | | | |
|---|---|---|---|---|---|---|---|---|---|---|---|
| | | VIOAR | | POLAV | | | | | | | |
| I.1 | naptalam | found | calculated | found | calculated | found | calculated | found | calculated | found | calculated |
| 62.5 | — | 0 | — | 70 | — | — | — | — | — | — | — |
| — | 100 | 65 | — | 75 | — | — | — | — | — | — | — |
| 62.5 | 100 | 70 | 65 | 98 | 93 | — | — | — | — | — | — |

| application rate a.i. in g/ha | | herbicidal activity 6 days after treatment against | | | | | | | |
|---|---|---|---|---|---|---|---|---|---|
| | | CONAR | | MATCH | | ABUTH | | KCHSC | |
| I.1 | naptalam | found | calculated | found | calculated | found | calculated | found | calculated |
| 31.25 | — | 5 | — | 0 | — | 35 | — | 10 | — |
| — | 100 | 80 | — | 65 | — | 85 | — | 85 | — |
| 31.25 | 100 | 95 | 81 | 70 | 65 | 95 | 90 | 95 | 87 |

| application rate a.i. in g/ha | | herbicidal activity 6 days after treatment against | | | | | | | | | |
|---|---|---|---|---|---|---|---|---|---|---|---|
| | | ERICA | | | | | | | | | |
| I.1 | naptalam | found | calculated | found | calculated | found | calculated | found | calculated | found | calculated |
| 125 | — | 70 | — | — | — | — | — | — | — | — | — |
| — | 50 | 80 | — | — | — | — | — | — | — | — | — |
| 125 | 50 | 98 | 94 | — | — | — | — | — | — | — | — |

| application rate a.i. in g/ha | | herbicidal activity 6 days after treatment against | | | | | | | |
|---|---|---|---|---|---|---|---|---|---|
| | | MATCH | | POLAV | | SASKR | | POLCO | |
| I.1 | naptalam | found | calculated | found | calculated | found | calculated | found | calculated |
| 62.5 | — | 10 | — | 70 | — | 65 | — | 70 | — |
| — | 50 | 30 | — | 70 | — | 70 | — | 75 | — |
| 62.5 | 50 | 70 | 37 | 95 | 91 | 95 | 90 | 98 | 93 |

-continued

| application rate a.i. in g/ha | | herbicidal activity 6 days after treatment against | | | | | | | |
|---|---|---|---|---|---|---|---|---|---|
| | | POLAV | | MATCH | | CONAR | | POLCO | |
| I.1 | naptalam | found | calculated | found | calculated | found | calculated | found | calculated |
| 31.25 | — | 70 | — | 0 | — | 5 | — | 35 | — |
| — | 50 | 70 | — | 30 | — | 80 | — | 75 | — |
| 31.25 | 50 | 98 | 91 | 70 | 30 | 95 | 81 | 90 | 84 |

Use Example 37: Synergistic Herbicidal Action of the Composition 1.96 Applied by the Post Emergence Method: Treatment by the Mixture of Compound (I.1)+Benzobicyclon (B.96)

| application rate a.i. in g/ha | | herbicidal activity 6 days after treatment against | | | | | | | |
|---|---|---|---|---|---|---|---|---|---|
| | | VIOAR | | SASKR | | CONAR | | | |
| I.1 | B.96 | found | calculated | found | calculated | found | calculated | found | calculated |
| 62.5 | — | 0 | — | 65 | — | 65 | — | — | — |
| — | 140 | 65 | — | 65 | — | 75 | — | — | — |
| 62.5 | 140 | 80 | 65 | 95 | 88 | 98 | 91 | | |

| application rate a.i. in g/ha | | herbicidal activity 6 days after treatment against | | | | | | | |
|---|---|---|---|---|---|---|---|---|---|
| | | POLAV | | IPOHE | | POLCO | | GALAP | |
| I.1 | B.96 | found | calculated | found | calculated | found | calculated | found | calculated |
| 62.5 | — | 70 | — | 80 | — | 70 | — | 65 | — |
| — | 140 | 70 | — | 70 | — | 80 | — | 80 | — |
| 62.5 | 140 | 95 | 91 | 98 | 94 | 98 | 94 | 98 | 93 |

| application rate a.i. in g/ha | | herbicidal activity 6 days after treatment against | | | | | | | |
|---|---|---|---|---|---|---|---|---|---|
| | | POLCO | | KCHSC | | VIOAR | | IPOHE | | SORVU |
| I.1 | B.96 | found | calculated | found | calculated | found | calculated | found | calculated | found | calculated |
| 31.25 | — | 35 | — | 10 | — | 0 | — | 70 | — | 0 | — |
| — | 140 | 80 | — | 55 | — | 65 | — | 70 | — | 60 | — |
| 31.25 | 140 | 95 | 87 | 70 | 60 | 70 | 65 | 95 | 91 | 65 | 60 |

| application rate a.i. in g/ha | | herbicidal activity 6 days after treatment against | | | | | | | |
|---|---|---|---|---|---|---|---|---|---|
| | | VIOAR | | POLAV | | POLCO | | GALAP | | KCHSC |
| I.1 | B.96 | found | calculated | found | calculated | found | calculated | found | calculated | found | calculated |
| 62.5 | — | 0 | — | 70 | — | 70 | — | 65 | — | 90 | — |
| — | 70 | 65 | — | 70 | — | 70 | — | 75 | — | 40 | — |
| 62.5 | 70 | 80 | 65 | 95 | 91 | 95 | 91 | 95 | 91 | 98 | 94 |

| application rate a.i. in g/ha | | herbicidal activity 6 days after treatment against | | | | | | | |
|---|---|---|---|---|---|---|---|---|---|
| | | POLCO | | KCHSC | | VIOAR | | IPOHE | | ABUTH |
| I.1 | B.96 | found | calculated | found | calculated | found | calculated | found | calculated | found | calculated |
| 31.25 | — | 35 | — | 10 | — | 0 | — | 70 | — | 35 | — |
| — | 70 | 70 | — | 40 | — | 65 | — | 70 | — | 85 | — |
| 31.25 | 70 | 90 | 81 | 85 | 46 | 70 | 65 | 95 | 91 | 95 | 90 |

-continued

| application rate | | herbicidal activity 6 days after treatment against | | | | | | | | |
|---|---|---|---|---|---|---|---|---|---|---|
| a.i. in g/ha | | VIOAR | | KCHSC | | | | | | |
| I.1 | B.96 | found | calculated | found | calculated | found | calculated | found | calculated | found | calculated |
| 62.5 | — | 0 | — | 90 | — | — | — | — | — | — | — |
| — | 35 | 65 | — | 35 | — | — | — | — | — | — | — |
| 62.5 | 35 | 80 | 65 | 98 | 94 | — | — | — | — | — | — |

| application rate | | herbicidal activity 6 days after treatment against | | | | | | | | |
|---|---|---|---|---|---|---|---|---|---|---|
| a.i. in g/ha | | POLPE | | KCHSC | | ABUTH | | | | |
| I.1 | B.96 | found | calculated | found | calculated | found | calculated | found | calculated | found | calculated |
| 31.25 | — | 10 | — | 10 | — | 35 | — | — | — | — | — |
| — | 35 | 85 | — | 35 | — | 80 | — | — | — | — | — |
| 31.25 | 35 | 98 | 87 | 85 | 42 | 95 | 87 | — | — | — | — |

| application rate | | herbicidal activity 6 days after treatment against | | | | | | | | |
|---|---|---|---|---|---|---|---|---|---|---|
| a.i. in g/ha | | VIOAR | | IPOHE | | STEME | | | | |
| I.1 | B.96 | found | calculated | found | calculated | found | calculated | found | calculated | found | calculated |
| 31.25 | — | 0 | — | 70 | — | 60 | — | — | — | — | — |
| — | 35 | 65 | — | 70 | — | 85 | — | — | — | — | — |
| 31.25 | 35 | 70 | 65 | 95 | 91 | 98 | 94 | — | — | — | — |

Use Example 38: Synergistic Herbicidal Action of the Composition 1.20 Applied by the Post Emergence Method: Treatment by the Mixture of Compound (I.1)+Bispyribac-Sodium (B.20)

| application rate | | herbicidal activity against | | | | | | | | |
|---|---|---|---|---|---|---|---|---|---|---|
| a.i. in g/ha | | ALOMY | | | | | | | | |
| I.1 | B.20 | Found | calculated | found | calculated | found | calculated | found | calculated | found | calculated |
| 125 | — | 30 | — | — | — | — | — | — | — | — | — |
| — | 4 | 55 | — | — | — | — | — | — | — | — | — |
| 125 | 4 | 80 | 69 | — | — | — | — | — | — | — | — |

| application rate | | herbicidal activity against | | | | | | | | |
|---|---|---|---|---|---|---|---|---|---|---|
| a.i. in g/ha | | ALOMY | | APESV | | | | | | |
| I.1 | B.20 | found | calculated | found | calculated | found | calculated | found | calculated | found | calculated |
| 62.5 | — | 25 | — | 20 | — | — | — | — | — | — | — |
| — | 4 | 55 | — | 60 | — | — | — | — | — | — | — |
| 62.5 | 4 | 70 | 66 | 75 | 68 | — | — | — | — | — | — |

| application rate | | herbicidal activity against | | | | | | | | |
|---|---|---|---|---|---|---|---|---|---|---|
| a.i. in g/ha | | ABUTH | | | | | | | | |
| I.1 | B.20 | found | calculated | found | calculated | found | calculated | found | calculated | found | calculated |
| 31.25 | — | 15 | — | — | — | — | — | — | — | — | — |
| — | 4 | 65 | — | — | — | — | — | — | — | — | — |
| 31.25 | 4 | 90 | 70 | — | — | — | — | — | — | — | — |

| application rate | | herbicidal activity against | | | | | | | | |
|---|---|---|---|---|---|---|---|---|---|---|
| a.i. in g/ha | | ALOMY | | | | | | | | |
| I.1 | B.20 | found | calculated | found | calculated | found | calculated | found | calculated | found | calculated |
| 125 | — | 30 | — | — | — | — | — | — | — | — | — |
| — | 2 | 30 | — | — | — | — | — | — | — | — | — |
| 125 | 2 | 60 | 51 | — | — | — | — | — | — | — | — |

-continued

| application rate a.i. in g/ha | | herbicidal activity against | | | | | | | |
|---|---|---|---|---|---|---|---|---|---|
| | | ABUTH | | IPOHE | | | | | |
| I.1 | B.20 | found | calculated | found | calculated | found | calculated | found | calculated |
| 31.25 | — | 15 | — | 25 | — | — | — | — | — |
| — | 2 | 35 | — | 30 | — | — | — | — | — |
| 31.25 | 2 | 60 | 45 | 60 | 48 | — | — | — | — |

Use Example 39: Synergistic Herbicidal Action of the Composition 1.24 Applied by the Post Emergence Method: Treatment by the Mixture of Compound (I.1)+Cyclosulfamuron (B.24)

| application rate a.i. in g/ha | | herbicidal activity against | | | | | | | |
|---|---|---|---|---|---|---|---|---|---|
| | | MATCH | | ALOMY | | | | | |
| I.1 | B.24 | found | calculated | found | calculated | found | calculated | found | calculated |
| 125 | — | 75 | — | 30 | — | — | — | — | — |
| — | 2 | 65 | — | 35 | — | — | — | — | — |
| 125 | 2 | 100 | 91 | 60 | 55 | — | — | — | — |

| application rate a.i. in g/ha | | herbicidal activity against | | | | | | | |
|---|---|---|---|---|---|---|---|---|---|
| | | MATCH | | KCHSC | | ABUTH | | | |
| I.1 | B.24 | found | calculated | found | calculated | found | calculated | found | calculated |
| 31.25 | — | 25 | — | 40 | — | 15 | — | — | — |
| — | 2 | 65 | — | 45 | — | 85 | — | — | — |
| 31.25 | 2 | 85 | 74 | 80 | 67 | 90 | 87 | — | — |

| application rate a.i. in g/ha | | herbicidal activity against | | | | | | | |
|---|---|---|---|---|---|---|---|---|---|
| | | ALOMY | | | | | | | |
| I.1 | B.24 | found | calculated | found | calculated | found | calculated | found | calculated |
| 125 | — | 30 | — | — | — | — | — | — | — |
| — | 1 | 25 | — | — | — | — | — | — | — |
| 125 | 1 | 55 | 48 | — | — | — | — | — | — |

| application rate a.i. in g/ha | | herbicidal activity against | | | | | | | |
|---|---|---|---|---|---|---|---|---|---|
| | | IPOHE | | KCHSC | | APESV | | | |
| I.1 | B.24 | found | calculated | found | calculated | found | calculated | found | calculated |
| 31.25 | — | 25 | — | 40 | — | 20 | — | — | — |
| — | 1 | 75 | — | 45 | — | 0 | — | — | — |
| 31.25 | 1 | 95 | 81 | 75 | 67 | 30 | 20 | — | — |

Use Example 40: Synergistic Herbicidal Action of the Composition 1.63 Applied by the Post Emergence Method: Treatment by the Mixture of Compound (I.1)+Tribenuron-Methyl (B.63)

| application rate a.i. in g/ha | | herbicidal activity against | | | | | | | |
|---|---|---|---|---|---|---|---|---|---|
| | | POLCO | | VIOAR | | | | | |
| I.1 | B.63 | found | calculated | found | calculated | found | calculated | found | calculated |
| 125 | — | 80 | — | 0 | — | — | — | — | — |
| — | 1 | 30 | — | 40 | — | — | — | — | — |
| 125 | 1 | 100 | 86 | 98 | 40 | — | — | — | — |

| application rate | herbicidal activity against | | | | | | | | |
|---|---|---|---|---|---|---|---|---|---|
| a.i. in g/ha | POLCO | | | | | | | | |
| I.1 | B.63 | found | calculated | found | calculated | found | calculated | found | calculated |
| 31.25 | — | 30 | — | | | | | | |
| — | 1 | 30 | — | | | | | | |
| 31.25 | 1 | 60 | 51 | | | | | | |

| application rate | herbicidal activity against | | | | | | | | |
|---|---|---|---|---|---|---|---|---|---|
| a.i. in g/ha | POLCO | | MATCH | | ALOMY | | | | |
| I.1 | B.63 | found | calculated | found | calculated | found | calculated | found | calculated |
| 125 | — | 80 | — | 75 | — | 30 | — | | |
| — | 0.5 | 20 | — | 30 | — | 0 | — | | |
| 125 | 0.5 | 100 | 84 | 100 | 83 | 60 | 30 | | |

| application rate | herbicidal activity against | | | | | | | | |
|---|---|---|---|---|---|---|---|---|---|
| a.i. in g/ha | VIOAR | | | | | | | | |
| I.1 | B.63 | found | calculated | found | calculated | found | calculated | found | calculated |
| 62.5 | — | 0 | — | | | | | | |
| — | 0.5 | 65 | — | | | | | | |
| 62.5 | 0.5 | 85 | 65 | | | | | | |

Use Example 41: Synergistic Herbicidal Action of the Composition 1.52 Applied by the Post Emergence Method: Treatment by the Mixture of Compound (I.1)+Penoxsulam (B.52)

| application rate | herbicidal activity against | | | | | | | | |
|---|---|---|---|---|---|---|---|---|---|
| a.i. in g/ha | VIOAR | | | | | | | | |
| I.1 | B.52 | found | calculated | found | calculated | found | calculated | found | calculated |
| 125 | — | 0 | — | | | | | | |
| — | 5 | 60 | — | | | | | | |
| 125 | 5 | 80 | 60 | | | | | | |

| application rate | herbicidal activity against | | | | | | | | |
|---|---|---|---|---|---|---|---|---|---|
| a.i. in g/ha | ERICA | | | | | | | | |
| I.1 | B.52 | found | calculated | found | calculated | found | calculated | found | calculated |
| 62.5 | — | 35 | — | | | | | | |
| — | 5 | 90 | — | | | | | | |
| 62.5 | 5 | 98 | 94 | | | | | | |

| application rate | herbicidal activity against | | | | | | | | |
|---|---|---|---|---|---|---|---|---|---|
| a.i. in g/ha | ABUTH | | ERICA | | | | | | |
| I.1 | B.52 | found | calculated | found | calculated | found | calculated | found | calculated |
| 31.25 | — | 15 | — | 0 | — | | | | |
| — | 5 | 90 | — | 90 | — | | | | |
| 31.25 | 5 | 98 | 92 | 98 | 90 | | | | |

| application rate | herbicidal activity against | | | | | | | | |
|---|---|---|---|---|---|---|---|---|---|
| a.i. in g/ha | ALOMY | | VIOAR | | APESV | | GERDI | | |
| I.1 | B.52 | found | calculated | found | calculated | found | calculated | found | calculated |
| 125 | — | 30 | — | 0 | — | 35 | — | 65 | — |
| — | 2.5 | 55 | — | 0 | — | 55 | — | 80 | — |
| 125 | 2.5 | 80 | 69 | 40 | 0 | 75 | 71 | 98 | 93 |

-continued

| application rate a.i. in g/ha | | herbicidal activity against | | | | | | | | |
|---|---|---|---|---|---|---|---|---|---|---|
| | | ALOMY | | APESV | | VIOAR | | ABUTH | | GERDI |
| I.1 | B.52 | found | calculated | found | calculated | found | calculated | found | calculated | found | calculated |
| 62.5 | — | 25 | — | 20 | — | 0 | — | 60 | — | 65 | — |
| — | 2.5 | 55 | — | 55 | — | 0 | — | 85 | — | 80 | — |
| 62.5 | 2.5 | 80 | 66 | 90 | 64 | 40 | 0 | 98 | 94 | 98 | 93 |

| application rate a.i. in g/ha | | herbicidal activity against ERICA | |
|---|---|---|---|
| I.1 | B.52 | found | calculated |
| 62.5 | — | 35 | — |
| — | 2.5 | 90 | — |
| 62.5 | 2.5 | 98 | 94 |

| application rate a.i. in g/ha | | herbicidal activity against | | | | | | | |
|---|---|---|---|---|---|---|---|---|---|
| | | ALOMY | | GERDI | | ERICA | | ABUTH | |
| I.1 | B.52 | found | calculated | found | calculated | found | calculated | found | calculated |
| 31.25 | — | 25 | — | 50 | — | 0 | — | 15 | — |
| — | 2.5 | 55 | — | 80 | — | 90 | — | 85 | — |
| 31.25 | 2.5 | 80 | 66 | 98 | 90 | 98 | 90 | 90 | 87 |

Use Example 42: Synergistic Herbicidal Action of the Composition 1.88 Applied by the Post Emergence Method: Treatment by the Mixture of Compound (I.1)+Flumioxazin (B.88)

| application rate a.i. in g/ha | | herbicidal activity against | | | | | | | |
|---|---|---|---|---|---|---|---|---|---|
| | | PAPRH | | APESV | | GERDI | | ALOMY | |
| I.1 | B.88 | found | calculated | found | calculated | found | calculated | found | calculated |
| 62.5 | — | 75 | — | 10 | — | 0 | — | 0 | — |
| — | 2 | 75 | — | 65 | — | 70 | — | 20 | — |
| 62.5 | 2 | 100 | 94 | 75 | 69 | 75 | 70 | 30 | 20 |

| application rate a.i. in g/ha | | herbicidal activity against | | | |
|---|---|---|---|---|---|
| | | PAPRH | | APESV | |
| I.1 | B.88 | found | calculated | found | calculated |
| 31.25 | — | 75 | — | 0 | — |
| — | 2 | 75 | — | 65 | — |
| 31.25 | 2 | 100 | 94 | 70 | 65 |

| application rate a.i. in g/ha | | herbicidal activity against | |
|---|---|---|---|
| | | PAPRH | |
| I.1 | B.88 | found | calculated |
| 15.62 | — | 70 | — |
| — | 2 | 75 | — |
| 15.62 | 2 | 100 | 93 |

| application rate a.i. in g/ha | | herbicidal activity against | | | | | | | | |
|---|---|---|---|---|---|---|---|---|---|---|
| | | PAPRH | | GERDI | | APESV | | ALOMY | | KCHSC |
| I.1 | B.88 | found | calculated | found | calculated | found | calculated | found | calculated | found | calculated |
| 62.5 | — | 75 | — | 0 | — | 10 | — | 0 | — | 80 | — |
| — | 1 | 25 | — | 70 | — | 25 | — | 0 | — | 85 | — |
| 62.5 | 1 | 100 | 90 | 70 | 55 | 33 | 40 | 0 | 100 | 97 | |

-continued

| application rate a.i. in g/ha | | herbicidal activity against | | | | | | | |
|---|---|---|---|---|---|---|---|---|---|
| | | PAPRH | | KCHSC | | APESV | | ABUTH | |
| I.1 | B.88 | found | calculated | found | calculated | found | calculated | found | calculated |
| 31.25 | — | 75 | — | 55 | — | 0 | — | 60 | — |
| — | 1 | 25 | — | 85 | — | 25 | — | 90 | — |
| 31.25 | 1 | 100 | 85 | 100 | 93 | 45 | 25 | 100 | 96 |

| application rate a.i. in g/ha | | herbicidal activity against | | | | | | | |
|---|---|---|---|---|---|---|---|---|---|
| | | KCHSC | | APESV | | | | | |
| I.1 | B.88 | found | calculated | found | calculated | found | calculated | found | calculated |
| 15.62 | — | 45 | — | 0 | — | | | | |
| — | 1 | 85 | — | 25 | — | | | | |
| 15.62 | 1 | 100 | 92 | 60 | 25 | | | | |

Use Example 43: Synergistic Herbicidal Action of the Composition 1.95 Applied by the Post Emergence Method: Treatment by the Mixture of Compound (I.1)+Trifludimoxazin (B.95)

| application rate a.i. in g/ha | | herbicidal activity against | | | | | | | |
|---|---|---|---|---|---|---|---|---|---|
| | | ECHCG | | GERDI | | MATCH | | ERICA | | GALAP | |
| I.1 | B.95 | found | calculated | found | calculated | found | calculated | found | calculated | found | calculated |
| 62.5 | — | 55 | — | 0 | — | 65 | — | 10 | — | 60 | |
| — | 2 | 45 | — | 65 | — | 65 | — | 45 | — | 75 | |
| 62.5 | 2 | 85 | 75 | 100 | 65 | 100 | 88 | 100 | 51 | 95 | 90 |

| application rate a.i. in g/ha | | herbicidal activity against | | | | | | | |
|---|---|---|---|---|---|---|---|---|---|
| | | MATCH | | ERICA | | GALAP | | | |
| I.1 | B.95 | found | calculated | found | calculated | found | calculated | found | calculated | found | calculated |
| 31.25 | — | 10 | — | 0 | — | 50 | — | | | | |
| — | 2 | 65 | — | 45 | — | 75 | — | | | | |
| 31.25 | 2 | 100 | 69 | 100 | 45 | 95 | 88 | | | | |

| application rate a.i. in g/ha | | herbicidal activity against | |
|---|---|---|---|
| | | ERICA | |
| I.1 | B.95 | found | calculated | found | calculated | found | calculated | found | calculated | found | calculated |
| 15.62 | — | 0 | — | | | | | | | | |
| — | 2 | 45 | — | | | | | | | | |
| 15.62 | 2 | 65 | 45 | | | | | | | | |

| application rate a.i. in g/ha | | herbicidal activity against | | | | | | | |
|---|---|---|---|---|---|---|---|---|---|
| | | ALOMY | | PAPRH | | ERICA | | GERDI | | APESV | |
| I.1 | B.95 | found | calculated | found | calculated | found | calculated | found | calculated | found | calculated |
| 62.5 | — | 0 | — | 75 | — | 10 | — | 0 | — | 10 | — |
| — | 1 | 25 | — | 35 | — | 40 | — | 65 | — | 30 | — |
| 62.5 | 1 | 60 | 25 | 100 | 84 | 60 | 46 | 75 | 65 | 55 | 37 |

| application rate a.i. in g/ha | | herbicidal activity against | | | | | | | |
|---|---|---|---|---|---|---|---|---|---|
| | | ALOMY | | PAPRH | | MATCH | | ERICA | | GALAP | |
| I.1 | B.95 | found | calculated | found | calculated | found | calculated | found | calculated | found | calculated |
| 31.25 | — | 0 | — | 75 | — | 10 | — | 0 | — | 50 | — |
| — | 1 | 25 | — | 35 | — | 30 | — | 40 | — | 75 | — |
| 31.25 | 1 | 55 | 25 | 100 | 84 | 100 | 37 | 55 | 40 | 90 | 85 |

| application rate a.i. in g/ha | | herbicidal activity against | | | | | | | |
|---|---|---|---|---|---|---|---|---|---|
| | | MATCH | | ERICA | | ECHCG | | APESV | |
| I.1 | B.95 | found | calculated | found | calculated | found | calculated | found | calculated |
| 15.62 | — | 10 | — | 0 | — | 10 | — | 0 | — |
| — | 1 | 30 | — | 40 | — | 25 | — | 30 | — |
| 15.62 | 1 | 55 | 37 | 55 | 40 | 45 | 33 | 40 | 30 |

Use Example 44: Synergistic Herbicidal Action of the Composition 1.57 Applied by the Post Emergence Method: Treatment by the Mixture of Compound (I.1)+Pyroxsulam (B.57)

| application rate a.i. in g/ha | | herbicidal activity against | | | | | | | |
|---|---|---|---|---|---|---|---|---|---|
| | | PAPRH | | ERICA | | | | | |
| I.1 | B.57 | found | calculated | found | calculated | found | calculated | found | calculated |
| 62.5 | — | 75 | — | 10 | — | — | — | — | — |
| — | 2 | 0 | — | 75 | — | — | — | — | — |
| 62.5 | 2 | 90 | 75 | 98 | 78 | | | | |

| application rate a.i. in g/ha | | herbicidal activity against | | | | | | | |
|---|---|---|---|---|---|---|---|---|---|
| | | IPOHE | | | | | | | |
| I.1 | B.57 | found | calculated | found | calculated | found | calculated | found | calculated |
| 62.5 | — | 30 | — | — | — | — | — | — | — |
| — | 1 | 80 | — | — | — | — | — | — | — |
| 62.5 | 1 | 98 | 86 | | | | | | |

Use Example 45: Synergistic Herbicidal Action of the Composition 1.89 Applied by the Post Emergence Method: Treatment by the Mixture of Compound (I.1)+Fomesafen (B.89)

| application rate a.i. in g/ha | | herbicidal activity against | | | | | | | |
|---|---|---|---|---|---|---|---|---|---|
| | | GERDI | | IPOHE | | ERICA | | | |
| I.1 | B.89 | found | calculated | found | calculated | found | calculated | found | calculated |
| 62.5 | — | 0 | — | 30 | — | 10 | — | — | — |
| — | 25 | 25 | — | 85 | — | 20 | — | — | — |
| 62.5 | 25 | 75 | 25 | 100 | 90 | 35 | 28 | | |

| application rate a.i. in g/ha | | herbicidal activity against | | | | | | | |
|---|---|---|---|---|---|---|---|---|---|
| | | STEME | | IPOHE | | ABUTH | | | |
| I.1 | B.89 | found | calculated | found | calculated | found | calculated | found | calculated |
| 31.25 | — | 0 | — | 25 | — | 60 | — | — | — |
| — | 25 | 0 | — | 85 | — | 90 | — | — | — |
| 31.25 | 25 | 65 | 0 | 100 | 89 | 100 | 96 | | |

| application rate a.i. in g/ha | | herbicidal activity against | | | | | | | | |
|---|---|---|---|---|---|---|---|---|---|---|
| | | STEME | | IPOHE | | GERDI | | | | |
| I.1 | B.89 | found | calculated | found | calculated | found | calculated | found | calculated | found | calculated |
| 15.62 | — | 0 | — | 25 | — | 0 | — | — | — | — | — |
| — | 25 | 0 | — | 85 | — | 25 | — | — | — | — | — |
| 15.62 | 25 | 20 | 0 | 100 | 89 | 35 | 25 | — | — | — | — |

| application rate a.i. in g/ha | | herbicidal activity against | | | | | | | | |
|---|---|---|---|---|---|---|---|---|---|---|
| | | ALOMY | | GERDI | | VIOAR | | IPOHE | | |
| I.1 | B.89 | found | calculated | found | calculated | found | calculated | found | calculated | found | calculated |
| 62.5 | — | 0 | — | 0 | — | 25 | — | 30 | — | — | — |
| — | 12.5 | 25 | — | 25 | — | 55 | — | 85 | — | — | — |
| 62.5 | 12.5 | 45 | 25 | 65 | 25 | 100 | 66 | 100 | 90 | — | — |

| application rate a.i. in g/ha | | herbicidal activity against | | | | | | | | |
|---|---|---|---|---|---|---|---|---|---|---|
| | | STEME | | | | | | | | |
| I.1 | B.89 | found | calculated | found | calculated | found | calculated | found | calculated | found | calculated |
| 31.25 | — | 0 | — | — | — | — | — | — | — | — | — |
| — | 12.5 | 0 | — | — | — | — | — | — | — | — | — |
| 31.25 | 12.5 | 20 | 0 | — | — | — | — | — | — | — | — |

| application rate a.i. in g/ha | | herbicidal activity against | | | | | | | | |
|---|---|---|---|---|---|---|---|---|---|---|
| | | POLCO | | | | | | | | |
| I.1 | B.89 | found | calculated | found | calculated | found | calculated | found | calculated | found | calculated |
| 15.62 | — | 0 | — | — | — | — | — | — | — | — | — |
| — | 12.5 | 95 | — | — | — | — | — | — | — | — | — |
| 15.62 | 12.5 | 100 | 95 | — | — | — | — | — | — | — | — |

Use Example 46: Synergistic Herbicidal Action of the Composition 1.167 Applied by the Post Emergence Method: Treatment by the Mixture of Compound (I.1)+Quinclorac (B.167)

| application rate a.i. in g/ha | | herbicidal activity against | | | | | | | |
|---|---|---|---|---|---|---|---|---|---|
| | | POLCO | | ABUTH | | GERDI | | MATCH | |
| I.1 | B.167 | found | calculated | found | calculated | found | calculated | found | calculated |
| 62.5 | — | 40 | — | 0 | — | 60 | — | 0 | — |
| — | 125 | 30 | — | 70 | — | 0 | — | 30 | — |
| 62.5 | 125 | 100 | 58 | 80 | 70 | 100 | 60 | 50 | 30 |

| application rate a.i. in g/ha | | herbicidal activity against | | | | | | | |
|---|---|---|---|---|---|---|---|---|---|
| | | ECHCG | | | | | | | |
| I.1 | B.167 | found | calculated | found | calculated | found | calculated | found | calculated | found | calculated |
| 31.25 | — | 10 | — | — | — | — | — | — | — | — | — |
| — | 125 | 20 | — | — | — | — | — | — | — | — | — |
| 31.25 | 125 | 50 | 28 | — | — | — | — | — | — | — | — |

| application rate a.i. in g/ha | | herbicidal activity against | | | | | | | | |
|---|---|---|---|---|---|---|---|---|---|---|
| | | POLCO | | ECHCG | | | | | | |
| I.1 | B.167 | found | calculated | found | calculated | found | calculated | found | calculated | found | calculated |
| 15.62 | — | 10 | — | 0 | — | — | — | — | — | — | — |
| — | 125 | 30 | — | 20 | — | — | — | — | — | — | — |
| 15.62 | 125 | 50 | 37 | 40 | 20 | | | | | | |

| application rate a.i. in g/ha | | herbicidal activity against | | | | | | | | |
|---|---|---|---|---|---|---|---|---|---|---|
| | | ABUTH | | MATCH | | POLCO | | KCHSC | | |
| I.1 | B.167 | found | calculated | found | calculated | found | calculated | found | calculated | found | calculated |
| 62.5 | — | 0 | — | 0 | — | 40 | — | 70 | — | — | — |
| — | 62.5 | 65 | — | 0 | — | 0 | — | 0 | — | — | — |
| 62.5 | 62.5 | 75 | 65 | 40 | 0 | 50 | 40 | 80 | 70 | | |

| application rate a.i. in g/ha | | herbicidal activity against | | | | | | | | |
|---|---|---|---|---|---|---|---|---|---|---|
| | | KCHSC | | | | | | | | |
| I.1 | B.167 | found | calculated | found | calculated | found | calculated | found | calculated | found | calculated |
| 31.25 | — | 30 | — | — | — | — | — | — | — | — | — |
| — | 62.5 | 0 | — | — | — | — | — | — | — | — | — |
| 31.25 | 62.5 | 60 | 30 | | | | | | | | |

| application rate a.i. in g/ha | | herbicidal activity against | | | | | | | | |
|---|---|---|---|---|---|---|---|---|---|---|
| | | POLCO | | | | | | | | |
| I.1 | B.167 | found | calculated | found | calculated | found | calculated | found | calculated | found | calculated |
| 15.62 | — | 10 | — | — | — | — | — | — | — | — | — |
| — | 62.5 | 0 | — | — | — | — | — | — | — | — | — |
| 15.62 | 62.5 | 50 | 10 | | | | | | | | |

Use Example 47: Synergistic Herbicidal Action of the Composition 1.103 Applied by the Post Emergence Method: Treatment by the Mixture of Compound (I.1)+Picolinafen (B.103)

| application rate a.i. in g/ha | | herbicidal activity against | | | | | | | |
|---|---|---|---|---|---|---|---|---|---|
| | | POLCO | | GERDI | | ERICA | | KCHSC | |
| I.1 | B.103 | found | calculated | found | calculated | found | calculated | found | calculated |
| 62.5 | — | 40 | — | 60 | — | 0 | — | 70 | — |
| — | 15 | 70 | — | 0 | — | 65 | — | 60 | — |
| 62.5 | 15 | 100 | 82 | 100 | 60 | 100 | 65 | 100 | 88 |

| application rate a.i. in g/ha | | herbicidal activity against | | | | | | | | |
|---|---|---|---|---|---|---|---|---|---|---|
| | | GERDI | | PAPRH | | ERICA | | IPOHE | | KCHSC | |
| I.1 | B.103 | found | calculated | found | calculated | found | calculated | found | calculated | found | calculated |
| 31.25 | — | 30 | — | 30 | — | 0 | — | 70 | — | 30 | — |
| — | 15 | 0 | — | 70 | — | 65 | — | 60 | — | 60 | — |
| 31.25 | 15 | 60 | 60 | 100 | 79 | 100 | 65 | 98 | 88 | 85 | 72 |

| application rate | | herbicidal activity against | | | | | | | | | |
|---|---|---|---|---|---|---|---|---|---|---|---|
| a.i. in g/ha | | STEME | | PAPRH | | | | | | | |
| I.1 | B.103 | found | calculated | found | calculated | found | calculated | found | calculated | found | calculated |
| 15.62 | — | 60 | — | 30 | — | | | | | | |
| — | 15 | 65 | — | 70 | — | | | | | | |
| 15.62 | 15 | 100 | 86 | 100 | 79 | | | | | | |

| application rate | | herbicidal activity against | | | | | | | | | |
|---|---|---|---|---|---|---|---|---|---|---|---|
| a.i. in g/ha | | POLCO | | GERDI | | ERICA | | KCHSC | | GALAP | |
| I.1 | B.103 | found | calculated | found | calculated | found | calculated | found | calculated | found | calculated |
| 62.5 | — | 40 | — | 60 | — | 0 | — | 70 | — | 50 | — |
| — | 7.5 | 40 | — | 0 | — | 25 | — | 60 | — | 70 | — |
| 62.5 | 7.5 | 100 | 64 | 100 | 60 | 40 | 25 | 100 | 88 | 95 | 85 |

| application rate | | herbicidal activity against | | | | | | | | | |
|---|---|---|---|---|---|---|---|---|---|---|---|
| a.i. in g/ha | | ECHCG | | GERDI | | KCHSC | | | | | |
| I.1 | B.103 | found | calculated | found | calculated | found | calculated | found | calculated | found | calculated |
| 31.25 | — | 10 | — | 30 | — | 30 | — | | | | |
| — | 7.5 | 20 | — | 0 | — | 60 | — | | | | |
| 31.25 | 7.5 | 40 | 28 | 100 | 30 | 85 | 72 | | | | |

| application rate | | herbicidal activity against | | | | | | | | | |
|---|---|---|---|---|---|---|---|---|---|---|---|
| a.i. in g/ha | | POLCO | | GERDI | | IPOHE | | | | | |
| I.1 | B.103 | found | calculated | found | calculated | found | calculated | found | calculated | found | calculated |
| 15.6 | — | 10 | — | 0 | — | 20 | — | | | | |
| — | 7.5 | 40 | — | 0 | — | 40 | — | | | | |
| 15.6 | 7.5 | 98 | 46 | 30 | 0 | 65 | 52 | | | | |

Use Example 48: Synergistic Herbicidal Action of the Composition 1.91 Applied by the Post Emergence Method: Treatment by the Mixture of Compound (I.1)+Oxyfluorfen (B.91)

| application rate | | herbicidal activity against | | | | | | | | |
|---|---|---|---|---|---|---|---|---|---|---|
| a.i. in g/ha | | ERICA | | | | | | | | |
| I.1 | B.91 | found | calculated | found | calculated | found | calculated | found | calculated |
| 62.5 | — | 0 | — | | | | | | | |
| — | 200 | 90 | — | | | | | | | |
| 62.5 | 200 | 100 | 90 | | | | | | | |

| application rate | | herbicidal activity against | | | | | | | | | |
|---|---|---|---|---|---|---|---|---|---|---|---|
| a.i. in g/ha | | ERICA | | | | | | | | | |
| I.1 | B.91 | found | calculated | found | calculated | found | calculated | found | calculated | found | calculated |
| 31.25 | — | 0 | — | | | | | | | | |
| — | 200 | 90 | — | | | | | | | | |
| 31.25 | 200 | 100 | 90 | | | | | | | | |

| application rate a.i. in g/ha | | herbicidal activity against | | | | | | | |
|---|---|---|---|---|---|---|---|---|---|
| | | ECHCG | | ERICA | | ALOMY | | | |
| I.1 | B.91 | found | calculated | found | calculated | found | calculated | found | calculated |
| 62.5 | — | 50 | — | 0 | — | 0 | — | — | — |
| — | 100 | 60 | — | 0 | — | 85 | — | — | — |
| 62.5 | 100 | 95 | 80 | 100 | 0 | 98 | 85 | — | — |

| application rate a.i. in g/ha | | herbicidal activity against | | | | | | | |
|---|---|---|---|---|---|---|---|---|---|
| | | ECHCG | | AMBEL | | ERICA | | ALMOY | |
| I.1 | B.91 | found | calculated | found | calculated | found | calculated | found | calculated |
| 31.25 | — | 10 | — | 0 | — | 0 | — | 0 | — |
| — | 100 | 60 | — | 70 | — | 0 | — | 85 | — |
| 31.25 | 100 | 90 | 64 | 98 | 70 | 90 | 0 | 95 | 85 |

| application rate a.i. in g/ha | | herbicidal activity against | | | | | | | |
|---|---|---|---|---|---|---|---|---|---|
| | | ECHCG | | AMBEL | | ERICA | | ALOMY | |
| I.1 | B.91 | found | calculated | found | calculated | found | calculated | found | calculated |
| 15.62 | — | 0 | — | 0 | — | 0 | — | 0 | — |
| — | 100 | 60 | — | 70 | — | 0 | — | 85 | — |
| 15.62 | 100 | 85 | 60 | 98 | 70 | 65 | 0 | 98 | 85 |

Use Example 49: Synergistic Herbicidal Action of the Composition 1.144 Applied by the Post Emergence Method: Treatment by the Mixture of Compound (I.1)+Aminopyralid (B.144)

| application rate a.i. in g/ha | | herbicidal activity against | | | | | | | |
|---|---|---|---|---|---|---|---|---|---|
| | | POLCO | | | | | | | |
| I.1 | B.144 | found | calculated | found | calculated | found | calculated | found | calculated |
| 62.5 | — | 40 | — | — | — | — | — | — | — |
| — | 8 | 98 | — | — | — | — | — | — | — |
| 62.5 | 8 | 100 | 99 | — | — | — | — | — | — |

| application rate a.i. in g/ha | | herbicidal activity against | | | | | | | |
|---|---|---|---|---|---|---|---|---|---|
| | | AMBEL | | KCHSC | | | | | |
| I.1 | B.144 | found | calculated | found | calculated | found | calculated | found | calculated |
| 31.25 | — | 0 | — | 30 | — | — | — | — | — |
| — | 8 | 75 | — | 0 | — | — | — | — | — |
| 31.25 | 8 | 85 | 75 | 55 | 30 | — | — | — | — |

| application rate a.i. in g/ha | | herbicidal activity against | | | | | | | |
|---|---|---|---|---|---|---|---|---|---|
| | | AMBEL | | KCHSC | | | | | |
| I.1 | B.144 | found | calculated | found | calculated | found | calculated | found | calculated |
| 15.625 | — | 0 | — | 0 | — | — | — | — | — |
| — | 8 | 75 | — | 0 | — | — | — | — | — |
| 15.625 | 8 | 85 | 75 | 20 | 0 | — | — | — | — |

-continued

| application rate a.i. in g/ha | | herbicidal activity against | | | | | | | | |
|---|---|---|---|---|---|---|---|---|---|---|
| | | APESV | | POLCO | | ABUTH | | GERDI | | KCHSC |
| I.1 | B.144 | found | calculated | found | calculated | found | calculated | found | calculated | found | calculated |
| 62.5 | — | 0 | — | 40 | — | 0 | — | 60 | — | 70 | — |
| — | 4 | 0 | — | 98 | — | 0 | — | 30 | — | 0 | — |
| 62.5 | 4 | 20 | 0 | 100 | 99 | 40 | 0 | 70 | 60 | 80 | 70 |

| application rate a.i. in g/ha | | herbicidal activity against | | | | | | | | |
|---|---|---|---|---|---|---|---|---|---|---|
| | | GERDI | | VIOLA | | | | | | |
| I.1 | B.144 | found | calculated | found | calculated | found | calculated | found | calculated | found | calculated |
| 15.625 | — | 0 | — | 0 | — | — | — | — | — | — | — |
| — | 4 | 0 | — | 0 | — | — | — | — | — | — | — |
| 15.625 | 4 | 20 | 0 | 35 | 0 | — | — | — | — | — | — |

Use Example 50: Synergistic Herbicidal Applied by the Post Emergence Method: Treatment by the Mixture of Compound (I.1)+DMTA

| application rate a.i. in g/ha | | herbicidal activity against | | | | | | | |
|---|---|---|---|---|---|---|---|---|---|
| | | GERDI | | IPOHE | | | | | |
| I.1 | DMTA | found | calculated | found | calculated | found | calculated | found | calculated |
| 125 | — | 70 | — | 95 | — | — | — | — | — |
| — | 350 | 60 | — | 25 | — | — | — | — | — |
| 125 | 350 | 95 | 88 | 98 | 96 | | | | |

| application rate a.i. in g/ha | | herbicidal activity against | | | | | |
|---|---|---|---|---|---|---|---|
| | | ALOMY | | POLCO | | MATCH | |
| I.1 | DMTA | found | calculated | found | calculated | found | calculated |
| 62.5 | — | 0 | — | 75 | — | 60 | — |
| — | 350 | 45 | — | 25 | — | 30 | — |
| 62.5 | 350 | 55 | 45 | 98 | 81 | 100 | 72 |

| application rate a.i. in g/ha | | herbicidal activity against | | | | | | | |
|---|---|---|---|---|---|---|---|---|---|
| | | ALOMY | | AMBEL | | GERDI | | MATCH | |
| I.1 | DMTA | found | calculated | found | calculated | found | calculated | found | calculated |
| 31.25 | — | 0 | — | 10 | — | 10 | — | 15 | — |
| — | 350 | 45 | — | 20 | — | 60 | — | 30 | — |
| 31.25 | 350 | 55 | 45 | 65 | 28 | 65 | 64 | 75 | 41 |

| application rate a.i. in g/ha | | herbicidal activity against | | | | | | | |
|---|---|---|---|---|---|---|---|---|---|
| | | ALOMY | | APESV | | GERDI | | VIOLA | |
| I.1 | DMTA | found | calculated | found | calculated | found | calculated | found | calculated |
| 125 | — | 25 | — | 0 | — | 70 | — | 30 | — |
| — | 175 | 0 | — | 95 | — | 30 | — | 0 | — |
| 125 | 175 | 40 | 25 | 100 | 95 | 95 | 79 | 80 | 30 |

| application rate a.i. in g/ha | | herbicidal activity against | | | | | | | | |
|---|---|---|---|---|---|---|---|---|---|---|
| | | ALOMY | | ECHCG | | VIOLA | | MATCH | | ERICA | |
| I.1 | DMTA | found | calculated | found | calculated | found | calculated | found | calculated | found | calculated |
| 62.5 | — | 0 | — | 15 | — | 20 | — | 60 | — | 10 | |
| — | 175 | 0 | — | 90 | — | 0 | — | 30 | — | 15 | |
| 65.5 | 175 | 20 | 0 | 95 | 92 | 30 | 20 | 80 | 72 | 75 | 24 |

| application rate a.i. in g/ha | | herbicidal activity against | | | | | | | | |
|---|---|---|---|---|---|---|---|---|---|---|
| | | POLCO | | AMBEL | | GERDI | | MATCH | | ERICA | |
| I.1 | DMTA | found | calculated | found | calculated | found | calculated | found | calculated | found | calculated |
| 31.25 | — | 20 | — | 10 | — | 10 | — | 15 | — | 10 | — |
| — | 175 | 0 | — | 0 | — | 30 | — | 30 | — | 15 | — |
| 31.25 | 175 | 40 | 20 | 35 | 10 | 55 | 37 | 60 | 41 | 35 | 15 |

Use Example 51: Synergistic Herbicidal Action of the Composition 1.178 Applied by the Post Emergence Method: Treatment by the Mixture of Compound (I.1)+Indaziflam (B.178)

| application rate a.i. in g/ha | | herbicidal activity against | | | | | | | |
|---|---|---|---|---|---|---|---|---|---|
| | | APESV | | GALAP | | GERDI | | | |
| I.1 | B.178 | found | calculated | found | calculated | found | calculated | found | calculated |
| 125 | — | 0 | — | 65 | — | 70 | — | — | — |
| — | 3 | 40 | — | 65 | — | 55 | — | — | — |
| 125 | 3 | 65 | 40 | 100 | 88 | 100 | 87 | | |

| application rate a.i. in g/ha | | herbicidal activity against | | | | | | | |
|---|---|---|---|---|---|---|---|---|---|
| | | ERICA | | KCHSC | | | | | |
| I.1 | B.178 | found | calculated | found | calculated | found | calculated | found | calculated |
| 62.5 | — | 10 | — | 60 | — | — | — | — | — |
| — | 3 | 15 | — | 15 | — | — | — | — | — |
| 62.5 | 3 | 35 | 24 | 85 | 66 | | | | |

| application rate a.i. in g/ha | | herbicidal activity against | | | | | | | |
|---|---|---|---|---|---|---|---|---|---|
| | | GERDI | | MATCH | | KCHSC | | | |
| I.1 | B.178 | found | calculated | found | calculated | found | calculated | found | calculated |
| 31.25 | — | 10 | — | 15 | — | 30 | — | — | — |
| — | 3 | 55 | — | 35 | — | 15 | — | — | — |
| 31.25 | 3 | 65 | 60 | 60 | 45 | 45 | 41 | | |

| application rate a.i. in g/ha | | herbicidal activity against | | | | | | | |
|---|---|---|---|---|---|---|---|---|---|
| | | ABUTH | | GALAP | | MATCH | | ERICA | |
| I.1 | B.178 | found | calculated | found | calculated | found | calculated | found | calculated |
| 62.5 | — | 55 | — | 65 | — | 60 | — | 10 | — |
| — | 6 | 60 | — | 60 | — | 65 | — | 60 | — |
| 62.5 | 6 | 90 | 82 | 90 | 86 | 100 | 86 | 100 | 64 |

| application rate | | herbicidal activity against | | | | | | | |
|---|---|---|---|---|---|---|---|---|---|
| a.i. in g/ha | | MATCH | | ABUTH | | AMBEL | | GERDI | |
| I.1 | B.178 | found | calculated | found | calculated | found | calculated | found | calculated |
| 31.25 | — | 15 | — | 0 | — | 10 | — | 10 | — |
| — | 6 | 35 | — | 60 | — | 70 | — | 55 | — |
| 31.25 | 6 | 60 | 45 | 65 | 60 | 85 | 73 | 60 | 60 |

Use Example 52: Synergistic Herbicidal Action of the Composition 1.130 Applied by the Post Emergence Method: Treatment by the Mixture of Compound (I.1)+Flufenacet (B.130)

| application rate | | herbicidal activity against | | | | | | | |
|---|---|---|---|---|---|---|---|---|---|
| a.i. in g/ha | | ALOMY | | | | | | | |
| I.1 | B.130 | found | calculated | found | calculated | found | calculated | found | calculated |
| 125 | — | 25 | — | — | — | — | — | — | — |
| — | 100 | 65 | — | — | — | — | — | — | — |
| 125 | 100 | 80 | 74 | | | | | | |

| application rate | | herbicidal activity against | | | | | | | |
|---|---|---|---|---|---|---|---|---|---|
| a.i. in g/ha | | ALOMY | | MATCH | | ECHCG | | | |
| I.1 | B.130 | found | calculated | found | calculated | found | calculated | found | calculated |
| 62.5 | — | 0 | — | 60 | — | 15 | — | — | — |
| — | 100 | 65 | — | 20 | — | 65 | — | — | — |
| 62.5 | 100 | 85 | 65 | 100 | 68 | 80 | 70 | | |

| application rate | | herbicidal activity against | | | | | | | |
|---|---|---|---|---|---|---|---|---|---|
| a.i. in g/ha | | ALOMY | | POLCO | | GERDI | | MATCH | |
| I.1 | B.130 | found | calculated | found | calculated | found | calculated | found | calculated |
| 31.25 | — | 0 | — | 20 | — | 10 | — | 15 | — |
| — | 100 | 65 | — | 10 | — | 10 | — | 20 | — |
| 31.25 | 100 | 85 | 65 | 40 | 28 | 45 | 19 | 55 | 32 |

| application rate | | herbicidal activity against | | | | | | | |
|---|---|---|---|---|---|---|---|---|---|
| a.i. in g/ha | | GERDI | | VIOAR | | | | | |
| I.1 | B.130 | found | calculated | found | calculated | found | calculated | found | calculated |
| 125 | — | 70 | — | 30 | — | — | — | — | — |
| — | 50 | 10 | — | 80 | — | — | — | — | — |
| 125 | 50 | 90 | 73 | 98 | 86 | | | | |

| application rate | | herbicidal activity against | | | | | | | |
|---|---|---|---|---|---|---|---|---|---|
| a.i. in g/ha | | MATCH | | ERICA | | KCHSC | | APESV | |
| I.1 | B.130 | found | calculated | found | calculated | found | calculated | found | calculated |
| 62.5 | — | 60 | — | 10 | — | 60 | — | 0 | — |
| — | 50 | 0 | — | 0 | — | 0 | — | 85 | — |
| 62.5 | 50 | 100 | 60 | 35 | 10 | 65 | 60 | 95 | 85 |

-continued

| application rate | | herbicidal activity against | | | | | | | | |
|---|---|---|---|---|---|---|---|---|---|---|
| a.i. in g/ha | | GERDI | | MATCH | | IPOHE | | POLCO | | ALOMY |
| I.1 | B.130 | found | calculated | found | calculated | found | calculated | found | calculated | found | calculated |
| 31.25 | — | 10 | — | 15 | — | 55 | — | 20 | — | 0 | — |
| — | 50 | 10 | — | 0 | — | 60 | — | 10 | — | 40 | — |
| 31.25 | 50 | 25 | 19 | 80 | 15 | 98 | 82 | 60 | 28 | 75 | 40 |

Use Example 53: Synergistic Herbicidal Action Applied by the Post Emergence Method: Treatment by the Mixture of Compound (I.1)+Cycloxidim

| application rate | | herbicidal activity against | | | | | | | | |
|---|---|---|---|---|---|---|---|---|---|---|
| a.i. in g/ha | | GALAP | | GERDI | | APESV | | | | |
| I.1 | cycloxidim | found | calculated | found | calculated | found | calculated | found | calculated | |
| 125 | — | 65 | — | 70 | — | 0 | — | — | — | |
| — | 5 | 25 | — | 20 | — | 30 | — | — | — | |
| 125 | 5 | 85 | 74 | 100 | 76 | 35 | 30 | | | |

| application rate | | herbicidal activity against | | | | | | | | |
|---|---|---|---|---|---|---|---|---|---|---|
| a.i. in g/ha | | MATCH | | | | | | | | |
| I.1 | cycloxidim | found | calculated | found | calculated | found | calculated | found | calculated | found | calculated |
| 62.5 | — | 60 | — | — | — | — | — | — | — | | |
| — | 5 | 65 | — | — | — | — | — | — | — | | |
| 62.5 | 5 | 100 | 86 | | | | | | | | |

| application rate | | herbicidal activity against | | | | | | | | |
|---|---|---|---|---|---|---|---|---|---|---|
| a.i. in g/ha | | GERDI | | APESV | | | | | | |
| I.1 | cycloxidim | found | calculated | found | calculated | found | calculated | found | calculated | found | calculated |
| 31.25 | — | 10 | — | 0 | — | — | — | — | — | | |
| — | 5 | 20 | — | 30 | — | — | — | — | — | | |
| 31.25 | 5 | 40 | 28 | 55 | 30 | | | | | | |

| application rate | | herbicidal activity against | | | | | | | | |
|---|---|---|---|---|---|---|---|---|---|---|
| a.i. in g/ha | | VIOAR | | GERDI | | | | | | |
| I.1 | cycloxidim | found | calculated | found | calculated | found | calculated | found | calculated | found | calculated |
| 125 | — | 30 | — | 70 | — | — | — | — | — | | |
| — | 2.5 | 0 | — | 0 | — | — | — | — | — | | |
| 125 | 2.5 | 80 | 30 | 75 | 70 | | | | | | |

| application rate | | herbicidal activity against | | | | | | | | |
|---|---|---|---|---|---|---|---|---|---|---|
| a.i. in g/ha | | VIOAR | | | | | | | | |
| I.1 | cycloxidim | found | calculated | found | calculated | found | calculated | found | calculated | found | calculated |
| 62.5 | — | 20 | — | — | — | — | — | — | — | | |
| — | 2.5 | 0 | — | — | — | — | — | — | — | | |
| 62.5 | 2.5 | 65 | 20 | | | | | | | | |

| application rate | | herbicidal activity against | | | | | | | | |
|---|---|---|---|---|---|---|---|---|---|---|
| a.i. in g/ha | | GERDI | | | | | | | | |
| I.1 | cycloxidim | found | calculated | found | calculated | found | calculated | found | calculated | found | calculated |
| 31.25 | — | 10 | — | — | — | — | — | — | — | | |
| — | 2.5 | 0 | — | — | — | — | — | — | — | | |
| 31.25 | 2.5 | 25 | 10 | | | | | | | | |

Use Example 54: Synergistic Herbicidal Action Applied by the Post Emergence Method: Treatment by the Mixture of Compound (I.1)+Metsulfuron

| application rate a.i. in g/ha | | herbicidal activity against | | | | | | | |
|---|---|---|---|---|---|---|---|---|---|
| | | APESV | | | | | | | |
| I.1 | metsulfuron | found | calculated | found | calculated | found | calculated | found | calculated |
| 62.5 | — | 0 | — | — | — | — | — | — | — |
| — | 0.25 | 30 | — | — | — | — | — | — | — |
| 62.5 | 0.25 | 40 | 30 | — | — | — | — | — | — |

| application rate a.i. in g/ha | | herbicidal activity against | | | | | | | |
|---|---|---|---|---|---|---|---|---|---|
| | | ECHCG | | ABUTH | | | | | |
| I.1 | metsulfuron | found | calculated | found | calculated | found | calculated | found | calculated |
| 31.25 | — | 0 | — | 0 | — | — | — | — | — |
| — | 0.25 | 25 | — | 80 | — | — | — | — | — |
| 31.25 | 0.25 | 30 | 25 | 85 | 80 | — | — | — | — |

| application rate a.i. in g/ha | | herbicidal activity against | | | | | | | |
|---|---|---|---|---|---|---|---|---|---|
| | | AMBEL | | POLCO | | | | | |
| I.1 | metsulfuron | found | calculated | found | calculated | found | calculated | found | calculated |
| 125 | — | 65 | — | 65 | — | — | — | — | — |
| — | 0.125 | 0 | — | 30 | — | — | — | — | — |
| 125 | 0.125 | 100 | 65 | 100 | 76 | — | — | — | — |

| application rate a.i. in g/ha | | herbicidal activity against | | | | | | | |
|---|---|---|---|---|---|---|---|---|---|
| | | ABUTH | | | | | | | |
| I.1 | metsulfuron | found | calculated | found | calculated | found | calculated | found | calculated |
| 62.5 | — | 65 | — | — | — | — | — | — | — |
| — | 0.125 | 20 | — | — | — | — | — | — | — |
| 62.5 | 0.125 | 100 | 72 | — | — | — | — | — | — |

| application rate a.i. in g/ha | | herbicidal activity against | | | | | | | |
|---|---|---|---|---|---|---|---|---|---|
| | | ABUTH | | GALAP | | ECHCG | | MATCH | |
| I.1 | metsulfuron | found | calculated | found | calculated | found | calculated | found | calculated |
| 31.25 | — | 0 | — | 50 | — | 0 | — | 0 | — |
| — | 0.125 | 20 | — | 10 | — | 0 | — | 0 | — |
| 31.25 | 0.125 | 55 | 20 | 60 | 55 | 30 | 0 | 90 | 0 |

Use Example 55: Synergistic Herbicidal Action of the Composition 1.93 Applied by the Post Emergence Method: Treatment by the Mixture of Compound (I.1)+Sulfentrazone (B.93)

| application rate a.i. in g/ha | | herbicidal activity against | | | | | | | |
|---|---|---|---|---|---|---|---|---|---|
| | | AMBEL | | MATCH | | POLCO | | | |
| I.1 | B.93 | found | calculated | found | calculated | found | calculated | found | calculated |
| 125 | — | 65 | — | 0 | — | 65 | — | — | — |
| — | 6 | 30 | — | 50 | — | 85 | — | — | — |
| 125 | 6 | 100 | 76 | 100 | 50 | 100 | 95 | — | — |

| application rate a.i. in g/ha | | herbicidal activity against | | | | | | | | |
|---|---|---|---|---|---|---|---|---|---|---|
| | | POLCO | | | | | | | | |
| I.1 | B.93 | found | calculated | found | calculated | found | calculated | found | calculated | found | calculated |
| 62.5 | — | 65 | — | — | | — | | — | | — | |
| — | 3 | 85 | — | — | | — | | — | | — | |
| 62.5 | 3 | 100 | 95 | — | | — | | — | | — | |

| application rate a.i. in g/ha | | herbicidal activity against | | | | | | | | |
|---|---|---|---|---|---|---|---|---|---|---|
| | | POLCO | | MATCH | | | | | | |
| I.1 | B.93 | found | calculated | found | calculated | found | calculated | found | calculated | found | calculated |
| 31.25 | — | 0 | — | 0 | — | | | | | | |
| — | 3 | 85 | — | 50 | — | | | | | | |
| 31.25 | 3 | 100 | 85 | 100 | 50 | | | | | | |

| application rate a.i. in g/ha | | herbicidal activity against | | | | | | | | |
|---|---|---|---|---|---|---|---|---|---|---|
| | | AMBEL | | MATCH | | APESV | | ALOMY | | |
| I.1 | B.93 | found | calculated | found | calculated | found | calculated | found | calculated | found | calculated |
| 125 | — | 65 | — | 0 | — | 0 | — | 15 | — | | |
| — | 1.5 | 20 | — | 0 | — | 10 | — | 0 | — | | |
| 125 | 1.5 | 85 | 72 | 100 | 0 | 40 | 10 | 25 | 15 | | |

| application rate a.i. in g/ha | | herbicidal activity against | | | | | | | | |
|---|---|---|---|---|---|---|---|---|---|---|
| | | GALAP | | APESV | | ALOMY | | | | |
| I.1 | B.93 | found | calculated | found | calculated | found | calculated | found | calculated | found | calculated |
| 62.5 | — | 80 | — | 0 | — | 0 | — | | | | |
| — | 1.5 | 45 | — | 10 | — | 0 | — | | | | |
| 62.5 | 1.5 | 98 | 89 | 30 | 10 | 20 | 0 | | | | |

| application rate a.i. in g/ha | | herbicidal activity against | | | | | | | | |
|---|---|---|---|---|---|---|---|---|---|---|
| | | PAPRH | | APESV | | ALOMY | | | | |
| I. | B.93 | found | calculated | found | calculated | found | calculated | found | calculated | found | calculated |
| 31.25 | — | 70 | — | 0 | — | 0 | — | | | | |
| — | 1.5 | 70 | — | 10 | — | 0 | — | | | | |
| 31.25 | 1.5 | 100 | 91 | 30 | 10 | 20 | 0 | | | | |

Use Example 56: Synergistic Herbicidal Action of the Composition 1.32 Applied by the Post Emergence Method: Treatment by the Mixture of Compound (I.1)+Imazapic (B.32)

| application rate a.i. in g/ha | | herbicidal activity against | | | | | | |
|---|---|---|---|---|---|---|---|---|
| | | AMBEL | | MATCH | | APESV | | |
| I.1 | B.32 | found | calculated | found | calculated | found | calculated | found | calculated |
| 125 | — | 65 | — | 0 | — | 0 | — | | |
| — | 6 | 65 | — | 30 | — | 80 | — | | |
| 125 | 6 | 100 | 88 | 100 | 30 | 85 | 80 | | |

| application rate | | herbicidal activity against | | | | | | | | |
|---|---|---|---|---|---|---|---|---|---|---|
| a.i. in g/ha | | APESV | | | | | | | | |
| I.1 | B.32 | found | calculated | found | calculated | found | calculated | found | calculated | found | calculated |
| 62.5 | — | 0 | — | — | — | — | — | — | — | — | — |
| — | 6 | 80 | — | — | — | — | — | — | — | — | — |
| 62.5 | 6 | 85 | 80 | — | — | — | — | — | — | — | — |

| application rate | | herbicidal activity against | | | | | | | | |
|---|---|---|---|---|---|---|---|---|---|---|
| a.i. in g/ha | | IPOHE | | ABUTH | | | | | | |
| I.1 | B.32 | found | calculated | found | calculated | found | calculated | found | calculated | found | calculated |
| 31.25 | — | 65 | — | 0 | — | — | — | — | — | — | — |
| — | 6 | 75 | — | 85 | — | — | — | — | — | — | — |
| 31.25 | 6 | 98 | 91 | 98 | 85 | — | — | — | — | — | — |

| application rate | | herbicidal activity against | | | | | | | | |
|---|---|---|---|---|---|---|---|---|---|---|
| a.i. in g/ha | | AMBEL | | MATCH | | | | | | |
| I.1 | B.32 | found | calculated | found | calculated | found | calculated | found | calculated | found | calculated |
| 125 | — | 65 | — | 0 | — | — | — | — | — | — | — |
| — | 3 | 0 | — | 0 | — | — | — | — | — | — | — |
| 125 | 3 | 100 | 65 | 100 | 0 | — | — | — | — | — | — |

| application rate | | herbicidal activity against | | | | | | | | |
|---|---|---|---|---|---|---|---|---|---|---|
| a.i. in g/ha | | ALOMY | | POLCO | | | | | | |
| I.1 | B.32 | found | calculated | found | calculated | found | calculated | found | calculated | found | calculated |
| 62.5 | — | 0 | — | 65 | — | — | — | — | — | — | — |
| — | 3 | 25 | — | 85 | — | — | — | — | — | — | — |
| 62.5 | 3 | 30 | 25 | 100 | 95 | — | — | — | — | — | — |

| application rate | | herbicidal activity against | | | | | | | | |
|---|---|---|---|---|---|---|---|---|---|---|
| a.i. in g/ha | | POLCO | | ALOMY | | APESV | | | | |
| I.1 | B.32 | found | calculated | found | calculated | found | calculated | found | calculated | found | calculated |
| 31.25 | — | 0 | — | 0 | — | 0 | — | — | — | — | — |
| — | 3 | 85 | — | 25 | — | 65 | — | — | — | — | — |
| 31.25 | 3 | 95 | 85 | 30 | 25 | 70 | 65 | — | — | — | — |

Use Example 57: Synergistic Herbicidal Action of the Composition 1.174 Applied by the Post Emergence Method: Treatment by the Mixture of Compound (I.1)+Diflufenzopyr (B.174)

| application rate | | herbicidal activity against | | | | | | | |
|---|---|---|---|---|---|---|---|---|---|
| a.i. in g/ha | | MATCH | | | | | | | |
| I.1 | B.174 | found | calculated | found | calculated | found | calculated | found | calculated |
| 125 | — | 0 | — | — | — | — | — | — | — |
| — | 40 | 70 | — | — | — | — | — | — | — |
| 125 | 40 | 100 | 70 | — | — | — | — | — | — |

-continued

| application rate | | herbicidal activity against | | | | | | | | |
|---|---|---|---|---|---|---|---|---|---|---|
| a.i. in g/ha | | STEME | | VIOAR | | | | | | |
| I.1 | B.174 | found | calculated | found | calculated | found | calculated | found | calculated | found | calculated |
| 31.25 | — | 30 | — | 0 | — | | — | | — | | — |
| — | 40 | 50 | — | 65 | — | | — | | — | | — |
| 31.25 | 40 | 80 | 65 | 75 | 65 | | | | | | |

| application rate | | herbicidal activity against | | | | | | | | |
|---|---|---|---|---|---|---|---|---|---|---|
| a.i. in g/ha | | MATCH | | APESV | | ALOMY | | | | |
| I.1 | B.174 | found | calculated | found | calculated | found | calculated | found | calculated | found | calculated |
| 125 | — | 0 | — | 0 | — | 15 | — | | — | | — |
| — | 20 | 70 | — | 0 | — | 0 | — | | — | | — |
| 125 | 20 | 100 | 70 | 35 | 0 | 40 | 15 | | | | |

| application rate | | herbicidal activity against | | | | | | | | |
|---|---|---|---|---|---|---|---|---|---|---|
| a.i. in g/ha | | KCHSC | | ALOMY | | | | | | |
| I.1 | B.174 | found | calculated | found | calculated | found | calculated | found | calculated | found | calculated |
| 62.5 | — | 85 | — | 0 | — | | — | | — | | — |
| — | 20 | 65 | — | 0 | — | | — | | — | | — |
| 62.5 | 20 | 100 | 95 | 10 | 0 | | | | | | |

| application rate | | herbicidal activity against | | | | | | | | |
|---|---|---|---|---|---|---|---|---|---|---|
| a.i. in g/ha | | KCHSC | | ABUTH | | POLCO | | ALOMY | | |
| I.1 | B.174 | found | calculated | found | calculated | found | calculated | found | calculated | found | calculated |
| 31.25 | — | 70 | — | 0 | — | 0 | — | 0 | — | | — |
| — | 20 | 65 | — | 85 | — | 30 | — | 0 | — | | — |
| 31.25 | 20 | 95 | 90 | 90 | 85 | 40 | 30 | 10 | 0 | | |

Use Example 58: Synergistic Herbicidal Action of the Composition 1.123 Applied by the Post Emergence Method: Treatment by the Mixture of Compound (I.1)+Pendimethalin (B.123)

| application rate | | herbicidal activity against | | | | | | | | |
|---|---|---|---|---|---|---|---|---|---|---|
| a.i. in g/ha | | ERICA | | POLCO | | | | | | |
| I.1 | B.123 | found | calculated | found | calculated | found | calculated | found | calculated |
| 125 | — | 75 | — | 85 | — | | — | | — |
| — | 1000 | 60 | — | 65 | — | | — | | — |
| 125 | 1000 | 100 | 90 | 100 | 95 | | | | |

| application rate | | herbicidal activity against | | | | | | | | |
|---|---|---|---|---|---|---|---|---|---|---|
| a.i. in g/ha | | ERICA | | | | | | | | |
| I.1 | B.123 | found | calculated | found | calculated | found | calculated | found | calculated | found | calculated |
| 62.5 | — | 75 | — | | — | | — | | — | | — |
| — | 1000 | 60 | — | | — | | — | | — | | — |
| 62.5 | 1000 | 100 | 90 | | | | | | | | |

| application rate | | herbicidal activity against | | | | | | | | |
|---|---|---|---|---|---|---|---|---|---|---|
| a.i. in g/ha | | GERDI | | | | | | | | |
| I. | B.123 | found | calculated | found | calculated | found | calculated | found | calculated | found | calculated |
| 31.25 | — | 65 | — | — | — | — | — | — | — | — | — |
| — | 1000 | 75 | — | — | — | — | — | — | — | — | — |
| 31.25 | 1000 | 100 | 91 | — | — | — | — | — | — | — | — |

| application rate | | herbicidal activity against | | | | | | | | |
|---|---|---|---|---|---|---|---|---|---|---|
| a.i. in g/ha | | ERICA | | | | | | | | |
| I.1 | B.123 | found | calculated | found | calculated | found | calculated | found | calculated | found | calculated |
| 125 | — | 75 | — | — | — | — | — | — | — | — | — |
| — | 500 | 30 | — | — | — | — | — | — | — | — | — |
| 125 | 500 | 100 | 83 | — | — | — | — | — | — | — | — |

| application rate | | herbicidal activity against | | | | | | | | |
|---|---|---|---|---|---|---|---|---|---|---|
| a.i. in g/ha | | ERICA | | | | | | | | |
| I.1 | B.123 | found | calculated | found | calculated | found | calculated | found | calculated | found | calculated |
| 62.5 | — | 75 | — | — | — | — | — | — | — | — | — |
| — | 500 | 30 | — | — | — | — | — | — | — | — | — |
| 62.5 | 500 | 100 | 83 | — | — | — | — | — | — | — | — |

| application rate | | herbicidal activity against | | | | | | | | |
|---|---|---|---|---|---|---|---|---|---|---|
| a.i. in g/ha | | ERICA | | | | | | | | |
| I.1 | B.123 | found | calculated | found | calculated | found | calculated | found | calculated | found | calculated |
| 31.25 | — | 70 | — | — | — | — | — | — | — | — | — |
| — | 500 | 30 | — | — | — | — | — | — | — | — | — |
| 31.25 | 500 | 100 | 79 | — | — | — | — | — | — | — | — |

Use Example 59: Synergistic Herbicidal Action of the Composition 1.97 Applied by the Post Emergence Method: Treatment by the Mixture of Compound (I.1)+Clomazone (B.97)

| application rate | | herbicidal activity against | | | | | | | |
|---|---|---|---|---|---|---|---|---|---|
| a.i. in g/ha | | ALOMY | | ERICA | | | | | |
| I.1 | B.97 | found | calculated | found | calculated | found | calculated | found | calculated |
| 125 | — | 65 | — | 75 | — | — | — | — | — |
| — | 750 | 60 | — | 65 | — | — | — | — | — |
| 125 | 750 | 95 | 86 | 100 | 97 | — | — | — | — |

| application rate | | herbicidal activity against | | | | | | | | |
|---|---|---|---|---|---|---|---|---|---|---|
| a.i. in g/ha | | ALOMY | | ERICA | | | | | | |
| I.1 | B.97 | found | calculated | found | calculated | found | calculated | found | calculated | found | calculated |
| 62.5 | — | 25 | — | 75 | — | — | — | — | — | — | — |
| — | 750 | 60 | — | 65 | — | — | — | — | — | — | — |
| 62.5 | 750 | 85 | 70 | 98 | 91 | — | — | — | — | — | — |

-continued

| application rate a.i. in g/ha | | herbicidal activity against | | | | | | | | |
|---|---|---|---|---|---|---|---|---|---|---|
| | | ERICA | | IPOHE | | ALOMY | | | | |
| I.1 | B.97 | found | calculated | found | calculated | found | calculated | found | calculated | found | calculated |
| 31.25 | — | 70 | — | 40 | — | 0 | — | — | — | — | — |
| — | 750 | 65 | — | 45 | — | 60 | — | — | — | — | — |
| 31.25 | 750 | 98 | 90 | 75 | 67 | 70 | 60 | | | | |

| application rate a.i. in g/ha | | herbicidal activity against | | | | | | | | |
|---|---|---|---|---|---|---|---|---|---|---|
| | | ERICA | | | | | | | | |
| I.1 | B.97 | found | calculated | found | calculated | found | calculated | found | calculated | found | calculated |
| 125 | — | 75 | — | — | — | — | — | — | — | — | — |
| — | 375 | 50 | — | — | — | — | — | — | — | — | — |
| 125 | 375 | 100 | 88 | | | | | | | | |

| application rate a.i. in g/ha | | herbicidal activity against | | | | | | | | |
|---|---|---|---|---|---|---|---|---|---|---|
| | | ERICA | | ALOMY | | VIOAR | | | | |
| I.1 | B.97 | found | calculated | found | calculated | found | calculated | found | calculated | found | calculated |
| 62.5 | — | 75 | — | 25 | — | 30 | — | — | — | — | — |
| — | 375 | 50 | — | 45 | — | 85 | — | — | — | — | — |
| 62.5 | 375 | 100 | 88 | 75 | 59 | 98 | 90 | | | | |

| application rate a.i. in g/ha | | herbicidal activity against | | | | | | | | |
|---|---|---|---|---|---|---|---|---|---|---|
| | | ALOMY | | VIOAR | | | | | | |
| I.1 | B.97 | found | calculated | found | calculated | found | calculated | found | calculated | found | calculated |
| 31.25 | — | 0 | — | 20 | — | — | — | — | — | — | — |
| — | 375 | 45 | — | 85 | — | — | — | — | — | — | — |
| 31.25 | 375 | 60 | 45 | 95 | 88 | | | | | | |

Use Example 60: Synergistic Herbicidal Action Applied by the Post Emergence Method: Treatment by the Mixture of Compound (I.1)+Halosulfuron Methyl

| application rate a.i. in g/ha | | herbicidal activity against | | | | | | | |
|---|---|---|---|---|---|---|---|---|---|
| | halosulfuron | ECHCG | | | | | | | |
| I.1 | methyl | found | calculated | found | calculated | found | calculated | found | calculated |
| 62.5 | — | 45 | — | — | — | — | — | — | — |
| — | 5 | 45 | — | — | — | — | — | — | — |
| 62.5 | 5 | 75 | 70 | | | | | | |

| application rate a.i. in g/ha | | herbicidal activity against | | | | | | | |
|---|---|---|---|---|---|---|---|---|---|
| | halosulfuron | ALOMY | | | | | | | |
| I.1 | methyl | found | calculated | found | calculated | found | calculated | found | calculated |
| 31.25 | — | 0 | — | — | — | — | — | — | — |
| — | 5 | 10 | — | — | — | — | — | — | — |
| 31.25 | 5 | 25 | 10 | | | | | | |

Use Example 61: Synergistic Herbicidal Action of the Composition 1.134 Applied by the Post Emergence Method: Treatment by the Mixture of Compound (I.1)+S-Metolachlor (B.134)

| application rate a.i. in g/ha | | herbicidal activity against | | | | | | | |
|---|---|---|---|---|---|---|---|---|---|
| | | ERICA | | POLCO | | | | | |
| I.1 | B.134 | found | calculated | found | calculated | found | calculated | found | calculated |
| 125 | — | 75 | — | 85 | — | — | — | — | — |
| — | 500 | 35 | — | 60 | — | — | — | — | — |
| 125 | 500 | 100 | 84 | 100 | 94 | — | — | — | — |

| application rate a.i. in g/ha | | herbicidal activity against | | | | | | | |
|---|---|---|---|---|---|---|---|---|---|
| | | ERICA | | ALOMY | | | | | |
| I.1 | B.134 | found | calculated | found | calculated | found | calculated | found | calculated |
| 62.5 | — | 75 | — | 25 | — | — | — | — | — |
| — | 500 | 35 | — | 20 | — | — | — | — | — |
| 62.5 | 500 | 100 | 84 | 50 | 40 | — | — | — | — |

| application rate a.i. in g/ha | | herbicidal activity against | | | | | | | |
|---|---|---|---|---|---|---|---|---|---|
| | | ERICA | | AMBEL | | GERDI | | VIOAR | | KCHSC | |
| I.1 | B.134 | found | calculated | found | calculated | found | calculated | found | calculated | found | calculated |
| 31.25 | — | 70 | — | 75 | — | 65 | — | 20 | — | 80 | — |
| — | 500 | 35 | — | 65 | — | 30 | — | 0 | — | 30 | — |
| 31.25 | 500 | 100 | 81 | 100 | 91 | 100 | 76 | 60 | 20 | 100 | 86 |

| application rate a.i. in g/ha | | herbicidal activity against | | | | | | | |
|---|---|---|---|---|---|---|---|---|---|
| | | ERICA | | POLCO | | GALAP | | VIOAR | | |
| I.1 | B.134 | found | calculated | found | calculated | found | calculated | found | calculated |
| 125 | — | 75 | — | 85 | — | 65 | — | 60 | — |
| — | 250 | 25 | — | 35 | — | 45 | — | 0 | — |
| 125 | 250 | 100 | 81 | 98 | 90 | 100 | 81 | 65 | 60 |

| application rate a.i. in g/ha | | herbicidal activity against | | | | | | | |
|---|---|---|---|---|---|---|---|---|---|
| | | VIOAR | | | | | | | |
| I.1 | B.134 | found | calculated | found | calculated | found | calculated | found | calculated |
| 62.5 | — | 30 | — | — | — | — | — | — | — |
| — | 250 | 0 | — | — | — | — | — | — | — |
| 62.5 | 250 | 35 | 30 | — | — | — | — | — | — |

| application rate a.i. in g/ha | | herbicidal activity against | | | | | | | |
|---|---|---|---|---|---|---|---|---|---|
| | | ABUTH | | AMBEL | | ALOMY | | | |
| I.1 | B.134 | found | calculated | found | calculated | found | calculated | found | calculated |
| 31.25 | — | 30 | — | 75 | — | 0 | — | — | — |
| — | 250 | 40 | — | 25 | — | 0 | — | — | — |
| 31.25 | 250 | 70 | 58 | 90 | 81 | 20 | 0 | — | — |

Use Example 62: Synergistic Herbicidal Action of the Composition 1.1 Applied by the Post Emergence Method: Treatment by the Mixture of Compound (I.1)+Clethodim (B.1)

| application rate a.i. in g/ha | | herbicidal activity against | | | | | | | |
|---|---|---|---|---|---|---|---|---|---|
| | | ABUTH | | GALAP | | | | | |
| I.1 | B.1 | found | calculated | found | calculated | found | calculated | found | calculated |
| 125 | — | 60 | — | 95 | — | — | — | — | — |
| — | 12 | 25 | — | 0 | — | — | — | — | — |
| 125 | 12 | 98 | 70 | 100 | 95 | | | | |

| application rate a.i. in g/ha | | herbicidal activity against | | | | | | | |
|---|---|---|---|---|---|---|---|---|---|
| | | ABUTH | | | | | | | |
| I.1 | B.1 | found | calculated | found | calculated | found | calculated | found | calculated |
| 62.5 | — | 50 | — | — | — | — | — | — | — |
| — | 12 | 25 | — | — | — | — | — | — | — |
| 62.5 | 12 | 80 | 63 | | | | | | |

| application rate a.i. in g/ha | | herbicidal activity against | | | | | | | |
|---|---|---|---|---|---|---|---|---|---|
| | | ABUTH | | GALAP | | ERICA | | | |
| I.1 | B.1 | found | calculated | found | calculated | found | calculated | found | calculated |
| 31.25 | — | 25 | — | 50 | — | 25 | — | — | — |
| — | 12 | 25 | — | 0 | — | 0 | — | — | — |
| 31.25 | 12 | 55 | 44 | 60 | 50 | 30 | 25 | | |

| application rate a.i. in g/ha | | herbicidal activity against | | | | | | | |
|---|---|---|---|---|---|---|---|---|---|
| | | ABUTH | | | | | | | |
| I.1 | B.1 | found | calculated | found | calculated | found | calculated | found | calculated |
| 125 | — | 60 | — | — | — | — | — | — | — |
| — | 6 | 0 | — | — | — | — | — | — | — |
| 125 | 6 | 98 | 60 | | | | | | |

| application rate a.i. in g/ha | | herbicidal activity against | | | | | | | |
|---|---|---|---|---|---|---|---|---|---|
| | | ABUTH | | APESV | | | | | |
| I. | B.1 | found | calculated | found | calculated | found | calculated | found | calculated |
| 62.5 | — | 50 | — | 15 | — | — | — | — | — |
| — | 6 | 0 | — | 75 | — | — | — | — | — |
| 62.5 | 6 | 80 | 50 | 90 | 79 | | | | |

| application rate a.i. in g/ha | | herbicidal activity against | | | | | | | |
|---|---|---|---|---|---|---|---|---|---|
| | | ABUTH | | POLCO | | | | | |
| I.1 | B.1 | found | calculated | found | calculated | found | calculated | found | calculated |
| 31.25 | — | 25 | — | 65 | — | — | — | — | — |
| — | 6 | 0 | — | 0 | — | — | — | — | — |
| 31.25 | 6 | 45 | 25 | 98 | 65 | | | | |

Use Example 63: Synergistic Herbicidal Action of the Composition 1.140 Applied by the Post Emergence Method: Treatment by the Mixture of Compound (I.1)+2,4-D (B.140)

| application rate a.i. in g/ha | | herbicidal activity against | | | | | | | |
|---|---|---|---|---|---|---|---|---|---|
| | | ALMOY | | ABUTH | | VIOAR | | | |
| I.1 | B.140 | found | calculated | found | calculated | found | calculated | found | calculated |
| 125 | — | 20 | — | 60 | — | 80 | — | — | — |
| — | 62.5 | 0 | — | 85 | — | 65 | — | — | — |
| 125 | 62.5 | 50 | 20 | 98 | 94 | 100 | 93 | — | — |

| application rate a.i. in g/ha | | herbicidal activity against | | | | | | | |
|---|---|---|---|---|---|---|---|---|---|
| | | ALOMY | | ABUTH | | GALAP | | VIOAR | |
| I.1 | B.140 | found | calculated | found | calculated | found | calculated | found | calculated |
| 62.5 | — | 10 | — | 50 | — | 90 | — | 0 | — |
| — | 62.5 | 0 | — | 85 | — | 0 | — | 65 | — |
| 62.5 | 62.5 | 20 | 10 | 98 | 93 | 98 | 90 | 70 | 65 |

| application rate a.i. in g/ha | | herbicidal activity against | | | | | | | |
|---|---|---|---|---|---|---|---|---|---|
| | | POLCO | | GALAP | | VIOAR | | ERICA | |
| I.1 | B.140 | found | calculated | found | calculated | found | calculated | found | calculated |
| 31.25 | — | 65 | — | 50 | — | 0 | — | 25 | — |
| — | 62.5 | 75 | — | 0 | — | 65 | — | 80 | — |
| 31.25 | 62.5 | 98 | 91 | 65 | 50 | 70 | 65 | 90 | 85 |

| application rate a.i. in g/ha | | herbicidal activity against | | | | | | | |
|---|---|---|---|---|---|---|---|---|---|
| | | ALOMY | | ABUTH | | | | | |
| I.1 | B.140 | found | calculated | found | calculated | found | calculated | found | calculated |
| 125 | — | 20 | — | 60 | — | — | — | — | — |
| — | 31.25 | 0 | — | 35 | — | — | — | — | — |
| 125 | 31.25 | 45 | 20 | 90 | 74 | — | — | — | — |

| application rate a.i. in g/ha | | herbicidal activity against | | | | | | | |
|---|---|---|---|---|---|---|---|---|---|
| | | ABUTH | | GALAP | | VIOAR | | | |
| I.1 | B.140 | found | calculated | found | calculated | found | calculated | found | calculated |
| 62.5 | — | 50 | — | 90 | — | 0 | — | — | — |
| — | 31.25 | 35 | — | 0 | — | 60 | — | — | — |
| 62.5 | 31.25 | 75 | 68 | 95 | 90 | 65 | 60 | — | — |

| application rate a.i. in g/ha | | herbicidal activity against | | | | | | | |
|---|---|---|---|---|---|---|---|---|---|
| | | POLCO | | GALAP | | ERICA | | ABUTH | | MATCH | |
| I.1 | B.140 | found | calculated | found | calculated | found | calculated | found | calculated | found | calculated |
| 31.25 | — | 65 | — | 50 | — | 25 | — | 25 | — | 25 | — |
| — | 31.25 | 65 | — | 0 | — | 70 | — | 35 | — | 0 | — |
| 31.25 | 31.25 | 100 | 88 | 65 | 50 | 85 | 78 | 55 | 51 | 30 | 25 |

Use Example 64: Synergistic Herbicidal Action Applied by the Post Emergence Method: Treatment by the Mixture of Compound (I.1)+Quizalofop-p-Ethyl

| application rate a.i. in g/ha | | herbicidal activity against | | | | | | | |
|---|---|---|---|---|---|---|---|---|---|
| | quizalofop- | ABUTH | | | | | | | |
| I.1 | p-ethyl | found | calculated | found | calculated | found | calculated | found | calculated |
| 125 | — | 60 | — | | | | | | |
| — | 15 | 25 | — | | | | | | |
| 125 | 15 | 98 | 70 | | | | | | |

| application rate a.i. in g/ha | | herbicidal activity against | | | | | | | |
|---|---|---|---|---|---|---|---|---|---|
| | quizalofop- | VIOAR | | | | | | | |
| I.1 | p-ethyl | found | calculated | found | calculated | found | calculated | found | calculated |
| 62.5 | — | 0 | — | | | | | | |
| — | 15 | 0 | — | | | | | | |
| 62.5 | 15 | 30 | 0 | | | | | | |

| application rate a.i. in g/ha | | herbicidal activity against | | | | | | | |
|---|---|---|---|---|---|---|---|---|---|
| | quizalofop- | PAPRH | | MATCH | | ERICA | | | |
| I.1 | p-ethyl | found | calculated | found | calculated | found | calculated | found | calculated |
| 31.25 | — | 65 | — | 25 | — | 25 | — | | |
| — | 15 | 50 | — | 0 | — | 20 | — | | |
| 31.25 | 15 | 98 | 83 | 55 | 25 | 55 | 40 | | |

| application rate a.i. in g/ha | | herbicidal activity against | | | | | | | |
|---|---|---|---|---|---|---|---|---|---|
| | quizalofop- | ABUTH | | VIOAR | | | | | |
| I.1 | p-ethyl | found | calculated | found | calculated | found | calculated | found | calculated |
| 125 | — | 60 | — | 80 | — | | | | |
| — | 7.5 | 15 | — | 0 | — | | | | |
| 125 | 7.5 | 98 | 66 | 98 | 80 | | | | |

| application rate a.i. in g/ha | | herbicidal activity against | | | | | | | |
|---|---|---|---|---|---|---|---|---|---|
| | quizalofop- | ABUTH | | ERICA | | | | | |
| I.1 | p-ethyl | found | calculated | found | calculated | found | calculated | found | calculated |
| 31.25 | — | 25 | — | 25 | — | | | | |
| — | 7.5 | 15 | — | 0 | — | | | | |
| 31.25 | 7.5 | 45 | 36 | 30 | 25 | | | | |

Use Example 65: Synergistic Herbicidal Action of the Composition 1.9 Applied by the Post Emergence Method: Treatment by the Mixture of Compound (I.1)+Profoxydim (B.9)

| application rate a.i. in g/ha | | herbicidal activity against | | | | | | | |
|---|---|---|---|---|---|---|---|---|---|
| | | ABUTH | | ALOMY | | | | | |
| I.1 | B.9 | found | calculated | found | calculated | found | calculated | found | calculated |
| 125 | — | 60 | — | 20 | — | — | — | — | — |
| — | 12 | 40 | — | 25 | — | — | — | — | — |
| 125 | 12 | 98 | 76 | 50 | 40 | — | — | — | — |

| application rate a.i. in g/ha | | herbicidal activity against | | | | | | | |
|---|---|---|---|---|---|---|---|---|---|
| | | ABUTH | | | | | | | |
| I.1 | B.9 | found | calculated | found | calculated | found | calculated | found | calculated |
| 62.5 | — | 50 | — | — | — | — | — | — | — |
| — | 12 | 40 | — | — | — | — | — | — | — |
| 62.5 | 12 | 98 | 70 | — | — | — | — | — | — |

| application rate a.i. in g/ha | | herbicidal activity against | | | | | | | |
|---|---|---|---|---|---|---|---|---|---|
| | | APESV | | POLCO | | | | | |
| I.1 | B.9 | found | calculated | found | calculated | found | calculated | found | calculated |
| 31.25 | — | 0 | — | 65 | — | — | — | — | — |
| — | 12 | 55 | — | 0 | — | — | — | — | — |
| 31.25 | 12 | 65 | 55 | 70 | 65 | — | — | — | — |

| application rate a.i. in g/ha | | herbicidal activity against | | | | | | | |
|---|---|---|---|---|---|---|---|---|---|
| | | ABUTH | | | | | | | |
| I.1 | B.9 | found | calculated | found | calculated | found | calculated | found | calculated |
| 125 | — | 60 | — | — | — | — | — | — | — |
| — | 6 | 0 | — | — | — | — | — | — | — |
| 125 | 6 | 98 | 60 | — | — | — | — | — | — |

| application rate a.i. in g/ha | | herbicidal activity against | | | | | | | |
|---|---|---|---|---|---|---|---|---|---|
| | | APESV | | ABUTH | | | | | |
| I.1 | B.9 | found | calculated | found | calculated | found | calculated | found | calculated |
| 62.5 | — | 15 | — | 50 | — | — | — | — | — |
| — | 6 | 15 | — | 0 | — | — | — | — | — |
| 62.5 | 6 | 45 | 28 | 60 | 50 | — | — | — | — |

| application rate a.i. in g/ha | | herbicidal activity against | | | | | | | |
|---|---|---|---|---|---|---|---|---|---|
| | | APESV | | ABUTH | | | | | |
| I.1 | B.9 | found | calculated | found | calculated | found | calculated | found | calculated |
| 31.25 | — | 0 | — | 25 | — | — | — | — | — |
| — | 6 | 15 | — | 0 | — | — | — | — | — |
| 31.25 | 6 | 50 | 15 | 45 | 25 | — | — | — | — |

Use Example 66: Synergistic Herbicidal Action Applied by the Post Emergence Method: Treatment by the Mixture of Compound (I.1)+Thiencarbazone

| application rate a.i. in g/ha | | herbicidal activity against | | | | | | |
|---|---|---|---|---|---|---|---|---|
| | | APESV | | ERICA | | | | |
| I.1 | thiencarbazone | found | calculated | found | calculated | found | calculated | found | calculated |
| 125 | — | 15 | — | 65 | — | — | | — | |
| — | 0.5 | 25 | — | 85 | — | — | | — | |
| 125 | 0.5 | 45 | 36 | 100 | 95 | — | | — | |

Use Example 67: Synergistic Herbicidal Action Applied by the Post Emergence Method: Treatment by the Mixture of Compound (I.1)+Propaquizafop

| application rate a.i. in g/ha | | herbicidal activity against | | | | | | | |
|---|---|---|---|---|---|---|---|---|---|
| | | ALOMY | | GALAP | | KCHSC | | | |
| I.1 | propaquizafop | found | calculated | found | calculated | found | calculated | found | calculated |
| 125 | — | 25 | — | 90 | — | 95 | — | — | — |
| — | 10 | 65 | — | 10 | — | 10 | — | — | — |
| 125 | 10 | 100 | 74 | 100 | 91 | 100 | 96 | | |

| application rate a.i. in g/ha | | herbicidal activity against | | | | | | | |
|---|---|---|---|---|---|---|---|---|---|
| | | ALOMY | | POLCO | | ABUTH | | | |
| I.1 | propaquizafop | found | calculated | found | calculated | found | calculated | found | calculated |
| 62.5 | — | 0 | — | 90 | — | 85 | — | — | — |
| — | 10 | 65 | — | 0 | — | 30 | — | — | — |
| 62.5 | 10 | 90 | 65 | 98 | 90 | 98 | 90 | | |

| application rate a.i. in g/ha | | herbicidal activity against | | | | | | | |
|---|---|---|---|---|---|---|---|---|---|
| | | ALOMY | | APESV | | ERICA | | GALAP | | KCHSC |
| I.1 | propaquizafop | found | calculated | found | calculated | found | calculated | found | calculated | found | calculated |
| 125 | — | 25 | — | 15 | — | 65 | — | 90 | — | 95 | — |
| — | 5 | 55 | — | 65 | — | 0 | — | 0 | — | 0 | — |
| 125 | 5 | 85 | 66 | 85 | 70 | 100 | 65 | 100 | 90 | 100 | 95 |

| application rate a.i. in g/ha | | herbicidal activity against | | | | | | |
|---|---|---|---|---|---|---|---|---|
| | | APESV | | POLCO | | ERICA | | |
| I.1 | propaquizafop | found | calculated | found | calculated | found | calculated | found | calculated |
| 62.5 | — | 0 | — | 90 | — | 75 | — | — | — |
| — | 5 | 65 | — | 0 | — | 0 | — | — | — |
| 62.5 | 5 | 85 | 65 | 98 | 90 | 100 | 75 | | |

Use Example 68: Synergistic Herbicidal Action of the Composition 1.169 Applied by the Post Emergence Method: Treatment by the Mixture of Compound (I.1)+Quinmerac (B.169)

| application rate a.i. in g/ha | | herbicidal activity against | | | | | | | |
|---|---|---|---|---|---|---|---|---|---|
| | | ERICA | | KCHSC | | | | | |
| I.1 | B.169 | found | calculated | found | calculated | found | calculated | found | calculated |
| 125 | — | 65 | — | 95 | — | — | — | — | — |
| — | 125 | 75 | — | 25 | — | — | — | — | — |
| 125 | 125 | 100 | 91 | 100 | 96 | — | — | — | — |

| application rate a.i. in g/ha | | herbicidal activity against | | | | | | | |
|---|---|---|---|---|---|---|---|---|---|
| | | ERICA | | KCHSC | | ALOMY | | APESV | |
| I.1 | B.169 | found | calculated | found | calculated | found | calculated | found | calculated |
| 125 | — | 65 | — | 95 | — | 25 | — | 15 | — |
| — | 62.5 | 65 | — | 10 | — | 0 | — | 0 | — |
| 125 | 62.5 | 100 | 88 | 100 | 96 | 35 | 25 | 25 | 15 |

| application rate a.i. in g/ha | | herbicidal activity against | | | | | | | |
|---|---|---|---|---|---|---|---|---|---|
| | | ECHCG | | | | | | | |
| I.1 | B.169 | found | calculated | found | calculated | found | calculated | found | calculated |
| 62.5 | — | 60 | — | — | — | — | — | — | — |
| — | 62.5 | 0 | — | — | — | — | — | — | — |
| 62.5 | 62.5 | 80 | 60 | — | — | — | — | — | — |

Use Example 69: Synergistic Herbicidal Action Applied by the Post Emergence Method: Treatment by the Mixture of Compound (I.1)+Aclonifen

| application rate a.i. in g/ha | | herbicidal activity against | | | | | | | |
|---|---|---|---|---|---|---|---|---|---|
| | | ERICA | | ALOMY | | | | | |
| I.1 | aclonifen | found | calculated | found | calculated | found | calculated | found | calculated |
| 125 | — | 65 | — | 35 | — | — | — | — | — |
| — | 1000 | 0 | — | 70 | — | — | — | — | — |
| 125 | 1000 | 100 | 65 | 90 | 81 | — | — | — | — |

| application rate a.i. in g/ha | | herbicidal activity against | | | | | | | |
|---|---|---|---|---|---|---|---|---|---|
| | | ERICA | | MATCH | | ALOMY | | | |
| I.1 | aclonifen | found | calculated | found | calculated | found | calculated | found | calculated |
| 62.5 | — | 70 | — | 30 | — | 0 | — | — | — |
| — | 1000 | 0 | — | 0 | — | 70 | — | — | — |
| 62.5 | 1000 | 100 | 70 | 100 | 30 | 80 | 70 | — | — |

| application rate a.i. in g/ha | | herbicidal activity against | | | | | | | |
|---|---|---|---|---|---|---|---|---|---|
| | | POLCO | | MATCH | | | | | |
| I.1 | aclonifen | found | calculated | found | calculated | found | calculated | found | calculated |
| 31.25 | — | 20 | — | 20 | — | — | — | — | — |
| — | 1000 | 85 | — | 0 | — | — | — | — | — |
| 31.25 | 1000 | 100 | 88 | 65 | 20 | — | — | — | — |

-continued

| application rate | | herbicidal activity against | | | | | | | |
|---|---|---|---|---|---|---|---|---|---|
| a.i. in g/ha | | ERICA | | | | | | | |
| I.1 | aclonifen | found | calculated | found | calculated | found | calculated | found | calculated |
| 125 | — | 65 | — | — | — | — | — | — | — |
| — | 500 | 0 | — | — | — | — | — | — | — |
| 125 | 500 | 100 | 65 | — | — | — | — | — | — |

| application rate | | herbicidal activity against | | | | | | | |
|---|---|---|---|---|---|---|---|---|---|
| a.i. in g/ha | | GERDI | | MATCH | | ALOMY | | | |
| I.1 | aclonifen | found | calculated | found | calculated | found | calculated | found | calculated |
| 62.5 | — | 55 | — | 30 | — | 0 | — | — | — |
| — | 500 | 70 | — | 0 | — | 60 | — | — | — |
| 62.5 | 500 | 100 | 87 | 100 | 30 | 70 | 60 | — | — |

| application rate | | herbicidal activity against | | | | | | | |
|---|---|---|---|---|---|---|---|---|---|
| a.i. in g/ha | | GERDI | | MATCH | | ECHCG | | POLCO | |
| I.1 | aclonifen | found | calculated | found | calculated | found | calculated | found | calculated |
| 31.25 | — | 50 | — | 20 | — | 70 | — | 20 | — |
| — | 500 | 70 | — | 0 | — | 80 | — | 95 | — |
| 31.25 | 500 | 100 | 85 | 100 | 20 | 100 | 94 | 100 | 96 |

| application rate | | herbicidal activity against | | | | | | | |
|---|---|---|---|---|---|---|---|---|---|
| a.i. in g/ha | | ERICA | | ALOMY | | ECHCG | | | |
| I.1 | aclonifen | found | calculated | found | calculated | found | calculated | found | calculated |
| 125 | — | 65 | — | 35 | — | 85 | — | — | — |
| — | 250 | 0 | — | 30 | — | 50 | — | — | — |
| 125 | 250 | 100 | 65 | 70 | 55 | 100 | 93 | — | — |

| application rate | | herbicidal activity against | | | | | | | |
|---|---|---|---|---|---|---|---|---|---|
| a.i. in g/ha | | GERDI | | MATCH | | ALOMY | | ECHCG | | GALAP | |
| I.1 | aclonifen | found | calculated | found | calculated | found | calculated | found | calculated | found | calculated |
| 62.5 | — | 55 | — | 30 | — | 0 | — | 85 | — | 60 | — |
| — | 250 | 30 | — | 0 | — | 30 | — | 50 | — | 80 | — |
| 62.5 | 250 | 100 | 69 | 100 | 30 | 65 | 30 | 100 | 93 | 98 | 92 |

| application rate | | herbicidal activity against | | | | | | | |
|---|---|---|---|---|---|---|---|---|---|
| a.i. in g/ha | | POLCO | | GERDI | | MATCH | | ALOMY | | ERICA | |
| I.1 | aclonifen | found | calculated | found | calculated | found | calculated | found | calculated | found | calculated |
| 31.25 | — | 20 | — | 50 | — | 20 | — | 0 | — | 50 | — |
| — | 250 | 85 | — | 30 | — | 0 | — | 30 | — | 90 | — |
| 31.25 | 250 | 100 | 88 | 100 | 65 | 100 | 20 | 60 | 30 | 100 | 95 |

Use Example 70: Synergistic Herbicidal Action of the Composition 1.135 Applied by the Post Emergence Method: Treatment by the Mixture of Compound (I.1)+Pretilachlor (B.135)

| application rate | | herbicidal activity against | | | | | | | |
|---|---|---|---|---|---|---|---|---|---|
| a.i. in g/ha | | ERICA | | | | | | | |
| I.1 | B.135 | found | calculated | found | calculated | found | calculated | found | calculated |
| 125 | — | 65 | — | — | — | — | — | — | — |
| — | 400 | 20 | — | — | — | — | — | — | — |
| 125 | 400 | 100 | 72 | — | — | — | — | — | — |

-continued

| application rate | | herbicidal activity against | | | | | | | | |
|---|---|---|---|---|---|---|---|---|---|---|
| a.i. in g/ha | | GERDI | | MATCH | | | | | | |
| I.1 | B.135 | found | calculated | found | calculated | found | calculated | found | calculated | found | calculated |
| 62.5 | — | 55 | — | 30 | — | — | | — | | — | |
| — | 400 | 0 | — | 0 | — | — | | — | | — | |
| 62.5 | 400 | 70 | 55 | 100 | 30 | | | | | | |

| application rate | | herbicidal activity against | | | | | | | | |
|---|---|---|---|---|---|---|---|---|---|---|
| a.i. in g/ha | | ABUTH | | GERDI | | MATCH | | | | |
| I.1 | B.135 | found | calculated | found | calculated | found | calculated | found | calculated | found | calculated |
| 31.25 | — | 20 | — | 50 | — | 20 | — | — | | — | |
| — | 400 | 0 | — | 0 | — | 0 | — | — | | — | |
| 31.25 | 400 | 40 | 20 | 65 | 50 | 60 | 20 | | | | |

| application rate | | herbicidal activity against | | | | | | | | |
|---|---|---|---|---|---|---|---|---|---|---|
| a.i. in g/ha | | ERICA | | | | | | | | |
| I.1 | B.135 | found | calculated | found | calculated | found | calculated | found | calculated | found | calculated |
| 125 | — | 65 | — | — | | — | | — | | — | |
| — | 200 | 0 | — | — | | — | | — | | — | |
| 125 | 200 | 100 | 65 | | | | | | | | |

| application rate | | herbicidal activity against | | | | | | | | |
|---|---|---|---|---|---|---|---|---|---|---|
| a.i. in g/ha | | GALAP | | GERDI | | MATCH | | ERICA | | |
| I.1 | B.135 | found | calculated | found | calculated | found | calculated | found | calculated | found | calculated |
| 62.5 | — | 60 | — | 55 | — | 30 | — | 70 | — | — | |
| — | 200 | 0 | — | 0 | — | 0 | — | 0 | — | — | |
| 62.5 | 200 | 80 | 60 | 100 | 55 | 100 | 30 | 95 | 70 | | |

| application rate | | herbicidal activity against | | | | | | | | |
|---|---|---|---|---|---|---|---|---|---|---|
| a.i. in g/ha | | POLCO | | ABUTH | | MATCH | | | | |
| I.1 | B.135 | found | calculated | found | calculated | found | calculated | found | calculated | found | calculated |
| 31.25 | — | 20 | — | 20 | — | 20 | — | — | | — | |
| — | 200 | 0 | — | 0 | — | 0 | — | — | | — | |
| 31.25 | 200 | 65 | 20 | 50 | 20 | 40 | 20 | | | | |

| application rate | | herbicidal activity against | | | | | | | | |
|---|---|---|---|---|---|---|---|---|---|---|
| a.i. in g/ha | | ERICA | | | | | | | | |
| I.1 | B.135 | found | calculated | found | calculated | found | calculated | found | calculated | found | calculated |
| 125 | — | 65 | — | — | | — | | — | | — | |
| — | 100 | 0 | — | — | | — | | — | | — | |
| 125 | 100 | 100 | 65 | | | | | | | | |

| application rate | | herbicidal activity against | | | | | | | | |
|---|---|---|---|---|---|---|---|---|---|---|
| a.i. in g/ha | | GERDI | | MATCH | | | | | | |
| I.1 | B.135 | found | calculated | found | calculated | found | calculated | found | calculated | found | calculated |
| 62.5 | — | 55 | — | 30 | — | — | | — | | — | |
| — | 100 | 0 | — | 0 | — | — | | — | | — | |
| 62.5 | 100 | 85 | 55 | 60 | 30 | | | | | | |

| application rate a.i. in g/ha | | herbicidal activity against | | | | | | | | |
|---|---|---|---|---|---|---|---|---|---|---|
| | | ABUTH | | GERDI | | MATCH | | | | |
| I.1 | B.135 | found | calculated | found | calculated | found | calculated | found | calculated | found | calculated |
| 31.25 | — | 20 | — | 50 | — | 20 | — | — | — | — | — |
| — | 100 | 0 | — | 0 | — | 0 | — | — | — | — | — |
| 31.25 | 100 | 50 | 20 | 65 | 50 | 40 | 20 | | | | |

Use Example 71: Synergistic Herbicidal Action Applied by the Post Emergence Method: Treatment by the Mixture of Compound (I.1)+Methyl Oleate

| application rate a.i. in g/ha | | herbicidal activity against | | | | | | | | |
|---|---|---|---|---|---|---|---|---|---|---|
| | methyl | ERICA | | | | | | | | |
| I.1 | oleate | found | calculated | found | calculated | found | calculated | found | calculated | found | calculated |
| 125 | — | 65 | — | — | — | — | — | — | — | — | — |
| — | 12 | 0 | — | — | — | — | — | — | — | — | — |
| 125 | 12 | 100 | 65 | | | | | | | | |

| application rate a.i. in g/ha | | herbicidal activity against | | | | | | | | |
|---|---|---|---|---|---|---|---|---|---|---|
| | methyl | GERDI | | MATCH | | | | | | |
| I.1 | oleate | found | calculated | found | calculated | found | calculated | found | calculated | found | calculated |
| 62.5 | — | 55 | — | 30 | — | — | — | — | — | — | — |
| — | 12 | 0 | — | 0 | — | — | — | — | — | — | — |
| 62.5 | 12 | 70 | 55 | 100 | 30 | | | | | | |

| application rate a.i. in g/ha | | herbicidal activity against | | | | | | | | |
|---|---|---|---|---|---|---|---|---|---|---|
| | methyl | POLCO | | ABUTH | | GALAP | | | | |
| I.1 | oleate | found | calculated | found | calculated | found | calculated | found | calculated | found | calculated |
| 31.25 | — | 20 | — | 20 | — | 60 | — | — | — | — | — |
| — | 12 | 0 | — | 0 | — | 0 | — | — | — | — | — |
| 31.25 | 12 | 40 | 20 | 30 | 20 | 65 | 60 | | | | |

| application rate a.i. in g/ha | | herbicidal activity against | | | | | | | | |
|---|---|---|---|---|---|---|---|---|---|---|
| | methyl | ERICA | | | | | | | | |
| I.1 | oleate | found | calculated | found | calculated | found | calculated | found | calculated | found | calculated |
| 125 | — | 65 | — | — | — | — | — | — | — | — | — |
| — | 6 | 0 | — | — | — | — | — | — | — | — | — |
| 125 | 6 | 90 | 65 | | | | | | | | |

| application rate a.i. in g/ha | | herbicidal activity against | | | | | | | | |
|---|---|---|---|---|---|---|---|---|---|---|
| | methyl | MATCH | | GERDI | | | | | | |
| I.1 | oleate | found | calculated | found | calculated | found | calculated | found | calculated | found | calculated |
| 62.5 | — | 30 | — | 55 | — | — | — | — | — | — | — |
| — | 6 | 0 | — | 0 | — | — | — | — | — | — | — |
| 62.5 | 6 | 100 | 30 | 65 | 55 | | | | | | |

-continued

| application rate a.i. in g/ha | | herbicidal activity against | | | | | | | | |
|---|---|---|---|---|---|---|---|---|---|---|
| | | POLCO | | ABUTH | | | | | | |
| I.1 | methyl oleate | found | calculated | found | calculated | found | calculated | found | calculated | found | calculated |
| 31.25 | — | 20 | — | 20 | — | — | — | — | — | — | — |
| — | 6 | 0 | — | 0 | — | — | — | — | — | — | — |
| 31.25 | 6 | 95 | 20 | 50 | 20 | — | — | — | — | — | — |

| application rate a.i. in g/ha | | herbicidal activity against | | | | | | | | |
|---|---|---|---|---|---|---|---|---|---|---|
| | | ERICA | | | | | | | | |
| I.1 | methyl oleate | found | calculated | found | calculated | found | calculated | found | calculated | found | calculated |
| 125 | — | 65 | — | — | — | — | — | — | — | — | — |
| — | 3 | 0 | — | — | — | — | — | — | — | — | — |
| 125 | 3 | 100 | 65 | — | — | — | — | — | — | — | — |

| application rate a.i. in g/ha | | herbicidal activity against | | | | | | | | |
|---|---|---|---|---|---|---|---|---|---|---|
| | | GERDI | | MATCH | | | | | | |
| I.1 | methyl oleate | found | calculated | found | calculated | found | calculated | found | calculated | found | calculated |
| 62.5 | — | 55 | — | 30 | — | — | — | — | — | — | — |
| — | 3 | 0 | — | 0 | — | — | — | — | — | — | — |
| 62.5 | 3 | 70 | 55 | 100 | 30 | — | — | — | — | — | — |

| application rate a.i. in g/ha | | herbicidal activity against | | | | | | | | |
|---|---|---|---|---|---|---|---|---|---|---|
| | | POLCO | | MATCH | | | | | | |
| I.1 | methyl oleate | found | calculated | found | calculated | found | calculated | found | calculated | found | calculated |
| 31.25 | — | 20 | — | 20 | — | — | — | — | — | — | — |
| — | 3 | 0 | — | 0 | — | — | — | — | — | — | — |
| 31.25 | 3 | 70 | 20 | 30 | 20 | — | — | — | — | — | — |

The invention claimed is:

1. A herbicidal composition comprising as component A) an isoxazolo[5,4-b]pyridine compound of formula I

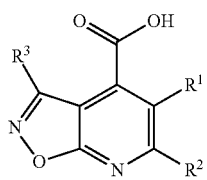

(I)

wherein the variables are as defined below:
$R^1$ is hydrogen;
$R^2$ is cyclopropyl;
$R^3$ is cyclopropyl or methyl;
or an agriculturally useful salt thereof;
and as component
B) at least one further herbicide selected from bleacher herbicides selected from the group consisting of pyrasulfotole, isoxaflutole, topramezone, benzobicyclon, bicyclopyrone, tembotrione, mesotrione, and tefuryltrione;
wherein the compound of formula I and the at least one further herbicide of component B are present in a synergistically effective amount and the weight ratio of component A to component B is from 75:1 to 1:75.

2. An agrochemical composition comprising the herbicidal composition of claim 1, at least one inert liquid and/or solid carrier and, if desired, at least one further additive.

3. The composition of claim 1, wherein component B is isoxaflutole.

4. The composition of claim 1, wherein component B is topramezone.

5. The composition of claim 1, wherein component B is benzobicyclon.

6. The composition of claim 1, wherein component B is tembotrione.

7. The composition of claim 1, wherein component B is mesotrione.

8. The composition of claim 1, wherein component B is pyrasulfotole.

9. A method for controlling unwanted vegetation, comprising allowing the composition of claim 1 to act on plants, their seeds and/or their habitat.

10. The method of claim 9 wherein the unwanted vegetation is controlled in a crop field where crop plants are cultivated.

11. The method of claim 10, wherein the crop plants are selected from cereals, corn, soybean, rice, millet, oilseed rape, cotton, sugarcane, potatoes, legumes, turf and permanent crops.

12. The method of claim 11, wherein component B is isoxaflutole.

13. The method of claim 11, wherein component B is topramezone.

14. The method of claim 11, wherein component B is benzobicyclon.

15. The method of claim 11, wherein component B is tembotrione.

16. The method of claim 11, wherein component B is mesotrione.

17. The method of claim 11, wherein component B is pyrasulfotole.

* * * * *